(12) United States Patent
An et al.

(10) Patent No.: US 10,761,088 B2
(45) Date of Patent: Sep. 1, 2020

(54) METHOD FOR IDENTIFYING HISTONE TAIL PROTEOLYSIS

(71) Applicant: University of Southern California, Los Angeles, CA (US)

(72) Inventors: Woojin An, Los Angeles, CA (US); Kyunghwan Kim, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/457,951

(22) Filed: Mar. 13, 2017

(65) Prior Publication Data

US 2017/0269069 A1 Sep. 21, 2017

Related U.S. Application Data

(60) Provisional application No. 62/308,100, filed on Mar. 14, 2016.

(51) Int. Cl.
*G01N 33/53* (2006.01)
*C12Q 1/68* (2018.01)
*C12Q 1/6804* (2018.01)

(52) U.S. Cl.
CPC ....... *G01N 33/5308* (2013.01); *C12Q 1/6804* (2013.01)

(58) Field of Classification Search
None
See application file for complete search history.

(56) References Cited

U.S. PATENT DOCUMENTS

2008/0069811 A1\* 3/2008 Zaidi ...................... C07K 16/26
424/130.1
2010/0183514 A1\* 7/2010 Glimcher ........... G01N 33/6893
424/9.1

OTHER PUBLICATIONS

Sundaram et al. (Experimental cell research 313.1 (2007): 168-178). (Year: 2007).\*
Azkur et al. (Oligonucleotides 15.2 (2005): 72-84.). (Year: 2005).\*
Soldi et al. (Journal of visualized experiments: JoVE 86 (2014) (Year: 2014).\*
Zhao et al. (Journal of molecular biology 383.5 (2008): 945-956.). (Year: 2008).\*
Ramos-DeSimone et al. (Journal of Biological Chemistry 274.19 (1999): 13066-13076.). (Year: 1999).\*
Chellaiah et al. (BioMed research international 2013 (2013); 13 pages). (Year: 2013).\*
Linn et al. ( Journal of Biological Chemistry 286.15 (2011): 13193-13204.) (Year: 2011).\*
Jin et al. (The EMBO journal 30.2 (2011): 249-262.). (Year: 2011).\*
Huang et al. (Stem cells and development 21.5 (2011): 778-789) (Year: 2011).\*

Asp, et al. "Genome-wide remodeling of the epigenetic landscape during myogenic differentiation", Proc Natl Acad Sci USA 108: E149-158, 2011.
Azad, et al., "Proteolytic clipping of histone tails: the emerging role of histone proteases in regulation of various biological processes", Molecular biology reports 41: 2717-2730, 2014.
Duncan, et al., "Cathepsin L proteolytically processes histone H3 during mouse embryonic stem cell differentiation", Cell 135: 284-294, 2008.
Khalkhali-Ellis, et al. "Cleavage of Histone 3 by Cathepsin D in the involuting mammary gland", PLoS One 9: e103230, 2014.
Nurse, et al., "Clipping of flexible tails of histones H3 and H4 affects the structure and dynamics of the nucleosome", Biophysical journal 104: 1081-1088, 2013.
Santos-Rosa, et al., "Histone H3 tail clipping regulates gene expression", Nature structural & molecular biology 16: 17-22, 2009.
Vossaert, et al., "Identification of histone H3 clipping activity in human embryonic stem cells", Stem cell research 13: 123-134, 2014.
Xue, et al., "PRB1 is required for clipping of the histone H3 N terminal tail in *Saccharomyces cerevisiae*", PLoS One 9: e90496, 2014.

\* cited by examiner

*Primary Examiner* — Tracy Vivlemore
*Assistant Examiner* — Sahana S Kaup
(74) *Attorney, Agent, or Firm* — Foley & Lardner LLP

(57) ABSTRACT

Although limited proteolysis of the histone H3 N-terminal tail (H3NT) is frequently observed during mammalian differentiation, the specific genomic sites targeted for H3NT proteolysis and the functional significance of H3NT cleavage remain largely unknown. Here Applicant reports the first method to identify and examine H3NT-cleaved regions in mammals, called ChIP of acetylated chromatin (ChIPac). By applying ChIPac-Seq to an established cell model of osteoclast differentiation, Applicant discovered that H3NT proteolysis is selectively targeted near transcription start sites of a small group of genes and that most H3NT-cleaved genes displayed significant expression changes during osteoclastogenesis. Applicant also discovered that the principal H3NT protease of osteoclastogenesis is matrix metalloproteinase 9 (MMP-9). In contrast to other known H3NT proteases, MMP-9 primarily cleaved H3K18-Q19 in vitro and in cells. Furthermore, Applicant's results support CBP/p300-mediated acetylation of H3K18 as a central regulator of MMP-9 H3NT protease activity both in vitro and at H3NT-cleavage sites during osteoclastogenesis. Importantly, Applicant found that abrogation of H3NT proteolysis impaired osteoclastogenic gene activation concomitant with defective osteoclast differentiation. Applicant's collective results support the necessity of MMP-9-dependent H3NT proteolysis in regulating gene pathways required for proficient osteoclastogenesis.

8 Claims, 15 Drawing Sheets
Specification includes a Sequence Listing.

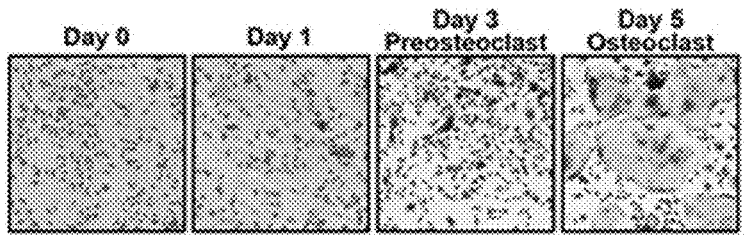
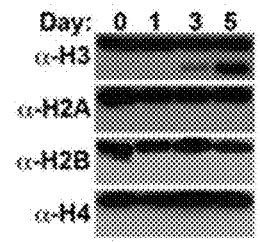
FIG. 1A
FIG. 1B
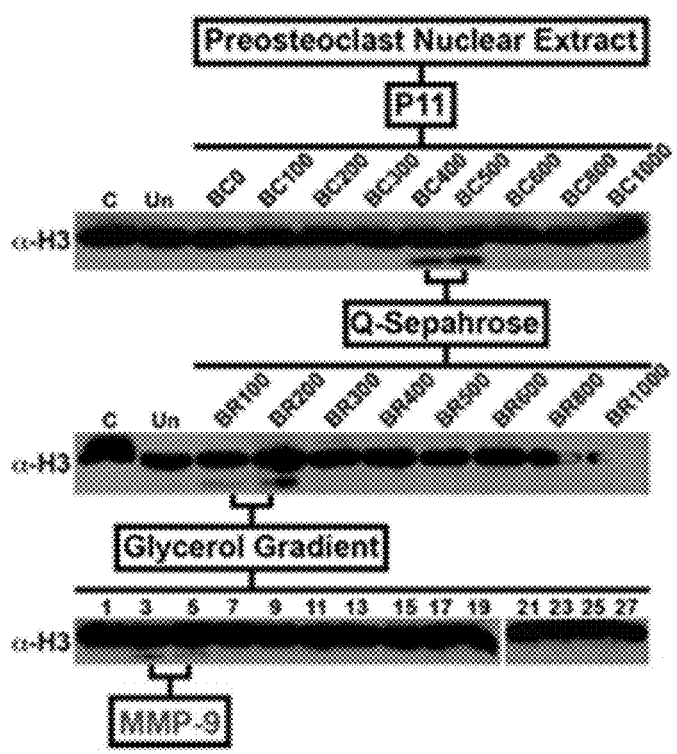
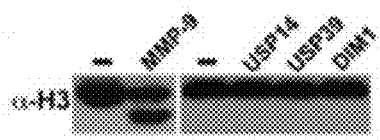
FIG. 1C
FIG. 1D
FIG. 1E
FIG. 1F
FIG. 1G

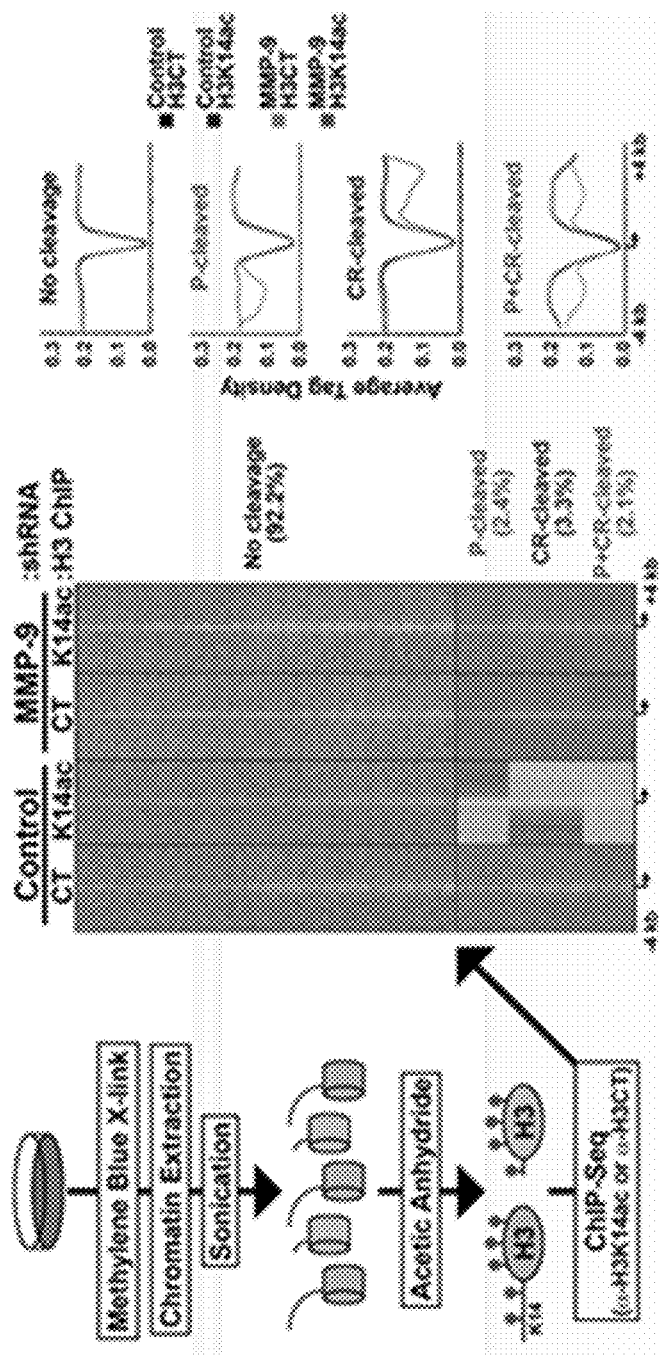

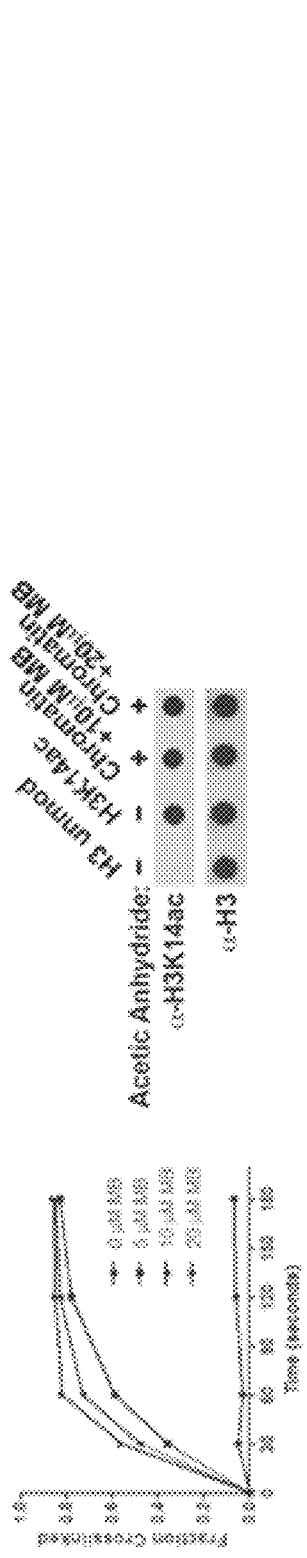
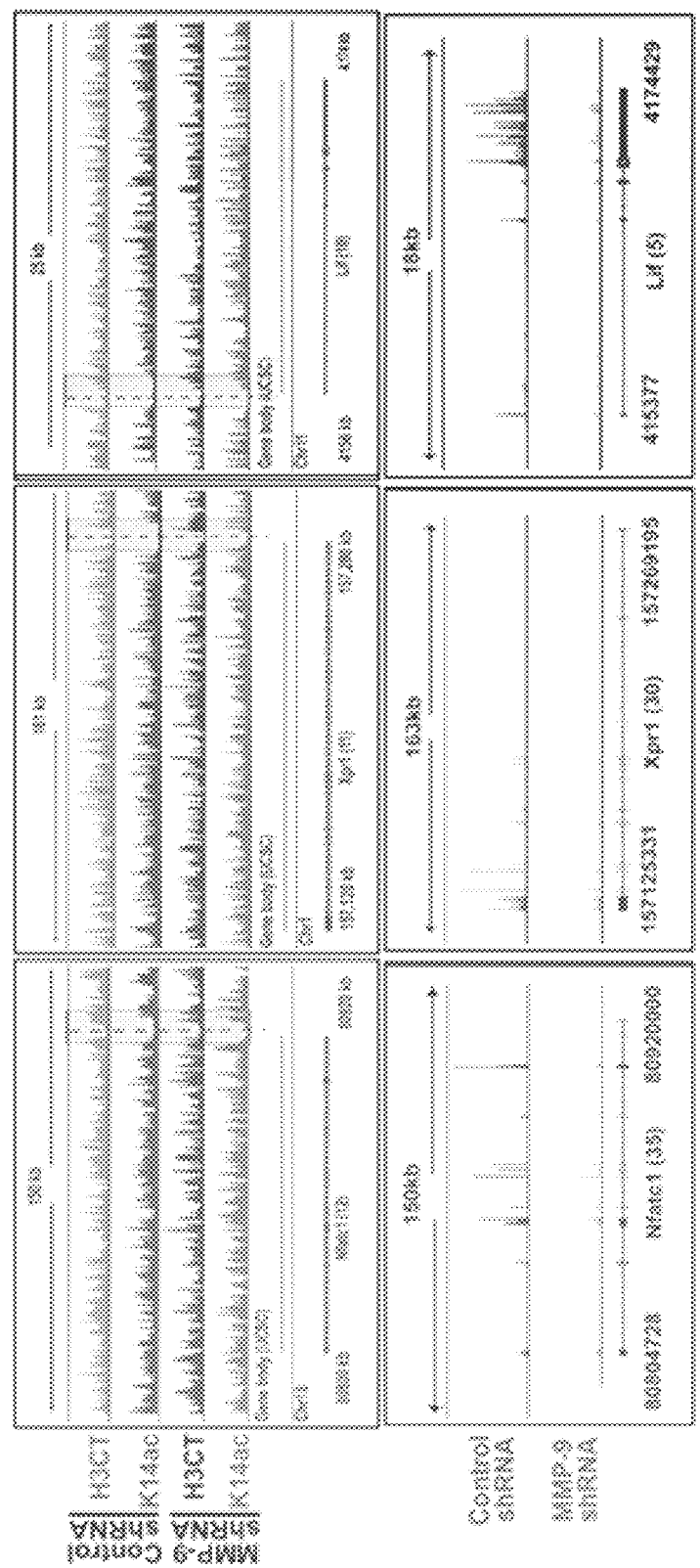
FIG. 13A
FIG. 13B
FIG. 13C

METHOD FOR IDENTIFYING HISTONE TAIL PROTEOLYSIS

CROSS-REFERENCE TO RELATED APPLICATIONS

This application claims priority under 35 U.S.C. § 119(e) to U.S. Provisional Application No. 62/308,100, filed Mar. 14, 2016, the contents of which is hereby incorporated by reference into the present disclosure.

STATEMENT OF GOVERNMENT SUPPORT

This invention was made with government support under Grant No. R01GM084209 awarded by National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on May 11, 2017, is named 064189-7551_SL.txt and is 15,462 bytes in size.

TECHNICAL FIELD

This invention embodies methods and kits related to epigenomics and medicine. In particular the invention is related to methods of identifying cleaved histones and treatment of bone conditions.

BACKGROUND

This disclosure references various publications, patents and published patent specifications by an identifying citation. The full citations for the disclosures are found immediately preceding the claims. The disclosures of these publications, patents and published patent specifications and all referenced documents are hereby incorporated by reference into the present disclosure in their entirety to more fully describe the state of the art to which this invention pertains.

The basic components that comprise the canonical nucleosome core particle are evolutionarily conserved in all eukaryotes. Within a living cell, however, there exists a remarkable degree of heterogeneity in nucleosome composition that influences chromatin structure and function (Luger et al. 2012). This is exemplified by the various covalent posttranslational modifications (PTMs) of the N-terminal tails (NT) of the core histone proteins (H3, H4, H2A, H2B) that alter nucleosome composition to regulate fundamental DNA-templated programs such as transcription (Zentner and Henikoff 2013). For example, acetylation of the H3NT can directly facilitate transcription by destabilizing nucleosome structure whereas methylation of the H3NT can indirectly regulate transcription by binding effector proteins that stimulate or repress transcription (Bannister et al. 2001; Shogren-Knaak et al. 2006). Recent landmark reports determined that differences in the "epigenomic signatures" of several H3NT PTMs are strongly correlated to the cell type-specific gene expression programs observed in >250 normal and diseased human tissues (Polak et al. 2015; Roadmap Epigenomics et al. 2015). These studies demonstrate that precise alterations of the epigenome are essential in the regulation of gene pathways necessary for the derivation of normal and aberrant cell types.

Altering epigenomic signatures by "erasing" H3NT PTMs can be achieved by several different enzymatic mechanisms. One mechanism is the selective removal of specific H3 PTMs by histone-modifying enzymes such as deacetylases and demethylases (Black et al. 2012; Seto and Yoshida 2014). A more extreme mechanism involves ATP-dependent deposition of a new H3 resulting in the removal of all pre-existing PTMs and associated interacting proteins (Narlikar et al. 2013). An alternative intermediate mechanism between the specific and complete erasure of H3 PTMs is proteolysis of the H3NT, which selectively removes pre-existing H3NT PTMs and associated interacting proteins without affecting the H3 core region (Azad and Tomar 2014; Dhaenens et al. 2015). While retention of the H3 core region preserves nucleosome structure, lack of the H3NT destabilizes intra- and inter-nucleosomal interactions that may increase DNA accessibility and facilitate factor binding (Allan et al. 1982; Andresen et al. 2013; Nurse et al. 2013). Therefore, H3NT cleavage provides an efficient means to rapidly and drastically alter chromatin structure and function both directly and indirectly.

Although proteolysis of histones within chromatin was first reported over 55 years ago, the mechanisms and biological functions of histone cleavage remain largely unknown (Phillips and Johns 1959). Proteolysis of the H3NT has been detected in various single and multi-cellular eukaryotes indicating that H3NT cleavage is an evolutionarily conserved process that likely functions in epigenetic regulation (Allis et al. 1980; Bortvin and Winston 1996; Duncan et al. 2008; Pauli et al. 2010; Duarte et al. 2014; Vossaert et al. 2014). Consistent with this, H3NT cleavage is frequently observed during mammalian developmental programs including embryonic stem cell differentiation, mammary gland development and myogenesis (Duncan et al. 2008; Asp et al. 2011; Khalkhali-Ellis et al. 2014; Vossaert et al. 2014). The recent identification of Cathepsin L and D as the principal H3NT protease during mouse embryonic stem cell differentiation and mammary gland development, respectively, suggests that precursor cells utilize different H3NT proteases in a differentiation-dependent context (Duncan et al. 2008; Khalkhali-Ellis et al. 2014). While these reports imply that targeted H3NT proteolysis at specific genomic regions facilitates differentiation, the lack of a method to identify H3NT-cleaved regions has precluded significant insights into the mechanistic functions of H3NT proteolysis. Thus, a need exists in the art and this disclosure satisfies this need and provides related advantages as well.

SUMMARY

In this disclosure Applicant demonstrates that matrix metalloproteinase 9 (MMP-9) is the principal H3NT protease of osteoclastogenesis. Applicant also developed the first method to map H3NT-cleaved regions in mammals, called "ChIP of acetylated chromatin (ChIPac)." Applicant further demonstrates the selective targeting of MMP-dependent H3NT proteolysis near transcription start sites of osteoclastogenic genes during differentiation. Consistent with H3NT cleavage-dependent gene activation reported in *S. cerevisiae*, Applicant discovered that H3NT proteolysis was strongly correlated with transcriptional activation (Santos-Rosa et al. 2009). Abrogation of MMP-9-dependent H3NT proteolysis resulted in impaired osteoclastogenic gene activation and defective osteoclast differentiation. Therefore, the results reported herein support a model whereby MMP- 9-dependent H3NT proteolysis at osteoclastogenic genes facilitates their activation necessary for proficient osteoclast differentiation.

The DNA in eukaryotic cells is hierarchically packaged by histones to form a highly repressive structure of chromatin. The basic unit of chromatin is the nucleosome, which consists of 147 bp of DNA wrapped around an H3-H4 tetramer and a pair of H2A-H2B dimers. Recent reports suggest that the dynamic modification of chromatin architecture plays fundamental roles in regulating specific gene expression programs. Chromatin architecture can be altered by several different enzymatic mechanisms. One mechanism is the removal of the N-terminal tail domain of histone H3 proteins by specific proteases. This mechanism selectively removes pre-existing H3 tail modifications and associated interacting proteins without affecting the H3 core regions. Thus, it is necessary to determine the genomic sites targeted for H3 N-terminal tail proteolysis to investigate the role of H3 tail cleavage in transcriptional regulation. Mapping these cleavage sites could be achieved by Chromatin Immunoprecipitation sequencing (ChIP-seq) analysis, but an antibody that has specific affinity for the H3 N-terminal tail of all H3 proteins, is not dependent on or inhibited by existing H3 posttranslational modifications and is validated for Chromatin Immunoprecipitation (ChIP) applications, is not available.

To overcome this technical barrier, Applicant developed a novel method, called ChIP of acetylated chromatin (ChIPac), for identification and examination of genetic loci bound by H3 with N-terminal tail-cleaved regions. The antibody recognizing H3 lysine 14 acetylation (H3K14ac) satisfies the criteria above for ChIP of the H3 N-terminal tail following complete lysine acetylation of crosslinked chromatin in vitro by acetic anhydride. First, cells were fixed with methylene blue to crosslink chromatin after brief exposure to white light. It should be noted that most ChIP protocols utilize formaldehyde to crosslink proteins to DNA in vivo. However, because formaldehyde reacts with lysine ε-amino side-chains, which likely precludes complete lysine acetylation by acetic anhydride, methylene blue was used as an alternative for cell fixation. Chromatin was isolated and the efficiency of crosslinking was confirmed by sodium dodecyl sulfate-chloroformisoamyl alcohol (SDS-CIA). Fragmented chromatin was then treated with acetic anhydride to completely acetylate all unmodified lysine residues in vitro. ChIPac using an H3K14ac-specific antibody selectively enriched H3 N-terminal tail-containing chromatin and simultaneously excluded chromatin lacking the H3 N-terminal tail. ChIPac using an H3 C-terminal tail antibody was performed in parallel as the normalization control. H3 N-terminal tail-cleaved regions were identified by the significant reduction in H3K14ac enrichment relative to control as determined by quantitative PCR (qPCR) or NextGen sequencing analysis.

Thus, in one aspect, provided herein is a method to identify and examine H3 N-terminal tail cleaved regions of a histone, the method comprising, or alternatively consisting essentially of, or yet further consisting of: a) contacting a cell containing chromatin with methylene blue or an equivalent thereof after exposure to white light or an equivalent of the white light to crosslink proteins in the cell; b) isolating the chromatin, c) acetylating all unmodified lysine residues by contacting the chromatin with acetic anhydride; d) conducing ChIPac with an H3 C-terminal tail antibody; and e) identifying H3 N-terminal tail-cleaved regions by detecting reduction in H3K14ac enrichment relative to a control.

In some aspects of the method, step e. is performed by a method comprising, or alternatively consisting essentially of, or yet further consisting of, quantitative PCR (qPCR) or NextGen sequencing analysis.

In another aspect, provided herein is a method to identify a polynucleotide fragment bound to an H3 histone comprising a cleaved N-terminal tail (H3NT) in a cell, the method comprising: a) crosslinking the genomic DNA of the cell to the histones of the cell, thereby producing crosslinked chromatin; b) generating fragments of the crosslinked chromatin; c) acetylating all unmodified lysine residues in the histones by contacting the fragmented, crosslinked chromatin with acetic anhydride or an equivalent thereof, d) conducting parallel chromatin immunoprecipitations on the acetylated chromatin produced in step c). with (1) an H3 C-terminal tail control antibody and (2) one or more antibodies directed to acetylated lysine residues in the cleaved region of the H3NT; and e) identifying the polynucleotide fragment bound to an H3NT by detecting reduction in polynucleotide fragment enrichment with the one or more antibodies directed to acetylated lysine residues in the cleaved region relative to polynucleotide fragment enrichment with the H3 C-terminal tail control antibody.

In other aspects, the method further comprises identifying a subject appropriate for therapeutic treatment with MMP-9.

In other aspects, the method further comprises identifying genetic loci at which a matrix metalloproteinase or other histone cleavage enzyme cleaves an H3 N terminal tail.

Also provided is a kit for identifying a polynucleotide fragment bound to an H3 histone comprising a cleaved N-terminal tail (H3NT) in a cell, the kit comprising: a) acetic anhydride or an equivalent thereof; b) an H3 C-terminal tail control antibody; c) a full length H3 N-tail detection antibody directed to an acetylated lysine residue; and d) instructions for use. In some embodiments, the full length H3 N-tail detection antibody is a H3K14ac antibody. In other embodiments, the antibody is an H3K4ac antibody or an H3K9ac antibody. In some embodiments, a mixture of one or more of H3K14ac antibody, H3K4ac antibody, and H3K9ac antibody are used to detect the full length acetylated H3 N-terminal tail. In some aspects, the kit may further comprise buffers, negative control antibodies, enzymes, methylene blue, and/or other reagents necessary to perform chromatin immunoprecipitation. The standard reagents necessary to perform chromatin immunoprecipitation, qPCR, and DNA seq are well known in the art.

Also provided is a method to modulate H3NT proteolysis during osteoclastogenesis in a cell, comprising, or alternatively consisting essentially of, or yet further consisting of, modulating the activity of MMP-9 in the cell. In one aspect, H3NT proteolysis is increased by increasing MMP-9 activity in the cell. In another aspect, the H3NT proteolysis is decreased by depletion or inhibit of MMP-9 activity in the cell. Diseases or pathological conditions associated with over- or under-osteoclastogenesis also can be treated by administering to a subject in need thereof an effective amount of the MMP-9 promoting or inhibiting agent. Agents that activate or promote MMP-9 activity include recombinant or isolated MMP-9 protein and epidermal growth factor has been shown to increase the expression and activity of MMP-9 (see WO 2002/045740).

Also provided herein is a method to modulate H3NT proteolysis in a cell, comprising modulating the activity of MMP-9 in the cell. In some aspects, H3NT proteolysis is increased by increasing MMP-9 activity in the nucleus of the cell. In further aspects, MMP-9 activity is increased by increasing nuclear localization of MMP-9, increasing acetylation of H3K18 residues, and/or overexpression of MMP-9. In other aspects, H3NT proteolysis is decreased by depletion or inhibition of MMP-9 activity in the cell. In further aspects, MMP-9 activity is decreased by knockdown of MMP-9 mRNA, treatment with CBP/p300 inhibitor, and/or treatment with a metalloprotease inhibitor. Knockdown of MMP-9 mRNA can comprise treatment with MMP-9 shRNA and/or treatment with a mesenchymal stem cell expressing MMP-9 shRNA.

In the above methods, a cell is a prokaryotic or a eukaryotic cell, and when an eukaryotic cell can be a mammalian cell, e.g., a mouse, canine, feline, ovine, simian or a human cell. In the above methods, a cell may be an osteoclast, an osteoclast precursor cell, or a stem or progenitor cell that can be differentiated into an osteoclast.

Also provided herein is a method to attenuate osteoclast formation and/or differentiation in a subject, comprising, or alternatively consisting essentially of, or yet further consisting of, administering to the subject an effective amount of a MMP-9 agent, inhibitor, or activator to the subject. In several aspects, the subject is a mammal, e.g., a mouse, a canine, a feline, an ovine, a simian or a human patient. These methods can be used therapeutically or in veterinary applications, or alternatively, as an animal model to assay for new therapies or treatments. The agents can be used alone or in combination with other known therapies.

Also provided herein is a method of treating a subject with low bone mineral density, comprising administering to the subject an agent that decreases or inhibiting the activity of MMP-9 in the subject. In several aspects, the subject is a mammal, e.g., a mouse, a canine, a feline, an ovine, a simian or a human patient. These methods can be used therapeutically or in veterinary applications, or alternatively, as an animal model to assay for new therapies or treatments. The agents can be used alone or in combination with other known therapies. In some aspects, the subject has a bone related disease or condition selected from osteoporosis, bone cancer, cancer that has metastasized to the bone, cancer-induced osteolysis, sepsis, rheumatoid arthritis, and periodontitis.

Also provided herein is a method of treating a subject with high bone mineral density, comprising administering to the subject an agent that increases the activity of MMP-9 in the subject. In several aspects, the subject is a mammal, e.g., a mouse, a canine, a feline, an ovine, a simian or a human patient. These methods can be used therapeutically or in veterinary applications, or alternatively, as an animal model to assay for new therapies or treatments. The agents can be used alone or in combination with other known therapies. In some aspects, the subject has a bone related disease or condition selected from osteopetrosis, pycondysostosis, osteopoikilosis, meloreostosis, sclerosteosis, van Buchem's disease, LRP5 high bone mass, LRP4 high bone mass, craniometaphyseal dysplasia, Camurati-Engelmann disease, Ghosal syndrome, bone cancer, cancer metastasized to the bone, fluorosis, renal osteodystrophy, acromegaly, hepatitis C-associated osteosclerosis, myelofibrosis, mastocytosis, osseous tuberous sclerosis, Paget's disease, and SAPHO syndrome.

BRIEF DESCRIPTION OF THE DRAWINGS

FIGS. 1A to 1G shows identification of MMP-9 as a novel H3NT protease.

FIGS. 1A-1G. FIG. 1A shows primary mouse OCP cells were cultured with RANKL to induce osteoclastogenesis. OCP-induced cells were fixed, stained for TRAP, and photographed under a light microscope (10×) at the indicated days. TRAP-positive cells containing 3 or more nuclei represent osteoclasts. FIG. 1B shows western blot analysis of chromatin extracted from OCP-induced cells using antibodies recognizing the C-terminal histone regions as indicated. FIG. 1C shows nuclear extracts from 3-day OCP-induced cells were fractionated on a P11 column by increased salt concentration, as indicated, and the in vitro H3NT cleavage assay was performed to identify H3NT active fractions by Western blot analysis using the H3CT antibody. The indicated H3NT active fractions were fractionated on a Q-Sepharose column followed by a 10-40% glycerol gradient. FIG. 1D shows H3NT cleavage assays of purified fractions #3-5 treated with different protease family inhibitors as indicated. FIG. 1E shows H3NT cleavage assays of purified fractions #3-5 treated with metalloproteinase inhibitors EDTA, CTT or a selective MMP-9 inhibitor. FIG. 1F shows Proteomic analysis of known proteases identified in purified fractions #3-5. FIG. 1G shows H3NT cleavage assays using recombinant MMP-9, USP14, USP39 and DIM1.

FIGS. 2A-2D. FIG. 2A shows western blot analysis for MMP-9 using whole cell (top) or nuclear (bottom) lysates isolated from OCP-induced cells at the indicated days. Proform and active MMP-9 are indicated. FIG. 2B shows gelatin zymography of nuclear lysates isolated from OCP-induced cells expressing a control (top) or MMP-9-specific (bottom) shRNA at the indicated days. FIG. 2C shows Western blot analysis of nuclear lysates from 3-day OCP-induced cells expressing a control (left) or MMP-9-specific (right) shRNA using the indicated antibodies. FIG. 2D shows OCP cells transduced with a control or MMP-9-specific shRNA (top) or treated with DMSO control or a selective MMP-9 inhibitor (bottom). H3NT cleavage was assessed at the indicated days post-induction.

FIGS. 3A-3D. FIG. 3A shows peptide sequences (SEQ ID NOS 25-37, respectively, in order of appearance) identified by LC-MS/MS of the gel-excised rH3 product (H3Δ19) generated by rMMP-9. FIG. 3B shows putative MMP-9 cleavage site identified in the H3NT (aa6-21) in silico. Amino acids that are more (light) or less (dark) conserved in the canonical MMP-9 consensus sequence are indicated. FIG. 3B discloses SEQ ID NO: 38. FIG. 3C shows H3NT cleavage assays using rMMP-9 and rH3 wild type (WT) or mutant substrates as indicated. FIG. 3D shows OCP cells were transduced with WT or mutant H3-FLAG. Chromatin was isolated on the indicated days post-induction for Western blot analysis using a FLAG antibody to specifically detect proteolysis of H3-FLAG.

FIGS. 4A-4E. FIG. 4A shows the indicated H3 peptides (aa10-35) were incubated with increasing concentrations of rMMP-9 (x-axis) and proteolysis was measured fluorometrically by reaction of free amino groups with fluorescamine (y-axis). The $V_{max}$ and $K_m$ values were obtained by non-linear regression fit. FIG. 4B shows H3NT cleavage assays using rMMP-9 and the indicated rH3 acetyl-lysine analogues substrates either alone (top) or as reconstituted nucleosome arrays (bottom). FIG. 4C shows H3NT cleavage assays using rMMP-9 and recombinant (top) or native (bottom) nucleosome array substrates. FIG. 4D shows Western blot analysis of nuclear lysates from 3-day OCP-induced cells expressing a control or CBP/p300-specific shRNA using the indicated antibodies. FIG. 4E shows OCP cells transduced with a control or CBP/p300-specific shRNA (top) or treated with DMSO control or a selective CBP/p300 inhibitor (bottom). H3NT cleavage was assessed at the indicated days post-induction.

FIGS. 5A-5D. FIG. 5A shows scatter plot of RNA-Seq normalized RPKM levels of annotated genes from 3-day OCP-induced cells expressing a control (x-axis) or MMP-9-specific (y-axis) shRNA. Genes with significantly increased (light gray) or decreased (dark gray) expression in MMP-9 depleted cells relative to control cells were defined based on FDR adjusted $p<0.05$ and log 2 ratio$\pm 0.7$. FIG. 5B shows GSEA of the 758 genes displaying impaired activation in MMP-9 depleted cells (x-axis) were ranked by increasing expression differences (light curve) relative to control cells (y-axis). FIG. 5C shows expression differences of the indicated 26 osteoclastogenic genes identified in FIG. 6B between control (left) and MMP-9 depleted (right) 3-day OCP-induced cells displayed as a heat map in the pseudo color scale indicated. FIG. 5D shows Visualization (10×) of TRAP stained 5-day OCP-induced cells expressing a control, MMP-9-specific or CBP/p300-specific shRNA (top) or treated with DMSO control, a selective MMP-9 inhibitor or a selective CBP/p300 inhibitor (bottom).

FIGS. 6A to 6C show selective targeting of MMP-9-dependent H3NT proteolysis near TSSs during osteoclastogenesis.

FIGS. 6A-6C. FIG. 6A shows schematic of ChIPac-Seq. Cells were fixed with methylene blue and chromatin extracted. Crosslinked chromatin was sonicated to generate nucleosomes containing full length (left) and NT-cleaved (right) H3. Acetic anhydride was used to artificially acetylate all unmodified lysines (indicated as lollipops on the H3). ChIPac was performed for H3CT control, to enrich all nucleosomes, or H3K14ac, to enrich only H3NT-containing nucleosomes. FIG. 6B shows Comparative ChIPac-Seq analyses of control (left) and MMP-9 depleted (right) 3-day OCP-induced cells for enrichment (dark) or depletion (light) of H3CT control (left) or H3K14ac (right) near TSS (+/−4 kb) of all known protein coding genes. K means clustering identified specific H3NT-cleaved TSSs at either promoters (P), coding regions (CR) or both (P+CR). FIG. 6C shows average tag density profiles (y-axis) of each H3NT-cleaved group near TSS (x-axis) for H3CT and H3K14ac in control and MMP-9 depleted 3-day OCP-induced cells as indicated.

FIGS. 7A-7D. FIG. 7A shows distribution of all H3NT-cleaved genes displaying no change (grey) or significantly changed expression (dark) between MMP-9 depleted and control 3-day OCP-induced cells (left). Distribution of H3NT-cleaved genes dependent on MMP-9 for activation (light) or repression (black) in 3-day OCP-induced cells (right). FIG. 7B shows fold expression changes (y-axis) of Nfatc1, Lif and Xpr1 normalized to β-actin in 3-day OCP-induced cells expressing a control (dark, first two bars in graph), MMP-9-specific (medium gray, middle two bars in each graph) or CBP/p300-specific (light gray, right two bars in each graph) shRNA relative to non-induced OCP cells. FIG. 7C shows ChIPac was performed with H3K14ac-specific (H3NT, left) and H3CT control (right) antibodies in 3-day control (−) or RANKL-induced (+) OCP cells express-ing a control, MMP-9-specific or CBP/p300-specific shRNA (x-axis). qPCR was performed at the promoters (P, left) and coding regions (CR, right) of Nfatc1 (P-cleaved), Lif (CR-cleaved) and Xpr1 (P+C-cleaved). Enrichments were plotted relative to non-induced control shRNA OCP cells (first column) (y-axis). Star indicates H3NT cleavage. FIG. 7D shows ChIP-qPCR analysis of H3K18ac as described above. Star indicates significantly increased H3K18ac enrichment.

FIG. 8A shows in vitro H3NT cleavage assays performed with the purified glycerol gradient fractions #3-5 (FIG. 1C) or recombinant MMP-9 (rMMP-9) as indicated. Substrates used in the assays were reconstituted recombinant histone octamer (left), reconstituted octamer containing purified native histones from HeLa cells (center) or reconstituted native nucleosome arrays (right). Western blot analysis was performed using antibodies that detect the C-terminal tail of each indicated core histone (left). FIG. 8B shows in vitro H3NT cleavage assays as described above using recombinant H3.1, H3.2 or H3.3 substrates in the absence (left) or presence (right) of rMMP-9.

FIG. 9A shows western blot analysis of cytosolic (left) and nuclear (right) lysates isolated in parallel from OCP-induced cells at the indicated days for MMP-9, GAPDH (cytosol control) and histone H4 (nucleus control). The volumes and total amount of protein (20 µg) loaded per lane were identical in all samples. FIG. 9B shows confocal microscopy of OCP-induced cells co-stained for MMP-9 and DAPI at the indicated days (left). OCP cells were grown on glass cover slips, fixed with 4% paraformaldehyde for 15 min and permeabilized with 0.25% Triton X-100 in phosphate-buffered saline (PBS) for 5 min. Cells were blocked with PBS+2% goat serum (GS) in PBS for 60 minutes prior to incubation with an MMP-9 antibody (Santa Cruz). Cells were washed with PBS+GS, incubated with a FITC conjugated secondary antibody (Jackson Laboratory) and mounted with VectaShield with DAPI (Vector Laboratories).

FIG. 10A shows the human histone H3 amino acid sequence (SEQ ID NO: 39) was analyzed by PROSPER (see prosper.erc.monash.edu.au) to identify predicted sites of H3 proteolysis (SEQ ID NOS 40-47, respectively, in order of appearance). The only potential cleavage site identified in the H3NT was K18, which was predicted to be cleaved by MMP-9 (inset). FIG. 10B shows the log-odds probabilities of amino acids (y-axis) in the P3-P2' position (x-axis) of substrates known to be proteolyzed by MMP-9 was generated from PMAP (www.proteolysis.org).

FIG. 11A shows recombinant H3 wild type (WT) and mono-, di- and trimethyl-lysine analogues (top) for H3K4, H3K9, H3K27 and H3K36 (left) were used as substrates in in vitro H3NT cleavage assays with rMMP-9. FIG. 11B shows OCP cells were transduced with H3K18 acetyltransferase-specific shRNAs as indicated. Knock-down specificity and efficiency of each acetyltransferase shRNA were determined by RT-qPCR to quantitate expression changes relative to control shRNA (y-axis) for each gene (x-axis). FIG. 11C shows chromatin was extracted from OCP cells expressing a control or acetyltransferase-specific shRNA (left) at the indicated days post-induction (top) for Western analysis with the H3CT antibody to detect H3NT proteolysis.

FIG. 12A shows genomic distribution of uniquely mapped RNA-Seq reads from control (dark) and MMP-9 (light) shRNA expressing 3-day OCP-induced cells was similar with most reads mapping to coding regions of the mouse genome. FIG. 12B shows gene body coverage plot between control (dark) and MMP-9 (light) shRNA expressing 3-day OCP-induced cells demonstrating a similar uniform coverage across gene bodies with no significant 5' or 3' bias. FIG. 12C shows gene ontology analysis of the 758 genes displaying impaired activation in MMP-9 depleted 3-day OCP-induced cells relative to control OCP cells. FIG. 12D shows OCP cells transduced with a control (grey), MMP-9-specific (dark) or CBP/p300-specific (light) shRNA (left) or cultured with DMSO control (grey), a MMP-9-specific inhibitor (dark) or a CBP/p300 inhibitor (light) (right) were treated with RANKL for 5 days (x-axis). Cells were fixed, stained with a TRAP kit (Sigma) and visualized by light microscopy (10×). The number of osteoclasts (y-axis) was determined by counting TRAP-positive cells containing 3 or more nuclei in each sample.

FIGS. 13A-13E. FIG. 13A shows OCP cells were cross-linked with different concentrations of methylene blue (0, 5, 10 and 20 µM) for the indicated times (x-axis). Chromatin was extracted and DNA-protein crosslinking efficiency was measured by SDS-chloroform-isoamyl alcohol (SDS-CIA) (y-axis). FIG. 13B shows unmodified and K14ac H3 peptides (aa10-35) and methylene blue crosslinked chromatin (10 or 20 µM) treated with acetic anhydride were spotted on nitrocellulose for Western analysis with the indicated antibodies. FIG. 13C shows genomic snapshots of the Nfatc1 (left), Xpr1 (center) and Lif (right) genes showing the normalized tracks of H3CT control and H3K14ac ChIPac-Seq data (top) and RNA-Seq data (bottom) from control and MMP-9 depleted 3-day OCP-induced cells as indicated. Numbers in parentheses indicate maximum sequencing depth for each sample. Grey boxes indicate the region near TSS (dashed line) displayed in FIG. 6D. FIG. 13D shows heat map showing one dimensional clustering in a single color channel of all genes displaying H3NT cleavage (FIG. 6B and Table 2). Euclidean distance and average linkage were used for clustering. Normalized read count values corresponding to each gene are plotted and colored proportional to the level of read counts as indicated in the color bar. FIG. 13E shows to investigate potential functional similarities and differences between the identified P, CR and P+CR H3NT-cleaved genes (Table 2), the Wikipathway database was queried and a ranked p-value was computed for each pathway from the Fisher exact test based on the bionomical distribution and independence for probability of any gene belonging to any enriched set. The RANKL and several osteoclastogenic pathways were significantly enriched ($p<0.0001$) when all H3NT-cleaved genes were analyzed (dark), consistent with RNA-Seq results (FIG. 12C). These pathways were also significantly enriched independently for P and CR H3NT-cleaved genes but not for P+CR (brown, $p>0.9$).

FIG. 14 shows OCP cells were treated with DMSO control (1), a selective MMP-9 inhibitor (2) or a selective CBP/p300 inhibitor (3) and cultured with (+) or without (−) RANKL for 3 days (x-axis). RT-qPCR was used to quantitatively measure fold expression changes (y-axis) of the osteoclastogenic genes Nfatc1, Lif and Xpr1 relative to non-induced control after normalization to β-actin expression.

DETAILED DESCRIPTION

Definitions

Figure 2A:
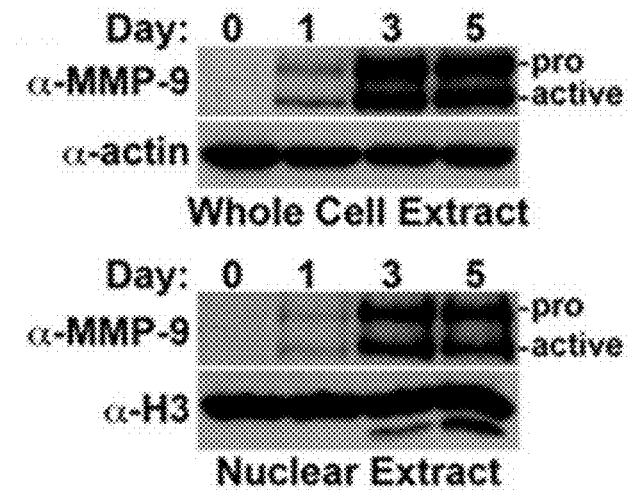
FIGS. 2A to 2D show MMP-9-dependent H3NT proteolysis during osteoclastogenesis.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (Cold Spring Harbor Laboratory Press (2002)); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Harlow and Lane, eds. (1999) Using Antibodies, A Laboratory Manual; Animal Cell Culture (R. I. Freshney, ed. (1987)); Zigova, Sanberg and Sanchez-Ramos, eds. (2002) Neural Stem Cells.

All numerical designations, e.g., pH, temperature, time, concentration, and molecular weight, including ranges, are approximations which are varied (+) or (−) by increments of 0.1 or 1 where appropriate. It is to be understood, although not always explicitly stated that all numerical designations are preceded by the term "about". The term "about" also includes the exact value "X" in addition to minor increments of "X" such as "X+0.1 or 1" or "X−0.1 or 1," where appropriate. It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this disclosure.

The term "isolated" as used herein with respect to proteins, polypeptides, cells, nucleic acids, such as DNA or RNA, refers to molecules separated from other proteins, polypeptides, cells, nucleic acids, such as DNA or RNA, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together. A recombinant polynucleotide is a polynucleotide created or replicated using techniques (chemical or using host cells) other than by a cell in its native environment.

"Cells," "host cells" or "recombinant host cells" are terms used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form. In some aspects of the disclosed methods, a "polynucleotide fragment" refers to a piece of genomic DNA that has been fragmented by a method such as sonication or enzymatic fragmentation. Such fragments may vary in size based on the conditions of the fragmentation. A polynucleotide fragment may be crosslinked to histones and other proteins associated with chromatin.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Amplify" "amplifying" or "amplification" of a polynucleotide sequence includes methods such as traditional cloning methodologies, PCR, ligation amplification (or ligase chain reaction, LCR) or other amplification methods. These methods are known and practiced in the art. See, e.g., U.S. Pat. Nos. 4,683,195 and 4,683,202 and Innis et al. (1990) Mol. Cell Biol. 10(11):5977-5982 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "genotype" refers to the specific allelic composition of an entire cell, a certain gene or a specific polynucleotide region of a genome, whereas the term "phenotype' refers to the detectable outward manifestations of a specific genotype.

As used herein, the term "gene" or "recombinant gene" refers to a nucleic acid molecule comprising an open reading frame and including at least one exon and (optionally) an intron sequence. A gene may also refer to a polymorphic or a mutant form or allele of a gene.

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov, last accessed on May 21, 2008. Biologically equivalent polynucleotides are those having the above-noted specified percent homology and encoding a polypeptide having the same or similar biological activity.

In one aspect, the term "equivalent" as it refers to polypeptides, proteins, or polynucleotides refers to polypeptides, proteins, or polynucleotides, respectively having a sequence having a certain degree of homology or identity with the reference sequence of the polypeptides, proteins, or polynucleotides (or complement thereof when referring to polynucleotides). A homolog of a double stranded nucleic acid is intended to include nucleic acids having a nucleotide sequence that has a certain degree of homology with or with the complement thereof. In one aspect, homologs of nucleic acids are capable of hybridizing to the nucleic acid or complement thereof. In one aspect, an equivalent has at least 70%, or at least 75% or at least 80%, or at least 85%, or at least 90%, or at least 95%, or at least 97%, or at least 98%, sequence identity to the reference polynucleotide or polypeptide.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

As used herein, the term "oligonucleotide" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection, sometimes called transduction), transfection, transformation or various other protein-based or lipid-based gene delivery complexes) as well as techniques facilitating the delivery of "naked" polynucleotides (such as electroporation, "gene gun" delivery and various other techniques used for the introduction of polynucleotides). Unless otherwise specified, the term transfected, transduced or transformed may be used interchangeably herein to indicate the presence of exogenous polynucleotides or the expressed polypeptide therefrom in a cell. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

The term "express" refers to the production of a gene product.

As used herein, "expression" refers to the process by which polynucleotides are transcribed into RNA such as mRNA and/or the process by which a transcribed mRNA is subsequently translated into peptides, polypeptides, or proteins. If the polynucleotide is derived from genomic DNA, expression may include splicing of the mRNA in an eukaryotic cell.

A "gene product" or alternatively a "gene expression product" refers to the amino acid (e.g., peptide or polypeptide) generated when a gene is transcribed and translated.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A cell that "stably expresses" an exogenous polypeptide is one that continues to express a polypeptide encoded by an exogenous gene introduced into the cell either after replication if the cell is dividing or for longer than a day, up to about a week, up to about two weeks, up to three weeks, up to four weeks, for several weeks, up to a month, up to two months, up to three months, for several months, up to a year or more.

As used herein, a "vector" is a vehicle for transferring genetic material into a cell. Examples of such include, but are not limited to plasmids and viral vectors. A viral vector is a virus that has been modified to transduct genetic material into a cell. A plasmid vector is made by splicing a DNA construct into a plasmid. As is apparent to those of skill in the art, the appropriate regulatory elements are included in the vectors to guide replication and/or expression of the genetic material in the selected host cell.

A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying et al. (1999) Nat. Med. 5(7):823-827.

In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, retroviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral Vectors, New York: Spring-Verlag Berlin Heidelberg.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., a cell surface marker found on stem cells.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmic vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacteria produces proteins to confer its antibiotic resistance, it can also be induced to produce large amounts of proteins from the inserted gene. This is a cheap and easy way of mass-producing a gene or the protein it then codes for.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. A eukaryotic host, including, for example, yeast, higher plant, insect and mammalian cells. Non-limiting examples include simian, bovine, ovine, porcine, murine, rats, canine, equine, feline, avian, reptilian and human.

"Prokaryotic cells" that usually lack a nucleus or any other membrane-bound organelles and are divided into two domains, bacteria and archaea. Additionally, instead of having chromosomal DNA, these cells' genetic information is in a circular loop called a plasmid. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to prokaryotic Cyanobacteria, *bacillus* bacteria, *E. coli* bacterium, and *Salmonella* bacterium.

The term "propagate" means to grow a cell or population of cells. The term "growing" also refers to the proliferation of cells in the presence of supporting media, nutrients, growth factors, support cells, or any chemical or biological compound necessary for obtaining the desired number of cells or cell type.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels are described and exemplified herein.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in MacPherson et al. (1991) PCR: A Practical Approach, IRL Press at Oxford University Press. All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra. The primers may optionall contain detectable labels and are exemplified and described herein.

As used herein, the term "detectable label" intends a directly or indirectly detectable compound or composition (other than a naturally occurring polynucleotide in its natural environment) that is conjugated directly or indirectly to the composition to be detected, e.g., polynucleotide or protein such as an antibody so as to generate an artificial, non-naturally occurring "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, *Lucifer* Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can by via a linker. Suitable binding pairs for use in indirectly linking the fluorescent label to the intermediate include, but are not limited to, antigens/antibodies, e.g., rhodamine/anti-rhodamine, biotin/avidin and biotin/strepavidin.

The phrase "solid support" refers to non-aqueous surfaces such as "culture plates" "gene chips" or "microarrays." Such gene chips or microarrays can be used for diagnostic and therapeutic purposes by a number of techniques known to one of skill in the art. In one technique, oligonucleotides are attached and arrayed on a gene chip for determining the DNA sequence by the hybridization approach, such as that outlined in U.S. Pat. Nos. 6,025,136 and 6,018,041. The polynucleotides of this invention can be modified to probes, which in turn can be used for detection of a genetic sequence. Such techniques have been described, for example, in U.S. Pat. Nos. 5,968,740 and 5,858,659. A probe also can be attached or affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarrays" and similar technologies are known in the art. Examples of such include, but are not limited to, LabCard (ACLARA Bio Sciences Inc.); GeneChip (Affymetric, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarry system that can dispense from 12 to 64 spots onto multiple glass slides (Intelligent Bio-Instruments); Molecular Biology Workstation and NanoChip (Nanogen, Inc.); a microfluidic glass chip (Orchid Biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu. Rev. Biomed. Eng. 4:129-153. Examples of "gene chips" or a "microarrays" are also described in U.S. Patent Publication Nos.: 2007/0111322; 2007/0099198; 2007/0084997; 2007/0059769 and 2007/0059765 and U.S. Pat. Nos. 7,138,506; 7,070,740 and 6,989,267.

In one aspect, "gene chips" or "microarrays" containing probes or primers homologous to a polynucleotide described herein are prepared. A suitable sample is obtained from the patient, extraction of genomic DNA, RNA, protein or any combination thereof is conducted and amplified if necessary. The sample is contacted to the gene chip or microarray panel under conditions suitable for hybridization of the gene(s) or gene product(s) of interest to the probe(s) or primer(s) contained on the gene chip or microarray. The probes or primers may be detectably labeled thereby identifying the sequence(s) of interest. Alternatively, a chemical or biological reaction may be used to identify the probes or primers which hybridized with the DNA or RNA of the gene(s) of interest. The genotypes or phenotype of the patient is then determined with the aid of the aforementioned apparatus and methods.

It is to be inferred without explicit recitation and unless otherwise intended, that when the present technology relates to a polypeptide, protein, polynucleotide or antibody, an equivalent or a biologically equivalent of such is intended within the scope of the present technology.

As used herein, the "administration" of an agent or drug to a subject or subject includes any route of introducing or delivering to a subject a compound to perform its intended function. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, vaginal, nasal administration, injection, topical application and by suppository. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

Administration can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician.

As used herein, the term "animal" is used synonymously with "patient" or "subject" and refers to living multi-cellular vertebrate organisms, a category that includes, for example, mammals and birds. The term "mammal" includes both human and non-human mammals. Similarly, the term "subject" or "patient" includes both human and veterinary subjects, for example, humans, non-human primates, dogs, cats, sheep, mice, horses, and cows.

The term "crosslinking" refers to a method of chemically joining two or more molecules by a covalent bond. Crosslinking methods allow for the stabilization of molecular structures and the capture of molecular interactions within a cell so that they can be preserved and studied. Crosslinking may also involve "fixation" of a cell or tissue by which said cell or tissue is preserved from decay and degradation, thus preventing cell lysis or putrefaction. Non-limiting examples of fixatives include heat fixation and chemical fixation. Chemical fixatives include crosslinking fixatives such as aldehydes which cause covalent chemical bonds between proteins and molecules in a cell, precipitating fixatives such as alcohols that reduce the solubility of protein molecules and acetic acid, oxidizing agents that react with protein side chains and other biological molecules to allow formation of crosslinks, mercurial, picrates that react with histones and basic proteins to form crystalline picrates with amino acids, and hepes-glutamic acid buffer-mediated organic solvent protection effect. Crosslinking reagents appropriate for use with the disclosed methods include but are not limited to formaldehyde, paraformaldehyde, methylene blue with or without exposure to white light, sodium fluorescein, acridine orange, cisplatin, dimethylarsinic acid, potassium chromate, ultraviolet light, and lasers.

The term "acetylation" generally refers to the chemical reaction which attaches one or more acetyl functional groups (chemical formula $CH_3CO$, sometimes referred to as the symbol "Ac") to a chemical compound. Acetylation may also refer to the status of a particular chemical moiety with respect to its degree of modification with acetyl groups. "Deacetylation" is the removal of an acetyl group from a chemical compound. An acetylation reaction involves the replacement of the hydrogen atom of a hydroxyl group with an acetyl group to yield an acetate ester. Lysine amino acid residues are common targets for protein acetylation. For example, histones are acetylated and deacetylated on lysine residues of their N-terminal tails. Such histone acetylation and deacetylation reactions can be catalyzed by a class of enzymes with histone acetyltransferase (HAT) activity or histone deacetylase (HDAC) activity, respectively. HAT enzymes include but are not limited to the GNAT superfamily including Gcn5, SAGA, SLIK, STAGA, ADA, A2, Gcn5L, p300/CREB-binding protein associated factor (PCAF), Elp3, HPA2, and HAT1), the MYST family including MOZ (Monocytic Leukemia Zinc Finger Protein), Ybf2/Sas3, Sas2, Tip60, Esa1, MOF, MORF, and HBO1, the p300/CBP family including adenoviral E1A associated protein of 300 kDa (p300) and te CREB-binding protein (CBP), and other HATs such as steroid receptor coactivator 1 (SRC 1), ATF-2, and TAFII250. Acetyl-Coenzyme A is a common source of the acetyl group transferred to a target histone lysine residue by HAT enzymes.

Acetic anhydride (also known as ethanoic anhydride, chemical formula $CH_3CO_2O$) is a common acetylating agent. Acetic anhydride acetylation reactions can occur in the presence of an acid or base catalyst. Metal salts and triflates such as $CoCl_2$, $TiCl4-AgCLO_4$, $TaCL_5$, $TaCl_5$—$SiO_2$, Ce(III) triflate, Sn(IV) porphyrine, $Sc(OTf)_3$, MeSiOTf, $In(OTf)_3$, $Cu(OTf)_2$, $Bi(OTf)_3$, bis(cyclopentadienyl) zirconium dichloride, $I_2$, and 1,3,-dibromo-5,5-dimethylhydentoin, trichloroisocyanuric acid can be used in combination with acid anhydride. Equivalents of acetic anhydride include but are not limited to HAT enzymes, priopionic anhydride, deuterated acetic anhydride, acetic acid, acetyl chloride, acetyl-CoA, and formic anhydride. An equivalent of acetic anhydride has the property of being the donating source of an acetyl group to modify a histone lysine residue and/or catalyzing a histone lysine acetylation reaction.

The term "chromatin" refers to the complex of biological molecules found in the nucleus of a cell, comprising, e.g., DNA, protein (including histones), and RNA. Histones are alkaline proetins found in nuclei that can function to package the nucleic acid. The fundamental unit of chromatin is the nucleosome which comprises about 146 base pairs of DNA wrapped about 1.7 times in a left-handed turn around a protein octamer of two each of the core histones H3, H4, H2A and H2B. Alternatively, the octamer may be comprised of one or more variant histones including H3.3,centromeric H3 variant (cenH3, called also CENPA), H3.1, H3.2, TS H3.4, H3.5, H3.Y, H2A.X, H2A.Z, H2A.Z.2, H2A.B, H2A.L, H2A.P, H2A.1, H2B.1, H2A.J, H2B.1, H2B.W, H2B.Z, H2B.E. H1 and H5 linker histones are generally located between nucleosomes. Histones can control accessibility and expression of the region of DNA (or specific locus) around which they are bound or regions of DNA with which they associate. For example, histones with repressive modifications to their N-terminal tails tend to promote tightly compacted chromatin that prevents transcriptional machinery from accessing the DNA. In contrast, histones with modifications to their N-terminal tails that increase access to the DNA tend to promote chromatin with high levels of gene expression. In addition to histones and nucleic acids, chromatin may also comprise proteins that associate with DNA such as transcription machinery (including RNA polymerases), DNA replication machinery, and transcription factors or repressors.

The term "chromatin immunoprecipitation" (ChIP) refers to a method used to study the interaction between nucleic acids and proteins in the chromatin of a cell. This method can be combined with DNA detection techniques to determine whether specific proteins or protein modifications are associated with specific genomic regions, or loci. In general, the DNA, RNA, and proteins of chromatin are first cross-linked together to preserve their interactions. Next, the crosslinked chromatin is sheared to break the DNA cross-linked to proteins into fragments. Then an antibody directed to a protein of interest is incubated with the fragmented chromatin. The antibody may be directly bound to a magnetic bead or a secondary antibody bound to a magnetic bead may be added. Alternatively, a non-magnetic purification strategy such as an affinity tag may be used. Next, the antibody-bound chromatin fragments are immunoprecipitated by purification with a magnetic column or an alternate purification method. Finally, the protein is unlinked from the precipitated chromatin and the DNA is purified. Standard detection techniques can be used to identify the precipitated DNA such as PCR, quantitative PCR, and DNA sequencing. Further details for ChIP techniques and optimization can be found in Chapter 20 of Sambrook and Russell eds. (2012) Molecular Cloning: A Laboratory Manual, 4th edition, incorporated by reference herein. In some aspects, the disclosed methods utilize specialized ChIP techniques to capture three dimensional chromatin structures as they occur in living cells. These specialized ChIP methods include but are not limited to Chromatin Conformation Capture (3C), Circularized Chromosome Conformation Capture (4C), Carbon Copy Chromosome Conformation Capture (5C), ChIP-Loop, Hi-C, and Capture-C. These methods are reviewed in de Wit et al. *Genes and Development* 2012 (26: 11-24), incorporated by reference herein.

The term "antibody" refers to a polyclonal, monoclonal, recombinant, or synthetic immunoglobulin molecule that specifically binds a target antigen. In one aspect, monoclonal antibodies are excluded. In another embodiment, polyclonal antibodies or other naturally occurring antibodies are excluded. The term includes intact immunoglobulin molecules, fragments or polymers of those immunoglobulin molecules, chimeric antibodies containing sequences from more than one species, class, or subclass of immunoglobulin, and human or humanized versions of immunoglobulin molecules or fragments thereof containing a least the idiotype of an immunoglobulin that specifically binds the target antigen. Target antigens relevant for the disclosed methods include but are not limited to the C-terminus of histone H3, H3 acetylated lysine residue 4, H3 acetylated lysine residue 9, and H3 acetylated lysine residue 14. Antibodies directed to the cleaved N-terminal tail and appropriate for use with the disclosed methods include but are not limited to Acetyl-Histone H3 (Lys9) Antibody (17H12L11), ABfinity Rabbit Monoclonal (ThermoFisher), Acetyl-Histone H3 (Lys9) Antibody (17HCLC), ABfinity Rabbit Oligoclonal (ThermoFisher), Acetyl-Histone H3 (Lys9) Antibody (2HCLC), Abfinity Rabbit Oligoclonal (ThermoFisher), Acetyl-Histone H3 (Lys14) Polyclonal Antibody (ThermoFisher), Acetyl-Histone H3 (Lys18) Polyclonal Antibody (ThermoFisher), Acetyl-Histone H3 (Lys9) Monoclonal Antibody (J.924.2) (ThermoFisher), Acetyl-Histone H3 (Lys9, Lys14) Polyclonal Antibody (ThermoFisher), Acetyl-Histone H3 (Lys4) Polyclonal Antibody (ThermoFisher), Acetyl-Histone H3 (Lys9) Polyclonal Antibody (ThermoFisher), Acetyl-Histone H3 (Lys9) Monoclonal Antibody (ThermoFisher), Acetyl-Histone H3 (Lys9, Lys14) Polyclonal Antibody (ThermoFisher), Anti-Histone H3 (acetyl K9) antibody—ChIP Grade (ab10812) (Abcam), Anti-Histone H3 (acetyl K9) antibody—ChIP Grade (ab4441) (abcam), Anti-Histone H3 (acetyl K18) antibody—ChIP Grade (ab1191) (abcam), Anti-Histone H3 (acetyl K14) antibody [EP964Y]—ChIP Grade (ab52946), and Anti-Histone H3 (acetyl K9) antibody [AH3-120]—ChIP Grade (ab12179) (abcam), or an equivalent of each thereof. An equivalent antibody is an antibody that has similar target reactivity (i.e. directed to an acetylated lysine residue in the N-terminal tail of histone H3), and can be used for chromatin immunoprecipitation. Equivalents also include antibodies with the same or similar target reactivity or idiotype that are conjugated to labels such as fluorochromes or epitope tags such as biotin.

The term "idiotype" refers to the portion of an immunoglobulin molecule that confers the molecule's ability to bind an antigen. The idiotype of an antibody is determined by the complementarity determining regions (CDRs) of the immunoglobulin variable domains ($V_L$ and $V_H$).

Matrix metallopeptidase 9 (MMP-9), also known as 92 kDa type IV collagenase, 92 kDa gelatinase or gelatinase B (GELB), is a matrixin, a class of enzymes that belong to the zinc-metalloproteinases family involved in the degradation of the extracellular matrix. The sequence of the human protein is found under GenBank reference number NP_004985 and the mRNA encoding the protein is found under NM_004994. The murine counterpart is found under NP_038627 and the mRNA is found under NM_013599. In some aspects, the protein sequence of MMP-9 is (SEQ ID NO: 22), disclosed below.

Additional matrix metallopeptidases that are relevant for the disclosed methods include: Matrix metalloproteinases with potential histone tail cleavage activity include but are not limited to MMP1 (interstitial collagenase, human mRNA: NM_002421, NM_001145938; protein: NP_001139410, NP_002412), MMP2 (Gelatinase-A, 72 kDa gelatinase, human mRNA: NM_004530, NM_001127891, NM_001302508, NM_001302509, NM_001302510; protein: NP_001121363, NP_001289437, NP_001289438, NP_001289439, NP_004521), MMP3 (Stromelysin 1, human mRNA: NM_002422; protein: NP_002413), MMP7, (Matrilysin, Pumpl, human mRNA: NM_002423; protein: NP_002414), MMP8 (Neutrophil collagenase, human mRNA: NM_001304441, NM_001304442, NM_002424; protein: NP_001291370, NP_001291371, NP_002415), MMP10 (Stromelysin 2, human mRNA: NM_002425; protein: NP_002416), MMP11 (Stromelysin 3, human mRNA: NM_005940; protein: NP_005931, NP_005931.2), MMP12 (Macrophage metalloelastase, human mRNA: NM_002426; protein: NP_002417), MMP13 (Collagenase3, human mRNA: NM_002427; protein: NP_002418), MMP14 (MT1-MMP, human mRNA: NM_004995; protein: NP_004986), MMP15 (MT2-MMP, human mRNA: NM_002428; protein: NP_002419), MMP16 (MT3-MMP, human mRNA: NM_005941, NM_022564, NM_032297; protein: NP_005932), MMP17 (MT4-MMP, human mRNA: NM_016155; protein: NP_057239, NP_057239.4), MMP18 (Collagenase 4, xcol4, *Xenopus* collagenase), MMP19 (RASI-1, Stromelysin 4, human mRNA: NM_001032360, NM_001272101, NM_002429, NM_022790, NM_022792; protein: NP_001259030, NP_002420), MMP20 (Enamelysin, human mRNA: NM_004771; protein: NP_004762), MMP21 (XMMP, human mRNA: NM_147191; protein: NP_671724), MMP23A (CA-MMP), MMP23B (human mRNA: NM_006983, protein: NP_008914), MMP24 (MT5-MMP, human mRNA: NM_006690; protein: NP_006681), MMP25 (MT6-MMP, human mRNA: NM_004142, NM_022468, NM_022718; protein: NP_071913), MMP26 (Matrilysin-2, endometase, human mRNA: NM_021801; protein: NP_068573), MMP27 (MMP-22, C-MMP, human mRNA: NM_022122; protein: NP_071405), MMP28 (Epilysin, human mRNA: NM_001032278, NM_024302, NM_032950, protein: NP_001027449, NP_077278, NP_116568, NP_116568.1).

The term "inhibitor" refers to a molecule (often a small molecule) that acts to block a function of a desired target protein. An equivalent of an MMP-9 inhibitor is one that blocks MMP-9 function and/or its import to the nucleus.

The term "peptide" or "polypeptide" can be used to refer to a natural or synthetic molecule comprising two or more amino acids linked by the carboxyl group of one amino acid to the alpha amino group of another. The peptide is not limited by length; thus "peptide" can include polypeptides and proteins.

The term "peptidomimetic" refers to a mimetic of a peptide which includes some alteration of the normal peptide chemistry. Peptidomimetics typically enhance some property of the original peptide, such as increase stability, increased efficacy, enhanced delivery, increased half life, etc.

The term "aptamer" refers to an oligonucleic acid molecule that specifically binds to a target molecule.

As used herein, the term "small molecule" refers to a compound having a molecular weight of less than 1000 Daltons, and typically between 300 and 700 Daltons. The term may include monomers or primary metabolites, secondary metabolites, a biological amine, a steroid, or synthetic or natural, non-peptide biological molecule(s). In the context of targeted imaging probes that are small molecules, the small molecule can specifically bind the molecular or cellular target.

The term "specifically recognizes" or "specifically binds" refers to the recognition or binding of a molecule to a target molecule, such as an antibody to its cognate antigen, while not significantly binding to other molecules. Preferably, a molecule "specifically binds" to a target molecule with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more) with the target molecule.

The term "subject" or "patient" refers to any individual who is the target of administration. The subject can be a vertebrate, for example, a mammal. Thus, the subject can be a human. The subject can be domesticated, agricultural, or zoo- or circus-maintained animals. Domesticated animals include, for example, mice, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses. The term does not denote a particular age or sex.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

In some aspects, the diseases or conditions that can be treated by the disclosed methods include but are not limited to low bone mineral density (BMP), high BMP, osteoporosis, bone cancer, cancer that has metastasized to the bone, cancer-induced osteolysis, sepsis, rheumatoid arthritis, periodontitis, osteopetrosis, pycondysostosis, osteopoikilosis, meloreostosis, sclerosteosis, van Buchem's disease, LRP5 high bone mass, LRP4 high bone mass, craniometaphyseal dysplasia, Camurati-Engelmann disease, Ghosal syndrome, bone cancer, cancer metastasized to the bone, fluorosis, renal osteodystrophy, acromegaly, hepatitis C-associated osteosclerosis, myelofibrosis, mastocytosis, osseous tuberous sclerosis, Paget's disease, and SAPHO syndrome. The disclosed methods can also be used to treat or identify a cell or tissue in need of histone N-terminal tail cleavage. In some aspects, the disclosed methods can be used to treat or identify a subject in of increased, decreased, or inhibited osteoclastogenesis.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. In one aspect, a biological equivalent of an antibody means one having the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov. Sequence identity and percent identity were determined by incorporating them into clustalW.

A "composition" as used herein, intends an active agent, such as a compound as disclosed herein and a carrier, inert or active. The carrier can be, without limitation, solid such as a biotin, a bead or a resin, or liquid, such as phosphate buffered saline.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks. Consistent with this definition and as used herein, the term "therapeutically effective amount" is an amount sufficient to treat a specified disorder or disease or alternatively to obtain a pharmacological response.

Modes for Carrying Out the Disclosure

This disclosure provides a method to identify to identify a polynucleotide fragment and or genomic locus bound to an H3 histone comprising a cleaved N-terminal tail (H3NT) in a cell, the method comprising, or alternatively consisting essentially of, or yet further consisting of the following steps: first crosslinking chromatin proteins including histones to the genomic DNA present in the cell by contacting the cell or a cell extract such as nuclear extract with an effective amount of methylene blue or an equivalent of methylene blue, subsequent to the cell having been exposed to white light or an equivalent of the white light. Methylene blue (chemical formula $C_{16}H_{18}ClN_3S$) is also known as methylthionium is a medication and a dye. Methylene blue is commercially available from number of vendors, for example Tocris, Spectrum, and MD Supplies. Non-limiting examples of an equivalent to methylene blue include sodium fluorescein, acridine orange, cisplatin, dimethylarsinic acid, potassium chromate, ultraviolet light, and lasers. Most ChIP protocols utilize formaldehyde to crosslink proteins to DNA in vivo. However, because formaldehyde reacts with lysine E-amino side-chains, which likely precludes complete lysine acetylation by acetic anhydride, methylene blue is used as an alternative for cell fixation. As used herein any cell containing chromatin can be used in the assay, e.g., a plant cell or a eukaryotic cell, and cells that are in culture. Non-limiting examples of eukaryotic cells include animal cell, mammalian cells (e.g. any species, canine, feline, equine) or human cells. In one aspect the cell is a human cell. In some aspects, the cell is an osteoclast, osteoclast precursor, or a progenitor cell or stem cell capable of differentiation into an osteoclast. Cells capable of differentiation into an osteoclast include but are not limited to embryonic stem cells, induced pluripotent cells, hematopoietic stem cells, myeloid stem cells, granulocyte-macrophage colony forming unit (GM-CFU), monocyte precursor (CFU-M), progenitor cells, and pre-osteoclasts.

After the chromatin in the cell is cross-linked, it is isolated from the cell and the efficiency of crosslinking is confirmed by any appropriate method, e.g., by sodium dodecyl sulfate-chloroformisoamyl alcohol (SDS-CIA). Unmodified lysine residues are acetylated by treatment or contacting with an effective amount of acetic anhydride or other acetylation agent. The fragmented chromatin is then contacted in parallel with either (1) an effective amount of an H3 C-terminal control antibody or (2) an effective amount of a H3K14ac-specific antibody. Alternatively, the chromatin may be contacted with another antibody specific for a lysine residue N-terminal (upstream) of the cleavage site of interest such as an H3K4ac or H3K9ac antibody. In another aspect, a mixture of two or more of H3K14ac, H3K4ac, and H3K9ac antibodies is used to enrich for uncleaved H3. The two parallel antibody-bound fragmented chromatin samples are then selectively enriched by immunoprecipitation. The antibody is a monoclonal or a polyclonal antibody. In one aspect, use of the H3 C-terminal tail antibody is performed in parallel with the normalization control. H3 N-terminal tail-cleaved regions are identified by the significant reduction in H3K14ac enrichment relative to control, e.g., as determined by quantitative PCR (qPCR) or NextGen DNA sequencing analysis.

Also provided herein is a method for identification and examination of genetic loci bound by H3 with N-terminal tail-cleaved regions. First, cells are fixed with methylene blue or an equivalent thereof to crosslink chromatin after brief exposure to white light. It should be noted that most ChIP protocols utilize formaldehyde to crosslink proteins to DNA in vivo. However, because formaldehyde reacts with lysine E-amino side-chains, which likely precludes complete lysine acetylation by acetic anhydride, methylene blue was used as an alternative for cell fixation. Chromatin was isolated and the efficiency of crosslinking was confirmed by sodium dodecyl sulfate-chloroformisoamyl alcohol (SDS-CIA). Fragmented chromatin was then treated with acetic anhydride to completely acetylate all unmodified lysine residues in vitro. ChIPac using an H3K14ac-specific antibody selectively enriched H3 N-terminal tail-containing chromatin and simultaneously excluded chromatin lacking the H3 N-terminal tail. ChIPac using an H3 C-terminal tail antibody was performed in parallel as the normalization control. H3 N-terminal tail-cleaved regions were identified by the significant reduction in H3K14ac enrichment relative to control as determined by quantitative PCR (qPCR) or NextGen sequencing analysis.

This method can also be used to identify and monitor other histone tail proteolysis processes. For example, the cysteine protease capthepsin L has been reported to cleave H3 in murine embryonic stem cells at several cleavage sites, including between alanine residue 21 and threonine residue 22 and between lysine residue 27 and serine residue 28. Because these cleavage sites are downstream (i.e. closer to the C-terminus of H3) of the recognition site for the detection antibodies used herein (i.e. H3K14, H3K9, and/or H3K4), the methods disclosed herein can be used to detect the location of capthepsinL cleaved histone H3 in the genome of a cell. As long as the detection antibody is directed to an acetylated residue upstream (i.e. closer to the N-terminus) of the putative H3 tail cleavage site, a cleaved histone genome binding location can be identified through the disclosed methods. Thus, the disclosed methods can be used detect the genomic loci of histone H3 cleaved at the following sites: alanine residue 21, arginine residue 26, or alanine residue 31 as reported in embryonic stem cells; between lysine 23 and alanine 24 or between lysine 27 and serine 28 as reported in chickens and catalyzed by the glutamate dehydrogenase enzyme; between alanine 21 and threonine 22 as reported in *Saccharomyces cerevisiae* and catalyzed by the purified vacuolar protease B enzyme; and between leucine 20 and alanine 21. In other aspects, this method can be used to identify and monitor lysis of other histone tails such as histone H2A, H2B, and H4 using antibodies specific to the cleaved portion of the H2A, H2B, or H4 in conjunction with antibodies to the C-terminal portion of these histones.

Thus, in one aspect, provided herein is a method to identify and examine H3 N-terminal tail cleaved regions of a histone, the method comprising, or alternatively consisting essentially of, or yet further consisting of: a) contacting a cell containing chromatin with methylene blue or an equivalent thereof after exposure to white light or an equivalent of the white light to crosslink proteins in the cell; b) isolating the chromatin, c) acetylating all unmodified lysine residues by contacting the chromatin with acetic anhydride; d) conducting ChIPac with an H3 C-terminal tail antibody; and e) identifying H3 N-terminal tail-cleaved regions by detecting reduction in H3K14ac enrichment relative to a control.

In some aspects of the method, step e. is performed by a method comprising, or alternatively consisting essentially of, or yet further consisting of, quantitative PCR (qPCR) or NextGen sequencing analysis.

In another aspect, provided herein is a method to identify a polynucleotide fragment bound to an H3 histone comprising a cleaved N-terminal tail (H3NT) in a cell, the method comprising: a) crosslinking the genomic DNA of the cell to the histones of the cell, thereby producing crosslinked chromatin; b) generating fragments of the crosslinked chromatin; c) acetylating all unmodified lysine residues in the histones by contacting the fragmented, crosslinked chromatin with acetic anhydride or an equivalent thereof, d) conducting parallel chromatin immunoprecipitations on the acetylated chromatin produced in step c). with (1) an H3 C-terminal tail control antibody and (2) one or more antibodies directed to acetylated lysine residues in the cleaved region of the H3NT; and e) identifying the polynucleotide fragment bound to an H3NT by detecting reduction in polynucleotide fragment enrichment with the one or more antibodies directed to acetylated lysine residues in the cleaved region relative to polynucleotide fragment enrichment with the H3 C-terminal tail control antibody.

In some aspects of the method, step a) is performed by fixation with methylene blue or an equivalent thereof.

In some aspects of the method, step b) is performed by sonication, enzymatic fragmentation, or an equivalent of each thereof.

In some aspects of the method, the one or more antibodies directed to acetylated lysine residues in the cleaved region of the H3NT in step d)(2) are selected from an an H3K4ac antibody, an H3K9ac antibody, and an H3K14ac antibody.

In some aspects of the method, the one or more antibodies directed to acetylated lysine residues in the cleaved region of the H3NT in step d)(2) is an H3K14ac antibody.

In some aspects of the method, step e) is performed by a method comprising quantitative PCR (qPCR) or NextGen sequencing analysis.

In other aspects, the method further comprises identifying a subject appropriate for therapeutic treatment with MMP-9.

In other aspects, the method further comprises identifying genetic loci at which a matrix metalloproteinase or other histone cleavage enzyme cleaves an H3 N terminal tail. Matrix metalloproteinases with potential histone tail cleavage activity include MMP1 (interstitial collagenase), MMP2 (Gelatinase-A, 72 kDa gelatinase), MMP3 (Stromelysin 1), MMP7, (Matrilysin, Pump 1), MMP8 (Neutrophil collagenase), MMP9 (Gelatinase-B, 92 kDa gelatinase), MMP10 (Stromelysin 2), MMP11 (Stromelysin 3), MMP12 (Macrophage metalloelastase), MMP13 (Collagenase3), MMP14 (MTI-MMP), MMP15 (MT2-MMP), MMP16 (MT3-MMP), MMP17 (MT4-MMP), MMPP18 (Collagenase 4, xcol4, *Xenopus* collagenase), MMP19 (RASI-1, Stromelysin 4), MMP20 (Enamelysin), MMP21 (XMMP), MMP23A (CA-MMP), MMP23B, MMP24 (MT5-MMP), MMP25 (MT6-MMP), MMP26 (Matrilysin-2, endometase), MMP27 (MMP-22, C-MMP), MMP28 (Epilysin).

Also provided is a kit for identifying a polynucleotide fragment bound to an H3 histone comprising a cleaved N-terminal tail (H3NT) in a cell, the kit comprising: a) acetic anhydride or an equivalent thereof, b) an H3 C-terminal tail control antibody; c) a full length H3 N-tail detection antibody directed to an acetylated lysine residue; and d) instructions for use. In some embodiments, the full length H3 N-tail detection antibody is a H3K14ac antibody. In other embodiments, the antibody is an H3K4ac antibody or an H3K9ac antibody. In some embodiments, a mixture of one or more of H3K14ac antibody, H3K4ac antibody, and H3K9ac antibody are used to detect the full length acetylated H3 N-terminal tail. In some aspects, the kit may further comprise buffers, negative control antibodies, enzymes, methylene blue, and/or other reagents necessary to perform chromatin immunoprecipitation. The standard reagents necessary to perform chromatin immunoprecipitation, qPCR, and DNA seq are well known in the art.

Also provided is a method to modulate H3NT proteolysis during osteoclastogenesis in a cell, comprising, or alternatively consisting essentially of, or yet further consisting of, modulating the activity of MMP-9 in the cell. In one aspect, H3NT proteolysis is increased by increasing MMP-9 activity in the cell. In another aspect, the H3NT proteolysis is decreased by depletion or inhibit of MMP-9 activity in the cell. Diseases or pathological conditions associated with over- or under-osteoclastogenesis also can be treated by administering to a subject in need thereof an effective amount of the MMP-9 promoting or inhibiting agent. Agents that activate or promote MMP-9 activity include recombinant or isolated MMP-9 protein and epidermal growth factor has been shown to increase the expression and activity of MMP-9 (see WO 2002/045740). In some aspects, the agent is selected from recombinant MMP-9, recombinant MMP-9 modified to include nuclear localization signals, a histone acetyltransferase enzyme with H3K18 specificity, and gene therapy with a polynucleotide encoding MMP-9. Agents that inhibit or decrease MMP-9 activity are known in the art, e.g., as described in US Patent Appl. No. 2017/0015647; 2013/0064878; and 2011/00114186, and incorporated herein by reference. In some aspects, the agent is selected from MMP-9 shRNA, a mesenchymal stem cell expressing MMP-9 shRNA, a CBP/p300 inhibitor, an MMP-9 inhibitor, or a metalloprotease inhibitor. In some aspects, inhibitors appropriate for use with the disclosed methods include but are not limited to inhibitors of MMP-9 such as 2-(N-Benzyl-4-methoxyphenylsulfonamido)-5-((diethylamino)methyl)-N-hydroxy-3-methylbenzamide, actinonin, marimastat, MMP Inhibitor V, Batimastat, Chlorhexidine, dihydrochloride, GM 6001, MMP Inhibitor II, cis-ACCP, SB-3CT, 4-Aminobenzoyl-Gly-Pro-D-Leu-D-Ala hydroxamic acid, keracyanin chloride, MMP2/MMP-9 Inhibitor I, MMP-2/MMP-9 Inhibitor II, MMP-9 Inhibitor I, MMP-9/MMP-13 inhibitor I, MMP-9/MMP-13 inhibitor II, MMP-2/MMP-9 Inhibitor V, CP 471474, Ageladine A, TFA, or an equivalent of each thereof. The above-listed MMP inhibitors are available from Abcam or Santa Cruz Biotech.

Also provided herein is a method to modulate H3NT proteolysis in a cell, comprising modulating the activity of MMP-9 in the cell. In some aspects, H3NT proteolysis is increased by increasing MMP-9 activity in the nucleus of the cell. In further aspects, MMP-9 activity is increased by increasing nuclear localization of MMP-9, increasing acetylation of H3K18 residues, and/or overexpression of MMP-9. In other aspects, H3NT proteolysis is decreased by depletion or inhibition of MMP-9 activity in the cell. In further aspects, MMP-9 activity is decreased by knockdown of MMP-9 mRNA, treatment with CBP/p300 inhibitor, and/or treatment with a metalloprotease inhibitor. Knockdown of MMP-9 mRNA can comprise treatment with MMP-9 shRNA and/or contacting the cell with an effective amount of a mesenchymal stem cell expressing MMP-9 shRNA.

In the above methods, a cell is a prokaryotic or a eukaryotic cell, and when an eukaryotic cell can be a mammalian cell, e.g., a mouse, canine, feline, ovine, simian or a human cell. In the above methods, a cell may be an osteoclast, an osteoclast precursor cell, or a stem or progenitor cell that can be differentiated into an osteoclast.

Also provided herein is a method to attenuate osteoclast formation and/or differentiation in a subject, comprising, or alternatively consisting essentially of, or yet further consisting of, administering to the subject an effective amount of a MMP-9 agent, inhibitor, or activator to the subject. In several aspects, the subject is a mammal, e.g., a mouse, a canine, a feline, an ovine, a simian or a human patient. These methods can be used therapeutically or in veterinary applications, or alternatively, as an animal model to assay for new therapies or treatments. The agents can be used alone or in combination with other known therapies.

Also provided herein is a method of treating a subject with low bone mineral density, administering an agent or inhibitor that decreases or inhibits the activity of MMP-9 in the subject. In several aspects, the subject is a mammal, e.g., a mouse, a canine, a feline, an ovine, a simian or a human patient. These methods can be used therapeutically or in veterinary applications, or alternatively, as an animal model to assay for new therapies or treatments. The agents can be used alone or in combination with other known therapies. In some aspects, the subject has a bone related disease or condition selected from osteoporosis, bone cancer, cancer that has metastasized to the bone, cancer-induced osteolysis, sepsis, rheumatoid arthritis, and periodontitis. Agents that inhibit or decrease MMP-9 activity are known in the art, e.g., as described in US Patent Appl. No. 2017/0015647; 2013/0064878; and 2011/00114186, and incorporated herein by reference. In some aspects, the agent is selected from MMP-9 shRNA, a mesenchymal stem cell expressing MMP-9 shRNA, a CBP/p300 inhibitor, an MMP-9 inhibitor, or a metalloprotease inhibitor. In some aspects, inhibitors appropriate for use with the disclosed methods include but are not limited to inhibitors of MMP-9 such as 2-(N-Benzyl-4-methoxyphenyl sulfonamido)-5-((diethylamino)methyl)-N-hydroxy-3-methylbenzamide, actinonin, marimastat, MMP Inhibitor V, Batimastat, Chlorhexidine, dihydrochloride, GM 6001, MMP Inhibitor II, cis-ACCP, SB-3CT, 4-Aminobenzoyl-Gly-Pro-D-Leu-D-Ala hydroxamic acid, keracyanin chloride, MMP2/MMP-9 Inhibitor I, MMP-2/

MMP-9 Inhibitor II, MMP-9 Inhibitor I, MMP-9/MMP-13 inhibitor I, MMP-9/MMP-13 inhibitor II, MMP-2/MMP-9 Inhibitor V, CP 471474, Ageladine A, TFA, or an equivalent of each thereof. The above-listed MMP inhibitors are available from Abcam or Santa Cruz Biotech.

Also provided herein is a method of treating a subject with high bone mineral density, comprising administering an agent that increases the activity of MMP-9 in the subject. In several aspects, the subject is a mammal, e.g., a mouse, a canine, a feline, an ovine, a simian or a human patient. These methods can be used therapeutically or in veterinary applications, or alternatively, as an animal model to assay for new therapies or treatments. The agents can be used alone or in combination with other known therapies. In some aspects, the subject has a bone related disease or condition selected from osteopetrosis, pycondysostosis, osteopoikilosis, meloreostosis, sclerosteosis, van Buchem's disease, LRP5 high bone mass, LRP4 high bone mass, craniometaphyseal dysplasia, Camurati-Engelmann disease, Ghosal syndrome, bone cancer, cancer metastasized to the bone, fluorosis, renal osteodystrophy, acromegaly, hepatitis C-associated osteosclerosis, myelofibrosis, mastocytosis, osseous tuberous sclerosis, Paget's disease, and SAPHO syndrome. Agents that increase MMP-9 activity in a cell include, for example, recombinant or isolated MMP-9 protein and epidermal growth factor (see WO 2002/045740). In some aspects, the agent is selected from recombinant MMP-9, recombinant MMP-9 modified to include nuclear localization signals, a histone acetyltransferase enzyme with H3K18 specificity, and gene therapy with a polynucleotide encoding MMP-9.

Also provided is method to modulate H3NT proteolysis during osteoclastogenesis in a cell, comprising, or alternatively consisting essentially of, or yet further consisting of, modulating the activity of MMP-9 in the cell. In one aspect, H3NT proteolysis is increased by increasing MMP-9 activity in the cell. Agents that increase MMP-9 activity in a cell include, for example, recombinant or isolated MMP-9 protein and epidermal growth factor (see WO 2002/045740). In another aspect, the H3NT proteolysis is decreased by depletion or inhibit of MMP-9 activity in the cell. Agents that inhibit or decrease MMP-9 activity are known in the art, e.g., as described in US Patent Appl. No. 2017/0015647; 2013/0064878; and 2011/00114186, and incorporated herein by reference. Cells that are suitably treated with the agents include without limitation a eukaryotic cell, a mammalian cell, e.g. a human cell, a equine cell, a canine cell, or a feline cell, an osteoclast, an osteoclast precursor, or a progenitor cell or stem cell capable of differentiation into an osteoclast. Cells capable of differentiation into an osteoclast include but are not limited to embryonic stem cells, induced pluripotent cells, hematopoietic stem cells, myeloid stem cells, granulocyte-macrophage colony forming unit (GM-CFU), monocyte precursor (CFU-M), progenitor cells, and pre-osteoclasts.

Descriptive Embodiments

Applicant discloses herein that MMP-9 is a novel H3NT protease required for H3NT proteolysis observed during osteoclastogenesis. This data demonstrate that RANKL-induced differentiation of primary mouse OCP cells facilitates the progressive nuclear accumulation and activity of MMP-9 concomitant with increased H3NT proteolysis. By applying Applicant's novel ChIPac-Seq method, App licant determined that many canonical osteoclastogenic genes are selectively targeted for H3NT proteolysis during osteoclastogenesis. Depletion of MMP-9 or inhibition of MMP-9 activity abrogated H3NT proteolysis concurrent with impaired osteoclastogenic gene activation and defective osteoclast differentiation. Applicant's data support a model whereby RANKL signaling induces MMP-9-dependent H3NT proteolysis at osteoclastogenic genes to regulate their expression necessary for proficient osteoclast differentiation. Consistent with this, it has been demonstrated that chemical inhibition of MMP-9 activity in vivo attenuates osteoclast formation in juvenile mouse clavaria and MMP-9-/- mice display delayed long bone development and defective bone fracture repair (Vu et al. 1998; Colnot et al. 2003; Cackowski et al. 2010; Franco et al. 2011).

Despite increasing evidence supporting H3NT proteolysis in epigenetic regulation, advances in the field have been significantly impeded by the lack of a method to define and investigate genomic regions targeted for H3NT proteolysis in mammalian cells. Applicant addresses this need by providing a ChIP of acetylated chromatin (ChIPac) method as a general approach to map and examine H3NT-cleaved regions. Since H3K14 resides within the H3NT-cleaved fragment and primarily exists in either an unmodified or acetylated state in mammals, an H3K14ac-specific antibody was used to selectively immunoprecipitate H3NT-containing nucleosomes from artificially acetylated crosslinked chromatin. ChIPac-Seq in MMP-9 depleted OCP cells that lack H3NT proteolysis validated the proficiency of the H3K14ac antibody to capture all nucleosomes, as the H3K14ac enrichment patterns were nearly identical to H3CT control. Furthermore, ChIPac-Seq in control 3-day OCP-induced cells that exhibit limited H3NT proteolysis identified a small number of genomic regions displaying significant reductions in H3K14ac enrichment, indicative of nucleosomes lacking the H3NT. Inhibition of H3NT proteolysis in 3-day OCP-induced cells rescued H3K14ac enrichment confirming that ChIPac with an H3K14ac-specific antibody identified sites selectively targeted for H3NT proteolysis during osteoclastogenesis. These results validate the ChIPac-Seq method to identify H3NT-cleaved sites that, most likely, can be utilized in other eukaryotic model systems. Application of ChIPac-Seq in this study resulted in the first demonstration of selective H3NT proteolysis at specific genomic sites during mammalian differentiation.

It was previously reported that proteolysis of the H3NT at gene promoters is directly correlated to transcriptional activation during yeast sporulation (Santos-Rosa et al. 2009). In this report, ChIPac-Seq similarly identified H3NT-cleaved regions surrounding the TSS of specific protein coding genes during osteoclastogenesis. Whereas H3NT proteolysis occurred at yeast promoters, mouse preosteoclasts displayed H3NT-cleaved regions that partitioned as those that were promoter-specific (P), coding region-specific (CR) or both (P+CR). The functional significance for these differences, if any, is unclear. Regardless of H3NT cleavage location (P, CR or P+CR), the majority of genes targeted for H3NT proteolysis during osteoclast differentiation displayed concomitant significant changes in expression. H3NT proteolysis correlated to transcriptional activation for >82% of these genes during osteoclastogenesis, similar to results in yeast, supporting the direct role of H3NT cleavage in gene activation. Several H3NT-cleaved genes were repressed and many others exhibited little difference in expression during differentiation, suggesting that H3NT proteolysis regulates activation of specific groups of genes in a context-dependent manner. In the context of RANKL signaling in OCP cells, the activation of a group of canonical osteoclastogenic genes necessary for osteoclast differentiation was directly correlated to the selective H3NT proteolysis near their TSSs.

Inhibition of H3NT proteolysis at these sites significantly impaired their activation, despite continuous RANKL signaling, resulting in defective osteoclast differentiation. Therefore, Applicant postulated that distinct signaling cues induce selective H3NT proteolysis to facilitate the rapid activation of specific developmental genes necessary for proficient differentiation.

Biochemical purification of preosteoclast nuclear extracts identified MMP-9 as a novel H3NT protease. Detailed investigation confirmed that MMP-9 is the principal histone protease in preosteoclasts that selectively cleaves the H3NT in vitro and in cells. Applicant's results strongly support a model whereby MMP-9 directly cleaves the H3NT to activate genes. Without being bound by theory, Applicant does not exclude the possibility that MMP-9 activity may also regulate unknown factors necessary to facilitate H3NT proteolysis and/or gene activation during osteoclastogenesis. However, these results demonstrate proteolysis of histones by a metalloproteinase that, therefore, expands the spectrum of histone proteases beyond the canonical serine and cysteine protease families (Dhaenens et al. 2015). Also without being bound by theory, these results suggest histone proteolysis by the remaining 22 MMPs. The primary P1 site of the yeast PRB1 serine protease and mouse Cathepsin cysteine proteases is H3A21 (Duncan et al. 2008; Duarte et al. 2014; Khalkhali-Ellis et al. 2014; Xue et al. 2014). In contrast, in silico analysis predicted H3K18 as the primary P1 site for MMP-9, which was confirmed experimentally. The MMP-9 and PRB1 endopeptidases generate a single major H3NT-cleaved product whereas Cathepsins generate progressively shorter H3 forms after T22 due to their additional aminopeptidase activity. These enzymatic and substrate differences support MMP-9 as the founding member of a novel class of H3K18 proteases.

Based on Applicants' findings and previous reports, Applicant looked to determine if specific classes of H3NT proteases are utilized in a context-dependent manner to facilitate distinct epigenetic mechanisms due to their particular H3NT proteolytic activities. In the context of mESC differentiation, the Cathepsin L H3A21 protease accumulates in the nucleus and is required for H3NT proteolysis (Duncan et al. 2008). The resulting H3Δ22 cleaved product impeded CBX7 chromodomain binding to H3K27me3 in vitro suggesting that proteolysis of H3 aa1-21 reduces the affinity of repressive H3K27me-binding proteins/complexes, thereby, facilitating gene activation in differentiating mESCs. This putative mechanism of epigenetic regulation may be conserved for H3A21 proteases but is less likely to apply to H3K18 proteases since an H3A18 peptide did not impair H3K27me3-CBX7 binding in vitro (Duncan et al. 2008). Although the primary mechanism of epigenetic regulation by H3K18 proteases remains unknown, the contrasting H3NT activities and epigenetic regulatory mechanisms observed between MMP-9 and Cathepsins may explain why each protease is selectively utilized during differentiation of distinct cell types.

During osteoclast differentiation, MMP-9 accumulates in the nucleus concomitant with gelatinase activity and H3NT proteolysis. Consistent with the disclosed results, increasing evidence demonstrates MMP-9 nuclear localization and activity in specific cell types and under certain physiological conditions (Mannello and Medda 2012). The mechanisms that facilitate MMP-9 nuclear translocation remain unknown but the lack of an NLS support the necessity of unidentified MMP-9-associated factors for transport. Applicant's results demonstrate that progressive MMP-9 nuclear accumulation during osteoclastogenesis is directly proportional to the extent of gelatinase activity and H3NT proteolysis. Robust gelatinase activity and H3NT proteolysis were not observed prior to preosteoclast formation, despite nuclear localization of the MMP-9 active form shortly after RANKL treatment, suggesting that a threshold of MMP-9 abundance regulates its nuclear protease activity. Furthermore, Applicant's results support H3K18 acetylation as a key regulator of MMP-9 activity. The specific acetylation of H3K18 was necessary and sufficient for MMP-9 H3NT proteolysis of nucleosome substrates in vitro and, in preosteoclasts, the sites and extent of H3NT cleavage were directly proportional to the level of acetylated H3K18. These results demonstrating that H3NT proteolysis is dependent on CBP/p300 activity, but not other canonical H3K18 acetyltransferases, support CBP/p300 as a central regulator of H3K18ac-dependent H3NT proteolysis.

It was recently reported that CBP recruitment and histone acetylation at the Nfatc1 promoter were directly correlated to Nfatc1 transcriptional activation during osteoclastogenesis, further supporting the necessity of CBP/p300-mediated H3K18 acetylation in regulating H3NT proteolysis and gene activation (Park-Min et al. 2014). Importantly, these results demonstrate that the targeted acetylation of H3K18 at the H3NT cleavage sites of Nfatc1, Lif and Xpr1 was insufficient to induce their expression during osteoclastogenesis, supporting H3NT cleavage as a prerequisite for their activation. Without being bound by theory, modulation of H3NT proteolysis by H3K18 acetylation is a conserved regulatory mechanism of many H3NT proteases, as Cathepsin L activity was also augmented by H3K18ac in vitro (Duncan et al. 2008).

Previous reports demonstrated that other histone modifications also regulate the activity of H3A21 proteases. Methylation of H3K27 augmented Cathepsin L activity in vitro whereas acetylated H3K23 abrogated H3 proteolysis in a dominant manner (Duncan et al. 2008). Similarly, H3K4me3 suppressed H3NT proteolysis in yeast consistent with the absence of H3K4me3 in the cleaved H3NT peptides isolated from differentiating mESCs (Santos-Rosa et al. 2009). In contrast to these reports, Applicant's results demonstrate that H3K4 methylation, H3K23 acetylation and H3K27 methylation are insufficient to regulate MMP-9 activity in vitro. These findings suggest that distinct H3NT proteases are differentially regulated by a specific "histone code" that stimulates or inhibits their activity (Strahl and Allis 2000). This may explain, in part, why only limited H3NT proteolysis is observed during differentiation and why MMP-9-dependent H3NT proteolysis is detected at only a small number of defined regions during osteoclastogenesis.

The H3NT proteases generate a cleaved H3 product that is transiently retained in chromatin during yeast sporulation and mESC differentiation (Duncan et al. 2008; Santos-Rosa et al. 2009). Although the rapid H3NT proteolysis identified at yeast promoters was insufficient for gene activation, the cleaved H3 facilitated subsequent nucleosome eviction at these promoters, by unknown mechanisms, concomitant with their activation. These findings suggest the similar requirement of cleaved H3-mediated nucleosome eviction for proficient gene activation during mammalian differentiation. However, Applicants' results demonstrate that cleaved H3 is retained within chromatin of differentiated osteoclasts and that robust activation of the H3NT-cleaved genes examined during osteoclastogenesis is independent of nucleosome eviction or histone replacement near their TSSs. While retention of cleaved H3 is observed in chromatin of terminally differentiated and senescent cells, the functional significance between retention and eviction/replacement of cleaved H3, as observed in differentiating mouse and human ESCs, remains unknown (Duncan et al. 2008; Asp et al. 2011; Duarte et al. 2014; Vossaert et al. 2014).

Experimental Details

Proteolysis of the Histone H3 N-Terminal Tail During Osteoclastogenesis

Since the epigenetic mechanisms that regulate mammalian osteoclastogenesis are largely unknown, an established ex vivo cell model was used to examine possible histone PTM changes during differentiation. Primary osteoclast precursor (OCP) cells derived from adult mouse long bone were cultured with the osteoclastogenic factor RANKL to induce synchronous osteoclast differentiation (An et al. 2014). As shown in FIG. 1A, nearly all 3-day OCP-induced cells were mononuclear preosteoclasts that fuse to form large multinuclear osteoclasts by day 5. Nuclei were isolated from OCP-induced cells at these time points and chromatin was extracted. Western blot analysis revealed an unexpected differentiation-dependent fast-migrating H3 band in chromatin of preosteoclasts with elevated levels detected in osteoclasts (FIG. 1B). Because an H3 C-terminal (H3CT) antibody was used in the Western blot analysis, the observed fast-migrating H3 band indicates specific proteolysis of the H3 N-terminal (H3NT). Fast-migrating bands of other nucleosome core histones were not observed demonstrating the selective, but limited, proteolysis of the H3NT during osteoclastogenesis (FIG. 1B).

MMP-9 is the Principal H3NT Protease in Preosteoclasts

Figure 8A:
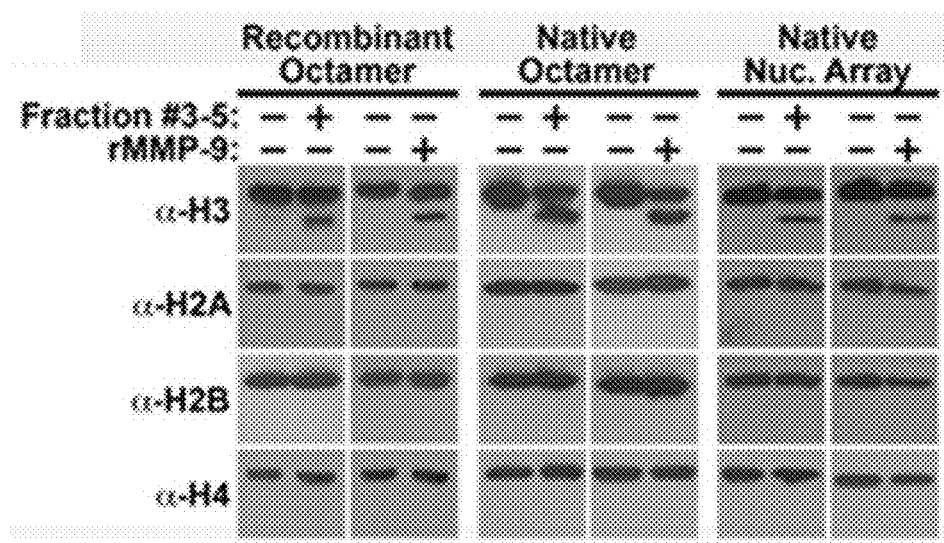
FIGS. 8A-8B.
Figure 8B:
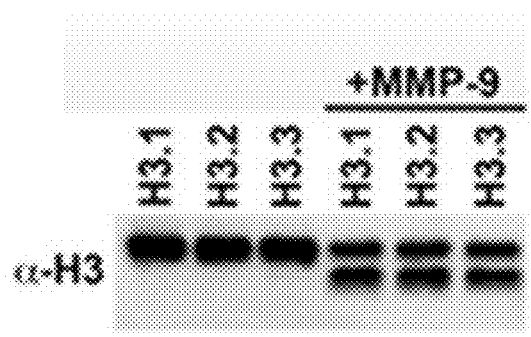

To identify the protease responsible for H3NT cleavage observed in preosteoclasts, nuclear extracts from 3-day OCP-induced cells were fractionated by a series of chromatography steps (FIG. 1C). An in vitro H3NT cleavage assay was developed using a recombinant H3 (rH3) substrate and Western blot analysis with the H3CT antibody to track and isolate nuclear fractions containing H3NT protease activity. Initial fractionation by P11 chromatography revealed that H3NT protease activity was largely restricted to two sequential fractions, BC400 and BC500, suggesting that a single protease cleaves the H3NT in preosteoclasts. These fractions were combined and fractionated on a Q-sepharose column where, again, H3NT protease activity was largely restricted to two sequential fractions, BR100 and BR200. The fractions were combined for glycerol gradient sedimentation resulting in the final purification of fractions (#3-5) containing H3NT protease activity. These purified fractions were initially incubated with different protease inhibitors to identify the family of proteases responsible for H3NT cleavage. Various serine and cysteine protease inhibitors failed to inhibit H3NT protease activity, which was highly unexpected as these families were reported to proteolyze the H3NT in yeast and mice, respectively (FIG. 1D) (Duncan et al. 2008; Khalkhali-Ellis et al. 2014; Xue et al. 2014). Further screening demonstrated that only metalloproteinase inhibition could abrogate H3NT cleavage activity (FIG. 1E). Consistent with these results, proteomic analysis of the purified fractions revealed that matrix metalloproteinase 9 (MMP-9) was the predominant of the four known proteases identified (FIG. 1F). In vitro H3NT cleavage assays using these recombinant proteases demonstrated that only rMMP-9 possessed H3NT protease activity (FIG. 1G). The purified fractions and rMMP-9 displayed similar H3NT protease activities for octamer and nucleosome array substrates as well as for H3.1, H3.2 and H3.3 substrates (FIGS. 8A-8B). Incubation of the purified fractions with a selective MMP-9 inhibitor abolished H3NT proteolysis confirming that MMP-9 activity is required for H3NT cleavage in vitro (FIG. 1E). These findings identify MMP-9 as a novel H3NT protease and the principal H3NT protease in preosteoclasts.

MMP-9 Activity is Required for H3NT Proteolysis During Osteoclastogenesis

Figure 2C:
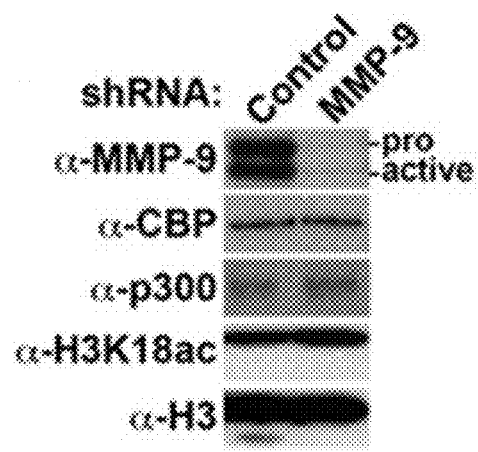
Figure 2B:
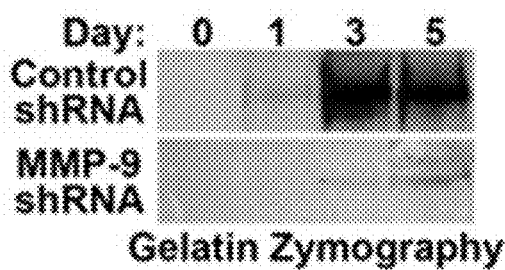
Figure 2D:
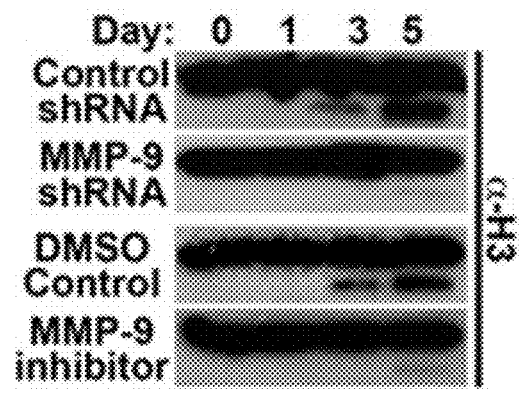
Figure 9A:
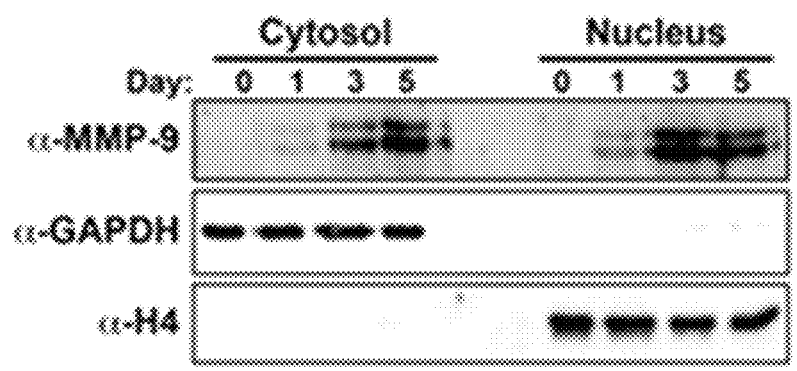
FIGS. 9A-9B.
Figure 9B:
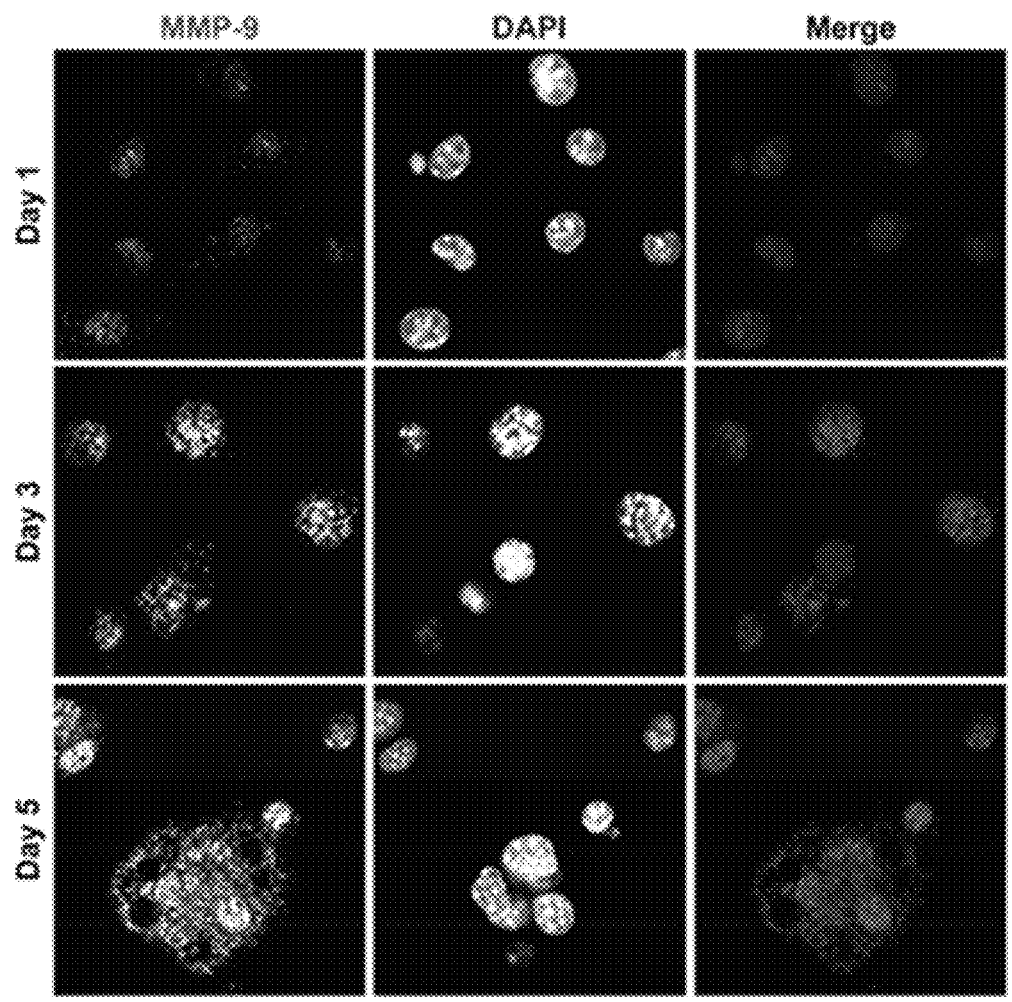

Matrix metalloproteinases are a large diverse family of zinc-dependent endopeptidases that function to remodel the pericellular space via proteolysis of extracellular matrix proteins (Nagase et al. 2006). MMP-9 and MMP-2 comprise the gelatinase sub-family of MMPs and are differentially expressed in osteoclasts and osteoblasts, respectively. MMP-9 is synthesized as an inactive/latent 92-kDa proenzyme and subsequently converted to an 82-kDa active form by proteolysis of its inhibitory N-terminal prodomain. Since MMP-9 is a secretory protein, Applicants' results demonstrating nuclear MMP-9 activity were unexpected. To address this discrepancy, MMP-9 localization dynamics were examined during osteoclastogenesis. Western blot analysis demonstrated that MMP-9 was absent in control OCP cells but both the pro- and active-forms of MMP-9 were detected in the nuclear compartment of 1-day OCP-induced cells (FIG. 2A and FIG. 9A). MMP-9 protein abundance was maximal by day 3 post-induction and was sustained in 5-day OCP-induced cells. Immunofluorescence microscopy confirmed the progressive nuclear accumulation of MMP-9 in OCP-induced cells (FIG. 9B). Gelatin zymography was performed using nuclear extracts isolated from OCP-induced cells to assess nuclear-specific MMP-9 gelatinase activity. Nuclear gelatinase activity mirrored the progressive nuclear accumulation of MMP-9 during osteoclastogenesis (FIG. 2B). These results indicate that maximal MMP-9 nuclear abundance and activity observed in 3-day OCP-induced cells directly correlate with H3NT proteolysis. To test the dependence of H3NT cleavage on MMP-9 during osteoclastogenesis, OCP cells were transduced with a control or MMP-9-specific shRNA to deplete MMP-9 prior to induction (FIG. 2C). MMP-9 depletion impeded nuclear gelatinase activity in OCP-induced cells concurrent with the significant and sustained impairment of H3NT proteolysis (FIGS. 2B and 2D). The continuous impairment of H3NT cleavage was similarly observed in OCP-induced cells treated with a selective MMP-9 inhibitor (FIG. 2D). These collective results support the dependence of H3NT proteolysis on nuclear MMP-9 activity during osteoclastogenesis.

H3K18 is the Primary P1 Site of MMP-9

Figure 3A:
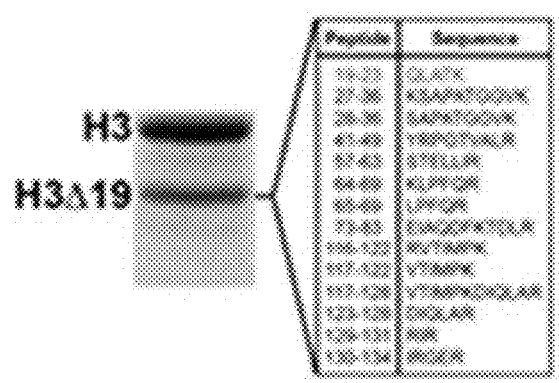
FIGS. 3A to 3D show H3K18 is the principal site of MMP-9 proteolysis.
Figure 3B:
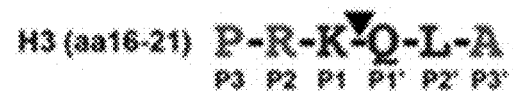
Figure 3C:
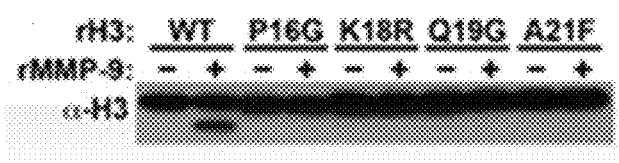
Figure 3D:
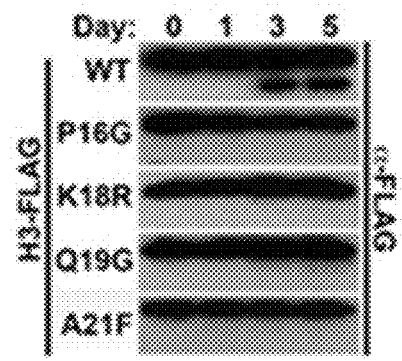
Figures 10A, 10B:
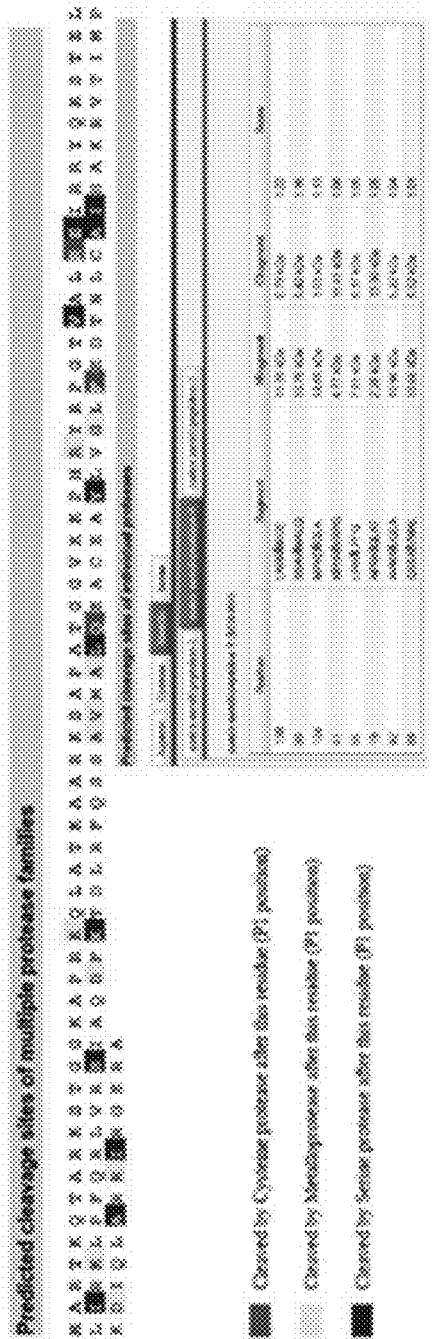
FIGS. 10A-10B.

Previous reports demonstrated that H3A21 is the primary cleavage site (P1) for cysteine and serine proteases, however, the H3NT P1 site of the MMP-9 metalloproteinase was unknown (Duncan et al. 2008; Santos-Rosa et al. 2009). In silico analysis of histone H3 identified K18 as the only potential P1 site on the H3NT, which was also predicted to be cleaved by MMP-9 (FIG. 10A) (Song et al. 2012). To test these predictions, LC-MS/MS of the gel-excised rH3-cleaved product generated by rMMP-9 was performed (FIG. 3A). Peptide fragments containing H3 residues prior to Q19 were not identified in the proteomic analysis, supporting H3K18 as the major P1 site of MMP-9. This result suggested that the sequence flanking H3K18 is a putative MMP-9 consensus site. To test this in vitro, rH3 containing mutated residues predicted necessary for MMP-9 activity were used as substrates in the H3NT cleavage assay (FIG. 3B and FIG. 10B). Mutation of rH3 at (P1, K18R; Pa', Q19G) or flanking (P3, P16G; P3', A21F) the cleavage site ablated H3NT proteolysis by rMMP-9, confirming that the H3 aa16-21 sequence is an MMP-9 consensus site in vitro (FIG. 3C). These results suggested that similar H3 mutations would ablate H3NT proteolysis during osteoclastogenesis. To test this, C-terminal FLAG-tag fusions of wild type H3 or the H3 mutants were transduced in OCP cells prior to induction. Western blot analysis of chromatin extracts confirmed proteolysis of wild type H3-FLAG in OCP-induced cells (FIG. 3D). Although mutant H3-FLAG proteins were also readily detected in chromatin extracts, each mutation of the MMP-9 consensus sequence abrogated H3NT proteolysis in OCP-induced cells. These findings support MMP-9 as the primary protease that directly cleaves H3K18-Q19 during osteoclastogeneis.

Acetylation of H3K18 Augments MMP-9 Activity

Figure 4A:
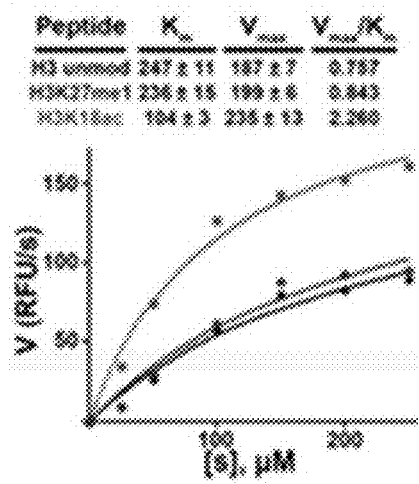
FIGS. 4A to 4E show acetylation status of H3K18 regulates MMP-9 activity.
Figure 4B:
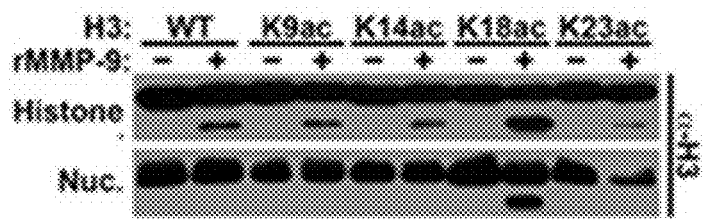
Figure 4C:
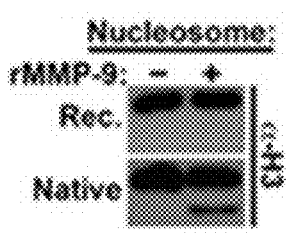
Figure 4D:
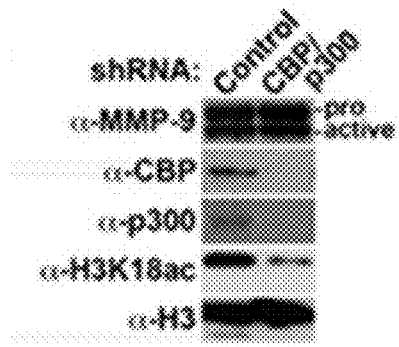
Figure 4E:
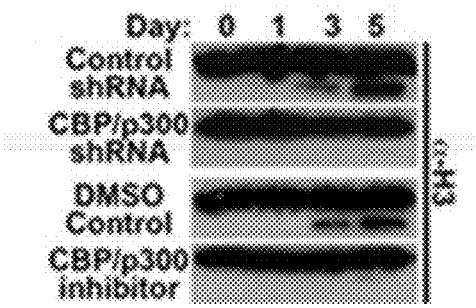
Figure 11A:
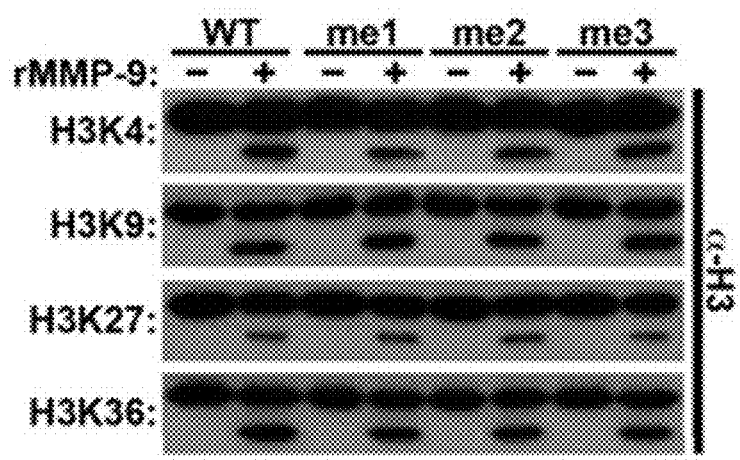
FIGS. 11A-11C.
Figure 11C:
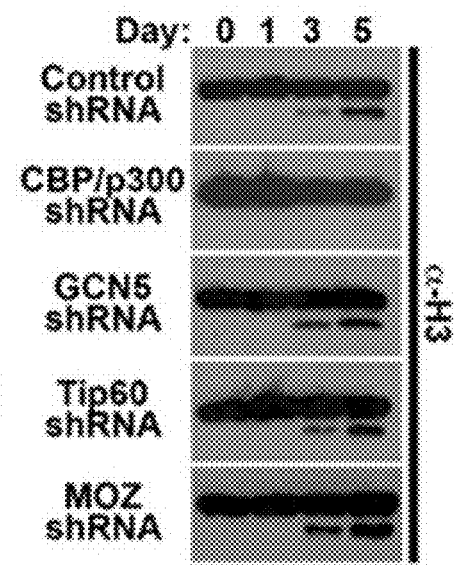
Figure 11B:
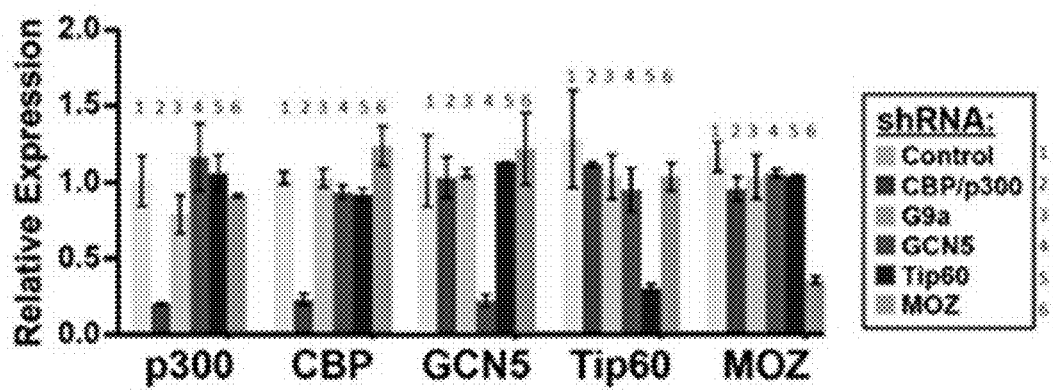

Analysis of the canonical MMP-9 consensus sequence indicated that MMP-9 preferentially cleaves uncharged residues over charged residues at the P1 site (FIG. 10B). Based on this, Applicants hypothesized that neutralizing the H3K18 charge by acetylation would augment MMP-9 activity. As predicted, kinetic analysis of MMP-9 activity using H3 peptide substrates confirmed that K18ac selectively amplified rMMP-9 activity resulting in a 3-fold increase of cleaved H3 compared to unmodified H3 or H3K27mea peptides (FIG. 4A). Consistent with these results, H3NT cleavage assays using rH3 acetyl-lysine analogues as substrates demonstrated that the specific acetylation of K18 robustly increased H3NT proteolysis by rMMP-9 (FIG. 4B) (Shogren-Knaak and Peterson 2004). MMP-9 activity with rH3 methyl-lysine analogues at K4, K9, K27 or K36 was nearly identical to rH3 control in all cases (FIG. 11A). These findings suggested that the acetylation of H3K18 facilitates MMP-9 activity in chromatin. To test this, nucleosome arrays containing unmodified rH3, the rH3 acetyl-lysine analogues or modified native histones purified from HeLa cells were generated in vitro and used as substrates in the H3NT cleavage assay (Kim et al. 2013a). Remarkably, unmodified nucleosome array substrates were completely resistant to rMMP-9 protease activity, in contrast to unmodified rH3 and octamer substrates (FIGS. 4B-4C and FIG. 8). Conversely, rMMP-9 displayed robust activity for modified native nucleosome arrays supporting the dependence of MMP-9 H3NT protease activity on specific histone PTMs in chromatin (FIG. 4C). Consistent with this, H3NT cleavage assays confirmed that the specific acetylation of H3K18 was both necessary and sufficient for H3NT cleavage by rMMP-9 in a nucleosome array context (FIG. 4B). These results suggested that acetylation of H3K18 was required for MMP-9-dependent H3NT cleavage during osteoclastogenesis. To test this, OCP cells were transduced with a control shRNA or an shRNA to deplete the CBP/p300 acetyltransferases, which are responsible for the majority of H3K18ac, prior to induction (Henry et al. 2013). Diminishment of H3K18ac in CBP/p300 depleted OCP-induced cells resulted in the sustained impairment of H3NT proteolysis without perturbing the nuclear abundance of active MMP-9 (FIGS. 4D-4E). Identical results were obtained from OCP-induced cells treated with a selective CBP/p300 inhibitor (FIG. 4E). Depletion of the known H3K18 acetyltransferases GCN5, Tip60 or MOZ did not impair H3NT proteolysis during osteoclastogenesis, in contrast to CBP/p300 depletion (FIGS. 11B-11C). These collective results support the regulation of MMP-9-dependent H3NT cleavage during osteoclastogenesis by the CBP/p300-mediated acetylation of H3K18.

Figure 5A:
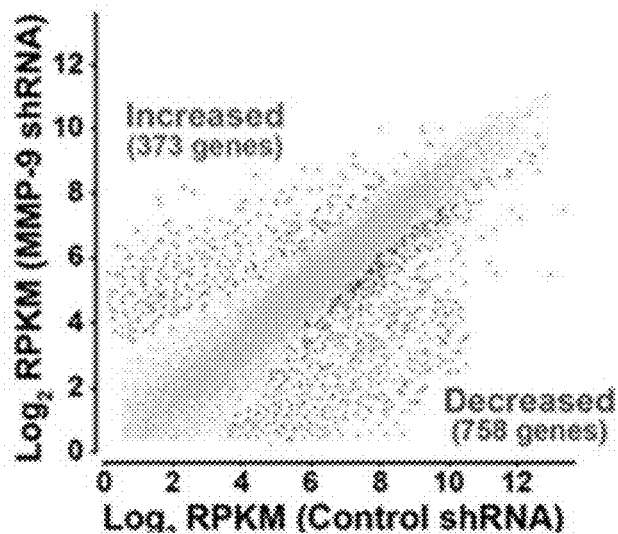
FIGS. 5A to 5D show MMP-9 is required for osteoclastogenic gene activation and proficient osteoclast differentiation.
Figure 5B:
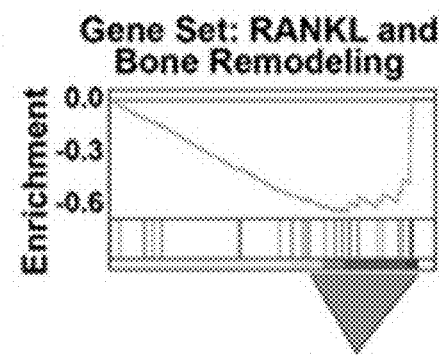
Figure 5C:
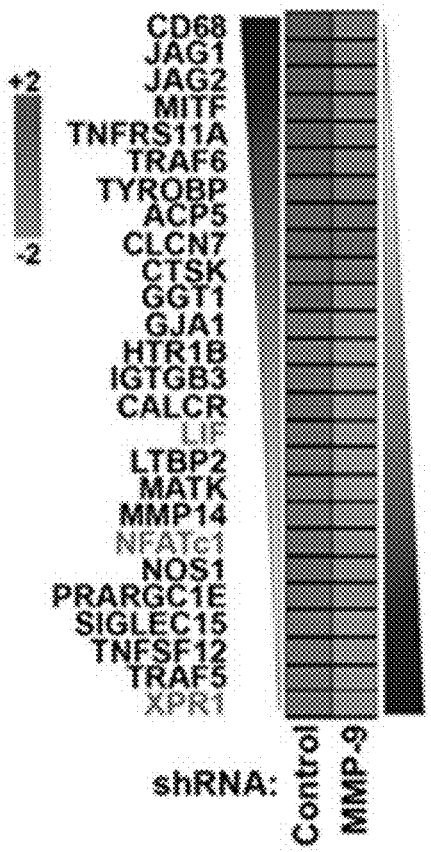
Figure 5D:
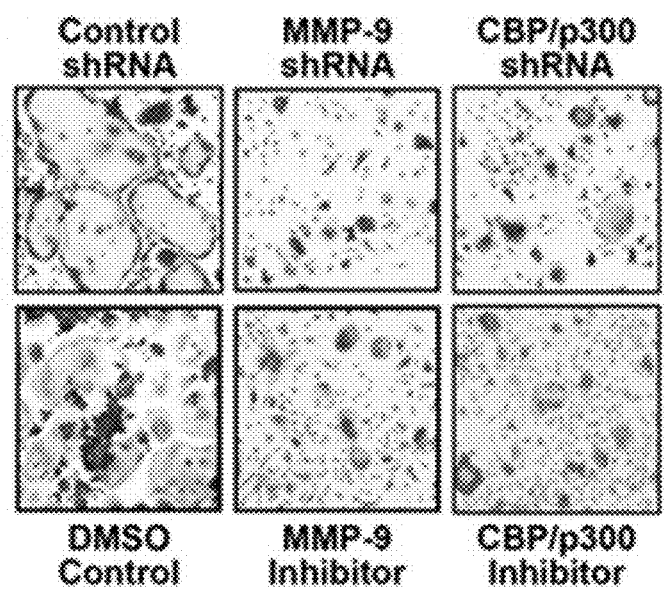
Figure 12A:
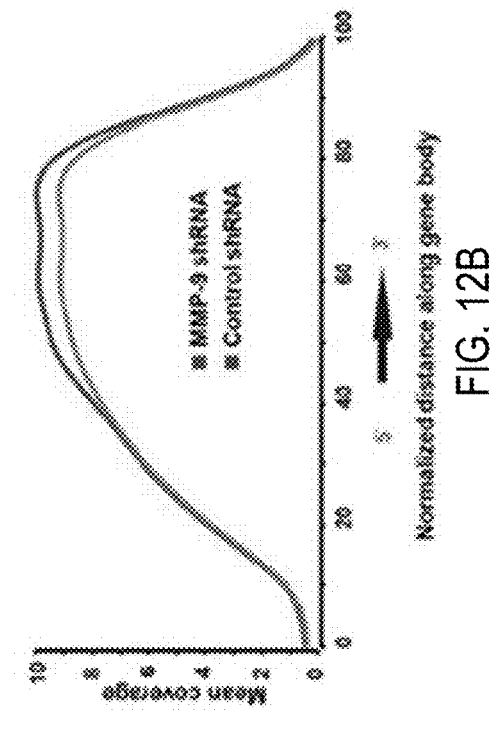
FIGS. 12A-12D.
Figure 12B:
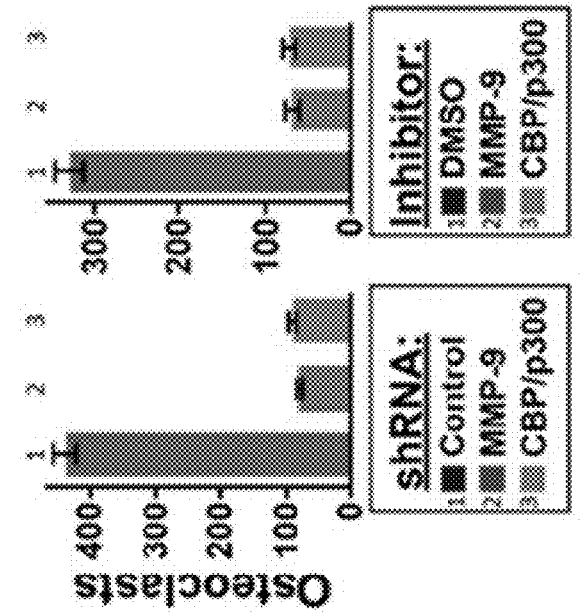
Figure 12C:
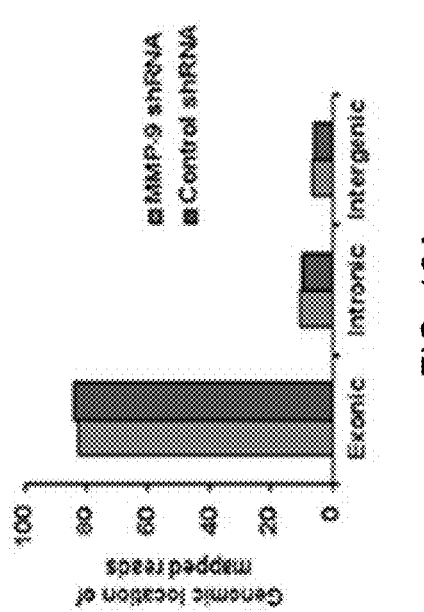
Figure 12D:
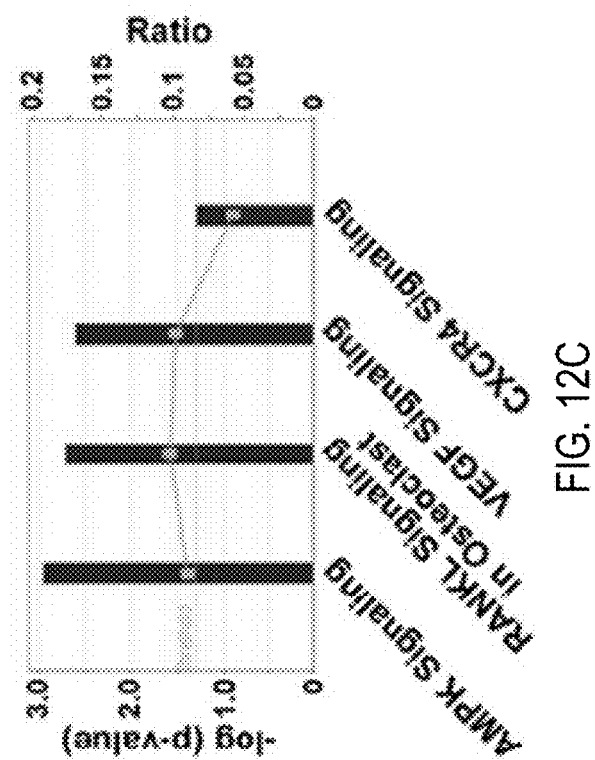

MMP-9 is Required for Osteoclastogenic Gene Activation and Proficient Osteoclastogenesis It was previously reported that H3NT cleavage facilitates gene activation in yeast during sporulation, suggesting that MMP-9-dependent H3NT proteolysis similarly functions in gene activation during osteoclastogenesis (Santos-Rosa et al. 2009). To test this, Applicants sought to identify the genes regulated by MMP-9 using RNA-Seq of total mRNA isolated from control or MMP-9 depleted 3-day OCP-induced cells (FIG. 2C). Comparative transcriptome analysis revealed 1,131 differentially expressed genes between the samples (Table 1 and FIGS. 12A-12B). Table 1 discloses "DEAH" as SEQ ID NO: 23 and "DEAD" as SEQ ID NO: 24). More than 67% of these genes displayed significantly reduced expression in MMP-9 depleted cells, supporting a function for MMP-9 in gene activation during osteoclastogenesis (FIG. 5A). Gene ontology analysis revealed that many of these genes are regulatory components of osteoclastogenic signaling pathways including the RANKL, AMPK and VEGF pathways (FIG. 12C). In addition, gene set enrichment analysis (GSEA) demonstrated that the expression of a large set of RANKL and bone remodeling pathway genes was significantly reduced in MMP-9 depleted cells compared to control cells (FIG. 5B). Examination of the leading-edge subset of these genes identified 26 canonical osteoclastogenic genes that required MMP-9 for their activation, including Nfatc1, Lifand Xpr1 (FIG. 5C) (Takayanagi et al. 2002; Bozec et al. 2008; Sharma et al. 2010). Importantly, the diminished H3NT cleavage and defective osteoclastogenic gene activation observed in MMP-9 depleted or inhibited 5-day OCP-induced cells were concurrent with a significant reduction of mature osteoclasts compared to control cells (FIG. 5D and FIG. 12D). Similar results obtained from CBP/p300 depleted or inhibited 5-day OCP-induced cells further support the dependence of osteoclastogenic gene activation and proficient osteoclast differentiation on H3NT proteolysis (FIG. 5D and FIG. 12D).

ChIPac-Seq: A Novel Approach to Identify H3NT-Cleaved Regions

The results suggested that MMP-9-dependent H3NT proteolysis directly regulates gene expression during osteoclastogenesis but the possible indirect effects of MMP-9 depletion on gene expression, independent of H3NT cleavage, could not be distinguished by transcriptomic analysis. Therefore, Applicants sought to determine the genomic sites targeted for H3NT proteolysis during osteoclastogenesis to directly investigate the role of H3NT cleavage in transcriptional regulation, however, a method to identify H3NT-cleaved sites in mammalian cells has not been reported. Applicants hypothesized that mapping these sites could be achieved by comparative ChIP-Seq analysis of the H3NT between control and MMP-9 depleted 3-day OCP-induced cells that exhibit or lack H3NT cleavage, respectively (FIG. 2D). Computational identification of genomic regions displaying significantly reduced H3NT enrichment in control versus MMP-9 depleted cells would indicate those regions selectively targeted for H3NT proteolysis during osteoclastogenesis. This ChIP approach requires an antibody that has specific affinity for the H3NT of all H3 proteins, is not dependent on or inhibited by existing H3 PTMs and is validated for ChIP applications, however, such an antibody is currently unavailable to the best of Applicants' knowledge. To bypass this technical barrier, established biochemical techniques were utilized to develop a novel method, called ChIP of acetylated chromatin (ChIPac), for identification and examination of H3NT-cleaved regions (FIG. 6A). Applicants reasoned that an H3K14 acetyl-specific antibody satisfies the criteria above for ChIP of the H3NT following complete lysine acetylation of crosslinked chromatin in vitro by acetic anhydride. First, cells were fixed with methylene blue to crosslink chromatin after brief exposure to white light (Tuite and Kelly 1993). Because formaldehyde reacts with lysine e-amino side-chains, which likely precludes complete lysine acetylation by acetic anhydride, methylene blue was used as an alternative for cell fixation (Metz et al. 2004). Chromatin was isolated and the efficiency of cross-linking was confirmed by SDS-CIA prior to sonication (FIG. 13A) (Lalwani et al. 1990). Fragmented chromatin was then treated with acetic anhydride to completely acetylate all unmodified lysine residues in vitro (FIG. 13B) (Nakayasu et al. 2014). ChIPac using an H3K14 acetyl-specific antibody selectively enriched H3NT-containing chromatin and simultaneously excluded chromatin lacking the H3NT. ChIPac using an H3CT antibody was performed in parallel as the normalization control. H3NT-cleaved regions were identified by the significant reduction in H3K14ac enrichment relative to control as determined by qPCR or NextGen sequencing analysis.

Specific Gene TSSs are Targeted for H3NT Proteolysis During Osteoclastogenesis

Figures 13D, 13E:
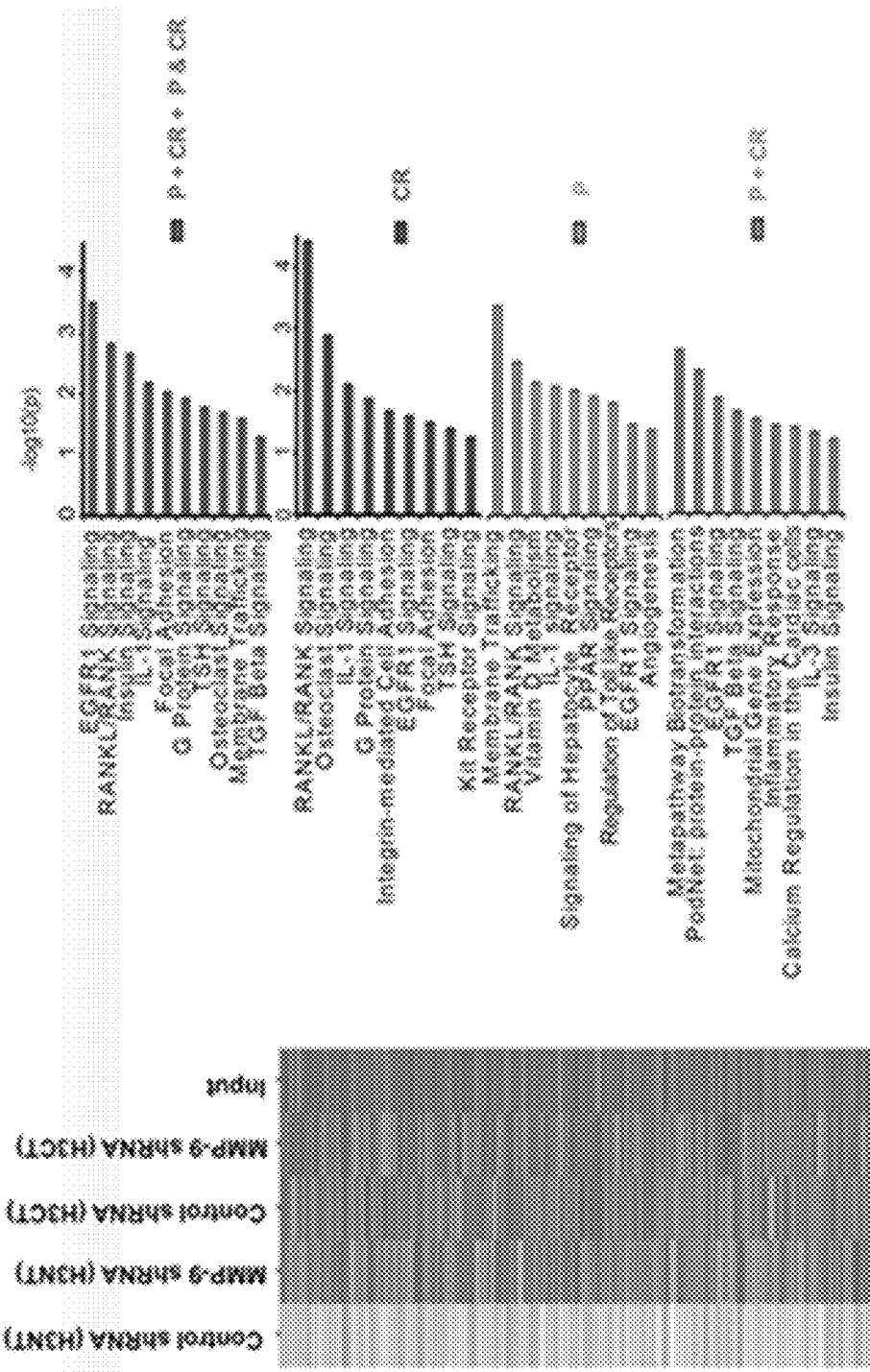

ChIPac-Seq was performed using control and MMP-9 depleted 3-day OCP-induced cells to identify the specific sites targeted for H3NT proteolysis during osteoclastogenesis. MMP-9 depleted cells that lack H3NT-cleaved chromatin displayed nearly indistinguishable enrichment patterns between H3K14ac and H3CT control, as predicted (FIG. 6B and FIGS. 13C-13D). These important results validated the ChIPac approach to purify all H3NT-containing chromatin using the H3K14ac-specific antibody. The capability of ChIPac-Seq to identify specific H3NT-cleaved regions was confirmed in control 3-day OCP-induced cells, which resulted in the identification of 1,233 regions displaying significantly reduced H3K14ac enrichment relative to MMP-9 depleted cells. The maximal peak of H3K14ac depletion within each H3NT-cleaved region and the gene nearest this peak were determined (Table 2) (Kim et al. 2013b). Applicant's subsequent computational analyses focused on the +/−4 kb region near gene transcription start sites (TSSs) since H3NT cleavage was previously reported at gene promoters in yeast (Santos-Rosa et al. 2009). K means clustering of TSSs revealed that <8% of all protein coding genes exhibited H3K14ac depletion near TSS indicating that these sites are selectively targeted for H3NT proteolysis during osteoclastogenesis (FIG. 6B and FIGS. 13C-13D). Strikingly, these genes partitioned into three distinct groups based on the location of H3NT cleavage: promoter-specific (P, 31%), coding region-specific (CR, 42%) or both (P+CR, 27%). Profiling the average tag densities in each group showed that H3NT cleavage typically peaks ~2 kb from TSS (FIG. 6C). Gene pathway analysis indicated that H3NT-cleaved genes are significantly linked to the RANKL and bone remodeling pathways (FIG. 13E). Several canonical osteoclastogenic genes were identified within each H3NT-cleaved group, including Nfatc1 (P), Lif (CR) and Xpr1 (P+CR). Notably, MMP-9 was required for H3NT cleavage near Nfatc1, Lif and Xpra TSSs and their concurrent activation during osteoclastogenesis, suggesting that H3NT proteolysis facilitates gene activation (FIG. 13C).

H3NT Cleavage Correlates with Gene Activation

Figure 7A:
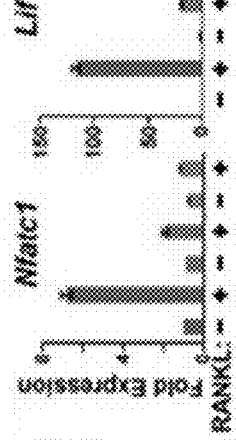
FIGS. 7A to 7D show CBP/p300-mediated acetylation of H3K18 regulates the sites and extent of MMP-9 H3NT proteolysis.
Figure 7B:
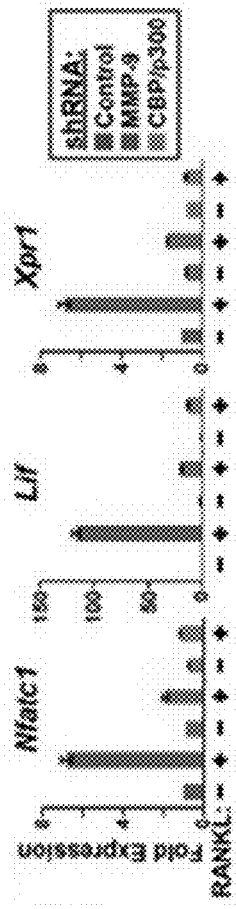
Figure 14:
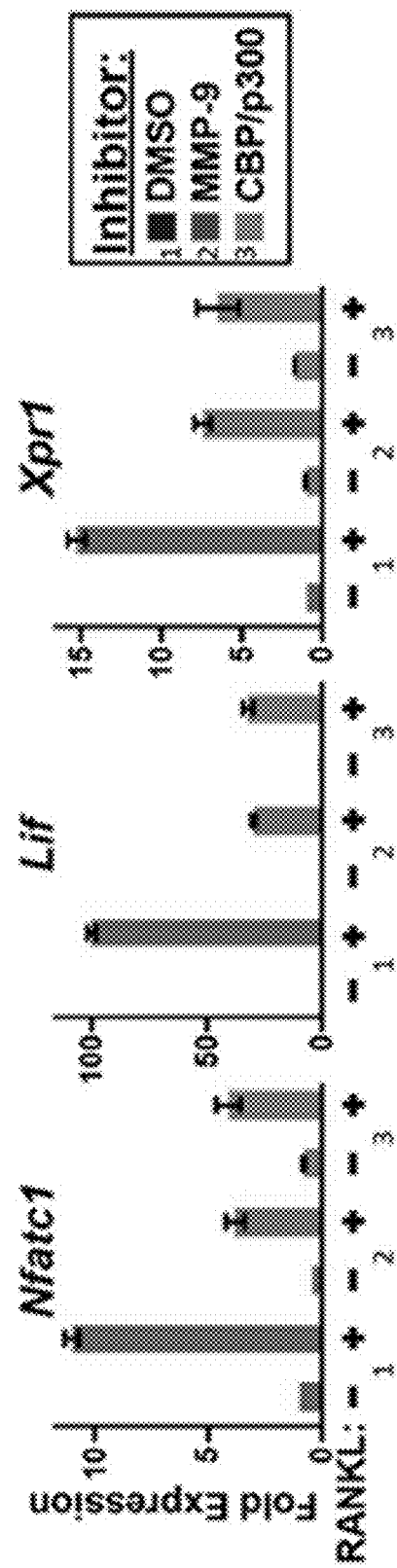
FIG. 14.

To broadly examine the association between H3NT cleavage and gene expression, the RNA-Seq data was analyzed for the 1,233 H3NT-cleaved genes identified in control and MMP-9 depleted 3-day OCP-induced cells. Comparative analyses revealed that most H3NT-cleaved genes (>53%) displayed significant expression differences in control versus MMP-9 depleted cells (FIG. 7A). The majority of these genes (>82%), including Nfatc1, Lif and Xpr1, exhibited significantly reduced expression in MMP-9 depleted cells indicating a strong functional correlation between MMP-9 and gene activation (FIG. 7A). To further investigate the MMP-9-dependent activation of these genes during osteoclastogenesis, RT-qPCR was performed in OCP cells transduced with a control or MMP-9-specific shRNA, or treated with DMSO control or a selective MMP-9 inhibitor, and cultured with or without RANKL for 3 days. Ablation of H3NT cleavage in MMP-9 depleted or inhibited 3-day OCP-induced cells significantly impaired Nfatc1, Lif and Xpr1 activation, suggesting that H3NT proteolysis directly facilitates their activation during osteoclastogenesis (FIGS. 2D, 7B and FIG. 14). Applicants reasoned that repeating these experiments in CBP/p300 depleted or inhibited 3-day OCP cells would test this hypothesis, as non-acetylated H3K18 impedes MMP-9 H3NT protease activity (FIG. 4). Consistent with the hypothesis, diminishment of H3K18 acetylation by CBP/p300 depletion or inhibition ablated H3NT cleavage and significantly impaired Nfatc1, Lif and Xpr1 activation, identical to the effects of MMP-9 depletion, but without altering nuclear abundance of the active MMP-9 enzyme (FIGS. 4D-4E, 7B and FIG. 14). These results further support the direct function of H3NT cleavage in gene activation and suggest that CBP/p300-mediated acetylation of H3K18 is a key regulator of MMP-9 H3NT protease activity during osteoclastogenesis.

Figure 7C:
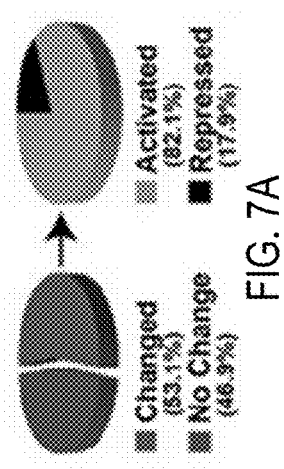
Figure 7D:
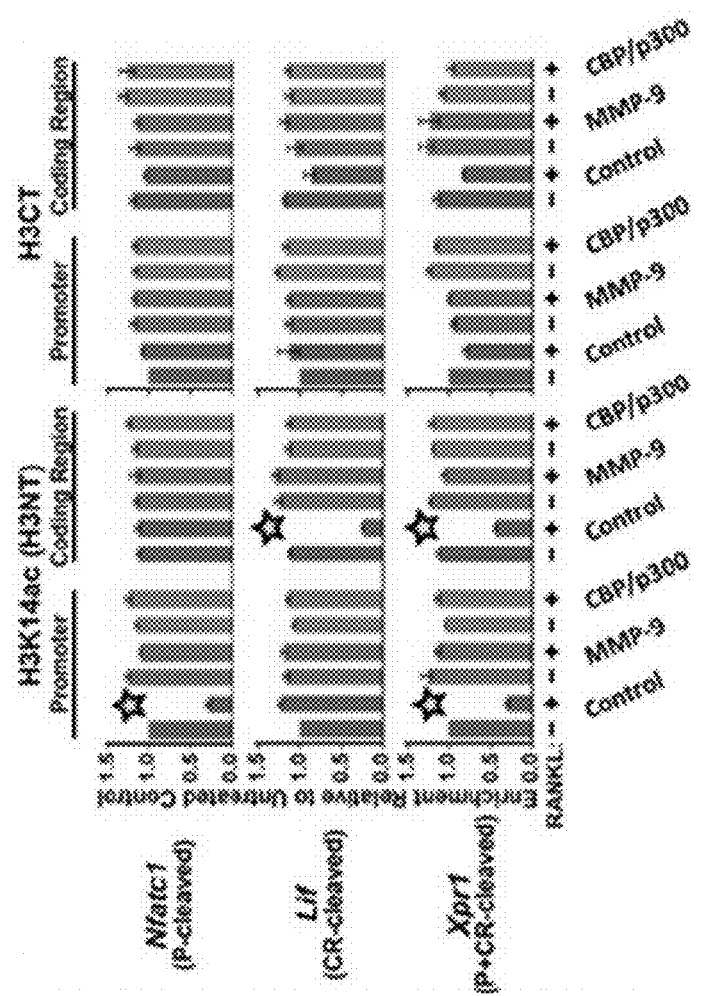

The Sites and Extent of H3NT Proteolysis are Directly Linked to H3K18 Acetylation Identification of the specific H3NT-cleaved sites at Nfatc1 (P), Lif (CR) and Xpra (P+CR) allowed us to directly examine the necessity of H3K18 acetylation on MMP-9 H3NT protease activity and gene activation during osteoclastogenesis. OCP cells were transduced with a control, MMP-9-specific or CBP/p300-specific shRNA, cultured with or without RANKL for 3 days and then processed for ChIPac or conventional ChIP using an H3K18ac-specific antibody. Subsequent qPCR confirmed the site-specific H3NT cleavage at Nfatca (P), Lif (CR) and Xpra (P+CR) in induced versus non-induced control shRNA cells (FIG. 7C). In contrast, H3K18ac enrichment at all sites examined were remarkably similar between induced and non-induced control shRNA cells (FIG. 7D). These results and the findings above suggested that H3NT cleavage sites are selectively targeted for H3K18 acetylation to activate MMP-9 H3K18-Q19 proteolysis, resulting in a tailless H3 that is exempt from enrichment by the H3K18ac ChIP. Consistent with this model, significantly increased H3K18ac enrichment at each H3NT cleavage site, but not the flanking non-cleavage sites, was concurrent with the ablation of H3NT cleavage at these sites in MMP-9 depleted 3-day OCP-induced cells (FIGS. 7C-7D). Notably, the relative increase of H3K18ac at each H3NT cleavage site observed in MMP-9 depleted cells was directly proportional to the relative decrease of H3K14ac observed in control shRNA cells, suggesting that H3K18 acetylation directly regulates the sites and extent of MMP-9 H3NT protease activity during osteoclastogenesis. Consistent with this, preclusion of H3K18 acetylation at each H3NT cleavage site was concurrent with the loss of H3NT cleavage at these sites in CBP/p300 depleted 3-day OCP-induced cells, despite the presence of active MMP-9 in the nucleus (FIGS. 4D and 7C-7D). The collective results indicate that the targeted CBP/p300-dependent acetylation of H3K18 at Nfatc1 (P), Lif (CR) and Xpr1 (P+CR) is prerequisite but insufficient for their expression, thereby, further supporting the necessity of H3NT proteolysis for their activation during osteoclastogenesis.

Cell Transduction and Inhibition

Retroviral particles were generated in Plat-E cells transfected with pMX-H3-Flag (Cell Biolabs) according to the manufacturers' instructions. Lentiviral particles were generated in HEK-293T cells by co-transfecting plasmids encoding VSV-G, NL-BH and pLKO.1-shRNA (Addgene) for MMP-9 (5'-GAGGCATACTTGTACCGCTAT (SEQ. ID NO: 19), p300 (5'-CCCTGGATTAAGTTTGATAAA (SEQ ID NO: 20)) or CBP (5'-TAACTCTGGCCATAGCTTAAT (SEQ ID NO: 21)). OCP cells were transduced and selected with puromycin (2 µg/ml) or cultured with DMSO, 10 nM MMP-9-INI (Santa Cruz) or 1.6 µM C646 (ApexBio) for 3 days prior to differentiation.

Chromatin Extraction and Western Blot Analysis

Chromatin was extracted by first resuspending cells in buffer A (10 mM HEPES, pH 7.4, 10 mM KCl, 1.5 mM MgCl2, 0.34 M sucrose, 10% glycerol, 1 mM DTT, 5 mM β-glycerophosphate, 10 mM NaF, protease inhibitors, and 0.2% Triton X-100) and incubating on ice for 8 min. Nuclei were isolated by centrifugation (1,300 g for 10' at 4° C.), resuspended in buffer B (3 mM EDTA, 0.2 mM EGTA, 1 mM DTT, 5 mM 3-glycerophosphate, 10 mM NaF, and protease inhibitors), centrifuged (1,700 g for 5 min at 4° C.) and the chromatin pellet was washed three times with buffer B prior to sonication in Laemmli buffer. Western blot analysis was performed using antibodies specific for H2A, H2B, H3 and H4 (Abcam); H3K9ac, H3K14ac, H3K18ac and H3K23ac (Active Motif); MMP-9, p300 (Santa Cruz) and CBP (BioLegend); His (Novagen) and FLAG (Sigma).

Recombinant Proteins and H3 Cleavage Assays

His-tagged proteins were generated in Rosetta 2 (DE3) pLysS $E.$ $coli$ (Novagen) and purified as previously described (Kim et al. 2008). MMP-9 (aa1115-730) was purified from inclusion bodies dissolved with lysis buffer (6 M urea, 0.5 M NaCl, 5 mM imidazole, 20 mM Tris, pH 7.9), refolded in 50 mM HEPES, 0.2 M NaCl, 1M NDSB201 (Sigma) and dialyzed in 50 mM Tris, pH 7.5, 0.1 M NaCl, 5 mM $CaCl_2$), 20 uM ZnCl2 and 30% glycerol. Recombinant and native histone octamers and nucleosome arrays were prepared as previously described (Kim et al. 2012). Cell extracts or recombinant proteins were incubated with histone octamer (1 rg) or nucleosomes (2 µg) in cleavage buffer (20 mM HEPES-KOH, pH 7.8, 1 mM $CaCl_2$), 20 mM KCl) for 0.5-2 hours at 37° C.+/−protease inhibitors aprotinin (10 µg/ml), bestatin (130 µm), EDTA (25 mM), leupeptin (100 µM), pepstatin A (1.5 M), PMSF (1 mM) or L006235 (20 nM). H3 tail peptides (aa10-35) were synthesized by solid-phase Fmoc/tBu chemistry and purity confirmed by ES-MS (EZBiolab). Peptides were incubated with rMMP-9 at seven different concentrations (0, 25, 50, 100, 150, 200, and 250 jM) in cleavage buffer, the reactions stopped by adding 20 mM o-phenanthroline (Sigma) and peptide hydrolysis was measured by adding 5 mM fluorescamine followed by detection at $\lambda_{ex}$ 365 nm and $\lambda_{em}$ 450 nm using a Plate Chameleon spectrofluorometer (Hidex). Kinetic parameters were determined by Michaelis-Menten analysis.

Chromatography

Nuclear extracts were fractionated on a P11 column (Pharmacia) equilibrated with BC100 buffer (20 mM HEPES-KOH, pH 7.9, 0.5 mM EDTA, 0.05% Nonidet P-40, 10% glycerol, 1 mM DTT, 100 mM KCl) as previously described (Kim et al. 2013b). H3NT active fractions were combined and dialyzed against Buffer R (10 mM HEPES-NaOH, pH7.6, 10 mM KCl, 1.5 mM MgCl2, 10% glycerol, 10 mM β-glycerophosphate, 1 mM DTT), loaded onto a Q-Sepharose column (Phamacia) and eluted with stepwise increased salt concentration in BR buffer. H3NT active fractions were combined and applied to a 5-ml 15-40% glycerol gradient in BR200 buffer containing 0.1% Nonidet P-40, centrifuged in an SW 55Ti rotor (150,000 g for 20 hours at 4° C.) and fractions (150 µl) were collected from the top of the tube. H3NT active fractions (#3-5) were combined for protein identification by LC-MS/MS analysis.

RNA-Seq

RNA Isolation and Library Preparation.

RNA was prepared using the Qiagen RNeasy kit (Qiagen, Valencia, Calif.) according to the manufacturer's instructions. For quality control, RNA purity and integrity were verified by denaturing gel electrophoresis, OD 260/280 ratio, and analysis on an Agilent 2100 Bioanalyzer (Agilent Technologies, Santa Clara, Calif.). Strand specific library perpetration was carried out using a KAPA Stranded mRNA-Seq Kit, with KAPA mRNA Capture Beads (KAPA Biosystem Wilmington, Mass.). Briefly, 30 ng of total RNA was reverse transcribed to cDNA using a T7 oligo(dT) primer. Second-strand cDNA was synthesized, in vitro transcribed, and labeled via incorporation of biotin-16-UTP. Validation of the library preparations was performed on an Agilent Bioanalyzer using the DNA1000 kit. Libraries were quantified using a Roche LightCycler96 with FastStart Essential DNA Green Master mix. Library concentrations were adjusted to 4 nM and pooled for multiplex sequencing. Pooled libraries were denatured and diluted to 15 pM and then clonally clustered onto the sequencing flow cell using the Illumina cBOT Cluster Generation Station and Cluster Kit v3-cBot-HS. The clustered flow cell was sequenced with 1×50 SE reads on the Illumina HiSeq2000 according to manufacturer's protocol. Base conversion was made using OLB version 1.9, de-multiplexed and converted to Fastq using CASAVA version 1.8 (Illumina). This resulted in approximately 50 million reads for control and MMP-9 shRNA expressing OCP cells. The library preparation and sequencing were performed in conjunction with the Sequencing Core Facility of UCLA, Los Angeles.

Bioinformatic Analyses of RNA-Seq.

To check the general quality of raw sequencing reads, Applicants used in-house RNA-seq workflow (University of Southern California, Epigenome Center) which consists of several open source tools. Briefly, to check the quality of sequencing reads in FastQC, reads were trimmed on both ends based on quality score (>38) of each sequence by using FASTX-Toolkit (http://hannonlab.cshl.edu). Adaptor sequences were also removed. High quality reads were aligned to the mm9 genome using TopHat-2 which uses Bowtie 2 at different steps, allowing one mismatch (in conjunction with gene model from Ensembl release 61) (Kim et al. 2013a). Potential PCR duplicated reads identified with the MarkDuplictaes using Picard (https://github.com) were excluded. Further alignment quality was checked using SamStat (Lassmann et al. 2011), RNA-seQC (DeLuca et al. 2012), Seqmonk, IGV and Qualimap (Garcia-Alcalde et al. 2012). A total of approximately 21 million unique mapped reads for each control and MMP-9 shRNA expressing OCP cells were obtained.

Transcript coverage. Applicants used coverage over the transcript plots to identify any problems associated with library preparation, sequencing process and distribution of reads across the genome or any bias in 5' or 3' expression using Qualimap and RNA-seQC packages. The majority of the reads (>80%) of all samples were within exonic regions and very low number of reads mapped to intronic or intergenic regions (FIG. 12A). To investigate any 5' or 3' bias in the expression, intronic positions were removed, coverage vectors for minus-strand genes were reversed, and remaining values divided into 100 non-overlapping bins were averaged to produce a uniform 100-column matrix of gene coverage for each sample. Genes <100 bp were not included in the analysis. Gene-wise trends in coverage bias and variability were studied by taking the coefficient of variance of the original coverage vector per gene and that of the ratio of the first-quarter mean depth (5' coverage) to fourth-quarter mean depth (3' coverage) on the gene body. Global coverage bias per sample was plotted against normalized coverage (FIG. 12B) as detailed previously (Graw et al. 2015). To obtain an overall robust gene expression, Applicants used an exon model by counting all reads mapped to only exons and combining all exons to a gene so that Applicants have read count per gene (RPKM) (Mortazavi et al. 2008). The RPKM values were adjusted globally by matching count distributions at the 75th percentile and then adjusting counts to a uniform distribution between samples. Finally differential expression was estimated by selecting transcripts that displayed significant changes (p<0.05) after Benjamini and Hochberg correction using a null model constructed from 1% of transcripts showing the closet average level of observation to estimate experimental noise (Ring et al. 2015). The gene list was further ranked using fold change criteria. GSEA and leading edge analyses were performed on the ranked list using gene sets from the C2 collection of the GSEA Molecular Signatures Database v3.0 and several gene sets associated with bone remodeling as detailed previously (Kim et al. 2015).

ChIPac-Seq

ChIP-ac.

Cells were fixed with 10 µM methylene blue (Sigma) on ice and exposed to white light from a 100 W incandescent bulb at a distance of 3 cm for 3'. Crosslinking was confirmed by SDS-chloroform-isoamyl alcohol (SDS-CIA) of extracted chromatin prior to dialyzation against acetylation buffer (50 mM $NaHCO_3$, pH 8.0, 150 mM NaCl, 0.01% SDS). Chromatin was acetylated with acetic anhydride (20 mM final) in an ice-bath for 1 h while maintaining the pH at 8.0-8.2 by addition of NaOH. Acetylated chromatin was immunoprecipitated with an H3K14ac-specific antibody (Active Motif) or an H3 C-terminal (H3CT) antibody (Abcam) as previously described (Kim et al. 2015).

Library Preparation.

DNA libraries were constructed from ~30 ng of DNA obtained from each ChIP sample. ChIP DNA and input DNA were first band-isolated on a 2% agarose gel to obtain fragments between 150 and 350 base pairs and DNA was extracted using the QIAquick gel extraction kit (Qiagen) and eluted in 35 µL elution buffer. For input, DNA was diluted 1:5 after gel extraction. The DNA was end-repaired and adapters were ligated to samples for 15 min at room temperature. Adapters in excess were eliminated by gel purification on a 2% agarose gel. A final size selection was performed using a 2% agarose gel to obtain a library with a median length of ~230 bp which is within the recommended size range for cluster generation on Illumina's flow cell. Following PCR, reactions were cleaned using magnetic beads and re-suspended in a small volume of 10 mM Tris 8.5 (Qiagen EB). Libraries were visualized by Agilent Bioanalyzer and quantified using the KAPA Biosystems Library Quantification Kit, according to manufacturer's instructions. Sequencing with 1×50 SE reads was carried out on the Illumina flow cell of HiSeq 2000 as recommended by manufacturer (Illumina). Image analysis and base calling were carried out using RTA 1.13.48.0. Final file formatting, de-multiplexing and fastq generation were carried out using CASAVA v 1.8.2.

ChIPac-Seq Quality Assessment.

All ChIP and input sample qualities were monitored using established strategies (Landt et al. 2012; Bailey et al. 2013). The quality matrices for raw sequence reads were obtained by FASTQc (http://www.bioinformatics.bbsrc.ac.uk). The reads were processed by Trim Galore (http://www.bioinformatics.babraham.ac.uk). The low sequencing quality nucleotides at the 3' end were removed, and only the reads longer than 75 bp were retained. Adaptor sequences were also removed using function cutadapt. The processed sequences were mapped to the mm9 genome using Burrows-Wheeler Aligner (Li et al. 2008). Further reads aligning to mitochondrial DNA, repetitive elements or unassigned sequences were discarded. This resulted in uniquely aligned reads from approximately 13 to 34 million reads covering the mouse genome. Applicants used deeptools (https://pypi.python.org/pypi/deepTools) to estimate distribution of ChIP signal from background noise (function-bamFingerprint) and cross-sample normalization was achieved by scaling read depths to reads using function-bamCoverage. Since the DNA polymerases, used in PCR-amplifications during the library preparation, prefer GC-rich regions and may influence the outcome of the sequencing, the GCbias was estimated in each sample but no correction was applied (data not shown). To validate the ChIPac-Seq approach, a function-bamFingerprint was used on uniquely mapped reads, which randomly samples genome regions into a specified length (10 bp bin) and counts the reads from indexed bam files that overlap with those regions. These counts were then sorted according to their rank (the bin with the highest number of reads will have the highest rank) and the cumulative sum of read counts was plotted (Diaz et al. 2012). In all cases it is possible to differentiate read density of the ChIPac sample from the input sample.

Establishment of Reference Loci.

To calculate the differential tag density of each ChIPac sample, Applicants used a binning approach (Diaz et al. 2012). Applicants normalized tag density to 1× coverage to compensate for the varying sequencing depth and mapping efficiency of each sample. Such normalization is achieved by first determining the actual read coverage (number of mapped reads*fragment length/effective genome size) and then using this number to determine the scaling factor that would yield a 1× coverage, as previously detailed (Kramer et al. 2011). Since each short read represents the end of an immunoprecipitated nucleosome, every read was extended 3' to a total of 200 bp to cover an entire nucleosome prior to analysis. Signal density was calculated in sliding 1 kb windows and normalized aligned reads were considered to be within a window of the midpoint of its estimated fragment. Mid-points in each window were counted, and empirical distributions of window counts were created. Genomic bins containing statistically significant regions were identified by comparison to a Poisson background model assuming that background reads are spread randomly throughout the genome (Kim et al. 2013c).

Identification and Analyses of H3NT-Cleaved Genes.

Applicants extracted the tag density in a ±4 kb window surrounding the TSSs using the program ngs.plot (https://github.com) (Shen et al. 2014) and Seqminer (Ye et al. 2011). To identify H3NT-cleaved regions in specific genomic loci, relative signal densities were defined as read counts per bin fixed divided by the total number of aligned reads in all bins. The loci which displayed differential read count in 1 kb windows between control shRNA H3K14ac over H3CT, as well as MMP-9 shRNA samples (H3K14ac and H3CT) with log 2 ratio >0.26 or absolute difference+1.2 were identified and annotated with closet gene (2000 bp in either direction). For visualization, alignment files were transformed into read coverage files (20 bp bin and smooth length 50 bp) to generate bigWig files. Seqmonk and IGV were used at different steps to visualize the data. Unless specified, command line option was used to extract data matrix and figures were generated in R (http://www.r-project.org). K-means clustering of tag densities+/−4 kb of TSSs was determined in R (http://www.r-project.org). Table 2 lists the H3NT-cleaved genes identified within each cluster. To study the functional significance of all H3NT-cleaved genes as well as the independent P, CR and P+CR clusters, Applicants quarried the Wikipathway database (Pico et al. 2008). A ranked p-value was computed from the fisher exact test based on the bionomical distribution and independence for probability of any gene belonging to any enriched set. As shown in FIG. 13E, all three clusters as well as P and CR clusters (but not P+CR, p>0.9) individually displayed a significant enrichment in RANKL and associated osteoclastogenic pathways (p<0.0001).

PCR qPCR was performed using PerfeCta® SYBR Green FastMix (Quanta BIOSCIENCES) and an iCycler IQ5 (Bio-Rad). Primers are: Nfatc1 (P: 5'-GAAGTGGTAGC-CCACGTGAT (SEQ ID NO: 1), 5'-TCTTGGCACCA-CATAAACCA (SEQ ID NO: 2); CR: 5'-GGGTCAGTGTGACCGAAGAT (SEQ ID NO: 3), 5'-GGAAGTCAGAAGTGGGTGGA (SEQ ID NO: 4); mRNA: 5'-CTCGAAAGACAGCACTGGAGCAT (SEQ ID NO: 5), 5'-CGGCTGCCTTCCGTCTCATAG) (SEQ ID NO: 6), Lif(P: 5'-CTCTGGCTGTCCTGGAACTC (SEQ ID NO: 7), 5'-CCAGGACCAGGTGAAACACT (SEQ ID NO: 8); CR: 5'-ATCTTGTGGCTTTGCCAACT (SEQ ID NO: 9), 5'-AGTCCTTGCCTGTCTTTCCA (SEQ ID NO: 10); mRNA: 5'-AGAAGGTCCTGAACCCCACT (SEQ ID NO: 11), 5'-AGAAGGTCCTGAACCCCACT-3' (SEQ ID NO: 12)) and Xpr1 (P: 5'-AGGACCTTCGGAAGAGCAGT (SEQ ID NO: 13), 5'-CAGCAAGCAGCTCATAACCA (SEQ ID NO: 14); CR: 5'-GGTGGGTTCCACT-GAAAGAA (SEQ ID NO: 15), 5'-GGTTCCTCTGAC-CAAAAGCA (SEQ ID NO: 16); mRNA: 5'-AGGAGCGT-GTCCAACATAGG (SEQ ID NO: 17), 5'-CCACGAGATGTTTCCAGGAT (SEQ ID NO: 18)). Specificity of amplification was determined by melting curve analysis and all samples were run in triplicate with results averaged.

Cell transduction, inhibition, chromatin extraction, Western blot analysis, antibodies, chromatography and PCR primers are detailed herein.

Cell Culture

Primary mouse OCP cells were derived, maintained and differentiated as previously described (An et al. 2014). Briefly, bone marrow (BM) cells were harvested by flushing femurs and tibias from 6- to 8-week-old C57BL/6 mice. Cells were cultured in a-minimum essential medium (α-MEM) supplemented with M-CSF (5 ng/ml) and 10% FBS for 16 hours. Non-adherent cells were harvested and cultured with M-CSF (30 ng/ml) for three days. Floating cells were removed. Adherent cells were used to generate osteoclasts. Adherent cells were cultured in the presence of M-CSF (30 ng/ml) and RANKL (50 ng/ml). On day 3, the cells were fixed and stained for tartrate-resistant acid phosphatase (TRAP) using a TRAP kit (Sigma).

Recombinant Proteins and H3 Cleavage Assays

His-tagged proteins were generated in Rosetta 2 (DE3) pLysS E. coli (Novagen) and purified as previously described (Kim et al. 2008). Recombinant and native histone octamers and nucleosome arrays were prepared as previously described (Kim et al. 2012). Cell extracts or recombinant proteins were incubated with histone octamer (1 µg) or nucleosomes (2 µg)+/−protease inhibitors and H3NT cleavage was determined by Western blot analysis. H3 peptides (aa10-35) were synthesized (EZBiolab) and incubated with rMMP-9 at increasing concentrations. Peptide hydrolysis was measured using a Plate Chameleon spectrofluorometer (Hidex) and kinetic parameters were determined by Michaelis-Menten analysis.

ChIPac-Seq

Cells were fixed with methylene blue (Sigma). Crosslinking was confirmed by SDS-chloroform-isoamyl alcohol (SDS-CIA) of extracted chromatin prior to acetylation with acetic anhydride. Acetylated chromatin was immunoprecipitated with an H3K14ac-specific antibody (Active Motif) or an H3 C-terminal (H3CT) antibody (Abcam). Libraries were constructed, sequenced and aligned to the mm9 reference genome (Li et al. 2008). Each read was extended in the sequencing orientation to a total of 200 bases to infer nucleosome coverage at each genomic position. Signal density was calculated in sliding 1 kb windows and aligned reads were considered to be within a window of the midpoint of its estimated fragment. Mid-points in each window were counted and empirical distributions of window counts were created. Genomic bins containing statistically significant regions were identified based on background distribution of randomized reads specific for each sample (Kim et al. 2013b). The ngs.plot was used to calculate the average coverage of TSSs and composite plots were generated by averaging reads in 200 bp windows (Shen et al. 2014). Peaks were annotated with non-overlapping genes from Ensembl. K-means clustering of tag densities+/−4 kb of TSSs was determined in R (http://www.r-project.org).

RNA-Seq

Libraries were generated from total RNA for sequencing. High quality reads were aligned to mm9 using TopHat in conjunction with gene model from Ensembl release 61 (Kim et al. 2013b). Data was quantitated by counting number of RPKM (Mortazavi et al. 2008). The values were adjusted globally by matching count distributions at the 15th percentile and then adjusting counts to a uniform distribution between samples. Differential expression was estimated by selecting transcripts that displayed significant changes (p<0.05) after Benjamini and Hochberg correction using null model constructed from 1% of transcripts showing the closet average level of observation to estimate experimental noise. The gene list was ranked using fold change criteria. GSEA and leading edge analysis was performed on the ranked list using gene sets from the C2 collection of the GSEA Molecular Signatures Database v3.0 and several gene sets associated with bone remodeling.

Treating a Subject with Abnormal Bone Mineral Density

The levels or function of MMP-9 can be modulated to treat a subject in need thereof. A subject in need of MMP-9 modulation includes a patient with low bone mineral density (BMD) or high BMD, and/or a subject with a bone related disease or condition selected from osteoporosis, bone cancer, cancer that has metastasized to the bone, cancer-induced osteolysis, sepsis, rheumatoid arthritis, periodontitis, osteopetrosis, pycondysostosis, osteopoikilosis, meloreostosis, sclerosteosis, van Buchem's disease, LRP5 high bone mass, LRP4 high bone mass, craniometaphyseal dysplasia, Camurati-Engelmann disease, Ghosal syndrome, bone cancer, cancer metastasized to the bone, fluorosis, renal osteodystrophy, acromegaly, hepatitis C-associated osteosclerosis, myelofibrosis, mastocytosis, osseous tuberous sclerosis, Paget's disease, and SAPHO syndrome. Patients with the above-listed diseases or conditions require either activation or suppression of osteoclastogenesis. For example, in a subject with low BMD, it is desirable to inhibit osteoclastogenesis to prevent loss of bone tissue. In a subject with high BMD, it is desirable to activate osteoclastogenesis to promote bone resorbtion.

Measurement of BMD is well known in the art. A common BMD test is a central dual-energy x-ray absorptiometry, or central DXA test. Normal BMD values vary based on age, gender, and other environmental factors but the World Health Organization generally defines normal as within one standard deviation (SD) of the young adult mean. Low bone mass is indicated by BMD values between 1 and 2.5 SD below the young adult mean. Osteoporosis is indicated by BMD more than 2.5 SD below the young adult mean. Success of treatment can be measured by restoring the subject's BMD to normal values or improving the subject's BMD closer to normal values.

To suppress osteoclastogenesis, an effective amount of an agent is administered to a subject to deplete or inhibit the function of MMP-9. MMP-9 can be directly depleted and/or inhibited by administration of an effective amount of an MMP-9 inhibitor, knockdown with interfering RNA directed to MMP-9 RNA and/or knockdown with shRNA delivered by contacting the cell, tissue, or subject with an effective amount of the shRNA, transfecting the cell, tissue, or subject with a polynucleotide expression vector that encodes the shRNA, or administering an effective amount of cells expressing the shRNA such as mesenchymal stem cells. MMP-9 function may also be inhibited by treatment with a broadly reactive metalloprotease inhibitor or by inhibition of enzymes that acetylate MMP-9's target cleavage site such as CBP/p300. Once MMP-9 function is attenuated, the osteoclastogenesis pathway in the cell, tissue, or subject will not be activated.

To activate osteoclastogenesis, MMP-9 function is activated and/or its expression levels are increased in a cell, tissue, or subject. MMP-9 function specific to osteoclastogenesis can be increased by promoting additional import of MMP-9 to the nucleus by adding nuclear localization signals to the enzyme. MMP-9 activity in the nucleus may also be increased by increasing the levels of acetylation at the MMP-9 target site and/or by over-expression of MMP-9. Subjects with abnormally high bone mineral density can be treated by administration of an effective amount of nuclear MMP-9 and/or administration of an effective amount of genetically engineered stem cells or osteoclast precursor cells that ectopically express MMP-9. Increased MMP-9 activity will then stimulate osteoclastogenesis which results in bone resorbtion.

Accession Numbers

Sequencing data sets were deposited at NCBI GEO (GSE72846 and GSE72957).

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The disclosures illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims. Thus, it should be understood that although the present disclosure has been specifically disclosed by preferred embodiments and optional features, modification and variation of the disclosures embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein. Other embodiments are within the following claims. In addition, where features or aspects of the disclosure are described in terms of Markush groups, those skilled in the art will recognize that the disclosure is also thereby described in terms of any individual member or subgroup of members of the Markush group.

SEQ ID NO. 22

MATRIX METALLOPROTEINASE-9 PREPROPROTEIN [*HOMO SAPIENS*]

NCBI Reference Sequence: NP_004985.2

LOCUS NP_004985 707 aa linear PRI 15 Mar. 2015

DEFINITION matrix metalloproteinase-9 preproprotein [*Homo sapiens*].

ACCESSION NP_004985

VERSION NP_004985.2 GI:74272287

DBSOURCE REFSEQ: accession NM_004994.2

KEYWORDS RefSeq.

SOURCE *Homo sapiens* (human)

ORGANISM *Homo sapiens*

Eukaryota; Metazoa; Chordata; Craniata; Vertebrata; Euteleostomi;

Mammalia; Eutheria; Euarchontoglires; Primates; Haplorrhini;

Catarrhini; Hominidae; Homo.

FEATURES Location/Qualifiers source 1..707

/organism="*Homo sapiens*"

/db xref="taxon:96(6"

/chromosome="20"

/map="20q13.12"

Protene 1..707

/product="matrix metalloproteinase-9 preproprotein"

/EC_number="3.4.24.35"

/note="type V collagenase; matrix metalloproteinase 9 (gelatinase B, 92 kDa gelatinase, 92 kDa type IV collagenase); macrophage gelatinase; matrix metallopeptidase 9 (gelatinase B, 92 kDa gelatinase, 92 kDa type IV collagenase)"

sig_peptide 1..19

/inference="COORDINATES: ab initio prediction:SignalP:4.0"

/calculated_mol_wt=2106 proprotein 20..707

/product="matrix metalloproteinase-9 proprotein"

/calculated_mol wt=76371

Site 59..60
/site_type="cleavage"
/experiment="experimental evidence, no additional details recorded"
/note="Cleavage, by MMP3; propagated from UniProtKB/Swiss-Prot (P14780.3)"
Region 97..104
/region_name="Cysteine switch. {ECO:0000250}"
/experiment="experimental evidence, no additional details recorded"
/note="propagated from UniProtKB/Swiss-Prot (P14780.3)"
Site 106..107
/site_type="cleavage"
/experiment="experimental evidence, no additional details recorded"
/note="Cleavage, by MMP3; propagated from UniProtKB/Swiss-Prot (P14780.3)"
mat_peptide 107..707
/product="82 kDa matrix metalloproteinase-9"
/experiment="experimental evidence, no additional details recorded"
/note="propagated from UniProtKB/Swiss-Prot (P14780.3)"
/calculated mol wt=66610
Region 115..444
/region_name="Peptidase_M10"
/note="Matrixin; pfam00413"
/db_xref="CDD:249842"
Region 115..444
/region_name="ZnMc_MMP"
/note="Zinc-dependent metalloprotease, matrix metalloproteinase (MMP) sub-family. MMPs are responsible for a great deal of pericellular proteolysis of extracellular matrix and cell surface molecules, playing crucial roles in morphogenesis, cell fate . . . ; cd04278"
/db_xref="CDD:239805"
Site order(167,179,186.. 192,201,401..402,411,421..423)
/site_type="other"
/note="TIMP-binding surface"
/db_xref="CDD:239805"
Region 224..271
/region_name="FN2"
/note="Fibronectin Type II domain: FN2 is one of three types of internal repeats which combine to form larger domains within fibmnectin. Fibronectin, a plasma protein that binds cell surfaces and various compounds including collagen, fibrin, heparin, DNA, and . . . ; cd00062"
/db_xref="CDD:280'19"
Site order(234,236,241,255,262,268,270)
/site_type="other"
/note="putative gelatin-binding site"
/db_xref="CDD:2330 19"
Region 282..329
/region_name="FN2"
/note="Fibronectin Type II domain: FN2 is one of three types of internal repeats which combine to form larger domains within fibronectin. Fibronectin, a plasma protein that binds cell surfaces and various compounds including collagen, fibrin, heparin, DNA, and . . . ; cd00062"
/db_xref="CDD:2380)19"
Site order(292,294,299,313,320,326,328)
/site_type="other"
/note="putative gelatin-binding site"
/db xref="CDD:2.38019"

Region 341..388
/region_name="FN2"
/note="Fibronectin Type II domain: FN2 is one of three types of internal repeats which combine to form larger domains within fibronectin. Fibronectin, a plasma protein that binds cell surfaces and various compounds including collagen, fibrin, heparin, DNA, and . . . ; cd00062"
/db xref="CDD:23801 9"
Site order(351,353,358,372,379,385,387)
/site_type="other"
/note="putative gelatin-binding site"
/db xref="CDD:238019"
Site order(401..402,405,411)
/site_type="active"
/db xref="CDD:239805"
Region 472..506
/region_name="PT"
/note="PT repeat; pfam04886"
/db xref="CDD:1 13652"
Region 514..704
/region_name="HX"
/note="Hemopexin-like repeats.; Hemopexin is a heme-binding protein that transports heme to the liver. Hemopexin-like repeats occur in vitronectin and some matrix metalloproteinases family (matrixins). The HX repeats of some matrixins bind tissue inhibitor of . . . ; cd00094"
/db_xref="CDD:238046"
Region 518..563
/region_name="Hemopexin 1"
/experiment="experimental evidence, no additional details recorded"
/note="propagated from UniProtKB/Swiss-Prot (P14780.3)"
Site order(522,524,568,570,614,616,662,664)
/site_type="metal-binding"
/note="Metal binding sites [ion binding]"
/db xref="CDD:2380,46"
Region 564..608
/region_name="Hemopexin 2"
/experiment="experimental evidence, no additional details recorded"
/note="propagated from UniProtKB/Swiss-Prot (P14780.3)"
Region 610..657
/region_name="Hemopexin 3"
/experiment="experimental evidence, no additional details recorded"
/note="propagated from UniProtKB/Swiss-Prot (P14780.3)"
Region 658..704
/region name="Hemopcxin 4"
/experiment="experimental evidence, no additional details recorded"
/note="propagated from UniProtKB/Swiss-Prot (P14780.3)"
CDS 1..707
/gene="MMP9"
/gene_synonym="CLG4B; GELB; MANDP2; MMP-9"
/coded_by="NM_004994.2:20..2143"
/db_xref="CCDS:CCDS13390.1"
/db_xref="GeneID:4318"
/db_xrcf="HGNC:HGNC7176"
/db_xref="MIM:120361"

ORIGIN (SEQ ID. NO: 22)

```
  1 mslwqplvlv llvlgccfaa prqrqstlvl fpgdlrtnlt drqlaeeyly rygytrvaem
 61 rgeskslgpa llllqkqlsl petgeldsat lkamrtprcg vpdlgrfqtf egdlkwhhhn
121 itywiqnyse dlpravidda farafalwsa vtpltftrvy srdadiviqf gvaehgdgyp
181 fdgkdgllah afppgpgiqg dahfdddelw slgkgvvvpt rfgnadgaac hfpfifegrs
241 ysacttdgrs dglpwcstta nydtddrfgf cpserlytqd gnadgkpcqf pfifqgqsys
301 acttdgrsdg yrwcattany drdklfgfcp tradstvmgg nsagelcvfp ftflgkeyst
361 ctsegrgdgr lwcattsnfd sdkkwgfcpd qgyslflvaa hefghalgld hssvpealmy
421 pmyrftegpp lhkddvngir hlygprpepe prppttttpq ptapptvcpt gpptvhpser
481 ptagptgpps agptgpptag pstattvpls pvddacnvni fdaiaeignq lylfkdgkyw
541 rfsegrgsrp qgpfliadkw palprkldsv feerlskklf ffsgrqvwvy tgasvlgprr
601 ldklglgadv aqvtgalrsg rgkmllfsgr rlwrfdvkaq mvdprsasev drmfpgvpld
661 thdvfqyrek ayfcqdrfyw rvssrselnq vdqvgyvtyd ilqcped.
```

REFERENCES

1. Allan J, Harborne N, Rau D C, Gould H. 1982. Participation of core histone "tails" in the stabilization of the chromatin solenoid. *The Journal of cell biology* 93: 285-297.
2. Allis C D, Bowen J K, Abraham G N, Glover C V, Gorovsky M A. 1980. Proteolytic processing of histone H3 in chromatin: a physiologically regulated event in Tetrahymena micronuclei. *Cell* 20: 55-64.
3. An D, Kim K, Lu W. 2014. Defective entry into mitosis 1 (Dima) negatively regulates osteoclastogenesis by inhibiting the expression of nuclear factor of activated T-cells, cytoplasmic, calcineurin-dependent 1 (NFATc1). *J Biol Chem* 289: 24366-24373.
4. Andresen K, Jimenez-Useche I, Howell S C, Yuan C, Qiu X. 2013. Solution scattering and FRET studies on nucleosomes reveal DNA unwrapping effects of H3 and H4 tail removal. *PLoS One* 8: e78587.
5. Asp P, Blum R, Vethantham V, Parisi F, Micsinai M, Cheng J, Bowman C, Kluger Y, Dynlacht B D. 2011. Genome-wide remodeling of the epigenetic landscape during myogenic differentiation. *Proc Natl Acad Sci U.S.A* 108: E149-158.
6. Azad G K, Tomar R S. 2014. Proteolytic clipping of histone tails: the emerging role of histone proteases in regulation of various biological processes. *Molecular biology reports* 41: 2717-2730.
7. Bannister A J, Zegerman P, Partridge J F, Miska E A, Thomas J O, Allshire R C, Kouzarides T. 2001. Selective recognition of methylated lysine 9 on histone H3 by the HP1 chromo domain. *Nature* 410: 120-124.
8. Black J C, Van Rechem C, Whetstine J R. 2012. Histone lysine methylation dynamics: establishment, regulation, and biological impact. *Mol Cell* 48: 491-507.
9. Bortvin A, Winston F. 1996. Evidence that Spt6p controls chromatin structure by a direct interaction with histones. *Science* 272: 1473-1476.
10. Bozec A, Bakiri L, Hoebertz A, Eferl R, Schilling A F, Komnenovic V, Scheuch H, Priemel M, Stewart C L, Amling M et al. 2008. Osteoclast size is controlled by Fra-2 through LIF/LIF-receptor signalling and hypoxia. *Nature* 454: 221-225.
11. Cackowski F C, Anderson J L, Patrene K D, Choksi R J, Shapiro S D, Windle J J, Blair H C, Roodman G D. 2010. Osteoclasts are important for bone angiogenesis. *Blood* 115: 140-149.
12. Colnot C, Thompson Z, Miclau T, Werb Z, Helms J A. 2003. Altered fracture repair in the absence of MMP9. *Development* 130: 4123-4133.
13. Dhaenens M, Glibert P, Meert P, Vossaert L, Deforce D. 2015. Histone proteolysis: a proposal for categorization into 'clipping' and 'degradation'. *BioEssays: news and reviews in molecular, cellular and developmental biology* 37: 70-79.
14. Duarte L F, Young A R, Wang Z, Wu H A, Panda T, Kou Y, Kapoor A, Hasson D, Mills N R, Ma'ayan A et al. 2014. Histone H3.3 and its proteolytically processed form drive a cellular senescence programme. *Nature communications* 5: 5210.
15. Duncan E M, Muratore-Schroeder T L, Cook R G, Garcia B A, Shabanowitz J, Hunt D F, Allis C D. 2008. Cathepsin L proteolytically processes histone H3 during mouse embryonic stem cell differentiation. *Cell* 135: 284-294.
16. Franco G C, Kajiya M, Nakanishi T, Ohta K, Rosalen P L, Groppo F C, Ernst C W, Boyesen J L, Bartlett J D, Stashenko P et al. 2011. Inhibition of matrix metalloproteinase-9 activity by doxycycline ameliorates RANK ligand-induced osteoclast differentiation in vitro and in vivo. *Experimental cell research* 317: 1454-1464.
17. Henry R A, Kuo Y M, Andrews A J. 2013. Differences in specificity and selectivity between CBP and p300 acetylation of histone H3 and H3/H4. *Biochemistry* 52: 5746-5759.
18. Khalkhali-Ellis Z, Goossens W, Margaryan N V, Hendrix M J. 2014. Cleavage of Histone 3 by Cathepsin D in the involuting mammary gland. *PLoS One* 9: e103230.
19. Kim K, Choi J, Heo K, Kim H, Levens D, Kohno K, Johnson E M, Brock H W, An W. 2008. Isolation and characterization of a novel H1.2 complex that acts as a repressor of p53-mediated transcription. *J Biol Chem* 283: 9113-9126.
20. Kim K, Heo K, Choi J, Jackson S, Kim H, Xiong Y, An W. 2012. Vpr-binding protein antagonizes p53-mediated transcription via direct interaction with H3 tail. *Mol Cell Biol* 32: 783-796.

21. Kim K, Kim J M, Kim J S, Choi J, Lee Y S, Neamati N, Song J S, Heo K, An W. 2013a. VprBP has intrinsic kinase activity targeting histone H2A and represses gene transcription. *Mol Cell* 52: 459-467.
22. Kim K, Punj V, Choi J, Heo K, Kim J M, Laird P W, An W. 2013b. Gene dysregulation by histone variant H2A.Z in bladder cancer. *Epigenetics & chromatin* 6: 34.
23. Lalwani R, Maiti S, Mukherji S. 1990. Visible light induced DNA-protein crosslinking in DNA-histone complex and sarcoma-180 chromatin in the presence of methylene blue. Journal of photochemistry and photobiology B, *Biology* 7: 57-73.
24. Li H, Ruan J, Durbin R. 2008. Mapping short DNA sequencing reads and calling variants using mapping quality scores. *Genome research* 18: 1851-1858.
25. Luger K, Dechassa M L, Tremethick D J. 2012. New insights into nucleosome and chromatin structure: an ordered state or a disordered affair? *Nature reviews Molecular cell biology* 13: 436-447.
26. Mannello F, Medda V. 2012. Nuclear localization of matrix metalloproteinases. *Progress in histochemistry and cytochemistry* 47: 27-58.
27. Metz B, Kersten G F, Hoogerhout P, Brugghe H F, Timmermans H A, de Jong A, Meiring H, ten Hove J, Hennink W E, Crommelin D J et al. 2004. Identification of formaldehyde-induced modifications in proteins: reactions with model peptides. *J Biol Chem* 279: 6235-6243.
28. Mortazavi A, Williams B A, McCue K, Schaeffer L, Wold B. 2008. Mapping and quantifying mammalian transcriptomes by RNA-Seq. *Nat Methods* 5: 621-628.
29. Nagase H, Visse R, Murphy G. 2006. Structure and function of matrix metalloproteinases and TIMPs. *Cardiovascular research* 69: 562-573.
30. Nakayasu E S, Wu S, Sydor M A, Shukla A K, Weitz K K, Moore R J, Hixson K K, Kim J S, Petyuk V A, Monroe M E et al. 2014. A method to determine lysine acetylation stoichiometries. *International journal of proteomics* 2014: 730725.
31. Narlikar G J, Sundaramoorthy R, Owen-Hughes T. 2013. Mechanisms and functions of ATP-dependent chromatin-remodeling enzymes. *Cell* 154: 490-503.
32. Nurse N P, Jimenez-Useche I, Smith I T, Yuan C. 2013. Clipping of flexible tails of histones H3 and H4 affects the structure and dynamics of the nucleosome. *Biophysical journal* 104: 1081-1088.
33. Park-Min K H, Lim E, Lee M J, Park S H, Giannopoulou E, Yarilina A, van der Meulen M, Zhao B, Smithers N, Witherington J et al. 2014. Inhibition of osteoclastogenesis and inflammatory bone resorption by targeting BET proteins and epigenetic regulation. *Nature communications* 5: 5418.
34. Pauli A, van Bemmel J G, Oliveira R A, Itoh T, Shirahige K, van Steensel B, Nasmyth K. 2010. A direct role for cohesin in gene regulation and ecdysone response in *Drosophila* salivary glands. *Curr Biol* 20: 1787-1798.
35. Phillips D M, Johns E W. 1959. A study of the proteinase content and the chromatography of thymus histones. *The Biochemical journal* 72: 538-544.
36. Polak P, Karlic R, Koren A, Thurman R, Sandstrom R, Lawrence M S, Reynolds A, Rynes E, Vlahovicek K, Stamatoyannopoulos J A et al. 2015. Cell-of-origin chromatin organization shapes the mutational landscape of cancer. *Nature* 518: 360-364.
37. Roadmap Epigenomics C, Kundaje A, Meuleman W, Ernst J, Bilenky M, Yen A, Heravi-Moussavi A, Kherad-pour P, Zhang Z, Wang J et al. 2015. Integrative analysis of 111 reference human epigenomes. *Nature* 518: 317-330.
38. Santos-Rosa H, Kirmizis A, Nelson C, Bartke T, Saksouk N, Cote J, Kouzarides T. 2009. Histone H3 tail clipping regulates gene expression. *Nature structural & molecular biology* 16: 17-22.
39. Seto E, Yoshida M. 2014. Erasers of histone acetylation: the histone deacetylase enzymes. *Cold Spring Harbor perspectives in biology* 6: a018713.
40. Sharma P, Patntirapong S, Hann S, Hauschka P V. 2010. RANKL-RANK signaling regulates expression of xenotropic and polytropic virus receptor (XPR1) in osteoclasts. *Biochemical and biophysical research communications* 399: 129-132.
41. Shen L, Shao N, Liu X, Nestler E. 2014. ngs.plot: Quick mining and visualization of next-generation sequencing data by integrating genomic databases. *BMC genomics* 15: 284.
42. Shogren-Knaak M, Ishii H, Sun J M, Pazin M J, Davie J R, Peterson C L. 2006. Histone H4-K16 acetylation controls chromatin structure and protein interactions. *Science* 311: 844-847.
43. Shogren-Knaak M A, Peterson C L. 2004. Creating designer histones by native chemical ligation. *Methods in enzymology* 375: 62-76.
44. Song J, Tan H, Perry A J, Akutsu T, Webb G I, Whisstock J C, Pike R N. 2012. PROSPER: an integrated feature-based tool for predicting protease substrate cleavage sites. *PLoS One* 7: e50300.
45. Strahl B D, Allis C D. 2000. The language of covalent histone modifications. *Nature* 403: 41-45.
46. Takayanagi H, Kim S, Koga T, Nishina H, Isshiki M, Yoshida H, Saiura A, Isobe M, Yokochi T, Inoue J et al. 2002. Induction and activation of the transcription factor NFATc1 (NFAT2) integrate RANKL signaling in terminal differentiation of osteoclasts. *Developmental cell* 3: 889-901.
47. Tuite E M, Kelly J M. 1993. Photochemical interactions of methylene blue and analogues with DNA and other biological substrates. Journal of photochemistry and photobiology B, *Biology* 21: 103-124.
48. Vossaert L, Meert P, Scheerlinck E, Glibert P, Van Roy N, Heindryckx B, De Sutter P, Dhaenens M, Deforce D. 2014. Identification of histone H3 clipping activity in human embryonic stem cells. *Stem cell research* 13: 123-134.
49. Vu T H, Shipley J M, Bergers G, Berger J E, Helms J A, Hanahan D, Shapiro S D, Senior R M, Werb Z. 1998. MMP-9/gelatinase B is a key regulator of growth plate angiogenesis and apoptosis of hypertrophic chondrocytes. *Cell* 93: 411-422.
50. Xue Y, Vashisht A A, Tan Y, Su T, Wohlschlegel J A. 2014. PRB1 is required for clipping of the histone H3 N terminal tail in *Saccharomyces cerevisiae*. *PLoS One* 9: e90496.
51. Zentner G E, Henikoff S. 2013. Regulation of nucleosome dynamics by histone modifications. *Nature structural & molecular biology* 20: 259-266.
52. Bailey T, Krajewski P, Ladunga I, Lefebvre C, Li Q, Liu T, Madrigal P, Taslim C, Zhang J. 2013. Practical guidelines for the comprehensive analysis of ChIP-seq data. *PLoS computational biology* 9: e1003326.
53. DeLuca D S, Levin J Z, Sivachenko A, Fennell T, Nazaire M D, Williams C, Reich M, Winckler W, Getz G. 2012. RNA-SeQC: RNA-seq metrics for quality control and process optimization. *Bioinformatics* 28: 1530-1532.

54. Diaz A, Park K, Lim D A, Song J S. 2012. Normalization, bias correction, and peak calling for ChIP-seq. *Statistical applications in genetics and molecular biology* 11: Article 9.
55. Garcia-Alcalde F, Okonechnikov K, Carbonell J, Cruz L M, Gotz S, Tarazona S, Dopazo J, Meyer T F, Conesa A. 2012. Qualimap: evaluating next-generation sequencing alignment data. *Bioinformatics* 28: 2678-2679.
56. Graw S, Meier R, Minn K, Bloomer C, Godwin A K, Fridley B, Vlad A, Beyerlein P, Chien J. 2015. Robust gene expression and mutation analyses of RNA-sequencing of formalin-fixed diagnostic tumor samples. *Scientific reports* 5: 12335.
57. Kim D, Pertea G, Trapnell C, Pimentel H, Kelley R, Salzberg S L. 2013a. TopHat2: accurate alignment of transcriptomes in the presence of insertions, deletions and gene fusions. Genome biology 14: R36.
58. Kim J M, Kim K, Schmidt T, Punj V, Tucker H, Rice J C, Ulmer T S, An W. 2015. Cooperation between SMYD3 and PC4 drives a distinct transcriptional program in cancer cells. *Nucleic acids research* 43: 8868-8883.
59. Kim K, Choi J, Heo K, Kim H, Levens D, Kohno K, Johnson E M, Brock H W, An W. 2008. Isolation and characterization of a novel H1.2 complex that acts as a repressor of p53-mediated transcription. *J Biol Chem* 283: 9113-9126.
60. Kim K, Heo K, Choi J, Jackson S, Kim H, Xiong Y, An W. 2012. Vpr-binding protein antagonizes p53-mediated transcription via direct interaction with H3 tail. *Mol Cell Biol* 32: 783-796.
61. Kim K, Lee B, Kim J, Choi J, Kim J M, Xiong Y, Roeder R G, An W. 2013b. Linker Histone H1.2 cooperates with Cul4A and PAF1 to drive H4K31 ubiquitylation-mediated transactivation. *Cell reports* 5: 1690-1703.
62. Kim K, Punj V, Choi J, Heo K, Kim J M, Laird P W, An W. 2013c. Gene dysregulation by histone variant H2A.Z in bladder cancer. *Epigenetics & chromatin* 6: 34.
63. Kramer J M, Kochinke K, Oortveld M A, Marks H, Kramer D, de Jong E K, Asztalos Z, Westwood J T, Stunnenberg H G, Sokolowski M B et al. 2011. Epigenetic regulation of learning and memory by Drosophila EHMT/G9a. *PLoS biology* 9: e1000569.
64. Landt S G, Marinov G K, Kundaje A, Kheradpour P, Pauli F, Batzoglou S, Bernstein B E, Bickel P, Brown J B, Cayting P et al. 2012. ChIP-seq guidelines and practices of the ENCODE and modENCODE consortia. *Genome research* 22: 1813-1831.
65. Lassmann T, Hayashizaki Y, Daub C O. 2011. SAMStat: monitoring biases in next generation sequencing data. *Bioinformatics* 27: 130-131.
66. Li H, Ruan J, Durbin R. 2008. Mapping short DNA sequencing reads and calling variants using mapping quality scores. *Genome research* 18: 1851-1858.
67. Mortazavi A, Williams B A, McCue K, Schaeffer L, Wold B. 2008. Mapping and quantifying mammalian transcriptomes by RNA-Seq. *Nat Methods* 5: 621-628.
68. Pico A R, Kelder T, van Iersel M P, Hanspers K, Conklin B R, Evelo C. 2008. WikiPathways: pathway editing for the people. *PLoS biology* 6: el 84.
69. Ring A, Mineyev N, Zhu W, Park E, Lomas C, Punj V, Yu M, Barrak D, Forte V, Porras T et al. 2015. EpCAM based capture detects and recovers circulating tumor cells from all subtypes of breast cancer except claudin-low. *Oncotarget*.
70. Shen L, Shao N, Liu X, Nestler E. 2014. ngs.plot: Quick mining and visualization of next-generation sequencing data by integrating genomic databases. *BMC genomics* 15: 284.
71. Ye T, Krebs A R, Choukrallah M A, Keime C, Plewniak F, Davidson I, Tora L. 2011. seqMINER: an integrated ChIP-seq data interpretation platform. *Nucleic acids research* 39: e35.

TABLE 1

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Tspan10 | 5.83763E−08 | ENSMUSG00000039691 | tetraspanin 10 | −7.4485833 | −5.3956246 | 2.0529587 | −7.4485833 |
| Gm13057 | 3.0793E−06 | ENSMUSG00000078514 | predicted gene 13057 | −7.171078 | −5.5476274 | 1.6234506 | −7.171078 |
| Gm13040 | 7.74498E−05 | ENSMUSG00000070616 | predicted gene 13040 | −7.171078 | −5.5476274 | 1.6234506 | −7.171078 |
| Rhov | 3.82912E−06 | ENSMUSG00000034226 | ras homolog gene family, member V | −6.6498415 | −5.3956246 | 1.2542169 | −6.6498415 |
| Itgb3 | 0.000171214 | ENSMUSG00000020689 | integrin beta 3 | −6.5923559 | −1.0736963 | 5.5186596 | −6.5923559 |
| Matk | 0.000250093 | ENSMUSG00000004933 | megakaryocyte-associated tyrosine kinase | −6.4593418 | −2.3956244 | 4.0637174 | −6.4593418 |
| Ctsk | 0.000214337 | ENSMUSG00000028111 | cathepsin K | −6.446837 | 5.423756 | 11.870593 | −6.446837 |
| Cldn11 | 7.28667E−05 | ENSMUSG00000037625 | claudin 11 | −5.5788259 | −0.2256994 | 5.3531265 | −5.5788259 |
| Bai1 | 0.000475161 | ENSMUSG00000034730 | brain-specific angiogenesis inhibitor 1 | −5.4648093 | −5.5476274 | −0.0828181 | −5.4648093 |
| Htr1b | 6.37744E−05 | ENSMUSG00000049511 | 5-hydroxytryptamine (serotonin) receptor 1B | −5.4282835 | −2.8106618 | 2.6176217 | −5.4282835 |
| D430036J16Rik | 0.000806317 | ENSMUSG00000085832 | RIKEN cDNA D430036J16 gene | −5.2213831 | −2.8106618 | 2.4107213 | −5.2213831 |
| Lif | 0.00083463 | ENSMUSG00000034394 | leukemia inhibitory factor | −5.2032929 | −0.6407369 | 4.562556 | −5.2032929 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Gm1123 | 0.013656123 | ENSMUSG00000044860 | predicted gene 1123 | −5.1941621 | −5.3956246 | −0.2014625 | −5.1941621 |
| Gm10696 | 0.015074948 | ENSMUSG00000074424 | predicted gene 10696 | −5.1710781 | −5.5476274 | −0.3765493 | −5.1710781 |
| Mmp9 | 5.50763E−09 | ENSMUSG00000017737 | matrix metallopeptidase 9 | −5.1696789 | 1.9531038 | 7.1227827 | −5.1696789 |
| Gm15448 | 0.002977603 | ENSMUSG00000074419 | predicted gene 15448 | −5.1237725 | −3.8106618 | 1.3131107 | −5.1237725 |
| Mapk4 | 0.016108619 | ENSMUSG00000024558 | mitogen-activated protein kinase 4 | −5.1237724 | −5.5476274 | −0.423855 | −5.1237724 |
| Zscan4c | 0.017287914 | ENSMUSG00000054272 | zinc finger and SCAN domain containing 4C | −5.1092732 | −5.3956246 | −0.2863514 | −5.1092732 |
| Gm13119 | 0.000839543 | ENSMUSG00000070619 | predicted gene 13119 | −5.0748629 | −5.5476274 | −0.4727645 | −5.0748629 |
| Atp2b3 | 0.017654449 | ENSMUSG00000031376 | ATPase, Ca++ transporting, plasma membrane 3 | −5.0748629 | −5.5476274 | −0.4727645 | −5.0748629 |
| Prss46 | 0.005045636 | ENSMUSG00000049719 | protease, serine, 46 | −5.0497718 | −2.8106618 | 2.23911 | −5.0497718 |
| Ccr3 | 0.000166384 | ENSMUSG00000035448 | chemokine (C-C motif) receptor 3 | −5.0467314 | −2.0736964 | 2.973035 | −5.0467314 |
| Dgki | 0.000827937 | ENSMUSG00000038665 | diacylglycerol kinase, iota | −5.0345051 | −2.8106618 | 2.2238433 | −5.0345051 |
| Gm7971 | 0.01710386 | ENSMUSG00000079422 | predicted gene 7971 | −5.0242368 | −5.5476274 | −0.5233907 | −5.0242368 |
| Gm16429 | 0.01720231 | ENSMUSG00000072823 | predicted gene 16429 | −5.0242368 | −5.5476274 | −0.5233907 | −5.0242368 |
| Opcml | 0.014594807 | ENSMUSG00000062257 | opioid binding protein/cell adhesion molecule-like | −5.0190754 | −4.3956246 | 0.62345076 | −5.0190754 |
| Zscan4d | 2.03004E−05 | ENSMUSG00000090714 | zinc finger and SCAN domain containing 4D | −5.0190753 | −5.3956246 | −0.3765493 | −5.0190753 |
| Mtus1 | 0.014655925 | ENSMUSG00000045636 | mitochondrial tumor suppressor 1 | −5.0190753 | −5.3956246 | −0.3765493 | −5.0190753 |
| Fam198b | 1.55975E−08 | ENSMUSG00000027955 | family with sequence similarity 198, member B | −5.003479 | 1.54689 | 6.550369 | −5.003479 |
| Chst1 | 0.015000206 | ENSMUSG00000027221 | carbohydrate (keratan sulfate Gal-6) sulfotransferase 1 | −4.9956165 | −4.3956246 | 0.59999186 | −4.9956165 |
| Calml4 | 0.001680683 | ENSMUSG00000032246 | calmodulin-like 4 | −4.977103 | −2.2256994 | 2.7514036 | −4.977103 |
| H1foo | 0.000716847 | ENSMUSG00000042279 | H1 histone family, member O, oocyte-specific | −4.9717696 | −5.3956246 | −0.423855 | −4.9717696 |
| Gm10424 | 0.014855926 | ENSMUSG00000072817 | predicted gene 10424 | −4.9717696 | −5.3956246 | −0.423855 | −4.9717696 |
| Ttll11 | 0.015697744 | ENSMUSG00000026885 | tubulin tyrosine ligase-like family, member 11 | −4.9717696 | −5.3956246 | −0.423855 | −4.9717696 |
| Ppef2 | 0.015779987 | ENSMUSG00000029410 | protein phosphatase, EF hand calcium-binding domain 2 | −4.9717696 | −5.3956246 | −0.423855 | −4.9717696 |
| D930048N14Rik | 0.015629802 | ENSMUSG00000052563 | RIKEN cDNA D930048N14 gene | −4.9717696 | −4.3956246 | 0.576145 | −4.9717696 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
| --- | --- | --- | --- | --- | --- | --- | --- |
| Slc4a3 | 0.01688572 | ENSMUSG00000006576 | solute carrier family 4 (anion exchanger), member 3 | -4.9717693 | -5.5476274 | -0.5758581 | -4.9717693 |
| BC061212 | 0.017009392 | ENSMUSG00000072822 | cDNA sequence BC061212 | -4.9717693 | -5.5476274 | -0.5758581 | -4.9717693 |
| Ccr1 | 1.08715E-10 | ENSMUSG00000025804 | chemokine (C-C motif) receptor 1 | -4.9647516 | 1.9081564 | 6.872908 | -4.9647516 |
| Rtkn2 | 9.62021E-10 | ENSMUSG00000037846 | rhotekin 2 | -4.9173215 | -5.5476274 | -0.6303059 | -4.9173215 |
| Plxna4 | 0.017766215 | ENSMUSG00000029765 | plexin A4 | -4.9173215 | -5.5476274 | -0.6303059 | -4.9173215 |
| Mpzl3 | 0.000349792 | ENSMUSG00000070305 | myelin protein zero-like 3 | -4.8696551 | -1.0736963 | 3.7959588 | -4.8696551 |
| C77080 | 4.56735E-08 | ENSMUSG00000050390 | expressed sequence C77080 | -4.8508598 | 2.1512702 | 7.00213 | -4.8508598 |
| Ano7 | 0.005485625 | ENSMUSG00000034107 | anoctamin 7 | -4.8349529 | -2.5882695 | 2.2466834 | -4.8349529 |
| Ckb | 3.7182E-09 | ENSMUSG00000001270 | creatine kinase, brain | -4.8318095 | 4.1141505 | 8.94596 | -4.8318095 |
| Sorbs2 | 0.005497429 | ENSMUSG00000031626 | sorbin and SH3 domain containing 2 | -4.8273795 | -2.5882695 | 2.23911 | -4.8273795 |
| Tdp0z5 | 0.026959086 | ENSMUSG00000074427 | TD and POZ domain containing 5 | -4.8018443 | -5.5476274 | -0.7457831 | -4.8018443 |
| Gm10697 | 0.02758078 | ENSMUSG00000074425 | predicted gene 10697 | -4.8018443 | -5.5476274 | -0.7457831 | -4.8018443 |
| Gm5286 | 0.028164925 | ENSMUSG00000090268 | predicted gene 5286 | -4.8018443 | -5.5476274 | -0.7457831 | -4.8018443 |
| Fam46c | 0.028858004 | ENSMUSG00000044468 | family with sequence similarity 46, member C | -4.8018443 | -5.5476274 | -0.7457831 | -4.8018443 |
| Gm6346 | 0.029553404 | ENSMUSG00000091252 | predicted gene 6346 | -4.8018443 | -5.5476274 | -0.7457831 | -4.8018443 |
| Cthrc1 | 0.030250954 | ENSMUSG00000054196 | collagen triple helix repeat containing 1 | -4.8018443 | -5.5476274 | -0.7457831 | -4.8018443 |
| Gm22 | 0.003586833 | ENSMUSG00000043903 | predicted gene 22 | -4.7791244 | -2.3956244 | 2.3835 | -4.7791244 |
| Adck3 | 4.30239E-06 | ENSMUSG00000026489 | aarF domain containing kinase 3 | -4.770136 | 1.1279377 | 5.8980737 | -4.770136 |
| Tnfsf12 | 0.000393042 | ENSMUSG00000090170 | tumor necrosis factor (ligand) superfamily, member 12 | -4.7429509 | -3.0736964 | 1.6692545 | -4.7429509 |
| Gpr176 | 0.001955719 | ENSMUSG00000040133 | G protein-coupled receptor 176 | -4.7408358 | -1.3956243 | 3.3452115 | -4.7408358 |
| Gm7978 | 0.02610885 | ENSMUSG00000072815 | predicted gene 7978 | -4.7404438 | -5.5476274 | -0.8071836 | -4.7404438 |
| Akr1c18 | 0.02618227 | ENSMUSG00000021214 | aldo-keto reductase family 1, member C18 | -4.7404438 | -5.5476274 | -0.8071836 | -4.7404438 |
| Gm15241 | 0.013268969 | ENSMUSG00000087505 | predicted gene 15241 | -4.7087353 | -4.3956246 | 0.31311068 | -4.7087353 |
| Eps8l2 | 0.018382147 | ENSMUSG00000025504 | EPS8-like 2 | -4.7087353 | -4.3956246 | 0.31311068 | -4.7087353 |
| Grb10 | 0.00447582 | ENSMUSG00000020176 | growth factor receptor bound protein 10 | -4.7087351 | -3.3956244 | 1.3131107 | -4.7087351 |
| Akap6 | 9.72033E-07 | ENSMUSG00000061603 | A kinase (PRKA) anchor protein 6 | -4.6948978 | 1.0638072 | 5.758705 | -4.6948978 |
| Sema7a | 0.001981256 | ENSMUSG00000038264 | sema domain, immunoglobulin domain (Ig), and GPI | -4.6631381 | -2.2256994 | 2.4374387 | -4.6631381 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| | | | membrane anchor, (semaphorin) 7A | | | | |
| Il34 | 0.023407776 | ENSMUSG00000031750 | interleukin 34 | −4.6498415 | −5.3956246 | −0.7457831 | −4.6498415 |
| BC050972 | 2.2733E−05 | ENSMUSG00000092131 | cDNA sequence BC050972 | −4.6498413 | −3.3956244 | 1.2542169 | −4.6498413 |
| Mras | 0.001684752 | ENSMUSG00000032470 | muscle and microspikes RAS | −4.6347343 | −1.3956243 | 3.23911 | −4.6347343 |
| Arhgap31 | 2.67619E−08 | ENSMUSG00000022799 | Rho GTPase activating protein 31 | −4.6253586 | 1.3048154 | 5.930174 | −4.6253586 |
| Tmcc3 | 0.012788476 | ENSMUSG00000020023 | transmembrane and coiled coil domains 3 | −4.619468 | −4.3956246 | 0.22384338 | −4.619468 |
| BC106179 | 0.02830728 | ENSMUSG00000045231 | cDNA sequence BC106179 | −4.6091994 | −5.5476274 | −0.938428 | −4.6091994 |
| Gabrg2 | 0.028566783 | ENSMUSG00000020436 | gamma-aminobutyric acid (GABA) A receptor, subunit gamma 2 | −4.6091994 | −5.5476274 | −0.938428 | −4.6091994 |
| Siglec15 | 1.04139E−13 | ENSMUSG00000091055 | sialic acid binding Ig-like lectin 15 | −4.6067727 | −1.3081615 | 3.2986112 | −4.6067727 |
| Cnn2 | 0.009360389 | ENSMUSG00000004665 | calponin 2 | −4.6062522 | −2.5882695 | 2.0179827 | −4.6062522 |
| Hist1h3f | 0.000460235 | ENSMUSG00000059309 | histone cluster 1, H3f | −4.588441 | −5.3956246 | −0.8071836 | −4.588441 |
| Msln | 0.014735865 | ENSMUSG00000063011 | mesothelin | −4.588441 | −4.3956246 | 0.19281639 | −4.588441 |
| B230206H07Rik | 0.015672518 | ENSMUSG00000086844 | RIKEN cDNA B230206H07 gene | −4.5567322 | −4.3956246 | 0.16110758 | −4.5567322 |
| Zscan4b | 0.028859515 | ENSMUSG00000091643 | zinc finger and SCAN domain containing 4B | −4.53881 | −5.5476274 | −1.0088174 | −4.53881 |
| Gm7682 | 0.029196529 | ENSMUSG00000074011 | predicted gene 7682 | −4.53881 | −5.5476274 | −1.0088174 | −4.53881 |
| Gm6468 | 0.029204158 | ENSMUSG00000072816 | predicted gene 6468 | −4.53881 | −5.5476274 | −1.0088174 | −4.53881 |
| Gpr64 | 0.034004346 | ENSMUSG00000031298 | G protein-coupled receptor 64 | −4.5243106 | −5.3956246 | −0.871314 | −4.5243106 |
| Cfhr2 | 0.002030646 | ENSMUSG00000033898 | complement factor H-related 2 | −4.5111351 | −1.4887338 | 3.0224013 | −4.5111351 |
| Myocd | 0.034741744 | ENSMUSG00000020542 | myocardin | −4.4648094 | −5.5476274 | −1.082818 | −4.4648094 |
| Gm7982 | 0.03488961 | ENSMUSG00000072814 | predicted gene 7982 | −4.4648094 | −5.5476274 | −1.082818 | −4.4648094 |
| Gm6509 | 0.035009217 | ENSMUSG00000074008 | predicted gene 6509 | −4.4648094 | −5.5476274 | −1.082818 | −4.4648094 |
| Gm6502 | 0.03512885 | ENSMUSG00000073498 | predicted gene 6502 | −4.4648094 | −5.5476274 | −1.082818 | −4.4648094 |
| Gm6351 | 0.035928585 | ENSMUSG00000072821 | predicted gene 6351 | −4.4648094 | −5.5476274 | −1.082818 | −4.4648094 |
| Slc18a1 | 1.86529E−06 | ENSMUSG00000036330 | solute carrier family 18 (vesicular monoamine), member 1 | −4.4627261 | 0.55857193 | 5.021298 | −4.4627261 |
| Rnf165 | 0.03428333 | ENSMUSG00000025427 | ring finger protein 165 | −4.4571966 | −5.3956246 | −0.938428 | −4.4571966 |
| Hist1h3b | 0.03678912 | ENSMUSG00000069267 | histone cluster 1, H3b | −4.4571966 | −5.3956246 | −0.938428 | −4.4571966 |
| Nos1ap | 9.11868E−06 | ENSMUSG00000038473 | nitric oxide synthase 1 (neuronal) adaptor protein | −4.3043447 | −5.5476274 | −1.2432827 | −4.3043447 |
| AA986860 | 2.02175E−11 | ENSMUSG00000042510 | expressed sequence AA986860 | −4.1523419 | −5.3956246 | −1.2432827 | −4.1523419 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Dmrtb1 | 4.996E−16 | ENSMUSG00000028610 | DMRT-like family B with proline-rich C-terminal, 1 | −4.1237723 | −5.5476274 | −1.4238551 | −4.1237723 |
| Apoa5 | 5.2547E−06 | ENSMUSG00000032079 | apolipoprotein A-V | −4.0648791 | −5.3956246 | −1.3307455 | −4.0648791 |
| Sphk1 | 0.000200649 | ENSMUSG00000061878 | sphingosine kinase 1 | −4.0097374 | −2.0736964 | 1.936041 | −4.0097374 |
| Acp5 | 0.001185123 | ENSMUSG00000001348 | acid phosphatase 5, tartrate resistant | −4.0066 | 6.829583 | 10.836183 | −4.0066 |
| Calcr | 1.58852E−06 | ENSMUSG00000023964 | calcitonin receptor | −3.9956162 | −2.3956244 | 1.5999918 | −3.9956162 |
| E130309D14Rik | 0.00390218 | ENSMUSG00000069814 | RIKEN cDNA E130309D14 gene | −3.9717695 | −5.3956246 | −1.4238551 | −3.9717695 |
| Gm3176 | 0.004518255 | ENSMUSG00000073509 | predicted gene 3176 | −3.9228601 | −4.3956246 | −0.4727645 | −3.9228601 |
| Kirrel2 | 0.000108978 | ENSMUSG00000036915 | kin of IRRE like 2 (*Drosophila*) | −3.9173215 | −5.5476274 | −1.6303059 | −3.9173215 |
| Gm4788 | 0.00511082 | ENSMUSG00000070594 | predicted gene 4788 | −3.9157354 | −2.5882695 | 1.3274659 | −3.9157354 |
| AI661453 | 6.6252E−10 | ENSMUSG00000034382 | expressed sequence AI661453 | −3.8722339 | −5.3956246 | −1.5233907 | −3.8722339 |
| Mrgpre | 1.63355E−07 | ENSMUSG00000048965 | MAS-related GPR, member E | −3.8722339 | −5.3956246 | −1.5233907 | −3.8722339 |
| Fam109a | 0.003682157 | ENSMUSG00000044134 | family with sequence similarity 109, member A | −3.8686511 | 3.3592632 | 7.2279143 | −3.8686511 |
| Nos1 | 0.002229427 | ENSMUSG00000029361 | nitric oxide synthase 1, neuronal | −3.8462386 | −3.3956244 | 0.45061424 | −3.8462386 |
| Ggt1 | 0.007170915 | ENSMUSG00000006345 | gamma-glutamyltransferase 1 | −3.8197665 | −4.3956246 | −0.5758581 | −3.8197665 |
| Pramef6 | 0.006200188 | ENSMUSG00000078512 | PRAME family member 6 | −3.8018444 | −5.5476274 | −1.745783 | −3.8018444 |
| Lilra6 | 0.001267628 | ENSMUSG00000030427 | leukocyte immunoglobulin-like receptor, subfamily A (with TM domain), member 6 | −3.7810859 | −2.5882695 | 1.1928164 | −3.7810859 |
| Gm10527 | 0.001781571 | ENSMUSG00000073525 | predicted gene 10527 | −3.7653187 | −5.3956246 | −1.6303059 | −3.7653187 |
| Gc | 0.010909459 | ENSMUSG00000035540 | group specific component | −3.7653187 | −5.3956246 | −1.6303059 | −3.7653187 |
| Cyp26b1 | 0.00299968 | ENSMUSG00000063415 | cytochrome P450, family 26, subfamily b, polypeptide 1 | −3.6763135 | −5.5476274 | −1.8713139 | −3.6763135 |
| Krba1 | 0.006188563 | ENSMUSG00000042810 | KRAB-A domain containing 1 | −3.6763135 | −5.5476274 | −1.8713139 | −3.6763135 |
| E230008N13Rik | 0.010172137 | ENSMUSG00000035539 | RIKEN cDNA E230008N13 gene | −3.6763135 | −5.5476274 | −1.8713139 | −3.6763135 |
| Clec4b1 | 5.68695E−05 | ENSMUSG00000030147 | C-type lectin domain family 4, member b1 | −3.6624414 | −1.1476969 | 2.5147445 | −3.6624414 |
| Src | 0.001090707 | ENSMUSG00000027646 | Rous sarcoma oncogene | −3.651526 | 4.082134 | 7.73366 | −3.651526 |
| Lrp2bp | 0.013656123 | ENSMUSG00000031637 | Lrp2 binding protein | −3.588441 | −4.3956246 | −0.8071836 | −3.588441 |
| Plekhg5 | 5.50763E−09 | ENSMUSG00000039713 | pleckstrin homology domain containing, family G (with | −3.5700286 | 0.18933822 | 3.7593668 | −3.5700286 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| | | | RhoGef domain) member 5 | | | | |
| 1700019D03Rik | 0.002977603 | ENSMUSG00000043629 | RIKEN cDNA 1700019D03 gene | -3.53881 | -5.5476274 | -2.0088174 | -3.53881 |
| Rnf43 | 0.017287914 | ENSMUSG00000034177 | ring finger protein 43 | -3.5243107 | -5.3956246 | -1.8713139 | -3.5243107 |
| Tmem220 | 0.017654449 | ENSMUSG00000050270 | transmembrane protein 220 | -3.5243107 | -5.3956246 | -1.8713139 | -3.5243107 |
| Ak1 | 0.000166384 | ENSMUSG00000026817 | adenylate kinase 1 | -3.4884204 | -0.186171 | 3.3022494 | -3.4884204 |
| Wipi1 | 0.005311127 | ENSMUSG00000041895 | WD repeat domain, phosphoinositide interacting 1 | -3.461769 | -1.4887338 | 1.9730352 | -3.461769 |
| Ndrg4 | 0.01720231 | ENSMUSG00000036564 | N-myc downstream regulated gene 4 | -3.4556536 | 3.251834 | 6.7074876 | -3.4556536 |
| Mmp14 | 0.01710386 | ENSMUSG00000000957 | matrix metallopeptidase 14 (membrane-inserted) | -3.4256262 | -1.9361928 | 1.4894334 | -3.4256262 |
| Gpr56 | 0.014594807 | ENSMUSG00000031785 | G protein-coupled receptor 56 | -3.3868072 | -5.3956246 | -2.0088174 | -3.3868072 |
| Pira5 | 0.014655925 | ENSMUSG00000074417 | paired-Ig-like receptor A5 | -3.3868071 | -2.0736964 | 1.3131107 | -3.3868071 |
| Gm13083 | 1.55975E-08 | ENSMUSG00000066688 | predicted gene 13083 | -3.3868069 | -5.5476274 | -2.1608205 | -3.3868069 |
| Smtnl2 | 0.001680683 | ENSMUSG00000045667 | smoothelin-like 2 | -3.3868069 | -5.5476274 | -2.1608205 | -3.3868069 |
| Hist1h1a | 0.014855926 | ENSMUSG00000049539 | histone cluster 1, H1a | -3.3868069 | -5.5476274 | -2.1608205 | -3.3868069 |
| Abcc2 | 0.015697744 | ENSMUSG00000025194 | ATP-binding cassette, sub-family C (CFTR/MRP), member 2 | -3.3868069 | -5.5476274 | -2.1608205 | -3.3868069 |
| Lctl | 0.01688572 | ENSMUSG00000032401 | lactase-like | -3.3352765 | 0.43726566 | 3.7725422 | -3.3352765 |
| Xpr1 | 0.017009392 | ENSMUSG00000026469 | xenotropic and polytropic retrovirus receptor 1 | -3.3232984 | 5.5578446 | 8.881143 | -3.3232984 |
| 41701 | 1.08715E-10 | ENSMUSG00000032656 | membrane-associated ring finger (C3HC4) 3 | -3.3128066 | -4.3956246 | -1.082818 | -3.3128066 |
| Adcy3 | 0.017891841 | ENSMUSG00000020654 | adenylate cyclase 3 | -3.2208839 | 0.94422567 | 4.1651096 | -3.2208839 |
| Cfhr1 | 0.000349792 | ENSMUSG00000057037 | complement factor H-related 1 | -3.2168819 | -5.5476274 | -2.3307455 | -3.2168819 |
| Tal2 | 0.005485625 | ENSMUSG00000028417 | T-cell acute lymphocytic leukemia 2 | -3.2168819 | -5.5476274 | -2.3307455 | -3.2168819 |
| Cyr61 | 0.005497429 | ENSMUSG00000028195 | cysteine rich protein 61 | -3.2168819 | -5.5476274 | -2.3307455 | -3.2168819 |
| Ltbp2 | 0.030250954 | ENSMUSG00000002020 | latent transforming growth factor beta binding protein 2 | -3.2023825 | -2.0736964 | 1.1286861 | -3.2023825 |
| Adamts14 | 0.026959086 | ENSMUSG00000059901 | a disintegrin-like and metallopeptidase (reprolysin type) with thrombospondin type 1 motif, 14 | -3.1987347 | -2.2256994 | 0.9730353 | -3.1987347 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Dnm1 | 0.02758078 | ENSMUSG00000026825 | dynamin 1 | −3.1965845 | −1.3081615 | 1.888423 | −3.1965845 |
| Pltp | 0.029553404 | ENSMUSG00000017754 | phospholipid transfer protein | −3.165339 | 2.4747405 | 5.6400795 | −3.165339 |
| Ggt6 | 1.80877E−07 | ENSMUSG00000040471 | gamma-glutamyltransferase 6 | −3.0648791 | −5.3956246 | −2.3307455 | −3.0648791 |
| Grin2d | 0.028858004 | ENSMUSG00000002771 | glutamate receptor, ionotropic, NMDA2D (epsilon 4) | −3.0648791 | −4.3956246 | −1.3307455 | −3.0648791 |
| Amz1 | 0.001955719 | ENSMUSG00000050022 | archaelysin family metallopeptidase 1 | −3.0345052 | 0.5112662 | 3.5457714 | −3.0345052 |
| Otx1 | 0.02610885 | ENSMUSG00000005917 | orthodenticle homolog 1 (*Drosophila*) | −3.0345052 | −2.8106618 | 0.22384338 | −3.0345052 |
| Lrrn4 | 0.001981256 | ENSMUSG00000043110 | leucine rich repeat neuronal 4 | −3.0242366 | −5.5476274 | −2.5233908 | −3.0242366 |
| Bpi | 0.00447582 | ENSMUSG00000052922 | bactericidal permeablility increasing protein | −3.0242366 | −5.5476274 | −2.5233908 | −3.0242366 |
| Kctd19 | 0.018382147 | ENSMUSG00000051648 | potassium channel tetramerisation domain containing 19 | −3.0242366 | −5.5476274 | −2.5233908 | −3.0242366 |
| Lipg | 0.005540829 | ENSMUSG00000053846 | lipase, endothelial | −3.0034782 | −2.8106618 | 0.19281639 | −3.0034782 |
| Acaa2 | 2.67619E−08 | ENSMUSG00000036880 | acetyl-Coenzyme A acyltransferase 2 (mitochondrial 3-oxoacyl-Coenzyme A thiolase) | −2.9547184 | 3.5845153 | 6.5392337 | −2.9547184 |
| 2410066E13Rik | 0.012788476 | ENSMUSG00000038065 | RIKEN cDNA 2410066E13 gene | −2.8722339 | −4.3956246 | −1.5233907 | −2.8722339 |
| Dlg2 | 0.009360389 | ENSMUSG00000052572 | discs, large homolog 2 (*Drosophila*) | −2.8722338 | −5.3956246 | −2.5233908 | −2.8722338 |
| 2810405K02Rik | 0.014735865 | ENSMUSG00000029059 | RIKEN cDNA 2810405K02 gene | −2.8722338 | −5.3956246 | −2.5233908 | −2.8722338 |
| Gm20442 | 0.02830728 | ENSMUSG00000092600 | predicted gene 20442 | −2.8722338 | −5.3956246 | −2.5233908 | −2.8722338 |
| Gja1 | 0.029196529 | ENSMUSG00000050953 | gap junction protein, alpha 1 | −2.8416021 | −0.3081615 | 2.5334406 | −2.8416021 |
| Hist1h4n | 0.029204158 | ENSMUSG00000069305 | histone cluster 1, H4n | −2.8018444 | −3.8106618 | −1.0088174 | −2.8018444 |
| Cd28 | 0.034004346 | ENSMUSG00000026012 | CD28 antigen | −2.8018444 | −5.5476274 | −2.745783 | −2.8018444 |
| Carns1 | 0.034741744 | ENSMUSG00000075289 | carnosine synthase 1 | −2.8018444 | −5.5476274 | −2.745783 | −2.8018444 |
| Wnt9a | 0.035009217 | ENSMUSG00000000126 | wingless-type MMTV integration site 9A | −2.8018444 | −5.5476274 | −2.745783 | −2.8018444 |
| Bcam | 0.035928585 | ENSMUSG00000002980 | basal cell adhesion molecule | −2.8018444 | −5.5476274 | −2.745783 | −2.8018444 |
| Emp1 | 0.042189736 | ENSMUSG00000030208 | epithelial membrane protein 1 | −2.7941766 | 3.9081564 | 6.702333 | −2.7941766 |
| Parp16 | 0.04001856 | ENSMUSG00000032392 | poly (ADP-ribose) polymerase family, member 16 | −2.7347302 | −0.9361927 | 1.7985375 | −2.7347302 |
| Clcn7 | 0.03428333 | ENSMUSG00000036636 | chloride channel 7 | −2.7234893 | 5.0524917 | 7.775981 | −2.7234893 |
| Eno2 | 0.03678912 | ENSMUSG00000004267 | enolase 2, gamma neuronal | −2.7158498 | 1.080109 | 3.7959588 | −2.7158498 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Cbr3 | 0.019589162 | ENSMUSG00000022947 | carbonyl reductase 3 | −2.6822627 | −0.9361927 | 1.74607 | −2.6822627 |
| Kdr | 9.9922E−09 | ENSMUSG00000062960 | kinase insert domain protein receptor | −2.6498416 | −5.3956246 | −2.745783 | −2.6498416 |
| Crip2 | 0.031184219 | ENSMUSG00000006356 | cysteine rich protein 2 | −2.6498416 | −5.3956246 | −2.745783 | −2.6498416 |
| Adcy5 | 0.032074198 | ENSMUSG00000022840 | adenylate cyclase 5 | −2.6498416 | −5.3956246 | −2.745783 | −2.6498416 |
| Tnfrsf25 | 0.037834987 | ENSMUSG00000024793 | tumor necrosis factor receptor superfamily, member 25 | −2.6498416 | −5.3956246 | −2.745783 | −2.6498416 |
| Nacc2 | 1.90741E−05 | ENSMUSG00000026932 | nucleus accumbens associated 2, BEN and BTB (POZ) domain containing | −2.6016853 | 0.64876974 | 3.250455 | −2.6016853 |
| Vwf | 0.007897177 | ENSMUSG00000001930 | Von Willebrand factor homolog | −2.6009319 | −3.0736964 | −0.4727645 | −2.6009319 |
| Npl | 0.03968443 | ENSMUSG00000042684 | N-acetylneuraminate pyruvate lyase | −2.5766314 | 0.6043756 | 3.181007 | −2.5766314 |
| Tmprss11bnl | 0.006505034 | ENSMUSG00000035861 | transmembrane protease, serine 11b N terminal like | −2.53881 | −5.5476274 | −3.0088174 | −2.53881 |
| Gfi1b | 0.006821152 | ENSMUSG00000026815 | growth factor independent 1B | −2.53881 | −5.5476274 | −3.0088174 | −2.53881 |
| Gm9222 | 0.024540374 | ENSMUSG00000091094 | predicted gene 9222 | −2.53881 | −5.5476274 | −3.0088174 | −2.53881 |
| Scn5a | 0.043510694 | ENSMUSG00000032511 | sodium channel, voltage-gated, type V, alpha | −2.53881 | −5.5476274 | −3.0088174 | −2.53881 |
| Celf6 | 0.04390951 | ENSMUSG00000032297 | CUGBP, Elav-like family member 6 | −2.53881 | −5.5476274 | −3.0088174 | −2.53881 |
| Gm6507 | 0.045192987 | ENSMUSG00000090013 | predicted gene 6507 | −2.53881 | −5.5476274 | −3.0088174 | −2.53881 |
| Tm7sf4 | 0.03066966 | ENSMUSG00000022303 | transmembrane 7 superfamily member 4 | −2.538506 | 4.3441563 | 6.8826623 | −2.538506 |
| Zbtb42 | 0.004560709 | ENSMUSG00000037638 | zinc finger and BTB domain containing 42 | −2.5282794 | −0.3512302 | 2.1770492 | −2.5282794 |
| Oprl1 | 0.04202406 | ENSMUSG00000027584 | opioid receptor-like 1 | −2.5243107 | −4.3956246 | −1.8713139 | −2.5243107 |
| Smpd1 | 0.040762037 | ENSMUSG00000037049 | sphingomyelin phosphodiesterase 1, acid lysosomal | −2.4983536 | 2.8851464 | 5.3835 | −2.4983536 |
| Copz2 | 0.04132218 | ENSMUSG00000018672 | coatomer protein complex, subunit zeta 2 | −2.4799163 | −3.8106618 | −1.3307455 | −2.4799163 |
| Rab13 | 0.014564358 | ENSMUSG00000027935 | RAB13, member RAS oncogene family | −2.4751628 | −1.1476969 | 1.3274659 | −2.4751628 |
| Ltbp3 | 1.11691E−09 | ENSMUSG00000024940 | latent transforming growth factor beta binding protein 3 | −2.4571964 | −3.3956244 | −0.938428 | −2.4571964 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Traf5 | 0.005175546 | ENSMUSG00000026637 | TNF receptor-associated factor 5 | −2.4035177 | 1.2908763 | 3.694394 | −2.4035177 |
| Rasgrp1 | 2.63666E−09 | ENSMUSG00000027347 | RAS guanyl releasing protein 1 | −2.3868072 | −5.3956246 | −3.0088174 | −2.3868072 |
| Cyp3a41b | 0.007969925 | ENSMUSG00000075552 | cytochrome P450, family 3, subfamily a, polypeptide 41B | −2.3868072 | −5.3956246 | −3.0088174 | −2.3868072 |
| H2-M10.4 | 0.008056933 | ENSMUSG00000048231 | histocompatibility 2, M region locus 10.4 | −2.3868072 | −5.3956246 | −3.0088174 | −2.3868072 |
| Brsk1 | 0.013945078 | ENSMUSG00000035390 | BR serine/threonine kinase 1 | −2.3868072 | −5.3956246 | −3.0088174 | −2.3868072 |
| Comp | 0.019483332 | ENSMUSG00000031849 | cartilage oligomeric matrix protein | −2.3868072 | −5.3956246 | −3.0088174 | −2.3868072 |
| Trp53i11 | 1.85071E−07 | ENSMUSG00000068735 | transformation related protein 53 inducible protein 11 | −2.3868071 | −3.0736964 | −0.6868893 | −2.3868071 |
| Gm17292 | 0.026323678 | ENSMUSG00000091500 | predicted gene, 17292 | −2.3868071 | −3.0736964 | −0.6868893 | −2.3868071 |
| Tmem92-ps | 0.012284395 | ENSMUSG00000075610 | transmembrane protein 92, pseudogene | −2.3603347 | −1.9361928 | 0.42414194 | −2.3603347 |
| Prnp | 0.028792284 | ENSMUSG00000079037 | prion protein | −2.3583783 | 0.9619277 | 3.320306 | −2.3583783 |
| Nos3 | 0.029377611 | ENSMUSG00000028978 | nitric oxide synthase 3, endothelial cell | −2.3279133 | −3.0736964 | −0.7457831 | −2.3279133 |
| Kifc3 | 0.02880698 | ENSMUSG00000031788 | kinesin family member C3 | −2.3243729 | 2.5987291 | 4.923102 | −2.3243729 |
| D930049A15Rik | 0.017146215 | ENSMUSG00000087535 | RIKEN cDNA D930049A15 gene | −2.3058869 | −1.9361928 | 0.3696941 | −2.3058869 |
| Dnajb13 | 0.04825035 | ENSMUSG00000030708 | DnaJ (Hsp40) related, subfamily B, member 13 | −2.2872711 | −3.8106618 | −1.5233907 | −2.2872711 |
| Ppargc1b | 0.047570087 | ENSMUSG00000033871 | peroxisome proliferative activated receptor, gamma, coactivator 1 beta | −2.2467025 | 2.9352925 | 5.181995 | −2.2467025 |
| Zan | 0.046040762 | ENSMUSG00000079173 | zonadhesin | −2.2348037 | −2.8106618 | −0.5758581 | −2.2348037 |
| Trpv4 | 2.0579E−08 | ENSMUSG00000014158 | transient receptor potential cation channel, subfamily V, member 4 | −2.2168817 | −5.5476274 | −3.3307457 | −2.2168817 |
| Gm5878 | 5.70138E−08 | ENSMUSG00000072952 | predicted gene 5878 | −2.2168817 | −5.5476274 | −3.3307457 | −2.2168817 |
| Morn3 | 0.01710776 | ENSMUSG00000029477 | MORN repeat containing 3 | −2.2168817 | −5.5476274 | −3.3307457 | −2.2168817 |
| Ccdc136 | 0.017162325 | ENSMUSG00000029769 | coiled-coil domain containing 136 | −2.2168817 | −5.5476274 | −3.3307457 | −2.2168817 |
| Pmel | 0.0373233 | ENSMUSG00000025359 | premelanosome protein | −2.2168817 | −5.5476274 | −3.3307457 | −2.2168817 |
| Exoc3l2 | 0.03821163 | ENSMUSG00000011263 | exocyst complex component 3-like 2 | −2.2168817 | −5.5476274 | −3.3307457 | −2.2168817 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Ctla4 | 0.04272519 | ENSMUSG00000026011 | cytotoxic T-lymphocyte-associated protein 4 | −2.2168817 | −5.5476274 | −3.3307457 | −2.2168817 |
| Eltd1 | 0.044563495 | ENSMUSG00000039167 | EGF, latrophilin seven transmembrane domain containing 1 | −2.2168817 | −5.5476274 | −3.3307457 | −2.2168817 |
| Agap1 | 0.006535044 | ENSMUSG00000055013 | ArfGAP with GTPase domain, ankyrin repeat and PH domain 1 | −2.2064753 | 2.5112662 | 4.7177415 | −2.2064753 |
| Gm16938 | 0.016329387 | ENSMUSG00000086325 | predicted gene, 16938 | −2.2023824 | −3.0736964 | −0.871314 | −2.2023824 |
| BC043934 | 0.016358571 | ENSMUSG00000056418 | cDNA sequence BC043934 | −2.1803559 | −2.8106618 | −0.6303059 | −2.1803559 |
| Atp6v1g1 | 0.03608559 | ENSMUSG00000039105 | ATPase, H+ transporting, lysosomal V1 subunit G1 | −2.1788064 | 5.2264276 | 7.405234 | −2.1788064 |
| Aebp1 | 1.28779E−07 | ENSMUSG00000020473 | AE binding protein 1 | −2.1523415 | −1.3956243 | 0.7567172 | −2.1523415 |
| Rgs10 | 2.5485E−06 | ENSMUSG00000030844 | regulator of G-protein signalling 10 | −2.1228371 | 3.7207193 | 5.8435564 | −2.1228371 |
| Hist1h2be | 0.011067117 | ENSMUSG00000047246 | histone cluster 1, H2be | −2.1207322 | −1.1476969 | 0.9730353 | −2.1207322 |
| Bcar1 | 0.005886043 | ENSMUSG00000031955 | breast cancer anti-estrogen resistance 1 | −2.1139732 | 0.6267435 | 2.7407167 | −2.1139732 |
| 2310035K24Rik | 0.016051397 | ENSMUSG00000068264 | RIKEN cDNA 2310035K24 gene | −2.0865737 | 1.9706978 | 4.0572715 | −2.0865737 |
| Spata9 | 8.47829E−07 | ENSMUSG00000021590 | spermatogenesis associated 9 | −2.0648791 | −4.3956246 | −2.3307455 | −2.0648791 |
| Cdh24 | 0.003821577 | ENSMUSG00000059674 | cadherin-like 24 | −2.0648791 | −4.3956246 | −2.3307455 | −2.0648791 |
| Ccr4 | 2.54713E−07 | ENSMUSG00000047898 | chemokine (C-C motif) receptor 4 | −2.0648789 | −5.3956246 | −3.3307457 | −2.0648789 |
| Trim15 | 5.39696E−05 | ENSMUSG00000050747 | tripartite motif-containing 15 | −2.0648789 | −5.3956246 | −3.3307457 | −2.0648789 |
| Cntn2 | 0.003975537 | ENSMUSG00000053024 | contactin 2 | −2.0648789 | −5.3956246 | −3.3307457 | −2.0648789 |
| Pacsin3 | 0.004444425 | ENSMUSG00000027257 | protein kinase C and casein kinase substrate in neurons 3 | −2.0648789 | −5.3956246 | −3.3307457 | −2.0648789 |
| Ptch2 | 0.004492317 | ENSMUSG00000028681 | patched homolog 2 | −2.0648789 | −5.3956246 | −3.3307457 | −2.0648789 |
| Gm3086 | 0.004751403 | ENSMUSG00000079076 | predicted gene 3086 | −2.0648789 | −5.3956246 | −3.3307457 | −2.0648789 |
| Gm13520 | 0.017877512 | ENSMUSG00000052403 | predicted gene 13520 | −2.0648789 | −5.3956246 | −3.3307457 | −2.0648789 |
| 4831440E17Rik | 0.047423657 | ENSMUSG00000091303 | RIKEN cDNA 4831440E17 gene | −2.0648789 | −5.3956246 | −3.3307457 | −2.0648789 |
| Olr1 | 0.02391179 | ENSMUSG00000030162 | oxidized low density lipoprotein (lectin-like) receptor 1 | −2.0648788 | −1.5882694 | 0.47660938 | −2.0648788 |
| Gpr68 | 0.014538036 | ENSMUSG00000047415 | G protein-coupled receptor 68 | −2.0587823 | 3.3013432 | 5.3601255 | −2.0587823 |
| Speg | 0.016736077 | ENSMUSG00000026207 | SPEG complex locus | −2.046822 | 2.2554274 | 4.3022494 | −2.046822 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Rab11fip5 | 0.002548879 | ENSMUSG00000051343 | RAB11 family interacting protein 5 (class I) | −1.9835787 | 1.7942002 | 3.7777789 | −1.9835787 |
| Kidins220 | 0.019567724 | ENSMUSG00000036333 | kinase D-interacting substrate 220 | −1.939535 | 6.379986 | 8.319521 | −1.939535 |
| Atp6v1e1 | 0.004245304 | ENSMUSG00000019210 | ATPase, H+ transporting, lysosomal V1 subunit E1 | −1.9293203 | 4.4885464 | 6.4178667 | −1.9293203 |
| Pvrl2 | 8.34206E−07 | ENSMUSG00000062300 | poliovirus receptor-related 2 | −1.9279968 | 0.4623566 | 2.3903534 | −1.9279968 |
| Tspan17 | 1.0474E−07 | ENSMUSG00000025875 | tetraspanin 17 | −1.9204887 | 0.5816556 | 2.5021443 | −1.9204887 |
| Gale | 0.019762464 | ENSMUSG00000028671 | galactose-4-epimerase, UDP | −1.8952713 | 1.7541227 | 3.649394 | −1.8952713 |
| Rcan1 | 0.01904115 | ENSMUSG00000022951 | regulator of calcineurin 1 | −1.874314 | 4.818695 | 6.693009 | −1.874314 |
| Gm11973 | 2.37392E−07 | ENSMUSG00000086839 | predicted gene 11973 | −1.8722338 | −0.8106618 | 1.061572 | −1.8722338 |
| Jag1 | 7.22295E−06 | ENSMUSG00000027276 | jagged 1 | −1.8641286 | 4.084156 | 5.9482846 | −1.8641286 |
| Pkn3 | 0.008641912 | ENSMUSG00000026785 | protein kinase N3 | −1.861691 | 3.7566605 | 5.6183515 | −1.861691 |
| Gpr137b-ps | 0.037627038 | ENSMUSG00000075118 | G protein-coupled receptor 137B, pseudogene | −1.8487921 | 5.7122464 | 7.5610385 | −1.8487921 |
| Gpr137b | 0.000425558 | ENSMUSG00000021306 | G protein-coupled receptor 137B | −1.8473807 | 6.3339963 | 8.181377 | −1.8473807 |
| Fastk | 0.025559984 | ENSMUSG00000028959 | Fas-activated serine/threonine kinase | −1.8316917 | 4.5629287 | 6.3946204 | −1.8316917 |
| Fhod1 | 0.021275658 | ENSMUSG00000014778 | formin homology 2 domain containing 1 | −1.83153 | 3.174231 | 5.005761 | −1.83153 |
| Klf10 | 0.025064955 | ENSMUSG00000037465 | Kruppel-like factor 10 | −1.8288834 | 2.3987916 | 4.227675 | −1.8288834 |
| Gm16170 | 0.025048712 | ENSMUSG00000086245 | predicted gene 16170 | −1.8018444 | −3.8106618 | −2.0088174 | −1.8018444 |
| Nrarp | 6.95089E−07 | ENSMUSG00000078202 | Notch-regulated ankyrin repeat protein | −1.8018444 | −5.5476274 | −3.745783 | −1.8018444 |
| Rab19 | 1.2671E−06 | ENSMUSG00000029923 | RAB19, member RAS oncogene family | −1.8018444 | −5.5476274 | −3.745783 | −1.8018444 |
| Hapln3 | 1.68935E−06 | ENSMUSG00000030606 | hyaluronan and proteoglycan link protein 3 | −1.8018444 | −5.5476274 | −3.745783 | −1.8018444 |
| Ccdc80 | 2.68412E−06 | ENSMUSG00000022665 | coiled-coil domain containing 80 | −1.8018444 | −5.5476274 | −3.745783 | −1.8018444 |
| Gm4841 | 3.87708E−06 | ENSMUSG00000068606 | predicted gene 4841 | −1.8018444 | −5.5476274 | −3.745783 | −1.8018444 |
| 4930412F09Rik | 4.95275E−06 | ENSMUSG00000085321 | RIKEN cDNA 4930412F09 gene | −1.8018444 | −5.5476274 | −3.745783 | −1.8018444 |
| Gm7694 | 2.55599E−05 | ENSMUSG00000079188 | predicted gene 7694 | −1.8018444 | −5.5476274 | −3.745783 | −1.8018444 |
| Mesp2 | 0.000146221 | ENSMUSG00000030543 | mesoderm posterior 2 | −1.8018444 | −5.5476274 | −3.745783 | −1.8018444 |
| Rnf152 | 0.000155408 | ENSMUSG00000047496 | ring finger protein 152 | −1.8018444 | −5.5476274 | −3.745783 | −1.8018444 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Gad1-ps | 0.000243773 | ENSMUSG00000090665 | glutamic acid decarboxylase 1, pseudogene | −1.8018444 | −5.5476274 | −3.745783 | −1.8018444 |
| Syngr3 | 0.000536011 | ENSMUSG00000007021 | synaptogyrin 3 | −1.8018444 | −5.5476274 | −3.745783 | −1.8018444 |
| Lrrc69 | 0.000857033 | ENSMUSG00000023151 | leucine rich repeat containing 69 | −1.8018444 | −5.5476274 | −3.745783 | −1.8018444 |
| Zfp352 | 0.000882844 | ENSMUSG00000070902 | zinc finger protein 352 | −1.8018444 | −5.5476274 | −3.745783 | −1.8018444 |
| Mapk8ip1 | 0.001025129 | ENSMUSG00000027223 | mitogen-activated protein kinase 8 interacting protein 1 | −1.8018444 | −5.5476274 | −3.745783 | −1.8018444 |
| Cplx2 | 0.001481371 | ENSMUSG00000025867 | complexin 2 | −1.8018444 | −5.5476274 | −3.745783 | −1.8018444 |
| 2310005G13Rik | 0.005757555 | ENSMUSG00000046748 | RIKEN cDNA 2310005G13 gene | −1.8018444 | −5.5476274 | −3.745783 | −1.8018444 |
| Ndst3 | 0.00595649 | ENSMUSG00000027977 | N-deacetylase/N-sulfotransferase (heparan glucosaminyl) 3 | −1.8018444 | −5.5476274 | −3.745783 | −1.8018444 |
| Cdhr2 | 0.008793266 | ENSMUSG00000034918 | cadherin-related family member 2 | −1.8018444 | −5.5476274 | −3.745783 | −1.8018444 |
| Tac4 | 0.009837943 | ENSMUSG00000020872 | tachykinin 4 | −1.8018444 | −5.5476274 | −3.745783 | −1.8018444 |
| Nexn | 0.011523547 | ENSMUSG00000039103 | nexilin | −1.8018444 | −5.5476274 | −3.745783 | −1.8018444 |
| Usp17l5 | 0.013230624 | ENSMUSG00000058976 | ubiquitin specific peptidase 17-like 5 | −1.8018444 | −5.5476274 | −3.745783 | −1.8018444 |
| 9430020K01Rik | 0.028962463 | ENSMUSG00000033960 | RIKEN cDNA 9430020K01 gene | −1.8018444 | −5.5476274 | −3.745783 | −1.8018444 |
| Rian | 0.032669194 | ENSMUSG00000091793 | RNA imprinted and accumulated in nucleus | −1.8018444 | −5.5476274 | −3.745783 | −1.8018444 |
| Fras1 | 0.03300434 | ENSMUSG00000034687 | Fraser syndrome 1 homolog (human) | −1.8018444 | −5.5476274 | −3.745783 | −1.8018444 |
| Rasgrp2 | 0.038632754 | ENSMUSG00000032946 | RAS, guanyl releasing protein 2 | −1.8018444 | −5.5476274 | −3.745783 | −1.8018444 |
| Gcnt2 | 0.042023577 | ENSMUSG00000021360 | glucosaminyl (N-acetyl) transferase 2, I-branching enzyme | −1.8018444 | −5.5476274 | −3.745783 | −1.8018444 |
| Pcdhb19 | 0.042246673 | ENSMUSG00000043313 | protocadherin beta 19 | −1.8018444 | −5.5476274 | −3.745783 | −1.8018444 |
| Cpt1c | 1.00434E−05 | ENSMUSG00000007783 | carnitine palmitoyltransferase 1c | −1.7653185 | −3.3956244 | −1.6303059 | −1.7653185 |
| Tcirg1 | 2.59394E−05 | ENSMUSG00000001750 | T-cell, immune regulator 1, ATPase, H+ transporting, lysosomal V0 protein A3 | −1.759994 | 7.245976 | 9.00597 | −1.759994 |
| Dguok | 0.030540211 | ENSMUSG00000014554 | deoxyguanosine kinase | −1.7519393 | 0.24823192 | 2.0001712 | −1.7519393 |
| Rnasek | 0.03223572 | ENSMUSG00000040904 | ribonuclease, RNase K | −1.7483242 | 2.9923928 | 4.740717 | −1.7483242 |
| Tmem170 | 0.004925352 | ENSMUSG00000031953 | transmembrane protein 170 | −1.7414716 | 0.53511304 | 2.2765846 | −1.7414716 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Cdkl4 | 2.17175E−05 | ENSMUSG00000033966 | cyclin-dependent kinase-like 4 | −1.7332573 | −0.5882695 | 1.1449878 | −1.7332573 |
| AA386476 | 0.00223168 | ENSMUSG00000074357 | expressed sequence AA386476 | −1.7169555 | −2.5882695 | −0.871314 | −1.7169555 |
| Efemp2 | 4.01625E−05 | ENSMUSG00000024909 | epidermal growth factor-containing fibulin-like extracellular matrix protein 2 | −1.7053364 | −1.3081615 | 0.39717492 | −1.7053364 |
| Atox1 | 0.00219727 | ENSMUSG00000018585 | ATX1 (antioxidant protein 1) homolog 1 (yeast) | −1.6888047 | 2.2978625 | 3.9866672 | −1.6888047 |
| Acot13 | 0.03344103 | ENSMUSG00000006717 | acyl-CoA thioesterase 13 | −1.655059 | 1.1279377 | 2.7829967 | −1.655059 |
| Zfand5 | 0.041743267 | ENSMUSG00000024750 | zinc finger, AN1-type domain 5 | −1.6533193 | 5.2987337 | 6.952053 | −1.6533193 |
| Gng8 | 6.13976E−05 | ENSMUSG00000063594 | guanine nucleotide binding protein (G protein), gamma 8 | −1.6498416 | −5.3956246 | −3.745783 | −1.6498416 |
| Ldb3 | 0.000180388 | ENSMUSG00000021798 | LIM domain binding 3 | −1.6498416 | −5.3956246 | −3.745783 | −1.6498416 |
| Tpm2 | 0.000303012 | ENSMUSG00000028464 | tropomyosin 2, beta | −1.6498416 | −4.3956246 | −2.745783 | −1.6498416 |
| Mamstr | 0.001821696 | ENSMUSG00000042918 | MEF2 activating motif and SAP domain containing transcriptional regulator | −1.6498416 | −5.3956246 | −3.745783 | −1.6498416 |
| 0610009L18Rik | 0.020528933 | ENSMUSG00000043644 | RIKEN cDNA 0610009L18 gene | −1.6498416 | −5.3956246 | −3.745783 | −1.6498416 |
| Wdr96 | 0.032827605 | ENSMUSG00000044948 | WD repeat domain 96 | −1.6498416 | −5.3956246 | −3.745783 | −1.6498416 |
| E030010A14Rik | 0.046596386 | ENSMUSG00000048572 | RIKEN cDNA E030010A14 gene | −1.6498416 | −5.3956246 | −3.745783 | −1.6498416 |
| Itih1 | 0.048211228 | ENSMUSG00000006529 | inter-alpha trypsin inhibitor, heavy chain 1 | −1.6498416 | −5.3956246 | −3.745783 | −1.6498416 |
| 1600016N20Rik | 1.96971E−06 | ENSMUSG00000025500 | RIKEN cDNA 1600016N20 gene | −1.6498414 | −3.3956244 | −1.745783 | −1.6498414 |
| AA543186 | 0.036252256 | ENSMUSG00000091706 | expressed sequence AA543186 | −1.6498413 | −3.0736964 | −1.4238551 | −1.6498413 |
| Adc | 0.004476923 | ENSMUSG00000028789 | arginine decarboxylase | −1.6296634 | −0.8106618 | 0.8190016 | −1.6296634 |
| Sh3bgrl3 | 0.003731431 | ENSMUSG00000028843 | SH3 domain binding glutamic acid-rich protein-like 3 | −1.6179714 | 6.1131606 | 7.731132 | −1.6179714 |
| B430212C06Rik | 0.014717348 | ENSMUSG00000046415 | RIKEN cDNA B430212C06 gene | −1.6009319 | −2.0736964 | −0.4727645 | −1.6009319 |
| Cblb | 0.000721993 | ENSMUSG00000022637 | Casitas B-lineage lymphoma b | −1.5841252 | 2.6377988 | 4.221924 | −1.5841252 |
| A530083I20Rik | 0.000124989 | ENSMUSG00000086343 | RIKEN cDNA A530083I20 gene | −1.5794521 | −2.5882695 | −1.0088174 | −1.5794521 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Cyb561 | 0.02012645 | ENSMUSG00000019590 | cytochrome b-561 | -1.5761316 | 1.0473192 | 2.6234508 | -1.5761316 |
| Uqcr10 | 0.034956805 | ENSMUSG00000059534 | ubiquinol-cytochrome c reductase, complex III subunit X | -1.5471251 | 3.6239665 | 5.1710916 | -1.5471251 |
| Cbx8 | 0.046324532 | ENSMUSG00000025578 | chromobox homolog 8 (Drosophila Pc class) | -1.5326578 | 0.15896448 | 1.6916223 | -1.5326578 |
| Comtd1 | 0.000179086 | ENSMUSG00000021773 | catechol-O-methyltransferase domain containing 1 | -1.526407 | 3.57016 | 5.096567 | -1.526407 |
| B430203G13Rik | 0.000268071 | ENSMUSG00000067356 | RIKEN cDNA B430203G13 gene | -1.5243105 | -3.3956244 | -1.8713139 | -1.5243105 |
| Tenc1 | 0.00078725 | ENSMUSG00000037003 | tensin like C1 domain-containing phosphatase | -1.5243105 | -3.3956244 | -1.8713139 | -1.5243105 |
| Fam71f2 | 0.04721271 | ENSMUSG00000079652 | family with sequence similarity 71, member F2 | -1.5243105 | -3.3956244 | -1.8713139 | -1.5243105 |
| Gnas | 0.002411892 | ENSMUSG00000027523 | GNAS (guanine nucleotide binding protein, alpha stimulating) complex locus | -1.5211316 | 5.855266 | 7.3763976 | -1.5211316 |
| Tsku | 1.447E-05 | ENSMUSG00000049580 | tsukushi | -1.5165749 | -0.3081615 | 1.2084134 | -1.5165749 |
| B3galt4 | 2.46354E-05 | ENSMUSG00000067370 | UDP-Gal:betaGlcNAc beta 1,3-galactosyltransferase, polypeptide 4 | -1.5096637 | -1.2256994 | 0.28396425 | -1.5096637 |
| Actg1 | 6.26977E-05 | ENSMUSG00000062825 | actin, gamma, cytoplasmic 1 | -1.504394 | 8.558754 | 10.063148 | -1.504394 |
| Slc39a13 | 0.042252257 | ENSMUSG00000002105 | solute carrier family 39 (metal ion transporter), member 13 | -1.5026059 | 4.2978625 | 5.8004684 | -1.5026059 |
| Pde8b | 0.000171998 | ENSMUSG00000021684 | phosphodiesterase 8B | -1.4957519 | 3.5321536 | 5.0279055 | -1.4957519 |
| Pla1a | 0.048690666 | ENSMUSG00000002847 | phospholipase A1 member A | -1.4945631 | 0.2190855 | 1.7136486 | -1.4945631 |
| Ihh | 0.000187296 | ENSMUSG00000006538 | Indian hedgehog | -1.4799163 | -3.8106618 | -2.3307455 | -1.4799163 |
| Bst1 | 0.027398707 | ENSMUSG00000029082 | bone marrow stromal cell antigen 1 | -1.4799163 | 1.9442257 | 3.424142 | -1.4799163 |
| Pmepa1 | 0.001784973 | ENSMUSG00000038400 | prostate transmembrane protein, androgen induced 1 | -1.4649818 | 3.0638072 | 4.528789 | -1.4649818 |
| Ostm1 | 0.000209975 | ENSMUSG00000038280 | osteopetrosis associated transmembrane protein 1 | -1.4622026 | 4.755392 | 6.2175946 | -1.4622026 |
| Pnkd | 0.002613748 | ENSMUSG00000026179 | paroxysmal nonkinesiogenic dyskinesia | -1.453757 | 1.9263037 | 3.3800607 | -1.453757 |
| Aldoc | 0.031371355 | ENSMUSG00000017390 | aldolase C, fructose-bisphosphate | -1.4523878 | 4.3742137 | 5.8266015 | -1.4523878 |
| Gpr157 | 0.002507451 | ENSMUSG00000047875 | G protein-coupled receptor 157 | -1.4509373 | 1.0638072 | 2.5147445 | -1.4509373 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
| --- | --- | --- | --- | --- | --- | --- | --- |
| Itm2c | 0.000136527 | ENSMUSG00000026223 | integral membrane protein 2C | −1.4433904 | 5.314321 | 6.7577114 | −1.4433904 |
| Pld1 | 0.001237733 | ENSMUSG00000027695 | phospholipase D1 | −1.4425491 | 1.6487699 | 3.091319 | −1.4425491 |
| Sun2 | 0.005151057 | ENSMUSG00000042524 | Sad1 and UNC84 domain containing 2 | −1.4423764 | 4.701091 | 6.1434674 | −1.4423764 |
| Cdon | 0.018776068 | ENSMUSG00000038119 | cell adhesion molecule-related/down-regulated by oncogenes | −1.4239599 | −0.8720624 | 0.55189747 | −1.4239599 |
| Cyp4f13 | 0.000314138 | ENSMUSG00000024055 | cytochrome P450, family 4, subfamily f, polypeptide 13 | −1.4210226 | 1.57016 | 2.9911826 | −1.4210226 |
| Gcc1 | 0.002457876 | ENSMUSG00000029708 | golgi coiled coil 1 | −1.4146862 | 2.9619274 | 4.3766136 | −1.4146862 |
| Grhpr | 0.004643564 | ENSMUSG00000035637 | glyoxylate reductase/hydroxypyruvate reductase | −1.4079125 | 1.1742313 | 2.5821438 | −1.4079125 |
| Traf6 | 0.04253863 | ENSMUSG00000027164 | TNF receptor-associated factor 6 | −1.3917976 | 4.262587 | 5.6543846 | −1.3917976 |
| Plcg1 | 0.027477618 | ENSMUSG00000016933 | phospholipase C, gamma 1 | −1.3875122 | 3.2803328 | 4.667845 | −1.3875122 |
| Gm711 | 0.000219044 | ENSMUSG00000049897 | predicted gene 711 | −1.3868072 | −4.3956246 | −3.0088174 | −1.3868072 |
| Gpr182 | 0.001226294 | ENSMUSG00000058396 | G protein-coupled receptor 182 | −1.386807 | −3.3956244 | −2.0088174 | −1.386807 |
| D2hgdh | 0.006610859 | ENSMUSG00000073609 | D-2-hydroxyglutarate dehydrogenase | −1.3820164 | 2.1042216 | 3.486238 | −1.3820164 |
| Tmem19 | 0.001470068 | ENSMUSG00000069520 | transmembrane protein 19 | −1.3742473 | 3.8874643 | 5.2617116 | −1.3742473 |
| Tmem120a | 0.018098773 | ENSMUSG00000039886 | transmembrane protein 120A | −1.3698108 | 3.3987916 | 4.7686024 | −1.3698108 |
| Tssk6 | 0.00016489 | ENSMUSG00000047654 | testis-specific serine kinase 6 | −1.3576605 | −0.0736962 | 1.2839643 | −1.3576605 |
| Camk1 | 7.14941E−05 | ENSMUSG00000030272 | calcium/calmodulin-dependent protein kinase I | −1.351926 | 3.342468 | 4.694394 | −1.351926 |
| Mitf | 0.001512894 | ENSMUSG00000035158 | microphthalmia-associated transcription factor | −1.350885 | 4.788011 | 6.138896 | −1.350885 |
| Hspa1b | 0.000582485 | ENSMUSG00000090877 | heat shock protein 1B | −1.3323592 | −0.6407369 | 0.69162226 | −1.3323592 |
| Hyal2 | 0.04322722 | ENSMUSG00000010047 | hyaluronoglucosaminidase 2 | −1.3124657 | 3.4052758 | 4.7177415 | −1.3124657 |
| Snapc5 | 0.001169527 | ENSMUSG00000032398 | small nuclear RNA activating complex, polypeptide 5 | −1.3058869 | −0.3512302 | 0.95465666 | −1.3058869 |
| Adcy9 | 0.000661473 | ENSMUSG00000005580 | adenylate cyclase 9 | −1.3011768 | 2.0719812 | 3.373158 | −1.3011768 |
| Sh3bgrl | 0.000909132 | ENSMUSG00000031246 | SH3-binding domain glutamic acid-rich protein like | −1.2961377 | 4.8391933 | 6.135331 | −1.2961377 |
| Trip10 | 0.03646866 | ENSMUSG00000019487 | thyroid hormone receptor interactor 10 | −1.2951012 | 2.9035838 | 4.198685 | −1.2951012 |
| Glis2 | 0.000204305 | ENSMUSG00000014303 | GLIS family zinc finger 2 | −1.2872714 | −2.2256994 | −0.938428 | −1.2872714 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| 4732465J04Rik | 0.000652129 | ENSMUSG00000071107 | RIKEN cDNA 4732465I04 gene | −1.287271 | −3.8106618 | −2.5233908 | −1.287271 |
| Dstn | 0.009541933 | ENSMUSG00000015932 | destrin | −1.2852877 | 6.1116743 | 7.396962 | −1.2852877 |
| Bad | 0.03586843 | ENSMUSG00000024959 | BCL2-associated agonist of cell death | −1.2839432 | 2.1435344 | 3.4274776 | −1.2839432 |
| Cbr1 | 0.04490556 | ENSMUSG00000051483 | carbonyl reductase 1 | −1.2796881 | 1.3725599 | 2.652248 | −1.2796881 |
| Cd180 | 0.04057961 | ENSMUSG00000021624 | CD180 antigen | −1.2769055 | 5.7043805 | 6.981286 | −1.2769055 |
| Kbtbd11 | 0.016952015 | ENSMUSG00000055675 | kelch repeat and BTB (POZ) domain containing 11 | −1.2746457 | 6.516142 | 7.7907877 | −1.2746457 |
| Rftn2 | 0.000334329 | ENSMUSG00000025978 | raftlin family member 2 | −1.2743322 | −1.3956243 | −0.1212921 | −1.2743322 |
| Bloc1s1 | 0.005817233 | ENSMUSG00000090247 | biogenesis of lysosome-related organelles complex-1, subunit 1 | −1.2713295 | 0.30481544 | 1.5761449 | −1.2713295 |
| Sdhc | 0.009144416 | ENSMUSG00000058076 | succinate dehydrogenase complex, subunit C, integral membrane protein | −1.26805 | 5.124012 | 6.392062 | −1.26805 |
| Fosl2 | 0.038066894 | ENSMUSG00000029135 | fos-like antigen 2 | −1.265212 | 8.133928 | 9.39914 | −1.265212 |
| Agap3 | 0.00044129 | ENSMUSG00000023353 | ArfGAP with GTPase domain, ankyrin repeat and PH domain 3 | −1.264696 | 5.073 | 6.337696 | −1.264696 |
| Gm16372 | 0.003350369 | ENSMUSG00000057160 | predicted pseudogene 16372 | −1.2619156 | −0.0380723 | 1.2238433 | −1.2619156 |
| Pip5k1b | 0.004221178 | ENSMUSG00000024867 | phosphatidylinositol-4-phosphate 5-kinase, type 1 beta | −1.258926 | 5.6555843 | 6.9145103 | −1.258926 |
| Avpi1 | 0.034654055 | ENSMUSG00000018821 | arginine vasopressin-induced 1 | −1.255085 | 2.6211839 | 3.8762689 | −1.255085 |
| Atp5j2 | 0.011021042 | ENSMUSG00000038690 | ATP synthase, H+ transporting, mitochondrial F0 complex, subunit F2 | −1.2517338 | 3.8162642 | 5.067998 | −1.2517338 |
| Cyc1 | 0.04513956 | ENSMUSG00000022551 | cytochrome c-1 | −1.2489853 | 5.1072073 | 6.3561926 | −1.2489853 |
| Tollip | 0.001564898 | ENSMUSG00000025139 | toll interacting protein | −1.2389507 | 4.1968327 | 5.4357834 | −1.2389507 |
| C330011M18Rik | 0.000299532 | ENSMUSG00000056753 | RIKEN cDNA C330011M18 gene | −1.2348039 | −3.3956244 | −2.1608205 | −1.2348039 |
| Fam108a | 0.003468877 | ENSMUSG00000003346 | family with sequence similarity 108, member A | −1.2336335 | 3.2873702 | 4.5210037 | −1.2336335 |
| Gm11273 | 0.003542103 | ENSMUSG00000079941 | predicted gene 11273 | −1.231031 | 3.715511 | 4.946542 | −1.231031 |
| Abhd14a | 0.001433305 | ENSMUSG00000042210 | abhydrolase domain containing 14A | −1.2276082 | 0.67046493 | 1.8980731 | −1.2276082 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Pccb | 0.000628514 | ENSMUSG00000032527 | propionyl Coenzyme A carboxylase, beta polypeptide | −1.2272532 | 2.8235443 | 4.0507975 | −1.2272532 |
| Sbno2 | 0.001419982 | ENSMUSG00000035673 | strawberry notch homolog 2 (*Drosophila*) | −1.223022 | 5.3650956 | 6.5881176 | −1.223022 |
| Yif1a | 0.008634817 | ENSMUSG00000024875 | Yip1 interacting factor homolog A (*S. cerevisiae*) | −1.2178903 | 1.7642471 | 2.9821374 | −1.2178903 |
| Pip5kl1 | 0.000696783 | ENSMUSG00000046854 | phosphatidylinositol-4-phosphate 5-kinase-like 1 | −1.2168817 | −5.5476274 | −4.3307457 | −1.2168817 |
| Tnfrsf17 | 0.001270444 | ENSMUSG00000022496 | tumor necrosis factor receptor superfamily, member 17 | −1.2168817 | −5.5476274 | −4.3307457 | −1.2168817 |
| Slc10a6 | 0.00129448 | ENSMUSG00000029321 | solute carrier family 10 (sodium/bile acid cotransporter family), member 6 | −1.2168817 | −5.5476274 | −4.3307457 | −1.2168817 |
| Rhox2d | 0.001357955 | ENSMUSG00000079634 | reproductive homeobox 2D | −1.2168817 | −5.5476274 | −4.3307457 | −1.2168817 |
| Adamts16 | 0.001422754 | ENSMUSG00000049538 | a disintegrin-like and metallopeptidase (reprolysin type) with thrombospondin type 1 motif, 16 | −1.2168817 | −5.5476274 | −4.3307457 | −1.2168817 |
| Adcy1 | 0.001623965 | ENSMUSG00000020431 | adenylate cyclase 1 | −1.2168817 | −5.5476274 | −4.3307457 | −1.2168817 |
| 4933402P03Rik | 0.002350824 | ENSMUSG00000044084 | RIKEN cDNA 4933402P03 gene | −1.2168817 | −5.5476274 | −4.3307457 | −1.2168817 |
| Gm16619 | 0.002409908 | ENSMUSG00000086303 | predicted gene, 16619 | −1.2168817 | −5.5476274 | −4.3307457 | −1.2168817 |
| Crb3 | 0.002483939 | ENSMUSG00000044279 | crumbs homolog 3 (*Drosophila*) | −1.2168817 | −5.5476274 | −4.3307457 | −1.2168817 |
| Fbxo17 | 0.002832668 | ENSMUSG00000030598 | F-box protein 17 | −1.2168817 | −5.5476274 | −4.3307457 | 4.2168817 |
| Podnl1 | 0.003043215 | ENSMUSG00000012889 | podocan-like 1 | −1.2168817 | −5.5476274 | −4.3307457 | −1.2168817 |
| Iglon5 | 0.003664683 | ENSMUSG00000013367 | IgLON family member 5 | −1.2168817 | −5.5476274 | −4.3307457 | −1.2168817 |
| Wdr16 | 0.004747208 | ENSMUSG00000020904 | WD repeat domain 16 | −1.2168817 | −5.5476274 | −4.3307457 | −1.2168817 |
| Slc28a1 | 0.004920505 | ENSMUSG00000025726 | solute carrier family 28 (sodium-coupled nucleoside transporter), member 1 | −1.2168817 | −5.5476274 | −4.3307457 | −1.2168817 |
| Hspg2 | 0.005137672 | ENSMUSG00000028763 | perlecan (heparan sulfate proteoglycan 2) | −1.2168817 | −5.5476274 | −4.3307457 | −1.2168817 |
| Cpne9 | 0.005249562 | ENSMUSG00000030270 | copine family member IX | −1.2168817 | −5.5476274 | −4.3307457 | −1.2168817 |
| Ttc23l | 0.006339658 | ENSMUSG00000022249 | tetratricopeptide repeat domain 23-like | −1.2168817 | −5.5476274 | −4.3307457 | −1.2168817 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
| --- | --- | --- | --- | --- | --- | --- | --- |
| Ppp1r1b | 0.007002014 | ENSMUSG00000061718 | protein phosphatase 1, regulatory (inhibitor) subunit 1B | −1.2168817 | −5.5476274 | −4.3307457 | −1.2168817 |
| Acsbg2 | 0.007208475 | ENSMUSG00000024207 | acyl-CoA synthetase bubblegum family member 2 | −1.2168817 | −5.5476274 | −4.3307457 | −1.2168817 |
| Peli3 | 0.014013367 | ENSMUSG00000024901 | pellino 3 | −1.2168817 | −5.5476274 | −4.3307457 | −1.2168817 |
| Myo15b | 0.018579457 | ENSMUSG00000034427 | myosin XVB | −1.2168817 | −5.5476274 | −4.3307457 | −1.2168817 |
| Scn4a | 0.018845024 | ENSMUSG00000001027 | sodium channel, voltage-gated, type IV, alpha | −1.2168817 | −5.5476274 | −4.3307457 | −1.2168817 |
| Sh3bp4 | 0.021253621 | ENSMUSG00000036206 | SH3-domain binding protein 4 | −1.2168817 | −5.5476274 | −4.3307457 | −1.2168817 |
| Gcom1 | 0.02231107 | ENSMUSG00000041361 | GRINL1A complex locus | −1.2168817 | −5.5476274 | −4.3307457 | −1.2168817 |
| Faim2 | 0.035814784 | ENSMUSG00000023011 | Fas apoptotic inhibitory molecule 2 | −1.2168817 | −5.5476274 | −4.3307457 | −1.2168817 |
| Sox10 | 0.04996452 | ENSMUSG00000033006 | SRY-box containing gene 10 | −1.2168817 | −5.5476274 | −4.3307457 | −1.2168817 |
| Letm1 | 0.001400281 | ENSMUSG00000005299 | leucine zipper-EF-hand containing transmembrane protein 1 | −1.207101 | 4.858223 | 6.065324 | −1.207101 |
| Obfc1 | 0.033878557 | ENSMUSG00000042694 | oligonucleotide/oligosaccharide-binding fold containing 1 | −1.2036425 | 3.3048155 | 4.508458 | −1.2036425 |
| Tnfaip3 | 0.002788399 | ENSMUSG00000019850 | tumor necrosis factor, alpha-induced protein 3 | −1.201921 | 4.3407774 | 5.5426984 | −1.201921 |
| Gnpda1 | 0.01936977 | ENSMUSG00000052102 | glucosamine-6-phosphate deaminase 1 | −1.1803564 | 4.0962286 | 5.276585 | −1.1803564 |
| 4921507L20Rik | 0.000400257 | ENSMUSG00000027196 | RIKEN cDNA 4921507L20 gene | −1.1803559 | −2.8106618 | −1.6303059 | −1.1803559 |
| Gcnt7 | 0.002288528 | ENSMUSG00000074569 | glucosaminyl (N-acetyl) transferase family member 7 | −1.1803559 | −2.8106618 | −1.6303059 | −1.1803559 |
| Gm16714 | 0.005287915 | ENSMUSG00000085339 | predicted gene, 16714 | −1.1803559 | −2.8106618 | −1.6303059 | −1.1803559 |
| Gm10642 | 0.004257144 | ENSMUSG00000074213 | predicted gene 10642 | −1.1803559 | 0.18933822 | 1.3696941 | −1.1803559 |
| Kif5a | 0.003976241 | ENSMUSG00000074657 | kinesin family member 5A | −1.1786551 | 3.4404259 | 4.619081 | −1.1786551 |
| Ucp2 | 0.018080156 | ENSMUSG00000033685 | uncoupling protein 2 (mitochondrial, proton carrier) | −1.174402 | 8.331445 | 9.505847 | −1.174402 |
| Stx4a | 0.001855345 | ENSMUSG00000030805 | syntaxin 4A (placental) | −1.1708516 | 4.2838554 | 5.454707 | −1.1708516 |
| Arpc4 | 0.04566701 | ENSMUSG00000079426 | actin related protein 2/3 complex, subunit 4 | −1.1692152 | 6.6474032 | 7.8166184 | −1.1692152 |
| Tyrobp | 0.006254981 | ENSMUSG00000030579 | TYRO protein tyrosine kinase | −1.1689372 | 6.1623178 | 7.331255 | −1.1689372 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| 1810014F10Rik | 0.006210305 | ENSMUSG00000025466 | binding protein RIKEN cDNA 1810014F10 gene | −1.1683084 | 1.813829 | 2.9821374 | −1.1683084 |
| Git1 | 0.017137151 | ENSMUSG00000011877 | G protein-coupled receptor kinase-interactor 1 | −1.1681207 | 5.449866 | 6.6179867 | −1.1681207 |
| Hemk1 | 0.00164007 | ENSMUSG00000032579 | HemK methyltransferase family member 1 | −1.1644144 | −1.5882694 | −0.423855 | −1.1644144 |
| Akr7a5 | 0.001301134 | ENSMUSG00000028743 | aldo-keto reductase family 7, member A5 (aflatoxin aldehyde reductase) | −1.1609256 | 1.7129 | 2.8738256 | −1.1609256 |
| Gng7 | 0.011786759 | ENSMUSG00000048240 | guanine nucleotide binding protein (G protein), gamma 7 | −1.1600361 | −0.9361927 | 0.22384338 | −1.1600361 |
| Lfng | 0.002728639 | ENSMUSG00000029570 | LFNG O-fucosylpeptide 3-beta-N-acetylglucosaminyl-transferase | −1.1599504 | 4.0801086 | 5.240059 | −1.1599504 |
| 4930481A15Rik | 0.00970437 | ENSMUSG00000086938 | RIKEN cDNA 4930481A15 gene | −1.1568013 | −0.1476968 | 1.0091045 | −1.1568013 |
| Sema4g | 0.009896757 | ENSMUSG00000025207 | sema domain, immunoglobulin domain (Ig), transmembrane domain (TM) and short cytoplasmic domain, (semaphorin) 4G | −1.1494124 | 1.4623566 | 2.611769 | −1.1494124 |
| Eef2k | 0.027855942 | ENSMUSG00000035064 | eukaryotic elongation factor-2 kinase | −1.148943 | 2.248232 | 3.397175 | −1.148943 |
| Marveld1 | 0.01568347 | ENSMUSG00000044345 | MARVEL (membrane-associating) domain containing 1 | −1.1408279 | 3.5142686 | 4.6550965 | −1.1408279 |
| Med29 | 0.000937494 | ENSMUSG00000003444 | mediator complex subunit 29 | −1.1378936 | 2.1200755 | 3.2579691 | −1.1378936 |
| Ndufv1 | 0.004069016 | ENSMUSG00000037916 | NADH dehydrogenase (ubiquinone) flavoprotein 1 | −1.1364661 | 5.3525686 | 6.4890347 | −1.1364661 |
| Idh3b | 0.001815378 | ENSMUSG00000027406 | isocitrate dehydrogenase 3 (NAD+) beta | −1.1333637 | 5.6107016 | 6.7440653 | −1.1333637 |
| Slc9a1 | 0.049830776 | ENSMUSG00000028854 | solute carrier family 9 (sodium/hydrogen exchanger), member 1 | −1.1203177 | 3.5262167 | 4.6465344 | −1.1203177 |
| 1110005A03Rik | 0.011171196 | ENSMUSG00000090266 | RIKEN cDNA 1110005A03 gene | −1.1139733 | 1.6267434 | 2.7407167 | −1.1139733 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Adamts10 | 0.003044179 | ENSMUSG00000024299 | a disintegrin-like and metallopeptidase (reprolysin type) with thrombospondin type 1 motif, 10 | −1.107314 | 1.6704649 | 2.7777789 | −1.107314 |
| Atp5e | 0.000939308 | ENSMUSG00000016252 | ATP synthase, H+ transporting, mitochondrial F1 complex, epsilon subunit | −1.1058641 | 3.9308052 | 5.0366693 | −1.1058641 |
| Sirt5 | 0.009139757 | ENSMUSG00000054021 | sirtuin 5 (silent mating type information regulation 2 homolog) 5 (S. cerevisiae) | −1.103014 | 1.4117305 | 2.5147445 | −1.103014 |
| 4930520O04Rik | 0.012646059 | ENSMUSG00000074039 | RIKEN cDNA 4930520O04 gene | −1.1023534 | 0.43726566 | 1.5396191 | −1.1023534 |
| Pydc4 | 0.02548906 | ENSMUSG00000073491 | pyrin domain containing 4 | −1.1018054 | 1.6811913 | 2.7829967 | −1.1018054 |
| Nfatc1 | 0.002607991 | ENSMUSG00000033016 | nuclear factor of activated T-cells, cytoplasmic, calcineurin-dependent 1 | −1.0996833 | 7.4641047 | 8.563788 | −1.0996833 |
| Sirt3 | 0.000476384 | ENSMUSG00000025486 | sirtuin 3 (silent mating type information regulation 2, homolog) 3 (S. cerevisiae) | −1.0970113 | 1.3987916 | 2.4958029 | −1.0970113 |
| Nkain1 | 0.026548363 | ENSMUSG00000078532 | Na+/K+ transporting ATPase interacting 1 | −1.0950936 | 2.166618 | 3.2617116 | −1.0950936 |
| Tmem179b | 0.004654881 | ENSMUSG00000079437 | transmembrane protein 179B | −1.0883923 | 2.3390853 | 3.4274776 | −1.0883923 |
| Egr1 | 0.011464391 | ENSMUSG00000038418 | early growth response 1 | −1.0853431 | 0.7336586 | 1.8190017 | −1.0853431 |
| Fdxr | 0.018414063 | ENSMUSG00000018861 | ferredoxin reductase | −1.0834726 | 3.332296 | 4.4157686 | −1.0834726 |
| Ptov1 | 0.003783276 | ENSMUSG00000038502 | prostate tumor over expressed gene 1 | −1.076344 | 3.743927 | 4.820271 | −1.076344 |
| Nradd | 0.0219546 | ENSMUSG00000032491 | neurotrophin receptor associated death domain | −1.0700967 | 1.7129 | 2.7829967 | −1.0700967 |
| A230051G13Rik | 0.031146139 | ENSMUSG00000049287 | RIKEN cDNA A230051G13 gene | −1.0672655 | 2.8427804 | 3.9100459 | −1.0672655 |
| Gm9982 | 0.001856765 | ENSMUSG00000055831 | predicted gene 9982 | −1.064879 | −3.0736964 | −2.0088174 | −1.064879 |
| Gm10645 | 0.004558912 | ENSMUSG00000074228 | predicted gene 10645 | −1.064879 | −3.0736964 | −2.0088174 | −1.064879 |
| Tas1r3 | 0.005695173 | ENSMUSG00000029072 | taste receptor, type 1, member 3 | −1.064879 | −2.0736964 | −1.0088174 | −1.064879 |
| Adcy6 | 0.001144709 | ENSMUSG00000022994 | adenylate cyclase 6 | −1.0648789 | −5.3956246 | −4.3307457 | −1.0648789 |
| Rgs12 | 0.002267373 | ENSMUSG00000029101 | regulator of G-protein signaling 12 | −1.0648789 | −3.3956244 | −2.3307455 | −1.0648789 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Olfr212 | 0.002351982 | ENSMUSG00000053251 | olfactory receptor 212 | −1.0648789 | −5.3956246 | −4.3307457 | −1.0648789 |
| 1700054O19Rik | 0.004014643 | ENSMUSG00000057293 | RIKEN cDNA 1700054O19 gene | −1.0648789 | −5.3956246 | −4.3307457 | −1.0648789 |
| Ccdc67 | 0.007290532 | ENSMUSG00000039977 | coiled-coil domain containing 67 | −1.0648789 | −5.3956246 | −4.3307457 | −1.0648789 |
| C4b | 0.008590216 | ENSMUSG00000073418 | complement component 4B (Childo blood group) | −1.0648789 | −2.3956244 | −1.3307455 | −1.0648789 |
| Arhgef17 | 0.009287045 | ENSMUSG00000032875 | Rho guanine nucleotide exchange factor (GEF) 17 | −1.0648789 | −3.3956244 | −2.3307455 | −1.0648789 |
| Slc36a3 | 0.013117594 | ENSMUSG00000049491 | solute carrier family 36 (proton/amino acid symporter), member 3 | −1.0648789 | −5.3956246 | −4.3307457 | −1.0648789 |
| Gm20468 | 0.013459157 | ENSMUSG00000092539 | predicted gene 20468 | −1.0648789 | −5.3956246 | −4.3307457 | −1.0648789 |
| 4930455G09Rik | 0.013695496 | ENSMUSG00000085761 | RIKEN cDNA 4930455G09 gene | −1.0648789 | −3.3956244 | −2.3307455 | −1.0648789 |
| Wap | 0.01899181 | ENSMUSG00000000381 | whey acidic protein | −1.0648789 | −5.3956246 | −4.3307457 | −1.0648789 |
| Ccdc54 | 0.028815286 | ENSMUSG00000050685 | coiled-coil domain containing 54 | −1.0648789 | −5.3956246 | −4.3307457 | −1.0648789 |
| Tmem130 | 0.03130156 | ENSMUSG00000043388 | transmembrane protein 130 | −1.0648789 | −5.3956246 | −4.3307457 | −1.0648789 |
| Nrcam | 0.045242175 | ENSMUSG00000020598 | neuron-glia-CAM-related cell adhesion molecule | −1.0648789 | −5.3956246 | −4.3307457 | −1.0648789 |
| Bfsp2 | 0.006345339 | ENSMUSG00000032556 | beaded filament structural protein 2, phakinin | −1.0648789 | −4.3956246 | −3.3307457 | −1.0648789 |
| Rab27b | 0.007012791 | ENSMUSG00000024511 | RAB27b, member RAS oncogene family | −1.0648789 | −4.3956246 | −3.3307457 | −1.0648789 |
| Aqp7 | 0.017064577 | ENSMUSG00000028427 | aquaporin 7 | −1.0648789 | −4.3956246 | −3.3307457 | −1.0648789 |
| 4930451E10Rik | 0.01750742 | ENSMUSG00000069223 | RIKEN cDNA 4930451E10 gene | −1.0648789 | −4.3956246 | −3.3307457 | −1.0648789 |
| Ms4a4b | 0.03696975 | ENSMUSG00000056290 | membrane-spanning 4-domains, subfamily A, member 4B | −1.0648789 | −4.3956246 | −3.3307457 | −1.0648789 |
| 4930529M08Rik | 0.037663873 | ENSMUSG00000037143 | RIKEN cDNA 4930529M08 gene | −1.0648789 | −4.3956246 | −3.3307457 | −1.0648789 |
| Rab11fip4 | 0.01102629 | ENSMUSG00000017639 | RAB11 family interacting protein 4 (class II) | −1.0648788 | −3.8106618 | −2.745783 | −1.0648788 |
| 41887 | 0.016744798 | ENSMUSG00000072214 | septin 5 | −1.0648788 | −3.8106618 | −2.745783 | −1.0648788 |
| Prx | 0.016224083 | ENSMUSG00000053198 | periaxin | −1.0648788 | −2.2256994 | −1.1608206 | −1.0648788 |
| Dlec1 | 0.03235247 | ENSMUSG00000038060 | deleted in lung and esophageal cancer 1 | −1.0648788 | −1.5882694 | −0.5233907 | −1.0648788 |
| Rpl10a-ps2 | 0.017712247 | ENSMUSG00000061988 | ribosomal protein L10A, pseudogene 2 | −1.0648787 | 1.9966931 | 3.0615718 | −1.0648787 |
| Cyfip2 | 0.009189907 | ENSMUSG00000020340 | cytoplasmic FMR1 | −1.0582762 | 2.3791628 | 3.437439 | −1.0582762 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Fgd6 | 0.005464029 | ENSMUSG00000020021 | FYVE, RhoGEF and PH domain containing 6 | −1.0570075 | 4.296119 | 5.3531265 | −1.0570075 |
| Spef1 | 0.006124181 | ENSMUSG00000027329 | sperm flagellar 1 | −1.0517034 | 0.38573536 | 1.4374388 | −1.0517034 |
| Rab34 | 0.023153191 | ENSMUSG00000002059 | RAB34, member of RAS oncogene family | −1.0480704 | 2.6211839 | 3.6692543 | −1.0480704 |
| Klc2 | 0.001976282 | ENSMUSG00000024862 | kinesin light chain 2 | −1.0417025 | 2.5759192 | 3.6176217 | −1.0417025 |
| Slc2a4 | 0.006559952 | ENSMUSG00000018566 | solute carrier family 2 (facilitated glucose transporter), member 4 | −1.0406312 | −0.4887338 | 0.55189747 | −1.0406312 |
| Map2k3 | 0.003899702 | ENSMUSG00000018932 | mitogen-activated protein kinase kinase 3 | −1.0403227 | 6.526588 | 7.5669107 | −1.0403227 |
| Dad1 | 0.00630479 | ENSMUSG00000022174 | defender against cell death 1 | −1.0402053 | 4.695811 | 5.7360163 | −1.0402053 |
| Gm14455 | 0.004350234 | ENSMUSG00000087633 | predicted gene 14455 | −1.0397879 | −0.5376434 | 0.50214446 | −1.0397879 |
| Ak3 | 0.006733093 | ENSMUSG00000024782 | adenylate kinase 3 | −1.0376728 | 4.4340982 | 5.471771 | −1.0376728 |
| Glce | 0.007387917 | ENSMUSG00000032252 | glucuronyl C5-epimerase | −1.032552 | 3.6239665 | 4.6565185 | −1.032552 |
| Mtap7d1 | 0.00833793 | ENSMUSG00000028849 | microtubule-associated protein 7 domain containing 1 | −1.031302 | 5.0462823 | 6.0775843 | −1.031302 |
| Ulk3 | 0.002965013 | ENSMUSG00000032308 | unc-51-like kinase 3 (*C. elegans*) | −1.0307307 | 2.022228 | 3.0529587 | −1.0307307 |
| Ppap2c | 0.01108149 | ENSMUSG00000052151 | phosphatidic acid phosphatase type 2C | −1.0295459 | 2.8805 | 3.9100459 | −1.0295459 |
| Anapc2 | 0.001523701 | ENSMUSG00000026965 | anaphase promoting complex subunit 2 | −1.0289692 | 4.8331943 | 5.8621635 | −1.0289692 |
| Aldoart1 | 0.013166931 | ENSMUSG00000059343 | aldolase 1A retrogene 1 | −1.028117 | 5.360098 | 6.388215 | −1.028117 |
| N4bp3 | 0.039391436 | ENSMUSG00000001053 | NEDD4 binding protein 3 | −1.0253504 | −0.186171 | 0.83917946 | −1.0253504 |
| Repin1 | 0.00851355 | ENSMUSG00000052751 | replication initiator 1 | −1.0077979 | 1.4623566 | 2.4701545 | −1.0077979 |
| Nudt14 | 0.003012999 | ENSMUSG00000002804 | nudix (nucleoside diphosphate linked moiety X)-type motif 14 | −1.0052901 | 2.0390038 | 3.0442939 | −1.0052901 |
| A830007P12Rik | 0.020650838 | ENSMUSG00000059555 | RIKEN cDNA A830007P12 gene | −0.9985294 | 4.9001446 | 5.898674 | −0.9985294 |
| Aldoa | 0.002948088 | ENSMUSG00000030695 | aldolase A, fructose-bisphosphate | −0.983461 | 8.502977 | 9.486438 | −0.983461 |
| Arc | 0.016652526 | ENSMUSG00000022602 | activity regulated cytoskeletal-associated protein | −0.9824167 | −1.2256994 | −0.2432828 | −0.9824167 |
| Rgl2 | 0.008882542 | ENSMUSG00000041354 | ral guanine nucleotide dissociation | −0.979752 | 5.2135544 | 6.1933064 | −0.979752 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| | | | stimulator-like 2 | | | | |
| Shpk | 0.019699099 | ENSMUSG00000005951 | sedoheptulokinase | −0.9781672 | 0.5112662 | 1.4894334 | −0.9781672 |
| Aga | 0.00395918 | ENSMUSG00000031521 | aspartylglucosaminidase | −0.9780013 | 1.8711622 | 2.8491635 | −0.9780013 |
| C230037L18Rik | 0.016271891 | ENSMUSG00000084915 | RIKEN cDNA C230037L18 gene | −0.977416 | −1.3081615 | −0.3307455 | −0.977416 |
| Il17rc | 0.018987024 | ENSMUSG00000030281 | interleukin 17 receptor C | −0.9750822 | 0.4623566 | 1.4374388 | −0.9750822 |
| Ocel1 | 0.019482028 | ENSMUSG00000002396 | occludin/ELL domain containing 1 | −0.9746046 | 2.8570411 | 3.8316457 | −0.9746046 |
| Il1rn | 0.004778137 | ENSMUSG00000026981 | interleukin 1 receptor antagonist | −0.973403 | 4.1836915 | 5.1570945 | −0.973403 |
| Rps16 | 0.04162411 | ENSMUSG00000037563 | ribosomal protein S16 | −0.97321 | 6.446333 | 7.419543 | −0.97321 |
| Zfp882 | 0.008488793 | ENSMUSG00000089857 | zinc finger protein 882 | −0.9717693 | −2.3956244 | −1.4238551 | −0.9717693 |
| Pold4 | 0.008677183 | ENSMUSG00000024854 | polymerase (DNA-directed), delta 4 | −0.9683707 | 1.0137666 | 1.9821373 | −0.9683707 |
| Man2b1 | 0.04088014 | ENSMUSG00000005142 | mannosidase 2, alpha B1 | −0.9667725 | 5.0232825 | 5.990055 | −0.9667725 |
| Athl1 | 0.00759034 | ENSMUSG00000062031 | ATH1, acid trehalase-like 1 (yeast) | −0.9665135 | 3.3857355 | 4.352249 | −0.9665135 |
| Fam195b | 0.012424714 | ENSMUSG00000061111 | family with sequence similarity 195, member B | −0.9629592 | 4.3971663 | 5.3601255 | −0.9629592 |
| Mtfp1 | 0.046913996 | ENSMUSG00000004748 | mitochondrial fission process 1 | −0.9624316 | 1.5585719 | 2.5210035 | −0.9624316 |
| Cyb561d2 | 0.010208104 | ENSMUSG00000037190 | cytochrome b-561 domain containing 2 | −0.9590102 | 2.3322961 | 3.2913063 | −0.9590102 |
| Tnfrsf11a | 0.010830157 | ENSMUSG00000026321 | tumor necrosis factor receptor superfamily, member 11a | −0.958003 | 6.045245 | 7.003248 | −0.958003 |
| 9230115E21Rik | 0.010104352 | ENSMUSG00000074354 | RIKEN cDNA 9230115E21 gene | −0.9579636 | −2.5882695 | −1.6303059 | −0.9579636 |
| Adamts1 | 0.022076081 | ENSMUSG00000022893 | a disintegrin-like and metallopeptidase (reprolysin type) with thrombospondin type 1 motif, 1 | −0.9579636 | −2.5882695 | −1.6303059 | −0.9579636 |
| Kif7 | 0.027391762 | ENSMUSG00000050382 | kinesin family member 7 | −0.9579635 | −1.5882694 | −0.6303059 | −0.9579635 |
| Capn12 | 0.012989306 | ENSMUSG00000054083 | calpain 12 | −0.9565671 | 2.9172585 | 3.8738256 | −0.9565671 |
| Gm16896 | 0.020594148 | ENSMUSG00000085988 | predicted gene, 16896 | −0.9511457 | 2.8805 | 3.8316457 | −0.9511457 |
| Naga | 0.004612528 | ENSMUSG00000022453 | N-acetyl galactosaminidase, alpha | −0.9453887 | 3.7966683 | 4.742057 | −0.9453887 |
| Aagab | 0.045944124 | ENSMUSG00000037257 | alpha- and gamma-adaptin binding protein | −0.9409665 | 5.1141505 | 6.055117 | −0.9409665 |
| Gm2895 | 0.013068641 | ENSMUSG00000091412 | predicted gene 2895 | −0.9393479 | −2.8106618 | −1.8713139 | −0.9393479 |
| Ccdc90a | 0.012132604 | ENSMUSG00000021371 | coiled-coil domain containing 90A | −0.9371602 | 3.0962288 | 4.033389 | −0.9371602 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Rgs11 | 0.011104016 | ENSMUSG00000024186 | regulator of G-protein signaling 11 | −0.9327752 | 0.9263038 | 1.859079 | −0.9327752 |
| Hyi | 0.028181328 | ENSMUSG00000006395 | hydroxypyruvate isomerase homolog (E. coli) | −0.9299492 | 0.99669313 | 1.9266423 | −0.9299492 |
| Gpr137 | 0.049236804 | ENSMUSG00000024958 | G protein-coupled receptor 137 | −0.9295592 | 3.1082015 | 4.0377607 | −0.9295592 |
| Ndufs3 | 0.006582539 | ENSMUSG00000005510 | NADH dehydrogenase (ubiquinone) Fe—S protein 3 | −0.9273753 | 3.8451672 | 4.7725425 | −0.9273753 |
| Acot11 | 0.010169235 | ENSMUSG00000034853 | acyl-CoA thioesterase 11 | −0.9219208 | 0.3322961 | 1.2542169 | −0.9219208 |
| Cirbp | 0.03442582 | ENSMUSG00000045193 | cold inducible RNA binding protein | −0.919633 | 3.076051 | 3.995684 | −0.919633 |
| Acvrl1 | 0.017487064 | ENSMUSG00000000530 | activin A receptor, type II-like 1 | −0.9193378 | 2.2337322 | 3.15307 | −0.9193378 |
| Ccdc114 | 0.036372237 | ENSMUSG00000040189 | coiled-coil domain containing 114 | −0.919028 | −0.6951846 | 0.22384338 | −0.919028 |
| Snn | 0.013385386 | ENSMUSG00000037972 | stannin | −0.9128759 | −3.0736964 | −2.1608205 | −0.9128759 |
| Msi1 | 0.014250691 | ENSMUSG00000054256 | Musashi homolog 1(Drosophila) | −0.9128759 | −3.0736964 | −2.1608205 | −0.9128759 |
| Cyth1 | 0.048440345 | ENSMUSG00000017132 | cytohesin 1 | −0.9122796 | 2.675838 | 3.5881176 | −0.9122796 |
| Aldh16a1 | 0.027805215 | ENSMUSG00000007833 | aldehyde dehydrogenase 16 family, member A1 | −0.909904 | 4.6811914 | 5.5910954 | −0.909904 |
| Rsph3a | 0.011015884 | ENSMUSG00000073471 | radial spoke 3A homolog (Chlamydomonas) | −0.9093094 | 2.4181566 | 3.327466 | −0.9093094 |
| Commd4 | 0.008752169 | ENSMUSG00000032299 | COMM domain containing 4 | −0.908303 | 2.9081564 | 3.8164594 | −0.908303 |
| Flcn | 0.008794582 | ENSMUSG00000032633 | folliculin | −0.9066836 | 4.4716544 | 5.378338 | −0.9066836 |
| 1700020I14Rik | 0.002356395 | ENSMUSG00000085438 | RIKEN cDNA 1700020I14 gene | −0.9060127 | 4.241 | 5.1470127 | −0.9060127 |
| Cd59b | 0.009062648 | ENSMUSG00000068686 | CD59b antigen | −0.8977688 | −0.3956244 | 0.50214446 | −0.8977688 |
| Gm15489 | 0.014427851 | ENSMUSG00000086942 | predicted gene 15489 | −0.8949539 | −2.2256994 | −1.3307455 | −0.8949539 |
| Taf10 | 0.016606517 | ENSMUSG00000043866 | TAF10 RNA polymerase II, TATA box binding protein (TBP)-associated factor | −0.8943495 | 4.8247538 | 5.7191033 | −0.8943495 |
| Eif2c4 | 0.011220387 | ENSMUSG00000042500 | eukaryotic translation initiation factor 2C, 4 | −0.8931125 | 2.804048 | 3.6971605 | −0.8931125 |
| 2810422J05Rik | 0.002751657 | ENSMUSG00000055553 | RIKEN cDNA 2810422J05 gene | −0.892449 | 7.259236 | 8.151685 | −0.892449 |
| Aldoart2 | 0.014008217 | ENSMUSG00000063129 | aldolase 1 A retrogene 2 | −0.889758 | 4.009517 | 4.899275 | −0.889758 |
| Fbrsl1 | 0.020696755 | ENSMUSG00000043323 | fibrosin-like 1 | −0.8856542 | 2.3458426 | 3.2314968 | −0.8856542 |
| Suv420h2 | 0.034955982 | ENSMUSG00000059851 | suppressor of variegation 4-20 homolog 2 (Drosophila) | −0.8856541 | 3.6677709 | 4.553425 | −0.8856541 |
| Rgs14 | 0.008254785 | ENSMUSG00000052087 | regulator of G-protein signaling 14 | −0.8804542 | 0.24823192 | 1.1286861 | −0.8804542 |
| Dhx34 | 0.016695064 | ENSMUSG00000006019 | DEAH (Asp-Glu-Ala-His) box | −0.8802828 | 3.1855762 | 4.065859 | −0.8802828 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| | | | polypeptide 34 | | | | |
| Orai2 | 0.01243197 | ENSMUSG00000039747 | ORAI calcium release-activated calcium modulator 2 | −0.8786246 | 4.897847 | 5.7764716 | −0.8786246 |
| Cope | 0.015722413 | ENSMUSG00000055681 | coatomer protein complex, subunit epsilon | −0.8782422 | 3.4020374 | 4.2802796 | −0.8782422 |
| Gm3550 | 0.006914831 | ENSMUSG00000078240 | predicted gene 3550 | −0.8767266 | 2.4435794 | 3.320306 | −0.8767266 |
| Tspyl1 | 0.010131083 | ENSMUSG00000047514 | testis-specific protein, Y-encoded-like 1 | −0.8765944 | 5.1190896 | 5.995684 | −0.8765944 |
| 1810013L24Rik | 0.008725129 | ENSMUSG00000022507 | RIKEN cDNA 1810013L24 gene | −0.876027 | 5.614204 | 6.490231 | −0.876027 |
| D4Wsu53e | 0.008402507 | ENSMUSG00000037266 | DNA segment, Chr 4, Wayne State University 53, expressed | −0.8759332 | 6.209855 | 7.0857882 | −0.8759332 |
| Ttn | 0.006356048 | ENSMUSG00000051747 | titin | −0.8746564 | 1.0137666 | 1.888423 | −0.8746564 |
| Tmem192 | 0.029768782 | ENSMUSG00000025521 | transmembrane protein 192 | −0.8737595 | 3.6811912 | 4.5549507 | −0.8737595 |
| Gm6189 | 0.006221308 | ENSMUSG00000090637 | predicted gene 6189 | −0.8722337 | −1.8106617 | −0.938428 | −0.8722337 |
| Atp6ap2 | 0.035808034 | ENSMUSG00000031007 | ATPase, H+ transporting, lysosomal accessory protein 2 | −0.872028 | 7.740566 | 8.612594 | −0.872028 |
| Zfp524 | 0.03309677 | ENSMUSG00000051184 | zinc finger protein 524 | −0.8684815 | 0.38573536 | 1.2542169 | −0.8684815 |
| Pgls | 0.016186675 | ENSMUSG00000031807 | 6-phosphogluconolactonase | −0.8678807 | 4.4197593 | 5.28764 | −0.8678807 |
| Nhlrc3 | 0.044700302 | ENSMUSG00000042997 | NHL repeat containing 3 | −0.8672788 | 3.1551225 | 4.0224013 | −0.8672788 |
| Slc9a5 | 0.017414166 | ENSMUSG00000014786 | solute carrier family 9 (sodium/hydrogen exchanger), member 5 | −0.8671144 | 2.523239 | 3.3903534 | −0.8671144 |
| Ctsz | 0.025800172 | ENSMUSG00000016256 | cathepsin Z | −0.8654295 | 8.136001 | 9.0014305 | −0.8654295 |
| Rps15 | 0.015647907 | ENSMUSG00000063457 | ribosomal protein S15 | −0.8634447 | 5.6838603 | 6.547305 | −0.8634447 |
| Gaa | 0.040927023 | ENSMUSG00000025579 | glucosidase, alpha, acid | −0.85985 | 5.17518 | 6.03503 | −0.85985 |
| Map3k10 | 0.011791729 | ENSMUSG00000040390 | mitogen-activated protein kinase kinase kinase 10 | −0.8566368 | 2.1435344 | 3.0001712 | −0.8566368 |
| Zfp526 | 0.029923318 | ENSMUSG00000046541 | zinc finger protein 526 | −0.8533748 | 2.4561245 | 3.3094993 | −0.8533748 |
| Hist1h3g | 0.014537657 | ENSMUSG00000062417 | histone cluster 1, H3g | −0.8491501 | −1.2256994 | −0.3765493 | −0.8491501 |
| Gm6055 | 0.032020975 | ENSMUSG00000062081 | predicted gene 6055 | −0.8490165 | 4.051459 | 4.9004755 | −0.8490165 |
| C030037D09Rik | 0.044817787 | ENSMUSG00000087574 | RIKEN cDNA C030037D09 gene | −0.8468781 | 0.9619277 | 1.8088058 | −0.8468781 |
| Zswim7 | 0.026769519 | ENSMUSG00000014243 | zinc finger, SWIM-type containing 7 | −0.8460816 | 1.9880799 | 2.8341615 | −0.8460816 |
| F420014N23Rik | 0.017114388 | ENSMUSG00000086597 | RIKEN cDNA F420014N23 gene | −0.8444889 | 0.5112662 | 1.3557551 | −0.8444889 |
| Ndufa9 | 0.005276035 | ENSMUSG00000000399 | NADH dehydrogenase (ubiquinone) | −0.843957 | 5.205218 | 6.049175 | −0.843957 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Nr4a2 | 0.012531522 | ENSMUSG00000026826 | 1 alpha subcomplex, 9 nuclear receptor subfamily 4, group A, member 2 | −0.8424864 | 1.1121702 | 1.9546566 | −0.8424864 |
| Gm20422 | 0.032568794 | ENSMUSG00000092544 | predicted gene 20422 | −0.8424863 | −0.0033069 | 0.83917946 | −0.8424863 |
| Map2k6 | 0.02493559 | ENSMUSG00000020623 | mitogen-activated protein kinase kinase 6 | −0.8424863 | −1.5882694 | −0.7457831 | −0.8424863 |
| Ulk1 | 0.02368065 | ENSMUSG00000029512 | Unc-51 like kinase 1 (*C. elegans*) | −0.8396657 | 2.6043756 | 3.4440413 | −0.8396657 |
| Slc39a3 | 0.01765952 | ENSMUSG00000046822 | solute carrier family 39 (zinc transporter), member 3 | −0.8366098 | 1.9619277 | 2.7985375 | −0.8366098 |
| Tbc1d23 | 0.022578219 | ENSMUSG00000022749 | TBC1 domain family, member 23 | −0.8355326 | 5.4475117 | 6.2830443 | −0.8355326 |
| Commd7 | 0.023516493 | ENSMUSG00000056941 | COMM domain containing 7 | −0.8331583 | 3.7233167 | 4.556475 | −0.8331583 |
| Gm6410 | 0.046976738 | ENSMUSG00000090435 | predicted gene 6410 | −0.8304137 | −2.0736964 | −1.2432827 | −0.8304137 |
| 1110032A03Rik | 0.019316237 | ENSMUSG00000037971 | RIKEN cDNA 1110032A03 gene | −0.8304134 | −0.0736962 | 0.7567172 | −0.8304134 |
| Pias4 | 0.04347021 | ENSMUSG00000004934 | protein inhibitor of activated STAT 4 | −0.8240743 | 2.9352925 | 3.7593668 | −0.8240743 |
| Zkscan4 | 0.02395805 | ENSMUSG00000054931 | zinc finger with KRAB and SCAN domains 4 | −0.8238707 | −0.1102221 | 0.7136486 | −0.8238707 |
| Tlcd2 | 0.02366598 | ENSMUSG00000038217 | TLC domain containing 2 | −0.8175689 | 0.7942001 | 1.611769 | −0.8175689 |
| Rap2a | 0.018936511 | ENSMUSG00000051615 | RAS related protein 2a | −0.8142681 | 2.1357572 | 2.9500253 | −0.8142681 |
| Snx7 | 0.01534647 | ENSMUSG00000028007 | sorting nexin 7 | −0.8141116 | 3.4020374 | 4.216149 | −0.8141116 |
| Nfam1 | 0.011470164 | ENSMUSG00000058099 | Nfat activating molecule with ITAM motif 1 | −0.813933 | 4.460801 | 5.274734 | −0.813933 |
| Paqr3 | 0.025071675 | ENSMUSG00000055725 | progestin and adipoQ receptor family member III | −0.8123367 | 2.7024078 | 3.5147445 | −0.8123367 |
| Orai2-ps | 0.02500956 | ENSMUSG00000090850 | ORAI calcium release-activated calcium modulator 2, pseudogene | −0.8119425 | 3.6838605 | 4.495803 | −0.8119425 |
| Epn2 | 0.017489249 | ENSMUSG00000001036 | epsin 2 | −0.8102112 | 4.6623673 | 5.4725785 | −0.8102112 |
| Bcl7b | 0.035148133 | ENSMUSG00000029681 | B-cell CLL/lymphoma 7B | −0.8095522 | 2.9966931 | 3.8062453 | −0.8095522 |
| 3110056O03Rik | 0.033237558 | ENSMUSG00000035206 | RIKEN cDNA 3110056O03 gene | −0.8087448 | 2.7942002 | 3.602945 | −0.8087448 |
| Mrpl22 | 0.048313465 | ENSMUSG00000020514 | mitochondrial ribosomal protein L22 | −0.8068106 | 1.4623566 | 2.2691672 | −0.8068106 |
| Relt | 0.013668023 | ENSMUSG00000008318 | RELT tumor necrosis factor receptor | −0.8055995 | 2.8664703 | 3.6720698 | −0.8055995 |
| Naaladl1 | 0.043300908 | ENSMUSG00000054999 | N-acetylated alpha-linked | −0.8018445 | −1.4887338 | −0.6868893 | −0.8018445 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| | | | acidic dipeptidase-like 1 | | | | |
| Mtss1l | 0.010499953 | ENSMUSG00000033763 | metastasis suppressor 1-like | −0.8018444 | −2.8106618 | −2.0088174 | −0.8018444 |
| 1600029O15Rik | 0.015520786 | ENSMUSG00000057818 | RIKEN cDNA 1600029O15 gene | −0.8018444 | −3.8106618 | −3.0088174 | −0.8018444 |
| Dao | 0.024370153 | ENSMUSG00000042096 | D-amino acid oxidase | −0.8018444 | −3.8106618 | −3.0088174 | −0.8018444 |
| BC125332 | 0.025244432 | ENSMUSG00000041358 | cDNA sequence BC125332 | −0.8018444 | −3.8106618 | −3.0088174 | −0.8018444 |
| Fat2 | 0.035712436 | ENSMUSG00000055333 | FAT tumor suppressor homolog 2 (*Drosophila*) | −0.8018444 | −3.8106618 | −3.0088174 | −0.8018444 |
| Cabp7 | 0.033022203 | ENSMUSG00000009075 | calcium binding protein 7 | −0.8018443 | −1.8106617 | −1.0088174 | −0.8018443 |
| Gm7353 | 0.019511756 | ENSMUSG00000055452 | predicted pseudogene 7353 | −0.8002038 | 3.6487699 | 4.4489737 | −0.8002038 |
| Rps8-ps1 | 0.014286589 | ENSMUSG00000071303 | ribosomal protein S8, pseudogene 1 | −0.799268 | 6.457295 | 7.256563 | −0.799268 |
| Alcam | 0.02590528 | ENSMUSG00000022636 | activated leukocyte cell adhesion molecule | −0.798258 | 5.32889 | 6.127148 | −0.798258 |
| Fos | 0.044314757 | ENSMUSG00000021250 | FBJ osteosarcoma oncogene | −0.7970984 | 5.28737 | 6.0844684 | −0.7970984 |
| Mtss1 | 0.036628574 | ENSMUSG00000022353 | metastasis suppressor 1 | −0.796156 | 5.59377 | 6.389926 | −0.796156 |
| Pcyox1 | 0.020175328 | ENSMUSG00000029998 | prenylcysteine oxidase 1 | −0.7958059 | 4.2732606 | 5.0690665 | −0.7958059 |
| Rnaseh2c | 0.022177652 | ENSMUSG00000024925 | ribonuclease H2, subunit C | −0.7937506 | 1.7642471 | 2.5579977 | −0.7937506 |
| Tab1 | 0.01681519 | ENSMUSG00000022414 | TGF-beta activated kinase 1/MAP3K7 binding protein 1 | −0.7932696 | 3.2661538 | 4.0594234 | −0.7932696 |
| Rps3 | 0.032059707 | ENSMUSG00000030744 | ribosomal protein S3 | −0.7917607 | 7.8012853 | 8.593046 | −0.7917607 |
| Gm5507 | 0.027941754 | ENSMUSG00000069376 | predicted gene 5507 | −0.7911568 | 5.7220187 | 6.5131755 | −0.7911568 |
| Mrp63 | 0.014859019 | ENSMUSG00000021967 | mitochondrial ribosomal protein 63 | −0.7907952 | 3.1240118 | 3.914807 | −0.7907952 |
| Solh | 0.027924877 | ENSMUSG00000037326 | small optic lobes homolog (*Drosophila*) | −0.7896872 | 3.3492093 | 4.1388965 | −0.7896872 |
| Adamts13 | 0.02814318 | ENSMUSG00000014852 | a disintegrin-like and metallopeptidase (reprolysin type) with thrombospondin type 1 motif, 13 | −0.7888179 | 2.6650715 | 3.4538894 | −0.7888179 |
| Lsm4 | 0.020239143 | ENSMUSG00000031848 | LSM4 homolog, U6 small nuclear RNA associated (*S. cerevisiae*) | −0.7882819 | 3.6071906 | 4.3954725 | −0.7882819 |
| Triobp | 0.014277731 | ENSMUSG00000033088 | TRIO and F-actin binding protein | −0.7874437 | 3.3955383 | 4.182982 | −0.7874437 |
| Gm16156 | 0.012805327 | ENSMUSG00000087436 | predicted gene 16156 | −0.787345 | 1.5112662 | 2.2986112 | −0.787345 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Kcnn4 | 0.024224881 | ENSMUSG00000054342 | potassium intermediate/ small conductance calcium- activated channel, subfamily N, member 4 | −0.784895 | 5.302212 | 6.087107 | −0.784895 |
| Trmt61a | 0.028067956 | ENSMUSG00000060950 | tRNA methyltransferase 61 homolog A (S. cerevisiae) | −0.783203 | 4.398792 | 5.181995 | −0.783203 |
| Tpra1 | 0.032772 | ENSMUSG00000002871 | transmembrane protein, adipocyte asscociated 1 | −0.7817533 | 2.1589644 | 2.9407177 | −0.7817533 |
| Adck4 | 0.028475156 | ENSMUSG00000003762 | aarF domain containing kinase 4 | −0.779902 | 2.9172585 | 3.6971605 | −0.779902 |
| Zfp189 | 0.02446675 | ENSMUSG00000039634 | zinc finger protein 189 | −0.7799019 | 0.3322961 | 1.112198 | −0.7799019 |
| Trak2 | 0.029910393 | ENSMUSG00000026028 | trafficking protein, kinesin binding 2 | −0.778933 | 5.470109 | 6.249042 | −0.778933 |
| Setd4 | 0.039261803 | ENSMUSG00000022948 | SET domain containing 4 | −0.7753723 | 2.0638072 | 2.8391795 | −0.7753723 |
| Ttc38 | 0.015144606 | ENSMUSG00000035944 | tetratricopeptide repeat domain 38 | −0.773416 | 1.54689 | 2.320306 | −0.773416 |
| Ccdc88c | 0.02540553 | ENSMUSG00000021182 | coiled-coil domain containing 88C | −0.7721902 | 3.7842848 | 4.556475 | −0.7721902 |
| Gm10159 | 0.017318606 | ENSMUSG00000069972 | predicted pseudogene 10159 | −0.770136 | 5.800363 | 6.570499 | −0.770136 |
| Aim1 | 0.02232682 | ENSMUSG00000019866 | absent in melanoma 1 | −0.7701057 | 5.5120173 | 6.282123 | −0.7701057 |
| Rab11b | 0.034848575 | ENSMUSG00000077450 | RAB11B, member RAS oncogene family | −0.7691937 | 4.3492093 | 5.118403 | −0.7691937 |
| Leprot | 0.02571553 | ENSMUSG00000035212 | leptin receptor overlapping transcript | −0.7679413 | 3.4654624 | 4.2334037 | −0.7679413 |
| Agap2 | 0.020851009 | ENSMUSG00000025422 | ArfGAP with GTPase domain, ankyrin repeat and PH domain 2 | −0.7653184 | −1.3956243 | −0.6303059 | −0.7653184 |
| Fbxl15 | 0.026200434 | ENSMUSG00000025226 | F-box and leucine-rich repeat protein 15 | −0.7637091 | 0.71290016 | 1.4766093 | −0.7637091 |
| Gm12942 | 0.024523953 | ENSMUSG00000070737 | predicted gene 12942 | −0.7623158 | 0.81382906 | 1.5761449 | −0.7623158 |
| Pts | 0.025246479 | ENSMUSG00000032067 | 6-pyruvoyl- tetrahydropterin synthase | −0.7604849 | 2.1279378 | 2.8884227 | −0.7604849 |
| 1110019D14Rik | 0.027602369 | ENSMUSG00000084931 | RIKEN cDNA 1110019D14 gene | −0.7600241 | −0.0033069 | 0.7567172 | −0.7600241 |
| B230312A22Rik | 0.015634464 | ENSMUSG00000036002 | RIKEN cDNA B230312A22 gene | −0.7591951 | 3.7413666 | 4.5005617 | −0.7591951 |
| Pik3r1 | 0.012770501 | ENSMUSG00000041417 | phosphatidylinositol 3- kinase, regulatory subunit, polypeptide 1 (p85 alpha) | −0.753873 | 4.502221 | 5.256094 | −0.753873 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Plekhh3 | 0.025038777 | ENSMUSG00000035172 | pleckstrin homology domain containing, family H (with MyTH4 domain) member 3 | −0.7507702 | 1.1279377 | 1.8787079 | −0.7507702 |
| Rbm42 | 0.016107807 | ENSMUSG00000036733 | RNA binding motif protein 42 | −0.743897 | 4.178023 | 4.92192 | −0.743897 |
| Gm16287 | 0.029231198 | ENSMUSG00000073739 | predicted gene 16287 | −0.7429509 | −3.0736964 | −2.3307455 | −0.7429509 |
| Psd2 | 0.024929984 | ENSMUSG00000024347 | pleckstrin and Sec7 domain containing 2 | −0.7429507 | −1.4887338 | −0.7457831 | −0.7429507 |
| Cyb561d1 | 0.019253794 | ENSMUSG00000048796 | cytochrome b-561 domain containing 1 | −0.7429507 | 3.2838557 | 4.0268064 | −0.7429507 |
| Mob2 | 0.022150464 | ENSMUSG00000025147 | MOB kinase activator 2 | −0.7429507 | 3.0348282 | 3.7777789 | −0.7429507 |
| 5830415F09Rik | 0.02634874 | ENSMUSG00000028331 | RIKEN cDNA 5830415F09 gene | −0.7429506 | 0.24823192 | 0.9911825 | −0.7429506 |
| AK157302 | 0.03351777 | ENSMUSG00000078139 | cDNA sequence AK157302 | −0.7418299 | 4.2572207 | 4.9990506 | −0.7418299 |
| Gm10154 | 0.026876133 | ENSMUSG00000066116 | predicted gene 10154 | −0.733413 | 6.259459 | 6.992872 | −0.733413 |
| Thap11 | 0.032562416 | ENSMUSG00000036442 | THAP domain containing 11 | −0.7276657 | 3.342468 | 4.0701337 | −0.7276657 |
| Ethe1 | 0.027350841 | ENSMUSG00000064254 | ethylmalonic encephalopathy 1 | −0.7267101 | 1.6704649 | 2.397175 | −0.7267101 |
| Rps26-ps1 | 0.041135248 | ENSMUSG00000059775 | ribosomal protein S26, pseudogene 1 | −0.7250665 | 5.626744 | 6.3518105 | −0.7250665 |
| Zfp523 | 0.021875188 | ENSMUSG00000024220 | zinc finger protein 523 | −0.7216739 | 1.3987916 | 2.1204655 | −0.7216739 |
| Klhl9 | 0.04047058 | ENSMUSG00000070923 | kelch-like 9 (Drosophila) | −0.7213396 | 4.7528524 | 5.474192 | −0.7213396 |
| Tmem198 | 0.024651697 | ENSMUSG00000051703 | transmembrane protein 198 | −0.7209243 | −0.3512302 | 0.3696941 | −0.7209243 |
| Rps8 | 0.04837038 | ENSMUSG00000047675 | ribosomal protein S8 | −0.7206627 | 6.4615793 | 7.182242 | −0.7206627 |
| Nudt13 | 0.026868425 | ENSMUSG00000021809 | nudix (nucleoside diphosphate linked moiety X)-type motif 13 | −0.7203802 | 1.8617636 | 2.5821438 | −0.7203802 |
| Psmb5 | 0.038760804 | ENSMUSG00000022193 | proteasome (prosome, macropain) subunit, beta type 5 | −0.720298 | 4.597314 | 5.317612 | −0.720298 |
| Polr2e | 0.0348101 | ENSMUSG00000004667 | polymerase (RNA) II (DNA directed) polypeptide E | −0.7191351 | 3.5142686 | 4.2334037 | −0.7191351 |
| Comt | 0.015054342 | ENSMUSG00000000326 | catechol-O-methyltransferase | −0.7187031 | 3.4181569 | 4.13686 | −0.7187031 |
| Fam100a | 0.021507928 | ENSMUSG00000039568 | family with sequence similarity 100, member A | −0.7178386 | 2.8186948 | 3.5365334 | −0.7178386 |
| Dusp28 | 0.011824952 | ENSMUSG00000047067 | dual specificity phosphatase 28 | −0.7169556 | 0.2190855 | 0.93604106 | −0.7169556 |
| 5730528L13Rik | 0.033186235 | ENSMUSG00000039693 | RIKEN cDNA 5730528L13 gene | −0.7158044 | 1.4372658 | 2.1530702 | −0.7158044 |
| Fbxl6 | 0.036996942 | ENSMUSG00000022559 | F-box and leucine-rich | −0.7127183 | 3.9508893 | 4.6636076 | −0.7127183 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Lrrc33 | 0.03724786 | ENSMUSG00000052384 | repeat protein 6 leucine rich repeat containing 33 | −0.7122502 | 5.7997475 | 6.5119977 | −0.7122502 |
| Pik3ca | 0.040598534 | ENSMUSG00000027665 | phosphatidylinositol 3-kinase, catalytic, alpha polypeptide | −0.712027 | 4.800363 | 5.51239 | −0.712027 |
| Sppl3 | 0.04645074 | ENSMUSG00000029550 | signal peptide peptidase 3 | −0.7106166 | 5.065855 | 5.7764716 | −0.7106166 |
| Rgs1 | 0.017007569 | ENSMUSG00000026358 | regulator of G-protein signaling 1 | −0.7068314 | 3.6971326 | 4.403964 | −0.7068314 |
| Gcap14 | 0.025004745 | ENSMUSG00000058690 | granule cell antiserum positive 14 | −0.706376 | 4.172332 | 4.878708 | −0.706376 |
| Rabgef1 | 0.045662638 | ENSMUSG00000025340 | RAB guanine nucleotide exchange factor (GEF) 1 | −0.705021 | 4.49464 | 5.199661 | −0.705021 |
| Vti1b | 0.029425714 | ENSMUSG00000021124 | vesicle transport through interaction with t-SNAREs 1B homolog | −0.7047739 | 6.4313216 | 7.1360955 | −0.7047739 |
| Pter | 0.029844783 | ENSMUSG00000026730 | phosphotriesterase related | −0.7043781 | 3.2410004 | 3.9453785 | −0.7043781 |
| Lrmp | 0.024810746 | ENSMUSG00000030263 | lymphoid-restricted membrane protein | −0.7032047 | 5.2572207 | 5.9604254 | −0.7032047 |
| Exoc7 | 0.024444766 | ENSMUSG00000020792 | exocyst complex component 7 | −0.7030464 | 3.73108 | 4.4341264 | −0.7030464 |
| 2400003C14Rik | 0.047920387 | ENSMUSG00000031729 | RIKEN cDNA 2400003C14 gene | −0.7017847 | 5.6838603 | 6.385645 | −0.7017847 |
| Gm8112 | 0.040240075 | ENSMUSG00000074859 | predicted gene 8112 | −0.6999323 | 3.3659267 | 4.065859 | −0.6999323 |
| Tjp3 | 0.023516202 | ENSMUSG00000034917 | tight junction protein 3 | −0.6987509 | 0.4623566 | 1.1611075 | −0.6987509 |
| Park7 | 0.040839158 | ENSMUSG00000028964 | Parkinson disease (autosomal recessive, early onset) 7 | −0.6974029 | 5.5694385 | 6.2668414 | −0.6974029 |
| Gm10063 | 0.036025446 | ENSMUSG00000059333 | predicted gene 10063 | −0.6958537 | 4.7743006 | 5.4701543 | −0.6958537 |
| Gm6788 | 0.020853998 | ENSMUSG00000090737 | predicted gene 6788 | −0.6952334 | 3.1161282 | 3.8113616 | −0.6952334 |
| Nmnat1 | 0.023781195 | ENSMUSG00000028992 | nicotinamide nucleotide adenylyltransferase 1 | −0.6944067 | 2.0137668 | 2.7081735 | −0.6944067 |
| Tbc1d10b | 0.039930627 | ENSMUSG00000042492 | TBC1 domain family, member 10b | −0.694137 | 5.522494 | 6.216631 | −0.694137 |
| Parp3 | 0.03246012 | ENSMUSG00000023249 | poly (ADP-ribose) polymerase family, member 3 | −0.6925622 | 2.535113 | 3.2276752 | −0.6925622 |
| Vps52 | 0.018454367 | ENSMUSG00000024319 | vacuolar protein sorting 52 (yeast) | −0.6916389 | 4.8355966 | 5.5272355 | −0.6916389 |
| Rps26 | 0.047893744 | ENSMUSG00000025362 | ribosomal protein S26 | −0.6903605 | 5.5454235 | 6.235784 | −0.6903605 |
| Immt | 0.030641051 | ENSMUSG00000052337 | inner membrane | −0.6881917 | 6.283416 | 6.9716077 | −0.6881917 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Adap2 | 0.040307727 | ENSMUSG00000020709 | protein, mitochondrial ArfGAP with dual PH domains 2 | −0.6863671 | −1.6951845 | −1.0088174 | −0.6863671 |
| Vps39 | 0.035322167 | ENSMUSG00000027291 | vacuolar protein sorting 39 (yeast) | −0.6844366 | 4.9988384 | 5.683275 | −0.6844366 |
| Fuca2 | 0.043429524 | ENSMUSG00000019810 | fucosidase, alpha-L-2, plasma | −0.6837888 | 4.6971326 | 5.3809214 | −0.6837888 |
| Dynlrb1 | 0.030277705 | ENSMUSG00000047459 | dynein light chain roadblock-type 1 | −0.6834495 | 2.2337322 | 2.9171817 | −0.6834495 |
| Mmgt2 | 0.04851589 | ENSMUSG00000048497 | membrane magnesium transporter 2 | −0.681381 | 4.133806 | 4.815187 | −0.681381 |
| Zfpl1 | 0.040050752 | ENSMUSG00000024792 | zinc finger like protein 1 | −0.6790388 | 3.1551225 | 3.8341613 | −0.6790388 |
| Gm20457 | 0.036167003 | ENSMUSG00000092187 | predicted gene 20457 | −0.6786962 | 0.64876974 | 1.3274659 | −0.6786962 |
| Fam82b | 0.048664004 | ENSMUSG00000028229 | family with sequence similarity 82, member B | −0.6786962 | 0.64876974 | 1.3274659 | −0.6786962 |
| H2-Eb1 | 0.037901763 | ENSMUSG00000060586 | histocompatibility 2, class II antigen E beta | −0.6778556 | −1.3081615 | −0.6303059 | −0.6778556 |
| Blvra | 0.0474667 | ENSMUSG00000001999 | biliverdin reductase A | −0.6718913 | 3.8475497 | 4.519441 | −0.6718913 |
| Srcrb4d | 0.0354348 | ENSMUSG00000029699 | scavenger receptor cysteine rich domain containing, group B (4 domains) | −0.6675433 | −0.6407369 | 0.02680641 | −0.6675433 |
| Glud1 | 0.04627992 | ENSMUSG00000021794 | glutamate dehydrogenase 1 | −0.6664464 | 6.44082 | 7.1072664 | −0.6664464 |
| Fdx1l | 0.04709346 | ENSMUSG00000079677 | ferredoxin 1-like | −0.6660187 | 4.133806 | 4.7998247 | −0.6660187 |
| 2610318N02Rik | 0.027701477 | ENSMUSG00000049916 | RIKEN cDNA 2610318N02 gene | −0.6646384 | 1.2042885 | 1.8689269 | −0.6646384 |
| Cbara1 | 0.025856437 | ENSMUSG00000020111 | calcium binding atopy-related autoantigen 1 | −0.6626866 | 4.2838554 | 4.946542 | −0.6626866 |
| AI837181 | 0.037062764 | ENSMUSG00000047423 | expressed sequence AI837181 | −0.6597565 | 2.7842848 | 3.4440413 | −0.6597565 |
| Agk | 0.028081048 | ENSMUSG00000029916 | acylglycerol kinase | −0.6595563 | 2.813829 | 3.4733853 | −0.6595563 |
| Slc44a2 | 0.027341165 | ENSMUSG00000057193 | solute carrier family 44, member 2 | −0.6587429 | 3.1627963 | 3.8215392 | −0.6587429 |
| Atp6v0d1 | 0.02142147 | ENSMUSG00000013160 | ATPase, H+ transporting, lysosomal V0 subunit D1 | −0.6567502 | 6.2455244 | 6.9022746 | −0.6567502 |
| Adat3 | 0.0407096 | ENSMUSG00000035370 | adenosine deaminase, tRNA-specific 3, TAD2 homolog (S. cerevisiae) | −0.6546907 | 1.2337323 | 1.888423 | −0.6546907 |
| Dlx4 | 0.029477518 | ENSMUSG00000020871 | distal-less homeobox 4 | −0.6498416 | −4.3956246 | −3.745783 | −0.6498416 |
| Fzd9 | 0.030664086 | ENSMUSG00000049551 | frizzled homolog 9 (Drosophila) | −0.6498416 | −4.3956246 | −3.745783 | −0.6498416 |
| Gm13031 | 0.03036407 | ENSMUSG00000087698 | predicted gene 13031 | −0.6498414 | −3.3956244 | −2.745783 | −0.6498414 |
| Jag2 | 0.041047707 | ENSMUSG00000002799 | jagged 2 | −0.6498413 | −2.0736964 | −1.4238551 | −0.6498413 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Gm5665 | 0.048196785 | ENSMUSG00000074863 | predicted gene 5665 | −0.6498413 | −2.8106618 | −2.1608205 | −0.6498413 |
| Cdk18 | 0.035990108 | ENSMUSG00000026437 | cyclin-dependent kinase 18 | −0.6487923 | 5.4451537 | 6.093946 | −0.6487923 |
| Wsb2 | 0.048568413 | ENSMUSG00000029364 | WD repeat and SOCS box-containing 2 | −0.6455825 | 5.747759 | 6.3933415 | −0.6455825 |
| Rpl14 | 0.04038221 | ENSMUSG00000025794 | ribosomal protein L14 | −0.645187 | 6.155603 | 6.80079 | −0.645187 |
| Gm11457 | 0.044966727 | ENSMUSG00000086453 | predicted gene 11457 | −0.6448752 | 1.2042885 | 1.8491637 | −0.6448752 |
| Adck5 | 0.025202971 | ENSMUSG00000022550 | aarF domain containing kinase 5 | −0.6416361 | 3.6514995 | 4.2931356 | −0.6416361 |
| Tmub2 | 0.04888207 | ENSMUSG00000034757 | transmembrane and ubiquitin-like domain containing 2 | −0.6409414 | 2.6865246 | 3.327466 | −0.6409414 |
| Atp5l-ps1 | 0.033605512 | ENSMUSG00000072460 | ATP synthase, H+ transporting, mitochondrial F0 complex, subunit g, pseudogene 1 | −0.6403808 | 3.2768009 | 3.9171817 | −0.6403808 |
| Rgs16 | 0.04644141 | ENSMUSG00000026475 | regulator of G-protein signaling 16 | −0.639681 | 4.759194 | 5.398875 | −0.639681 |
| Rpl21-ps14 | 0.04064617 | ENSMUSG00000062152 | ribosomal protein L21, pseudogene 14 | −0.6384003 | 3.3254747 | 3.963875 | −0.6384003 |
| Snx11 | 0.046817992 | ENSMUSG00000020876 | sorting nexin 11 | −0.634604 | 3.0514588 | 3.6860628 | −0.634604 |
| Nln | 0.048038434 | ENSMUSG00000021710 | neurolysin (metallopeptidase M3 family) | −0.6335058 | 4.5365906 | 5.1700964 | −0.6335058 |
| Acss2 | 0.039891824 | ENSMUSG00000027605 | acyl-CoA synthetase short-chain family member 2 | −0.6298728 | 3.2042885 | 3.8341613 | −0.6298728 |
| Gm16744 | 0.04230707 | ENSMUSG00000086002 | predicted gene, 16744 | −0.6287797 | −0.8720624 | −0.2432828 | −0.6287797 |
| 1110051M20Rik | 0.042616416 | ENSMUSG00000040591 | RIKEN cDNA 1110051M20 gene | −0.627511 | 4.2536316 | 4.8811426 | −0.627511 |
| Rab1b | 0.042926516 | ENSMUSG00000024870 | RAB1B, member RAS oncogene family | −0.6267397 | 5.902438 | 6.5291777 | −0.6267397 |
| Ndufs5 | 0.027461376 | ENSMUSG00000028648 | NADH dehydrogenase (ubiquinone) Fe—S protein 5 | −0.6264772 | 1.979415 | 2.6058922 | −0.6264772 |
| Tmem42 | 0.034604322 | ENSMUSG00000066233 | transmembrane protein 42 | −0.6259945 | 1.535113 | 2.1611075 | −0.6259945 |
| Mapkapk2 | 0.03941688 | ENSMUSG00000016528 | MAP kinase-activated protein kinase 2 | −0.6252842 | 6.7155113 | 7.3407955 | −0.6252842 |
| Stambpl1 | 0.035237126 | ENSMUSG00000024776 | STAM binding protein like 1 | −0.6250782 | 5.4197593 | 6.0448375 | −0.6250782 |
| Pgam2 | 0.039034486 | ENSMUSG00000020475 | phosphoglycerate mutase 2 | −0.6243063 | −1.1476969 | −0.5233907 | −0.6243063 |
| Fam160b1 | 0.04417353 | ENSMUSG00000033478 | family with sequence similarity 160, member B1 | −0.6238462 | 3.7336588 | 4.357505 | −0.6238462 |
| Ttll12 | 0.048118092 | ENSMUSG00000016757 | tubulin tyrosine ligase-like | −0.6235144 | 4.5365906 | 5.160105 | −0.6235144 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Nudt15 | 0.033909168 | ENSMUSG00000033405 | nudix (nucleoside diphosphate linked moiety X)-type motif 15 family, member 12 | −0.6220963 | 1.7336587 | 2.355755 | −0.6220963 |
| Tram2 | 0.049381044 | ENSMUSG00000041779 | translocating chain-associating membrane protein 2 | −0.6220071 | 1.8989964 | 2.5210035 | −0.6220071 |
| Ociad2 | 0.0425186 | ENSMUSG00000029153 | OCIA domain containing 2 | −0.6212722 | −1.3081615 | −0.6868893 | −0.6212722 |
| Bloc1s3 | 0.04529189 | ENSMUSG00000057667 | biogenesis of lysosome-related organelles complex-1, subunit 3 | −0.620094 | 2.2190855 | 2.8391795 | −0.620094 |
| Rassf1 | 0.037896954 | ENSMUSG00000010067 | Ras association (RalGDS/AF-6) domain family member 1 | −0.6198733 | 3.4309242 | 4.0507975 | −0.6198733 |
| Sntb2 | 0.038723968 | ENSMUSG00000041308 | syntrophin, basic 2 | −0.619171 | 4.99991 | 5.619081 | −0.619171 |
| Kcnab2 | 0.037089523 | ENSMUSG00000028931 | potassium voltage-gated channel, shaker-related subfamily, beta member 2 | −0.6191615 | 4.422958 | 5.0421195 | −0.6191615 |
| Rragc | 0.04885698 | ENSMUSG00000028646 | Ras-related GTP binding C | −0.6159734 | 6.085671 | 6.7016444 | −0.6159734 |
| Irf3 | 0.038443018 | ENSMUSG00000003184 | interferon regulatory factor 3 | −0.615951 | 3.2554274 | 3.8713784 | −0.615951 |
| 3110043O21Rik | 0.046679143 | ENSMUSG00000028300 | RIKEN cDNA 3110043O21 gene | −0.6140154 | 5.588082 | 6.2020974 | −0.6140154 |
| Tnfaip8 | 0.036621507 | ENSMUSG00000062210 | tumor necrosis factor, alpha-induced protein 8 | −0.613772 | 4.529188 | 5.14296 | −0.613772 |
| Dscr3 | 0.034768607 | ENSMUSG00000022898 | Down syndrome critical region gene 3 | −0.6132714 | 4.3169026 | 4.930174 | −0.6132714 |
| Ppp1r16a | 0.034497265 | ENSMUSG00000033819 | protein phosphatase 1, regulatory (inhibitor) subunit 16A | −0.6129417 | 3.6487699 | 4.2617116 | −0.6129417 |
| Rpl17-ps3 | 0.041614436 | ENSMUSG00000069392 | ribosomal protein L17, pseudogene 3 | −0.609239 | 6.650135 | 7.259374 | −0.609239 |
| 5430403G16Rik | 0.04923931 | ENSMUSG00000072763 | RIKEN cDNA 5430403G16 gene | −0.6085005 | 0.4870187 | 1.0955192 | −0.6085005 |
| Mpst | 0.04476959 | ENSMUSG00000071711 | mercaptopyruvate sulfurtransferase | −0.6077339 | 2.2264276 | 2.8341615 | −0.6077339 |
| Rab14 | 0.04740811 | ENSMUSG00000026878 | RAB14, member RAS oncogene family | −0.6071036 | 6.0426474 | 6.649751 | −0.6071036 |
| Rtkn | 0.04634605 | ENSMUSG00000034930 | rhotekin | −0.6054473 | −1.9361928 | −1.3307455 | −0.6054473 |
| Gm11788 | 0.048462883 | ENSMUSG00000086929 | predicted gene 11788 | −0.6054473 | −1.9361928 | −1.3307455 | −0.6054473 |
| BC024978 | 0.045672644 | ENSMUSG00000078786 | cDNA sequence BC024978 | −0.605103 | 2.6377988 | 3.2429018 | −0.605103 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
| --- | --- | --- | --- | --- | --- | --- | --- |
| Tmem86b | 0.042776905 | ENSMUSG00000045282 | transmembrane protein 86B | −0.603745 | 0.3322961 | 0.93604106 | −0.603745 |
| 2510039O18Rik | 0.03078932 | ENSMUSG00000044496 | RIKEN cDNA 2510039O18 gene | −0.601857 | 5.210781 | 5.812638 | −0.601857 |
| Ankmy2 | 0.038953494 | ENSMUSG00000036188 | ankyrin repeat and MYND domain containing 2 | −0.6018472 | 2.9531038 | 3.554951 | −0.6018472 |
| Txndc11 | 0.026081089 | ENSMUSG00000022498 | thioredoxin domain containing 11 | −0.6013887 | 4.539541 | 5.1409297 | −0.6013887 |
| Nhp2 | 0.047920577 | ENSMUSG00000001056 | NHP2 ribonucleoprotein homolog (yeast) | −0.601229 | 4.57879 | 5.180019 | −0.601229 |
| Oxa1l | 0.044693552 | ENSMUSG00000000959 | oxidase assembly 1-like | −0.6010437 | 4.9848366 | 5.5858803 | −0.6010437 |
| Plcb3 | 0.040368132 | ENSMUSG00000024960 | phospholipase C, beta 3 | −0.5995494 | 4.0962286 | 4.695778 | −0.5995494 |
| Mylip | 0.040585697 | ENSMUSG00000038175 | myosin regulatory light chain interacting protein | −0.5987937 | 2.9531038 | 3.5518975 | −0.5987937 |
| Psmd5 | 0.047061477 | ENSMUSG00000026869 | proteasome (prosome, macropain) 26S subunit, non-ATPase, 5 | −0.5970666 | 5.0473194 | 5.644386 | −0.5970666 |
| Gss | 0.049137637 | ENSMUSG00000027610 | glutathione synthetase | −0.5966295 | 4.0922155 | 4.688845 | −0.5966295 |
| Grin1 | 0.04237296 | ENSMUSG00000026959 | glutamate receptor, ionotropic, NMDA1 (zeta 1) | −0.5953935 | −2.2256994 | −1.6303059 | −0.5953935 |
| Rpl17 | 0.000773 | ENSMUSG00000062328 | ribosomal protein L17 | −0.5925903 | 6.0826397 | 6.67523 | −0.5925903 |
| Rab5b | 0.041810345 | ENSMUSG00000000711 | RAB5B, member RAS oncogene family | −0.5925451 | 4.6446652 | 5.2372103 | −0.5925451 |
| Kat2b | 0.048757337 | ENSMUSG00000000708 | K(lysine) acetyltransferase 2B | −0.5910521 | 3.1893382 | 3.7803903 | −0.5910521 |
| Rrbp1 | 0.04895402 | ENSMUSG00000027422 | ribosome binding protein 1 | −0.5907982 | 6.131364 | 6.7221622 | −0.5907982 |
| Serpinb9b | 0.046480495 | ENSMUSG00000021403 | serine (or cysteine) peptidase inhibitor, clade B, member 9b | −0.5884407 | −1.3956243 | −0.8071836 | −0.5884407 |
| BC030307 | 0.045264874 | ENSMUSG00000044937 | cDNA sequence BC030307 | −0.5857109 | 0.12793766 | 0.7136486 | −0.5857109 |
| Pcyt2 | 0.04845 | ENSMUSG00000025137 | phosphate cytidylyltransferase 2, ethanolamine | −0.585105 | 4.362599 | 4.947704 | −0.585105 |
| Map2k7 | 0.047179256 | ENSMUSG00000002948 | mitogen-activated protein kinase kinase 7 | −0.4015106 | 5.2838554 | 5.685366 | −0.4015106 |
| Fbxo33 | 0.044220295 | ENSMUSG00000035329 | F-box protein 33 | 1.066019 | 5.693826 | 4.627807 | 1.066019 |
| Adam15 | 0.049121536 | ENSMUSG00000028041 | a disintegrin and metallopeptidase domain 15 (metargidin) | 1.1044345 | 6.393909 | 5.2894745 | 1.1044345 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Slc25a33 | 0.04958606 | ENSMUSG00000028982 | solute carrier family 25, member 33 | 1.1154347 | 4.7272034 | 3.6117687 | 1.1154347 |
| Lilrb4 | 0.044434078 | ENSMUSG00000062593 | leukocyte immunoglobulin-like receptor, subfamily B, member 4 | 1.1315183 | 5.5951886 | 4.4636703 | 1.1315183 |
| Phgdh | 0.043934878 | ENSMUSG00000053398 | 3-phosphoglycerate dehydrogenase | 1.1419146 | 8.229285 | 7.0873704 | 1.1419146 |
| Itgam | 0.04708623 | ENSMUSG00000030786 | integrin alpha M | 1.1575141 | 6.4313216 | 5.2738075 | 1.1575141 |
| Papd7 | 0.045507006 | ENSMUSG00000034575 | PAP associated domain containing 7 | 1.1577465 | 5.6149035 | 4.457157 | 1.1577465 |
| Slc2a3 | 0.048934277 | ENSMUSG00000003153 | solute carrier family 2 (facilitated glucose transporter), member 3 | 1.1751518 | 4.8415856 | 3.6664338 | 1.1751518 |
| Rin2 | 0.043170445 | ENSMUSG00000001768 | Ras and Rab interactor 2 | 1.2039381 | 4.8331943 | 3.6292562 | 1.2039381 |
| Sorl1 | 0.038947 | ENSMUSG00000049313 | sortilin-related receptor, LDLR class A repeats-containing | 1.2207785 | 5.069942 | 3.8491635 | 1.2207785 |
| Tlr2 | 0.043592107 | ENSMUSG00000027995 | toll-like receptor 2 | 1.225015 | 6.882244 | 5.657229 | 1.225015 |
| Mycn | 0.040442508 | ENSMUSG00000037169 | v-myc myelocytomatosis viral related oncogene, neuroblastoma derived (avian) | 1.2253772 | 7.345843 | 6.1204658 | 1.2253772 |
| Ifi203 | 0.0450752 | ENSMUSG00000039997 | interferon activated gene 203 | 1.2263527 | 5.3914623 | 4.1651096 | 1.2263527 |
| Psph | 0.047209337 | ENSMUSG00000029446 | phosphoserine phosphatase | 1.2327685 | 5.4157505 | 4.182982 | 1.2327685 |
| Tcof1 | 0.044333804 | ENSMUSG00000024613 | Treacher Collins Franceschetti syndrome 1, homolog | 1.2456369 | 6.1352696 | 4.8896327 | 1.2456369 |
| Adar | 0.03601896 | ENSMUSG00000027951 | adenosine deaminase, RNA-specific | 1.266367 | 6.79049 | 5.524123 | 1.266367 |
| Ogfr | 0.02613318 | ENSMUSG00000049401 | opioid growth factor receptor | 1.2672534 | 5.8403897 | 4.5731363 | 1.2672534 |
| Nfkbid | 0.030824393 | ENSMUSG00000036931 | nuclear factor of kappa light polypeptide gene enhancer in B-cells inhibitor, delta | 1.2704837 | 5.5672717 | 4.296788 | 1.2704837 |
| Gm6736 | 0.024999972 | ENSMUSG00000071414 | predicted gene 6736 | 1.2907186 | 8.271154 | 6.9804354 | 1.2907186 |
| Fads2 | 0.026953876 | ENSMUSG00000024665 | fatty acid desaturase 2 | 1.3091817 | 5.6204877 | 4.311306 | 1.3091817 |
| E330016A19Rik | 0.042681493 | ENSMUSG00000032344 | RIKEN cDNA E330016A19 gene | 1.3128021 | 4.629515 | 3.3167129 | 1.3128021 |
| Bcat1 | 0.039503414 | ENSMUSG00000030268 | branched chain | 1.3130115 | 7.048355 | 5.7353435 | 1.3130115 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Sh3bp5 | 0.02677949 | ENSMUSG00000021892 | aminotransferase 1, cytosolic SH3-domain binding protein 5 (BTK-associated) | 1.3191829 | 4.8307877 | 3.5116048 | 1.3191829 |
| Ncf1 | 0.033802066 | ENSMUSG00000015950 | neutrophil cytosolic factor 1 | 1.3297525 | 6.17518 | 4.8454275 | 1.3297525 |
| Clec5a | 0.03368596 | ENSMUSG00000029915 | C-type lectin domain family 5, member a | 1.3339666 | 5.980501 | 4.6465344 | 1.3339666 |
| Tnip3 | 0.046092596 | ENSMUSG00000044162 | TNFAIP3 interacting protein 3 | 1.35819 | 5.035873 | 3.677683 | 1.35819 |
| Fam129a | 0.038229138 | ENSMUSG00000026483 | family with sequence similarity 129, member A | 1.358445 | 4.789251 | 3.430806 | 1.358445 |
| 4731419I09Rik | 0.031881414 | ENSMUSG00000091513 | RIKEN cDNA 4731419I09 gene | 1.3631143 | 5.4396367 | 4.0765224 | 1.3631143 |
| Stom | 0.028415862 | ENSMUSG00000026880 | stomatin | 1.386817 | 5.465462 | 4.078645 | 1.386817 |
| Adam17 | 0.012626361 | ENSMUSG00000052593 | a disintegrin and metallopeptidase domain 17 | 1.3891568 | 6.7518983 | 5.3627415 | 1.3891568 |
| Psat1 | 0.047628995 | ENSMUSG00000024640 | phosphoserine aminotransferase 1 | 1.401087 | 8.7339 | 7.332813 | 1.401087 |
| Zw10 | 0.020814842 | ENSMUSG00000032264 | ZW10 homolog (*Drosophila*), centromere/kinetochore protein | 1.423672 | 5.65898 | 4.235308 | 1.423672 |
| Ripk2 | 0.035168238 | ENSMUSG00000041135 | receptor (TNFRSF)-interacting serine-threonine kinase 2 | 1.427343 | 4.539541 | 3.112198 | 1.427343 |
| Pcyox1l | 0.027063185 | ENSMUSG00000024579 | prenylcysteine oxidase 1 like | 1.4283414 | 3.8186948 | 2.3903534 | 1.4283414 |
| Rbpsuhrs3 | 0.018088786 | ENSMUSG00000079575 | recombining binding protein suppressor of hairless (*Drosophila*), related sequence 3 | 1.4293184 | 6.848442 | 5.4191236 | 1.4293184 |
| Cd74 | 0.0275401 | ENSMUSG00000024610 | CD74 antigen (invariant polypeptide of major histocompatibility complex, class II antigen-associated) | 1.4491129 | 7.1620784 | 5.7129655 | 1.4491129 |
| Clec4e | 0.03084233 | ENSMUSG00000030142 | C-type lectin domain family 4, member e | 1.4540292 | 3.8781712 | 2.424142 | 1.4540292 |
| Sash1 | 0.020445129 | ENSMUSG00000015305 | SAM and SH3 domain containing 1 | 1.4577389 | 4.98808 | 3.5303411 | 1.4577389 |
| Parp12 | 0.016752578 | ENSMUSG00000038507 | poly (ADP-ribose) polymerase family, member 12 | 1.4689444 | 6.2917514 | 4.822807 | 1.4689444 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Daam1 | 0.014327282 | ENSMUSG00000034574 | dishevelled associated activator of morphogenesis 1 | 1.4692431 | 5.6343527 | 4.1651096 | 1.4692431 |
| Gm15645 | 0.04660924 | ENSMUSG00000086414 | predicted gene 15645 | 1.4707485 | 5.332296 | 3.8615475 | 1.4707485 |
| Mt2 | 0.021577373 | ENSMUSG00000031762 | metallothionein 2 | 1.4811826 | 3.8851466 | 2.403964 | 1.4811826 |
| Slfn4 | 0.020475224 | ENSMUSG00000000204 | schlafen 4 | 1.4817953 | 6.2803326 | 4.7985373 | 1.4817953 |
| Rbpj | 0.036361992 | ENSMUSG00000039191 | recombination signal binding protein for immunoglobulin kappa J region | 1.4903395 | 7.8968415 | 6.406502 | 1.4903395 |
| Ptplb | 0.019518027 | ENSMUSG00000035376 | protein tyrosine phosphatase-like (proline instead of catalytic arginine), member b | 1.4923386 | 4.991316 | 3.4989774 | 1.4923386 |
| Asph | 0.026277151 | ENSMUSG00000028207 | aspartate-beta-hydroxylase | 1.4966014 | 7.1630354 | 5.666434 | 1.4966014 |
| Spata13 | 0.01995978 | ENSMUSG00000021990 | spermatogenesis associated 13 | 1.500841 | 5.070962 | 3.570121 | 1.500841 |
| Gp49a | 0.01797235 | ENSMUSG00000089672 | glycoprotein 49 A | 1.52455 | 5.52696 | 4.00241 | 1.52455 |
| Glrx | 0.020311931 | ENSMUSG00000021591 | glutaredoxin | 1.5271039 | 3.8758385 | 2.3487346 | 1.5271039 |
| Slc6a4 | 0.015190769 | ENSMUSG00000020838 | solute carrier family 6 (neurotransmitter transporter, serotonin), member 4 | 1.5354503 | 6.4502573 | 4.914807 | 1.5354503 |
| Setdb2 | 0.023574898 | ENSMUSG00000071350 | SET domain, bifurcated 2 | 1.5376244 | 4.5600257 | 3.0224013 | 1.5376244 |
| Eif2ak2 | 0.00837484 | ENSMUSG00000024079 | eukaryotic translation initiation factor 2-alpha kinase 2 | 1.551614 | 6.850225 | 5.298611 | 1.551614 |
| Stat2 | 0.022812009 | ENSMUSG00000040033 | signal transducer and activator of transcription 2 | 1.5807465 | 4.598729 | 3.0179825 | 1.5807465 |
| Herpud1 | 0.009253571 | ENSMUSG00000031770 | homocysteine-inducible, endoplasmic reticulum stress-inducible, ubiquitin-like domain member 1 | 1.58482 | 5.684527 | 4.099707 | 1.58482 |
| Tmem2 | 0.01044533 | ENSMUSG00000024754 | transmembrane protein 2 | 1.585879 | 6.534744 | 4.948865 | 1.585879 |
| Bmf | 0.03913493 | ENSMUSG00000040093 | BCL2 modifying factor | 1.6214382 | 4.1298966 | 2.5084584 | 1.6214382 |
| Mitd1 | 0.020194989 | ENSMUSG00000026088 | MIT, microtubule interacting and transport, domain containing 1 | 1.6276122 | 4.689184 | 3.0615718 | 1.6276122 |
| Slfn3 | 0.017630316 | ENSMUSG00000018986 | schlafen 3 | 1.6345547 | 4.6744967 | 3.039942 | 1.6345547 |
| Tasp1 | 0.017170591 | ENSMUSG00000039033 | taspase, threonine aspartase 1 | 1.6429404 | 4.678517 | 3.0355766 | 1.6429404 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Ifi35 | 0.013708029 | ENSMUSG00000010358 | interferon-induced protein 35 | 1.6526694 | 3.8688183 | 2.2161489 | 1.6526694 |
| Slc11a1 | 0.002501 | ENSMUSG00000026177 | solute carrier family 11 (proton-coupled divalent metal ion transporters), member 1 | 1.6735306 | 5.9848366 | 4.311306 | 1.6735306 |
| Ssh2 | 0.012622531 | ENSMUSG00000037926 | slingshot homolog 2 (Drosophila) | 1.691286 | 5.652862 | 3.961576 | 1.691286 |
| Parp10 | 0.015827406 | ENSMUSG00000063268 | poly (ADP-ribose) polymerase family, member 10 | 1.6941132 | 4.7076635 | 3.0135503 | 1.6941132 |
| Uba7 | 0.016567297 | ENSMUSG00000032596 | ubiquitin-like modifier activating enzyme 7 | 1.7041156 | 4.98808 | 3.2839644 | 1.7041156 |
| Fam49a | 0.014623731 | ENSMUSG00000020589 | family with sequence similarity 49, member A | 1.7116549 | 4.9956193 | 3.2839644 | 1.7116549 |
| Dennd2d | 0.031796068 | ENSMUSG00000027901 | DENN/MADD domain containing 2D | 1.7250655 | 4.427743 | 2.7026775 | 1.7250655 |
| Pld4 | 0.015250916 | ENSMUSG00000052160 | phospholipase D family, member 4 | 1.7269177 | 5.590929 | 3.8640113 | 1.7269177 |
| Fosl1 | 0.03473085 | ENSMUSG00000024912 | fos-like antigen 1 | 1.7354727 | 3.2873702 | 1.5518975 | 1.7354727 |
| Ugcg | 0.015557361 | ENSMUSG00000028381 | UDP-glucose ceramide glucosyltransferase | 1.7373785 | 4.746483 | 3.0091045 | 1.7373785 |
| Slc7a5 | 0.014336524 | ENSMUSG00000040010 | solute carrier family 7 (cationic amino acid transporter, y+ system), member 5 | 1.7564154 | 7.282095 | 5.5256796 | 1.7564154 |
| Odc1 | 0.003826073 | ENSMUSG00000011179 | ornithine decarboxylase, structural 1 | 1.7847224 | 8.635129 | 6.8504066 | 1.7847224 |
| Gch1 | 0.032283947 | ENSMUSG00000037580 | GTP cyclohydrolase 1 | 1.7982392 | 3.3254747 | 1.5272355 | 1.7982392 |
| Slc6a9 | 0.012537855 | ENSMUSG00000028542 | solute carrier family 6 (neurotransmitter transporter, glycine), member 9 | 1.8009172 | 4.5629287 | 2.7620115 | 1.8009172 |
| Phf15 | 0.006952753 | ENSMUSG00000020387 | PHD finger protein 15 | 1.803466 | 6.181804 | 4.378338 | 1.803466 |
| Gpr179 | 0.027233575 | ENSMUSG00000070337 | G protein-coupled receptor 179 | 1.812993 | 3.749034 | 1.936041 | 1.812993 |
| Sp110 | 0.008639846 | ENSMUSG00000070034 | Sp110 nuclear body protein | 1.8445542 | 4.076051 | 2.2314968 | 1.8445542 |
| Tpst1 | 0.032691307 | ENSMUSG00000034118 | protein-tyrosine sulfotransferase 1 | 1.8491342 | 4.3575926 | 2.5084584 | 1.8491342 |
| Qsox1 | 0.007972689 | ENSMUSG00000033684 | quiescin Q6 sulfhydryl oxidase 1 | 1.8776744 | 4.7805486 | 2.9028742 | 1.8776744 |
| Ier3 | 0.014196688 | ENSMUSG00000003541 | immediate early response 3 | 1.890267 | 4.981586 | 3.091319 | 1.890267 |
| Ets2 | 0.006089266 | ENSMUSG00000022895 | E26 avian leukemia | 1.8925752 | 5.7541227 | 3.8615475 | 1.8925752 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Zc3h12c | 0.004831877 | ENSMUSG00000035164 | oncogene 2, 3' domain zinc finger CCCH type containing 12C | 1.8958522 | 6.226885 | 4.3310328 | 1.8958522 |
| Ccdc24 | 0.030835103 | ENSMUSG00000078588 | coiled-coil domain containing 24 | 1.8994296 | 3.6239665 | 1.7245369 | 1.8994296 |
| Plk2 | 0.008188616 | ENSMUSG00000021701 | polo-like kinase 2 (*Drosophila*) | 1.9049172 | 5.0740175 | 3.1691003 | 1.9049172 |
| Stat1 | 0.007773834 | ENSMUSG00000026104 | signal transducer and activator of transcription 1 | 1.9285366 | 5.6984534 | 3.7699168 | 1.9285366 |
| Chac1 | 0.031882036 | ENSMUSG00000027313 | ChaC, cation transport regulator-like 1 (*E. coli*) | 1.9297678 | 3.6758378 | 1.74607 | 1.9297678 |
| Gng2 | 0.035535995 | ENSMUSG00000043004 | guanine nucleotide binding protein (G protein), gamma 2 | 1.9435497 | 3.6128042 | 1.6692545 | 1.9435497 |
| Grap | 0.003583301 | ENSMUSG00000004837 | GRB2-related adaptor protein | 1.9460665 | 6.5101385 | 4.564072 | 1.9460665 |
| Pycr1 | 0.025833854 | ENSMUSG00000025140 | pyrroline-5-carboxylate reductase 1 | 1.95558527 | 2.7541227 | 0.79853743 | 1.95558527 |
| Trim12c | 0.012106774 | ENSMUSG00000057143 | tripartite motif-containing 12C | 1.9593374 | 4.2135544 | 2.254217 | 1.9593374 |
| Clec4d | 0.007304858 | ENSMUSG00000030144 | C-type lectin domain family 4, member d | 1.9701681 | 4.1551223 | 2.1849542 | 1.9701681 |
| Cpd | 0.002164662 | ENSMUSG00000020841 | carboxypeptidase D | 1.990618 | 8.797824 | 6.807206 | 1.990618 |
| Dtx3l | 0.002565308 | ENSMUSG00000049502 | deltex 3-like (*Drosophila*) | 2.010299 | 5.4739695 | 3.4636705 | 2.010299 |
| Car12 | 0.015473221 | ENSMUSG00000032373 | carbonic anyhydrase 12 | 2.0304694 | 4.0306406 | 2.0001712 | 2.0304694 |
| Lrrc17 | 0.006864152 | ENSMUSG00000039883 | leucine rich repeat containing 17 | 2.038969 | 5.394724 | 3.355755 | 2.038969 |
| Gm17549 | 0.002010584 | ENSMUSG00000091543 | predicted gene, 17549 | 2.0470712 | 5.278568 | 3.2314968 | 2.0470712 |
| Fyb | 0.001659938 | ENSMUSG00000022148 | FYN binding protein | 2.0631156 | 6.3173323 | 4.2542167 | 2.0631156 |
| Ccl3 | 0.003072253 | ENSMUSG00000000982 | chemokine (C-C motif) ligand 3 | 2.0781493 | 7.3361187 | 5.2579694 | 2.0781493 |
| Trim5 | 0.028752334 | ENSMUSG00000060441 | tripartite motif-containing 5 | 2.0891548 | 2.9081564 | 0.8190016 | 2.0891548 |
| Dusp2 | 0.001119755 | ENSMUSG00000027368 | dual specificity phosphatase 2 | 2.097596 | 6.005255 | 3.907659 | 2.097596 |
| Lyz1 | 0.001480785 | ENSMUSG00000069515 | lysozyme 1 | 2.1054833 | 5.294374 | 3.1888907 | 2.1054833 |
| Dhrs3 | 0.002936547 | ENSMUSG00000066026 | dehydrogenase/reductase (SDR family) member 3 | 2.1068875 | 4.804048 | 2.6971605 | 2.1068875 |
| Slc1a4 | 0.00929272 | ENSMUSG00000020142 | solute carrier family 1 (glutamate/neutral amino acid transporter), member 4 | 2.1085265 | 4.301343 | 2.1928165 | 2.1085265 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Epsti1 | 0.044788834 | ENSMUSG00000022014 | epithelial stromal interaction 1 (breast) | 2.11605915 | 2.6432946 | 0.52723545 | 2.11605915 |
| H2-T24 | 0.001531115 | ENSMUSG00000053835 | histocompatibility 2, T region locus 24 | 2.1219106 | 5.3534074 | 3.2314968 | 2.1219106 |
| Zc3h12a | 0.001478526 | ENSMUSG00000042677 | zinc finger CCCH type containing 12A | 2.1227481 | 4.1318526 | 2.0091045 | 2.1227481 |
| Sass6 | 0.001012042 | ENSMUSG00000027959 | spindle assembly 6 homolog (C. elegans) | 2.123662 | 6.059703 | 3.936041 | 2.123662 |
| Abcc4 | 0.007724259 | ENSMUSG00000032849 | ATP-binding cassette, sub-family C (CFTR/MRP), member 4 | 2.1336435 | 5.597314 | 3.4636705 | 2.1336435 |
| Mef2c | 0.000477217 | ENSMUSG00000005583 | myocyte enhancer factor 2C | 2.1434676 | 6.121061 | 3.9775934 | 2.1434676 |
| Mpeg1 | 0.000799983 | ENSMUSG00000046805 | macrophage expressed gene 1 | 2.1497637 | 6.5332637 | 4.3835 | 2.1497637 |
| Rnf213 | 0.007161953 | ENSMUSG00000070327 | ring finger protein 213 | 2.15004 | 10.065887 | 7.915847 | 2.15004 |
| Dusp5 | 0.009104466 | ENSMUSG00000034765 | dual specificity phosphatase 5 | 2.1525025 | 3.5082576 | 1.3557551 | 2.1525025 |
| Irf9 | 0.008142755 | ENSMUSG00000002325 | interferon regulatory factor 9 | 2.1531142 | 5.075034 | 2.9219198 | 2.1531142 |
| Tlr9 | 0.007655328 | ENSMUSG00000045322 | toll-like receptor 9 | 2.1671071 | 4.3441563 | 2.1770492 | 2.1671071 |
| Rapgef5 | 0.018954162 | ENSMUSG00000041992 | Rap guanine nucleotide exchange factor (GEF) 5 | 2.177482 | 3.789251 | 1.611769 | 2.177482 |
| Akap5 | 0.001063172 | ENSMUSG00000021057 | A kinase (PRKA) anchor protein 5 | 2.202505 | 5.302212 | 3.099707 | 2.202505 |
| Serpine1 | 0.005375954 | ENSMUSG00000037411 | serine (or cysteine) peptidase inhibitor, clade E, member 1 | 2.204582 | 5.140623 | 2.936041 | 2.204582 |
| Xylt2 | 0.003379382 | ENSMUSG00000020868 | xylosyltransferase II | 2.2256849 | 5.0190606 | 2.7933757 | 2.2256849 |
| Sash3 | 0.000824317 | ENSMUSG00000031101 | SAM and SH3 domain containing 3 | 2.2435947 | 6.8015924 | 4.5579977 | 2.2435947 |
| B4galt6 | 0.0185172 | ENSMUSG00000056124 | UDP-Gal:betaGlcNAc beta 1,4-galactosyltransferase, polypeptide 6 | 2.2701052 | 3.7207193 | 1.4506141 | 2.2701052 |
| Herc6 | 0.012329049 | ENSMUSG00000029798 | hect domain and RLD 6 | 2.2897381 | 3.543955 | 1.2542169 | 2.2897381 |
| Lgals3bp | 0.001605042 | ENSMUSG00000033880 | lectin, galactoside-binding, soluble, 3 binding protein | 2.3190542 | 5.550551 | 3.2314968 | 2.3190542 |
| Slfn5 | 0.001191921 | ENSMUSG00000054404 | schlafen 5 | 2.3321457 | 5.6738253 | 3.3416796 | 2.3321457 |
| Cd52 | 0.035810307 | ENSMUSG00000000682 | CD52 antigen | 2.3386994 | 3.3117347 | 0.9730353 | 2.3386994 |
| Ggta1 | 0.019090641 | ENSMUSG00000035778 | glycoprotein galactosyltransferase alpha 1, 3 | 2.3622925 | 3.8259628 | 1.4636703 | 2.3622925 |
| Tlr7 | 0.02658981 | ENSMUSG00000044583 | toll-like receptor 7 | 2.37990606 | 2.804048 | 0.42414194 | 2.37990606 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Fli1 | 0.007515412 | ENSMUSG000000016087 | Friend leukemia integration 1 | 2.3803927 | 3.9685104 | 1.5881177 | 2.3803927 |
| Oasl1 | 0.000525786 | ENSMUSG000000041827 | 2'-5' oligoadenylate synthetase-like 1 | 2.3906102 | 7.1178565 | 4.7272463 | 2.3906102 |
| Mndal | 0.004260393 | ENSMUSG000000090272 | myeloid nuclear differentiation antigen like | 2.3974011 | 4.5902176 | 2.1928165 | 2.3974011 |
| Gas7 | 0.000438789 | ENSMUSG000000033066 | growth arrest specific 7 | 2.4181176 | 7.49464 | 5.0765224 | 2.4181176 |
| Stab1 | 0.031446114 | ENSMUSG000000042286 | stabilin 1 | 2.4637601 | 3.342468 | 0.8787079 | 2.4637601 |
| Lck | 0.008432007 | ENSMUSG000000000409 | lymphocyte protein tyrosine kinase | 2.47206192 | 2.9486713 | 0.47660938 | 2.47206192 |
| Pdcd1 | 0.024454752 | ENSMUSG000000026285 | programmed cell death 1 | 2.47214922 | 2.813829 | 0.34167978 | 2.47214922 |
| Otub2 | 0.03326988 | ENSMUSG000000021203 | OTU domain, ubiquitin aldehyde binding 2 | 2.47428 | 3.1435344 | 0.6692544 | 2.47428 |
| Tanc2 | 0.03190521 | ENSMUSG000000053580 | tetratricopeptide repeat, ankyrin repeat and coiled-coil containing 2 | 2.50528675 | 2.789251 | 0.28396425 | 2.50528675 |
| Gm7676 | 0.042453267 | ENSMUSG000000068631 | predicted gene 7676 | 2.54145726 | 3.2768009 | 0.73534364 | 2.54145726 |
| Cp | 0.039974507 | ENSMUSG000000003617 | ceruloplasmin | 2.5422796 | 2.6377988 | 0.0955192 | 2.5422796 |
| Pck2 | 0.000345685 | ENSMUSG000000040618 | phosphoenol pyruvate carboxykinase 2 (mitochondrial) | 2.5555408 | 5.9458942 | 3.3903534 | 2.5555408 |
| Lyl1 | 0.011417538 | ENSMUSG00000034041 | lymphoblastomic leukemia 1 | 2.5561529 | 3.5291882 | 0.9730353 | 2.5561529 |
| BC006779 | 0.000513289 | ENSMUSG00000027580 | cDNA sequence BC006779 | 2.5614315 | 6.8995705 | 4.338139 | 2.5614315 |
| Dab2 | 0.0005445 | ENSMUSG00000022150 | disabled homolog 2 (Drosophila) | 2.5665724 | 5.390645 | 2.8240726 | 2.5665724 |
| Cd36 | 0.000197919 | ENSMUSG00000002944 | CD36 antigen | 2.5687684 | 7.523425 | 4.9546566 | 2.5687684 |
| Gm885 | 0.000151064 | ENSMUSG00000040528 | predicted gene 885 | 2.5931254 | 4.3709044 | 1.777779 | 2.5931254 |
| Cxcl16 | 0.040038653 | ENSMUSG00000018920 | chemokine (C—X—C motif) ligand 16 | 2.617381 | 2.7129002 | 0.0955192 | 2.617381 |
| Samd9l | 0.001224701 | ENSMUSG00000047735 | sterile alpha motif domain containing 9-like | 2.6175766 | 5.347527 | 2.7299504 | 2.6175766 |
| Ifitm3 | 0.000167685 | ENSMUSG00000025492 | interferon induced transmembrane protein 3 | 2.6401358 | 7.2650404 | 4.6249046 | 2.6401358 |
| Tlr1 | 0.000515847 | ENSMUSG00000044827 | toll-like receptor 1 | 2.644155 | 4.99991 | 2.355755 | 2.644155 |
| Icosl | 0.0499492 | ENSMUSG00000000732 | icos ligand | 2.6630416 | 0.3322961 | −2.3307455 | 2.6630416 |
| 5730469M10Rik | 0.008745185 | ENSMUSG00000021792 | RIKEN cDNA 5730469M10 gene | 2.6663043 | 3.979415 | 1.3131107 | 2.6663043 |
| Oas1a | 5.18934E−06 | ENSMUSG00000052776 | 2'-5' oligoadenylate synthetase 1A | 2.6766694 | 6.7122464 | 4.035577 | 2.6766694 |
| Prss16 | 0.029725667 | ENSMUSG00000006179 | protease, serine, 16 (thymus) | 2.73307769 | 2.8617637 | 0.12868601 | 2.73307769 |
| Pla2g5 | 0.044189025 | ENSMUSG00000041193 | phospholipase A2, group V | 2.73704227 | 2.6542242 | −0.0828181 | 2.73704227 |
| Pros1 | 0.044148285 | ENSMUSG00000022912 | protein S (alpha) | 2.74788957 | 2.6650715 | −0.0828181 | 2.74788957 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Gm4902 | 0.038773473 | ENSMUSG00000091649 | predicted gene 4902 | 2.75766276 | 2.1818047 | −0.5758581 | 2.75766276 |
| Ptgs2 | 0.000652096 | ENSMUSG00000032487 | prostaglandin-endoperoxide synthase 2 | 2.7881889 | 4.6071906 | 1.8190017 | 2.7881889 |
| D330045A20Rik | 0.03840468 | ENSMUSG00000042498 | RIKEN cDNA D330045A20 gene | 2.82533312 | 2.3525686 | −0.4727645 | 2.82533312 |
| Gbp7 | 0.001749768 | ENSMUSG00000040253 | guanylate binding protein 7 | 2.8321975 | 4.384095 | 1.5518975 | 2.8321975 |
| Abcc3 | 0.04643164 | ENSMUSG00000020865 | ATP-binding cassette, sub-family C (CFTR/MRP), member 3 | 2.83324138 | 2.54689 | −0.2863514 | 2.83324138 |
| Lsp1 | 0.006437104 | ENSMUSG00000018819 | lymphocyte specific 1 | 2.8433657 | 3.6623673 | 0.8190016 | 2.8433657 |
| Fads6 | 0.03632363 | ENSMUSG00000044788 | fatty acid desaturase domain family, member 6 | 2.85568675 | 2.3322961 | −0.5233907 | 2.85568675 |
| Dlg4 | 0.015582533 | ENSMUSG00000020886 | discs, large homolog 4 (*Drosophila*) | 2.8627704 | 2.0555868 | −0.8071836 | 2.8627704 |
| Spire2 | 0.04822587 | ENSMUSG00000010154 | spire homolog 2 (*Drosophila*) | 2.86800703 | 0.99669313 | −1.8713139 | 2.86800703 |
| Parp9 | 3.87374E−05 | ENSMUSG00000022906 | poly (ADP-ribose) polymerase family, member 9 | 2.8685094 | 5.217244 | 2.3487346 | 2.8685094 |
| Spred3 | 0.020723633 | ENSMUSG00000037239 | sprouty-related, EVH1 domain containing 3 | 2.8737209 | 2.1279378 | −0.7457831 | 2.8737209 |
| Oas1c | 0.04526947 | ENSMUSG00000001166 | 2'-5' oligoadenylate synthetase 1C | 2.8841373 | 1.7233167 | −1.1608206 | 2.8841373 |
| Procr | 0.029140951 | ENSMUSG00000027611 | protein C receptor, endothelial | 2.886866 | 1.804048 | −1.082818 | 2.886866 |
| Plek | 0.000116704 | ENSMUSG00000020120 | pleckstrin | 2.9145183 | 7.8633833 | 4.948865 | 2.9145183 |
| Soat2 | 0.04084924 | ENSMUSG00000023045 | sterol O-acyltransferase 2 | 2.91756277 | 2.5410135 | −0.3765493 | 2.91756277 |
| Bst2 | 0.000290517 | ENSMUSG00000046718 | bone marrow stromal cell antigen 2 | 2.9644963 | 5.522494 | 2.5579977 | 2.9644963 |
| Oas1g | 4.99617E−06 | ENSMUSG00000066861 | 2'-5' oligoadenylate synthetase 1G | 2.9733734 | 6.706023 | 3.7326496 | 2.9733734 |
| Acsbg1 | 0.011451526 | ENSMUSG00000032281 | acyl-CoA synthetase bubblegum family member 1 | 2.97743206 | 3.6239665 | 0.64653444 | 2.97743206 |
| Srgn | 0.000519223 | ENSMUSG00000020077 | serglycin | 2.9888318 | 4.8379955 | 1.8491637 | 2.9888318 |
| Cd300lf | 0.048743 | ENSMUSG00000047798 | CD300 antigen like family member F | 2.99401476 | 0.83319426 | −2.1608205 | 2.99401476 |
| Btg2 | 0.013627362 | ENSMUSG00000020423 | B-cell translocation gene 2, anti-proliferative | 3.04782124 | 3.0390038 | −0.0088174 | 3.04782124 |
| Lyz2 | 0.000114821 | ENSMUSG00000069516 | lysozyme 2 | 3.0592905 | 8.7250185 | 5.665728 | 3.0592905 |
| Tmem176a | 0.001501859 | ENSMUSG00000023367 | transmembrane protein 176A | 3.0797794 | 4.3339963 | 1.2542169 | 3.0797794 |
| Cd300ld | 0.006088423 | ENSMUSG00000034641 | CD300 molecule-like | 3.08196247 | 3.1435344 | 0.06157193 | 3.08196247 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Ikbke | 0.011466974 | ENSMUSG00000042349 | family member d inhibitor of kappaB kinase epsilon | 3.0988679 | 3.468562 | 0.3696941 | 3.0988679 |
| Sepw1 | 0.021194948 | ENSMUSG00000041571 | selenoprotein W, muscle 1 | 3.10504645 | 2.8617637 | −0.2432828 | 3.10504645 |
| Hap1 | 0.006396474 | ENSMUSG00000006930 | huntingtin-associated protein 1 | 3.10895079 | 3.1357572 | 0.02680641 | 3.10895079 |
| Trim34a | 0.03032563 | ENSMUSG00000056144 | tripartite motif-containing 34A | 3.10989568 | 2.8235443 | −0.2863514 | 3.10989568 |
| Ccl5 | 0.025789276 | ENSMUSG00000035042 | chemokine (C-C motif) ligand 5 | 3.1330606 | 1.8897779 | −1.2432827 | 3.1330606 |
| Phf11 | 0.033611197 | ENSMUSG00000044703 | PHD finger protein 11 | 3.16393976 | 0.83319426 | −2.3307455 | 3.16393976 |
| Sp100 | 6.08582E−05 | ENSMUSG00000026222 | nuclear antigen Sp100 | 3.1818978 | 4.8955464 | 1.7136486 | 3.1818978 |
| Gstt1 | 3.95629E−06 | ENSMUSG00000001663 | glutathione S-transferase, theta 1 | 3.1898814 | 5.8534894 | 2.663608 | 3.1898814 |
| Irgm1 | 1.61702E−05 | ENSMUSG00000046879 | immunity-related GTPase family M member 1 | 3.1988442 | 6.315182 | 3.1163378 | 3.1988442 |
| Tnf | 1.1853E−05 | ENSMUSG00000024401 | tumor necrosis factor | 3.2128252 | 6.417355 | 3.2045298 | 3.2128252 |
| Trib3 | 0.008661835 | ENSMUSG00000032715 | tribbles homolog 3 (Drosophila) | 3.24853782 | 3.5902176 | 0.34167978 | 3.24853782 |
| Mcf2l | 0.029599534 | ENSMUSG00000031442 | mcf.2 transforming sequence-like | 3.2570492 | 1.0962287 | −2.1608205 | 3.2570492 |
| Gm2619 | 0.027174171 | ENSMUSG00000091199 | predicted gene 2619 | 3.27751335 | 2.7541227 | −0.5233907 | 3.27751335 |
| Ccl2 | 2.73529E−05 | ENSMUSG00000035385 | chemokine (C-C motif) ligand 2 | 3.2992415 | 5.2446203 | 1.9453788 | 3.2992415 |
| Gm7592 | 0.001554758 | ENSMUSG00000090186 | predicted gene 7592 | 3.31135076 | 4.1704297 | 0.85907894 | 3.31135076 |
| Slamf9 | 0.02308799 | ENSMUSG00000026548 | SLAM family member 9 | 3.31978506 | 2.743927 | −0.5758581 | 3.31978506 |
| P2ry6 | 0.017429588 | ENSMUSG00000048779 | pyrimidinergic receptor P2Y, G-protein coupled, 6 | 3.3331523 | 2.5873692 | −0.7457831 | 3.3331523 |
| Slc9a4 | 0.007401402 | ENSMUSG00000026065 | solute carrier family 9 (sodium/hydrogen exchanger), member 4 | 3.3680806 | 2.3592632 | −1.0088174 | 3.3680806 |
| Cth | 1.06479E−06 | ENSMUSG00000028179 | cystathionase (cystathionine gamma-lyase) | 3.376959 | 4.760459 | 1.3835 | 3.376959 |
| Tmem176b | 9.82651E−08 | ENSMUSG00000029810 | transmembrane protein 176B | 3.4009837 | 6.739123 | 3.3381393 | 3.4009837 |
| Hao1 | 0.010638081 | ENSMUSG00000027261 | hydroxyacid oxidase 1, liver | 3.40718967 | 3.0306404 | −0.3765493 | 3.40718967 |
| Socs3 | 0.004106858 | ENSMUSG00000053113 | suppressor of cytokine signaling 3 | 3.41114926 | 3.8617635 | 0.45061424 | 3.41114926 |
| Gm5431 | 0.03143841 | ENSMUSG00000058163 | predicted gene 5431 | 3.4162479 | 1.6704649 | −1.745783 | 3.4162479 |
| Slc7a11 | 5.55815E−05 | ENSMUSG00000027737 | solute carrier family 7 (cationic amino acid | 3.4173804 | 6.241453 | 2.8240726 | 3.4173804 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
| --- | --- | --- | --- | --- | --- | --- | --- |
| | | | transporter, y+ system), member 11 | | | | |
| Cd14 | 1.38458E−06 | ENSMUSG00000051439 | CD14 antigen | 3.428314 | 7.3783393 | 3.9500253 | 3.428314 |
| Cx3cr1 | 0.010204745 | ENSMUSG00000052336 | chemokine (C—X3—C) receptor 1 | 3.45128475 | 3.208002 | −0.2432828 | 3.45128475 |
| Gna15 | 0.022787878 | ENSMUSG00000034792 | guanine nucleotide binding protein, alpha 15 | 3.4586832 | 1.1279377 | −2.3307455 | 3.4586832 |
| Tifa | 0.03074038 | ENSMUSG00000046688 | TRAF-interacting protein with forkhead-associated domain | 3.4756895 | 1.6043756 | −1.8713139 | 3.4756895 |
| Slc2a6 | 0.007765551 | ENSMUSG00000036067 | solute carrier family 2 (facilitated glucose transporter), member 6 | 3.4897101 | 2.4808927 | −1.0088174 | 3.4897101 |
| Gm12185 | 0.0202251 | ENSMUSG00000048852 | predicted gene 12185 | 3.50280586 | 0.97941506 | −2.5233908 | 3.50280586 |
| Ccl22 | 0.01904264 | ENSMUSG00000031779 | chemokine (C-C motif) ligand 22 | 3.5061447 | 2.8758388 | −0.6303059 | 3.5061447 |
| Gm7609 | 0.002328847 | ENSMUSG00000079457 | predicted pseudogene 7609 | 3.51338906 | 3.937531 | 0.42414194 | 3.51338906 |
| 9930111J21Rik1 | 0.015952412 | ENSMUSG00000069893 | RIKEN cDNA 9930111J21 gene 1 | 3.5533596 | 2.8664703 | −0.6868893 | 3.5533596 |
| Oas1b | 0.006014395 | ENSMUSG00000029605 | 2'-5' oligoadenylate synthetase 1B | 3.55350672 | 3.2227612 | −0.3307455 | 3.55350672 |
| Oas2 | 4.47082E−05 | ENSMUSG00000032690 | 2'-5' oligoadenylate synthetase 2 | 3.5568339 | 6.3605146 | 2.8036807 | 3.5568339 |
| C3ar1 | 1.90141E−05 | ENSMUSG00000040552 | complement component 3a receptor 1 | 3.5586367 | 5.8717475 | 2.3131108 | 3.5586367 |
| Xk | 0.016647717 | ENSMUSG00000015342 | Kell blood group precursor (McLeod phenotype) homolog | 3.587198 | 1.0638072 | −2.5233908 | 3.587198 |
| Rcsd1 | 0.00644401 | ENSMUSG00000040723 | RCSD domain containing 1 | 3.6429406 | 2.2190855 | −1.4238551 | 3.6429406 |
| Gm17446 | 1.97358E−07 | ENSMUSG00000090648 | predicted gene, 17446 | 3.6493672 | 6.604024 | 2.9546568 | 3.6493672 |
| Ms4a6c | 0.012355432 | ENSMUSG00000079419 | membrane-spanning 4-domains, subfamily A, member 6C | 3.6525339 | 2.022228 | −1.6303059 | 3.6525339 |
| Gbp3 | 0.00609057 | ENSMUSG00000028268 | guanylate binding protein 3 | 3.66391947 | 3.2873702 | −0.3765493 | 3.66391947 |
| Irf8 | 0.005833246 | ENSMUSG00000041515 | interferon regulatory factor 8 | 3.66485538 | 3.2410004 | −0.423855 | 3.66485538 |
| 9930111J21Rik2 | 0.002968723 | ENSMUSG00000069892 | RIKEN cDNA 9930111J21 gene 2 | 3.66551388 | 3.3791625 | −0.2863514 | 3.66551388 |
| Nxf7 | 0.026874818 | ENSMUSG00000031410 | nuclear RNA export factor 7 | 3.6684755 | 1.6596581 | −2.0088174 | 3.6684755 |
| 4933421A08Rik | 0.04371277 | ENSMUSG00000086443 | RIKEN cDNA 4933421A08 gene | 3.6900088 | −0.6407369 | −4.3307457 | 3.6900088 |
| Nfkbiz | 0.000338256 | ENSMUSG00000035356 | nuclear factor of kappa light | 3.69558076 | 4.4309244 | 0.73534364 | 3.69558076 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| | | | polypeptide gene enhancer in B-cells inhibitor, zeta | | | | |
| Cd33 | 0.003050802 | ENSMUSG00000004609 | CD33 antigen | 3.7085288 | 3.804048 | 0.0955192 | 3.7085288 |
| Tmem132a | 0.015127231 | ENSMUSG00000024736 | transmembrane protein 132A | 3.764706 | 2.9575224 | −0.8071836 | 3.764706 |
| Isg20 | 0.012284132 | ENSMUSG00000039236 | interferon-stimulated protein | 3.8299389 | 1.4991934 | −2.3307455 | 3.8299389 |
| Oas3 | 4.73984E−09 | ENSMUSG00000032661 | 2'-5' oligoadenylate synthetase 3 | 3.8306523 | 7.3947244 | 3.5640721 | 3.8306523 |
| Gm5483 | 0.03113538 | ENSMUSG00000079597 | predicted gene 5483 | 3.84201193 | −0.4887338 | −4.3307457 | 3.84201193 |
| Cd40 | 0.008479672 | ENSMUSG00000017652 | CD40 antigen | 3.8493916 | 3.2190857 | −0.6303059 | 3.8493916 |
| Rab3il1 | 0.002127681 | ENSMUSG00000024663 | RAB3A interacting protein (rabin3)-like 1 | 3.8658585 | 2.535113 | −1.3307455 | 3.8658585 |
| Atf3 | 0.010065816 | ENSMUSG00000026628 | activating transcription factor 3 | 3.8931904 | 3.1474073 | −0.7457831 | 3.8931904 |
| Neurl3 | 0.002695141 | ENSMUSG00000047180 | neuralized homolog 3 homolog (Drosophila) | 3.93512115 | 3.4117305 | −0.5233907 | 3.93512115 |
| Gm216 | 0.047322746 | ENSMUSG00000073650 | predicted gene 216 | 3.9351214 | −1.3956243 | −5.3307457 | 3.9351214 |
| Aox3l1 | 0.04825851 | ENSMUSG00000079554 | aldehyde oxidase 3-like 1 | 3.9351214 | −1.3956243 | −5.3307457 | 3.9351214 |
| Slc39a4 | 0.000711307 | ENSMUSG00000063354 | solute carrier family 39 (zinc transporter), member 4 | 3.94382097 | 3.5672717 | −0.3765493 | 3.94382097 |
| Trim30d | 0.012037092 | ENSMUSG00000057596 | tripartite motif-containing 30D | 3.94794524 | 3.0095172 | −0.938428 | 3.94794524 |
| Trim30a | 1.61687E−07 | ENSMUSG00000030921 | tripartite motif-containing 30A | 3.971755 | 6.3483686 | 2.3766136 | 3.971755 |
| Cd244 | 0.047936272 | ENSMUSG00000004709 | CD244 natural killer cell receptor 2B4 | 3.9940152 | −1.4887338 | −5.482749 | 3.9940152 |
| Adam33 | 0.048501696 | ENSMUSG00000027318 | a disintegrin and metallopeptidase domain 33 | 3.9940152 | −1.4887338 | −5.482749 | 3.9940152 |
| Art3 | 0.049302656 | ENSMUSG00000034842 | ADP-ribosyltransferase 3 | 3.9940152 | −1.4887338 | −5.482749 | 3.9940152 |
| Evl | 0.01699222 | ENSMUSG00000021262 | Ena-vasodilator stimulated phosphoprotein | 4.0225842 | 0.6918385 | −3.3307457 | 4.0225842 |
| BC049352 | 0.019156335 | ENSMUSG00000091996 | cDNA sequence BC049352 | 4.0225842 | −0.3081615 | −4.3307457 | 4.0225842 |
| Ms4a7 | 0.04587867 | ENSMUSG00000024672 | membrane-spanning 4-domains, subfamily A, member 7 | 4.0225842 | −1.3081615 | −5.3307457 | 4.0225842 |
| Cnrip1 | 0.04739232 | ENSMUSG00000044629 | cannabinoid receptor interacting protein 1 | 4.0225842 | −1.3081615 | −5.3307457 | 4.0225842 |
| Gbp2 | 0.04953059 | ENSMUSG00000028270 | guanylate binding protein 2 | 4.0225842 | −1.3081615 | −5.3307457 | 4.0225842 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Rbpms | 0.017674573 | ENSMUSG00000031586 | RNA binding protein gene with multiple splicing | 4.0644043 | 0.7336586 | −3.3307457 | 4.0644043 |
| Leprel1 | 0.015996631 | ENSMUSG00000038168 | leprecan-like 1 | 4.06440437 | −0.2663413 | −4.3307457 | 4.06440437 |
| Adam3 | 0.009531343 | ENSMUSG00000031553 | a disintegrin and metallopeptidase domain 3 (cyritestin) | 4.0726246 | 1.0638072 | −3.0088174 | 4.0726246 |
| Trim34b | 0.007744697 | ENSMUSG00000090215 | tripartite motif-containing 34B | 4.0807986 | 2.0719812 | −2.0088174 | 4.0807986 |
| Pilrb1 | 0.0480939 | ENSMUSG00000066684 | paired immunoglobin-like type 2 receptor beta 1 | 4.0871247 | −1.3956243 | −5.482749 | 4.0871247 |
| Prickle1 | 0.048321296 | ENSMUSG00000036158 | prickle homolog 1 (*Drosophila*) | 4.0871247 | −1.3956243 | −5.482749 | 4.0871247 |
| Ccrl2 | 0.048543822 | ENSMUSG00000043953 | chemokine (C-C motif) receptor-like 2 | 4.0871247 | −1.3956243 | −5.482749 | 4.0871247 |
| 1700003M07Rik | 0.0489742 | ENSMUSG00000085389 | RIKEN cDNA 1700003M07 gene | 4.0871247 | −1.3956243 | −5.482749 | 4.0871247 |
| Nphs2 | 0.04948828 | ENSMUSG00000026602 | nephrosis 2 homolog, podocin (human) | 4.0871247 | −1.3956243 | −5.482749 | 4.0871247 |
| Il10ra | 0.003073455 | ENSMUSG00000032089 | interleukin 10 receptor, alpha | 4.10113089 | 4.1279373 | 0.02680641 | 4.10113089 |
| Gadd45a | 0.043100644 | ENSMUSG00000036390 | growth arrest and DNA-damage-inducible 45 alpha | 4.1050463 | −1.2256994 | −5.3307457 | 4.1050463 |
| 6530402F18Rik | 0.044838425 | ENSMUSG00000079499 | RIKEN cDNA 6530402F18 gene | 4.1050463 | −1.2256994 | −5.3307457 | 4.1050463 |
| Irgm2 | 1.04727E−05 | ENSMUSG00000069874 | immunity-related GTPase family M member 2 | 4.1400689 | 4.509763 | 0.3696941 | 4.1400689 |
| Gpr84 | 2.75089E−05 | ENSMUSG00000063234 | G protein-coupled receptor 84 | 4.14575538 | 3.859404 | −0.2863514 | 4.14575538 |
| Atp8b4 | 2.32191E−07 | ENSMUSG00000060131 | ATPase, class I, type 8B, member 4 | 4.1493087 | 6.0280166 | 1.8787079 | 4.1493087 |
| Pi16 | 0.04246121 | ENSMUSG00000024011 | peptidase inhibitor 16 | 4.1830488 | −1.1476969 | −5.3307457 | 4.1830488 |
| 9430070O13Rik | 0.042740114 | ENSMUSG00000026601 | RIKEN cDNA 9430070O13 gene | 4.1830488 | −1.1476969 | −5.3307457 | 4.1830488 |
| Xaf1 | 0.004594872 | ENSMUSG00000040483 | XIAP associated factor 1 | 4.1863461 | 3.3791625 | −0.8071836 | 4.1863461 |
| Gbp9 | 0.009429601 | ENSMUSG00000029298 | guanylate-binding protein 9 | 4.1956487 | 1.4498657 | −2.745783 | 4.1956487 |
| Aldh1l2 | 9.31273E−08 | ENSMUSG00000020256 | aldehyde dehydrogenase 1 family, member L2 | 4.268145 | 6.0248623 | 1.7567173 | 4.268145 |
| Ceacam19 | 0.01110833 | ENSMUSG00000049848 | carcinoembryonic antigen-related cell adhesion molecule 19 | 4.2690218 | 1.5232388 | −2.745783 | 4.2690218 |
| Siglec1 | 0.000273761 | ENSMUSG00000027322 | sialic acid binding Ig-like lectin 1, sialoadhesin | 4.26931259 | 4.296119 | 0.02680641 | 4.26931259 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
| --- | --- | --- | --- | --- | --- | --- | --- |
| Nhsl1 | 0.007009061 | ENSMUSG00000039835 | NHS-like 1 | 4.3043549 | 1.5585719 | −2.745783 | 4.3043549 |
| Mx1 | 0.014547019 | ENSMUSG00000000386 | myxovirus (influenza virus) resistance 1 | 4.32743881 | −0.0033069 | −4.3307457 | 4.32743881 |
| Il1b | 0.038834058 | ENSMUSG00000027398 | interleukin 1 beta | 4.3350521 | −1.1476969 | −5.482749 | 4.3350521 |
| Emr1 | 1.82451E−06 | ENSMUSG00000004730 | EGF-like module containing, mucin-like, hormone receptor-like sequence 1 | 4.360369 | 5.65898 | 1.298611 | 4.360369 |
| Parp14 | 1.93595E−08 | ENSMUSG00000034422 | poly (ADP-ribose) polymerase family, member 14 | 4.3674735 | 6.3035145 | 1.936041 | 4.3674735 |
| D14Ertd668e | 1.30197E−05 | ENSMUSG00000068245 | DNA segment, Chr 14, ERATO Doi 668, expressed | 4.36899129 | 4.4976773 | 0.12868601 | 4.36899129 |
| Igtp | 0.001563031 | ENSMUSG00000078853 | interferon gamma induced GTPase | 4.3773436 | 3.57016 | −0.8071836 | 4.3773436 |
| Gstt4 | 0.011173716 | ENSMUSG00000009093 | glutathione S-transferase, theta 4 | 4.3780647 | 2.0473192 | −2.3307455 | 4.3780647 |
| Stap1 | 2.50132E−07 | ENSMUSG00000029254 | signal transducing adaptor family member 1 | 4.3900233 | 6.239187 | 1.8491637 | 4.3900233 |
| Tpbg | 0.03382182 | ENSMUSG00000035274 | trophoblast glycoprotein | 4.4090527 | −1.0736963 | −5.482749 | 4.4090527 |
| Wdr66 | 0.013581607 | ENSMUSG00000029442 | WD repeat domain 66 | 4.45868316 | 0.71290016 | −3.745783 | 4.45868316 |
| Hunk | 0.01660839 | ENSMUSG00000053414 | hormonally upregulated Neu-associated kinase | 4.48971018 | 0.15896448 | −4.3307457 | 4.48971018 |
| Saa3 | 0.025470588 | ENSMUSG00000040026 | serum amyloid A 3 | 4.5200839 | −0.8106618 | −5.3307457 | 4.5200839 |
| Ifih1 | 7.52283E−06 | ENSMUSG00000026896 | interferon induced with helicase C domain 1 | 4.52452936 | 4.9486713 | 0.42414194 | 4.52452936 |
| Tlr13 | 0.004782067 | ENSMUSG00000033777 | toll-like receptor 13 | 4.5446259 | 3.3013432 | −1.2432827 | 4.5446259 |
| Trim30eps1 | 0.029862829 | ENSMUSG00000073929 | tripartite motif-containing 30E, pseudogene 1 | 4.6106866 | −0.8720624 | −5.482749 | 4.6106866 |
| Six4 | 0.006483047 | ENSMUSG00000034460 | sine oculis-related homeobox 4 homolog (*Drosophila*) | 4.63556084 | 0.88977784 | −3.745783 | 4.63556084 |
| Cybb | 1.95579E−07 | ENSMUSG00000015340 | cytochrome b-245, beta polypeptide | 4.7431125 | 5.752217 | 1.0091045 | 4.7431125 |
| BC013712 | 0.000281571 | ENSMUSG00000037731 | cDNA sequence BC013712 | 4.7587783 | 3.8874643 | −0.871314 | 4.7587783 |
| Galnt3 | 0.00355866 | ENSMUSG00000026994 | No description | 4.7595498 | 2.0137668 | −2.745783 | 4.7595498 |
| Tnnt2 | 0.02091825 | ENSMUSG00000026414 | troponin T2, cardiac | 4.7875644 | −0.6951846 | −5.482749 | 4.7875644 |
| Fabp4 | 0.021602802 | ENSMUSG00000062515 | fatty acid binding | 4.7875644 | −0.6951846 | −5.482749 | 4.7875644 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Slpi | 0.01807874 | ENSMUSG00000017002 | protein 4, adipocyte secretory leukocyte peptidase inhibitor | 4.7931023 | 0.4623566 | −4.3307457 | 4.7931023 |
| Ifi44 | 1.53211E−14 | ENSMUSG00000028037 | interferon-induced protein 44 | 4.8898906 | 8.224481 | 3.3345904 | 4.8898906 |
| AI504432 | 0.019602522 | ENSMUSG00000056145 | expressed sequence AI504432 | 4.8944795 | −0.5882695 | −5.482749 | 4.8944795 |
| Ddx60 | 0.000261457 | ENSMUSG00000037921 | DEAD (Asp-Glu-Ala-Asp) box polypeptide 60 | 4.923806 | 3.178023 | −1.745783 | 4.923806 |
| Slc9a9 | 0.020172823 | ENSMUSG00000031129 | solute carrier family 9 (sodium/hydrogen exchanger), member 9 | 4.9451056 | −0.5376434 | −5.482749 | 4.9451056 |
| Ccl7 | 0.000610965 | ENSMUSG00000035373 | chemokine (C-C motif) ligand 7 | 4.9591955 | 3.3288896 | −1.6303059 | 4.9591955 |
| Ddx58 | 3.12944E−11 | ENSMUSG00000040296 | DEAD (Asp-Glu-Ala-Asp) box polypeptide 58 | 4.9671744 | 7.1678104 | 2.200636 | 4.9671744 |
| I830012O16Rik | 0.004567375 | ENSMUSG00000062488 | RIKEN cDNA I830012O16 gene | 4.9940149 | 1.2482319 | −3.745783 | 4.9940149 |
| Irf7 | 8.24433E−07 | ENSMUSG00000025498 | interferon regulatory factor 7 | 5.01074876 | 5.4348907 | 0.42414194 | 5.01074876 |
| Htra4 | 0.017311335 | ENSMUSG00000037406 | HtrA serine peptidase 4 | 5.04132096 | −0.441428 | −5.482749 | 5.04132096 |
| Siglece | 0.00169967 | ENSMUSG00000030474 | sialic acid binding Ig-like lectin E | 5.0807986 | 2.0719812 | −3.0088174 | 5.0807986 |
| Aqp9 | 0.000577649 | ENSMUSG00000032204 | aquaporin 9 | 5.088251 | 3.342468 | −1.745783 | 5.088251 |
| Adh7 | 0.002669529 | ENSMUSG00000055301 | alcohol dehydrogenase 7 (class IV), mu or sigma polypeptide | 5.1050461 | 1.3592631 | −3.745783 | 5.1050461 |
| Slc30a2 | 0.014447143 | ENSMUSG00000028836 | solute carrier family 30 (zinc transporter), member 2 | 5.10504635 | −0.2256994 | −5.3307457 | 5.10504635 |
| Cd86 | 0.00104289 | ENSMUSG00000022901 | CD86 antigen | 5.1249457 | 2.7942002 | −2.3307455 | 5.1249457 |
| Hsh2d | 0.009497254 | ENSMUSG00000062007 | hematopoietic SH2 domain containing | 5.16393996 | 0.83319426 | −4.3307457 | 5.16393996 |
| Ccnd2 | 0.000857036 | ENSMUSG00000000184 | cyclin D2 | 5.1779776 | 3.7541225 | −1.4238551 | 5.1779776 |
| Asb2 | 0.008776278 | ENSMUSG00000021200 | ankyrin repeat and SOCS box-containing 2 | 5.1830489 | 0.8523032 | −4.3307457 | 5.1830489 |
| Gm1966 | 0.009493642 | ENSMUSG00000073902 | predicted gene 1966 | 5.20190794 | 0.87116224 | −4.3307457 | 5.20190794 |
| Col14a1 | 0.012412123 | ENSMUSG00000022371 | collagen, type XIV, alpha 1 | 5.21640767 | −0.2663413 | −5.482749 | 5.21640767 |
| Clec4a1 | 0.003088675 | ENSMUSG00000049037 | C-type lectin domain family 4, member a1 | 5.2205235 | 2.4747405 | −2.745783 | 5.2205235 |
| Gm11711 | 0.000704584 | ENSMUSG00000089722 | predicted gene 11711 | 5.2926734 | 2.7692826 | −2.5233908 | 5.2926734 |
| Gbp5 | 0.012722499 | ENSMUSG00000040264 | guanylate binding protein 5 | 5.29657803 | −0.186171 | −5.482749 | 5.29657803 |
| Gm11710 | 0.000707052 | ENSMUSG00000069609 | predicted gene 11710 | 5.2976914 | 2.7743006 | −2.5233908 | 5.2976914 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Cd300lh | 0.000719966 | ENSMUSG00000069607 | CD300 antigen like family member H | 5.3026922 | 2.7793014 | −2.5233908 | 5.3026922 |
| Kcna3 | 0.007314483 | ENSMUSG00000047959 | potassium voltage-gated channel, shaker-related subfamily, member 3 | 5.36138606 | 0.03064036 | −5.3307457 | 5.36138606 |
| Niacr1 | 0.000542988 | ENSMUSG00000045502 | niacin receptor 1 | 5.3709405 | 2.8475497 | −2.5233908 | 5.3709405 |
| Dhx58 | 1.07756E−08 | ENSMUSG00000017830 | DEXH (Asp-Glu-X-His) box polypeptide 58 | 5.41137727 | 5.034828 | −0.3765493 | 5.41137727 |
| Cmpk2 | 1.21268E−06 | ENSMUSG00000020638 | cytidine monophosphate (UMP-CMP) kinase 2, mitochondrial | 5.42365352 | 4.950889 | −0.4727645 | 5.42365352 |
| Irak3 | 0.000561619 | ENSMUSG00000020227 | interleukin-1 receptor-associated kinase 3 | 5.4246825 | 3.9012918 | −1.5233907 | 5.4246825 |
| Lysmd2 | 0.007453424 | ENSMUSG00000032184 | LysM, putative peptidoglycan-binding, domain containing 2 | 5.42697442 | 0.09622872 | −5.3307457 | 5.42697442 |
| Cxcl10 | 0.000436733 | ENSMUSG00000034855 | chemokine (C—X—C motif) ligand 10 | 5.4269746 | 2.9035838 | −2.5233908 | 5.4269746 |
| C5ar1 | 8.91278E−05 | ENSMUSG00000049130 | complement component 5a receptor 1 | 5.4794421 | 4.055587 | −1.4238551 | 5.4794421 |
| Ifit2 | 0.000635787 | ENSMUSG00000045932 | interferon-induced protein with tetratricopeptide repeats 2 | 5.4802343 | 3.8499284 | −1.6303059 | 5.4802343 |
| Gm15655 | 0.009071947 | ENSMUSG00000086717 | predicted gene 15655 | 5.51338936 | 0.03064036 | −5.482749 | 5.51338936 |
| Apol9b | 0.000853888 | ENSMUSG00000057346 | apolipoprotein L 9b | 5.5350342 | 2.2042885 | −3.3307457 | 5.5350342 |
| 4930438A08Rik | 0.008135167 | ENSMUSG00000069873 | RIKEN cDNA 4930438A08 gene | 5.54655632 | 0.06380732 | −5.482749 | 5.54655632 |
| Slamf7 | 0.008154977 | ENSMUSG00000038179 | SLAM family member 7 | 5.54655632 | 0.06380732 | −5.482749 | 5.54655632 |
| Trem3 | 0.007723238 | ENSMUSG00000041754 | triggering receptor expressed on myeloid cells 3 | 5.57897772 | 0.09622872 | −5.482749 | 5.57897772 |
| Il10 | 0.006503063 | ENSMUSG00000016529 | interleukin 10 | 5.61068666 | 0.12793766 | −5.482749 | 5.61068666 |
| Itga9 | 0.006992263 | ENSMUSG00000039115 | integrin alpha 9 | 5.61068666 | 0.12793766 | −5.482749 | 5.61068666 |
| Rnase4 | 0.000401531 | ENSMUSG00000021876 | ribonuclease, RNase A family 4 | 5.7743251 | 2.4435794 | −3.3307457 | 5.7743251 |
| Rtp4 | 2.66731E−08 | ENSMUSG00000033355 | receptor transporter protein 4 | 5.78130823 | 5.6204877 | −0.1608205 | 5.78130823 |
| Itgal | 8.11603E−08 | ENSMUSG00000030830 | integrin alpha L | 5.80660638 | 5.520255 | −0.2863514 | 5.80660638 |
| Isg15 | 4.77137E−05 | ENSMUSG00000035692 | ISG15 ubiquitin-like modifier | 5.8244175 | 4.9531035 | −0.871314 | 5.8244175 |
| Cd300e | 0.000227213 | ENSMUSG00000048498 | CD300e antigen | 5.9200143 | 2.1742313 | −3.745783 | 5.9200143 |
| Zbp1 | 0.000939954 | ENSMUSG00000027514 | Z-DNA binding protein 1 | 5.9463487 | 1.615603 | −4.3307457 | 5.9463487 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Ifit3 | 0.00091502 | ENSMUSG00000074896 | interferon-induced protein with tetratricopeptide repeats 3 | 5.9574891 | 1.6267434 | −4.3307457 | 5.9574891 |
| Gpr65 | 8.52311E−06 | ENSMUSG00000021886 | G-protein coupled receptor 65 | 5.9849697 | 3.6542242 | −2.3307455 | 5.9849697 |
| Gm11428 | 0.001755864 | ENSMUSG00000069792 | predicted gene 11428 | 6.04132093 | 0.55857193 | −5.482749 | 6.04132093 |
| Ccl4 | 8.01905E−11 | ENSMUSG00000018930 | chemokine (C-C motif) ligand 4 | 6.04364554 | 6.54579 | 0.50214446 | 6.04364554 |
| Gm14085 | 0.000702213 | ENSMUSG00000079071 | predicted gene 14085 | 6.0644043 | 0.7336586 | −5.3307457 | 6.0644043 |
| Lcn2 | 0.000630766 | ENSMUSG00000026822 | lipocalin 2 | 6.2164076 | 0.7336586 | −5.482749 | 6.2164076 |
| Apol9a | 0.000453771 | ENSMUSG00000068246 | apolipoprotein L 9a | 6.2660382 | 2.9352925 | −3.3307457 | 6.2660382 |
| Tnfrsf13b | 0.000442462 | ENSMUSG00000010142 | tumor necrosis factor receptor superfamily, member 13b | 6.3317263 | 3.0009806 | −3.3307457 | 6.3317263 |
| Maf | 3.9675E−06 | ENSMUSG00000055435 | avian musculoaponeurotic fibrosarcoma (v-maf) AS42 oncogene homolog | 6.3557831 | 3.6100001 | −2.745783 | 6.3557831 |
| Gm4070 | 9.03925E−07 | ENSMUSG00000078606 | predicted gene 4070 | 6.3693103 | 5.2864923 | −1.082818 | 6.3693103 |
| Gvin1 | 7.25705E−07 | ENSMUSG00000045868 | GTPase, very large interferon inducible 1 | 6.3885 | 5.305682 | −1.082818 | 6.3885 |
| Usp18 | 4.19049E−11 | ENSMUSG00000030107 | ubiquitin specific peptidase 18 | 6.46699962 | 6.690843 | 0.22384338 | 6.46699962 |
| Slc28a2 | 0.000986595 | ENSMUSG00000027219 | solute carrier family 28 (sodium-coupled nucleoside transporter), member 2 | 6.564478 | 1.2337323 | −5.3307457 | 6.564478 |
| Slc15a3 | 1.36526E−11 | ENSMUSG00000024737 | solute carrier family 15, member 3 | 6.58377798 | 6.159923 | −0.423855 | 6.58377798 |
| Gm11547 | 0.000421104 | ENSMUSG00000085604 | predicted gene 11547 | 6.6106867 | 1.1279377 | −5.482749 | 6.6106867 |
| Il18rap | 1.85857E−05 | ENSMUSG00000026068 | interleukin 18 receptor accessory protein | 6.6765883 | 2.3458426 | −4.3307457 | 6.6765883 |
| 2010002M12Rik | 0.000675854 | ENSMUSG00000067297 | RIKEN cDNA 2010002M12 gene | 6.7453361 | 1.2625871 | −5.482749 | 6.7453361 |
| Batf | 0.00066985 | ENSMUSG00000034266 | basic leucine zipper transcription factor, ATF-like | 6.75955 | 1.276801 | −5.482749 | 6.75955 |
| Irg1 | 3.31171E−11 | ENSMUSG00000022126 | immunoresponsive gene 1 | 6.81480982 | 6.3420453 | −0.4727645 | 6.81480982 |
| Serinc2 | 0.000244017 | ENSMUSG00000023232 | serine incorporator 2 | 6.8737206 | 3.1279376 | −3.745783 | 6.8737206 |
| Csf3 | 0.001778822 | ENSMUSG00000038067 | colony stimulating factor 3 (granulocyte) | 6.9351213 | 1.6043756 | −5.3307457 | 6.9351213 |
| Gm14275 | 0.001133265 | ENSMUSG00000085949 | predicted gene 14275 | 6.9451056 | 1.4623566 | −5.482749 | 6.9451056 |
| H28 | 1.20005E−05 | ENSMUSG00000039146 | histocompatibility 28 | 6.9781485 | 4.647403 | −2.3307455 | 6.9781485 |

TABLE 1-continued

| Gene | p-value | ID | Description | Differential expressin (log2 ratio) | MMP-9sh 3d RANKL | NCsh 3d RNAKL | MMP9sh vs NCsh (log2 ratio) |
|---|---|---|---|---|---|---|---|
| Gm11709 | 0.001331092 | ENSMUSG00000089753 | predicted gene 11709 | 7.0012106 | 1.6704649 | −5.3307457 | 7.0012106 |
| Cxcl2 | 6.37467E−06 | ENSMUSG00000058427 | chemokine (C—X—C motif) ligand 2 | 7.0361591 | 4.5127683 | −2.5233908 | 7.0361591 |
| Gm8979 | 0.000989941 | ENSMUSG00000091928 | predicted gene 8979 | 7.226676 | 1.743927 | −5.482749 | 7.226676 |
| Gm8989 | 0.001071625 | ENSMUSG00000091567 | predicted gene 8989 | 7.226676 | 1.743927 | −5.482749 | 7.226676 |
| Lgals9 | 1.50607E−06 | ENSMUSG00000001123 | lectin, galactose binding, soluble 9 | 7.357186 | 4.611403 | −2.745783 | 7.357186 |
| Rsad2 | 2.21866E−08 | ENSMUSG00000020641 | radical S-adenosyl methionine domain containing 2 | 7.438284 | 5.692501 | −1.745783 | 7.438284 |
| Oasl2 | 0.000192137 | ENSMUSG00000029561 | 2'-5' oligoadenylate synthetase-like 2 | 7.5275784 | 2.1968327 | −5.3307457 | 7.5275784 |
| Zfp811 | 0.00022262 | ENSMUSG00000055202 | zinc finger protein 811 | 7.5869706 | 2.1042216 | −5.482749 | 7.5869706 |
| Lancl3 | 1.56193E−05 | ENSMUSG00000047344 | LanC lantibiotic synthetase component C-like 3 (bacterial) | 7.7806113 | 2.4498656 | −5.3307457 | 7.7806113 |
| Ppfibp2 | 1.1878E−06 | ENSMUSG00000036528 | PTPRF interacting protein, binding protein 2 (liprin beta 2) | 7.8349816 | 5.0891986 | −2.745783 | 7.8349816 |
| Mx2 | 2.73356E−05 | ENSMUSG00000023341 | myxovirus (influenza virus) resistance 2 | 7.8539847 | 2.523239 | −5.3307457 | 7.8539847 |
| Pou2f2 | 5.15218E−06 | ENSMUSG00000008496 | POU domain, class 2, transcription factor 2 | 8.2065845 | 2.8758388 | −5.3307457 | 8.2065845 |
| Ifit1 | 8.33396E−06 | ENSMUSG00000034459 | interferon-induced protein with tetratricopeptide repeats 1 | 8.227443 | 3.8966973 | −4.3307457 | 8.227443 |
| Nos2 | 2.15861E−09 | ENSMUSG00000020826 | nitric oxide synthase 2, inducible | 8.6715229 | 6.3407774 | −2.3307455 | 8.6715229 |
| Fcgr1 | 1.58442E−08 | ENSMUSG00000015947 | Fc receptor, IgG, high affinity I | 8.9574893 | 3.4747403 | −5.482749 | 8.9574893 |

TABLE 2

| Peak | Gene | log$_2$ normalized Read count | | | | | log$_2$ ratio NCsh (N) vs input |
|---|---|---|---|---|---|---|---|
| | | NCsh (N) | NCsh (C) | MMP-9sh (N) | MMP-9sh (C) | Input | |
| Promoter Cleavage | | | | | | | |
| Chr1:129640001-129641000 | Acmsd | 3.452 | 3.345 | 3.723 | 4.892 | 4.644 | −1.192 |
| Chr1:130156001-130157000 | Ubxn4 | 2.867 | 3.831 | 4.045 | 3.754 | 3.907 | −1.040 |
| Chr1:132640001-132641000 | AA986860 | 2.452 | 3.345 | 3.308 | 4.240 | 3.585 | −1.133 |

TABLE 2-continued

| Peak | Gene | log₂ normalized Read count | | | | | log₂ ratio NCsh (N) vs input |
| --- | --- | --- | --- | --- | --- | --- | --- |
| | | NCsh (N) | NCsh (C) | MMP-9sh (N) | MMP-9sh (C) | Input | |
| Chr1:132971001-132972000 | Mapkapk2 | 2.867 | 4.608 | 3.308 | 4.602 | 3.907 | −1.040 |
| Chr1:134423001-134424000 | Cntn2 | 1.867 | 1.023 | 4.308 | 1.433 | 3.459 | −1.592 |
| Chr1:135147001-135148000 | Plekha6 | 2.452 | 3.608 | 3.308 | 3.754 | 3.459 | −1.007 |
| Chr1:136022001-136023000 | Chit1 | 3.189 | 4.193 | 4.893 | 4.754 | 4.585 | −1.396 |
| Chr1:155379001-155380000 | Npl | 1.867 | 4.345 | 2.723 | 3.017 | 3.322 | −1.455 |
| Chr1:173073001-173074000 | Sdhc | 2.452 | 3.608 | 3.308 | 4.433 | 4.000 | −1.548 |
| Chr1:175560001-175561000 | Pyhin1 | 1.867 | 4.608 | 3.723 | 2.433 | 3.700 | −1.833 |
| Chr1:179681001-179682000 | 1700016C15Rik | 2.867 | 4.345 | 4.723 | 3.433 | 4.248 | −1.381 |
| Chr1:182164001-182165000 | Psen2 | 2.867 | 3.023 | 3.723 | 4.017 | 3.907 | −1.040 |
| Chr1:184064001-184065000 | Srp9 | 2.867 | 3.831 | 3.723 | 4.240 | 4.170 | −1.303 |
| Chr1:188482001-188483000 | Tgfb2 | 1.867 | 3.608 | 1.723 | 3.433 | 3.807 | −1.940 |
| Chr1:193904001-193905000 | Traf5 | 1.867 | 3.345 | 2.723 | 3.017 | 3.807 | −1.940 |
| Chr1:74383001-74384000 | Pnkd | 2.867 | 3.345 | 3.723 | 4.017 | 3.907 | −1.040 |
| Chr1:87941001-87942000 | 2810459M11Rik | 2.452 | 3.345 | 3.723 | 3.754 | 4.000 | −1.548 |
| Chr1:89474001-89475000 | Neu2 | 3.452 | 4.345 | 5.308 | 3.017 | 4.524 | −1.072 |
| Chr1:90985001-90986000 | Sh3bp4 | 1.867 | 3.345 | 1.723 | 3.433 | 3.000 | −1.133 |
| Chr10:126473001-126474000 | Fam119b | 2.452 | 3.345 | 4.045 | 3.017 | 3.459 | −1.007 |
| Chr10:127188001-127189000 | Gpr182 | 1.867 | 4.193 | 3.308 | 4.240 | 3.907 | −2.040 |
| Chr10:127669001-127670000 | Gm17292 | 0.867 | 3.608 | 1.723 | 3.433 | 2.000 | −1.133 |
| Chr10:127719001-127720000 | Stat2 | 3.189 | 3.023 | 3.308 | 4.892 | 4.322 | −1.133 |
| Chr10:127753001-127754000 | Pan2 | 1.867 | 2.608 | 3.308 | 4.017 | 3.322 | −1.455 |
| Chr10:128362001-128363000 | Bloc1s1 | 2.452 | 2.023 | 4.308 | 3.754 | 4.392 | −1.940 |
| Chr10:18728001-18729000 | Tnfaip3 | 2.452 | 3.345 | 3.308 | 4.017 | 4.248 | −1.796 |
| Chr10:39706001-39707000 | BC021785 | 2.452 | 3.608 | 3.308 | 4.017 | 3.700 | −1.248 |
| Chr10:79539001-79540000 | Sbno2 | 2.867 | 3.345 | 1.723 | 4.754 | 4.087 | −1.220 |
| Chr10:80327001-80328000 | 3110056O03Rik | 2.452 | 2.023 | 3.723 | 3.754 | 3.585 | −1.133 |
| Chr10:80619001-80620000 | Pias4 | 1.867 | 3.608 | 3.308 | 2.433 | 4.000 | −2.133 |
| Chr10:80643001-80644000 | Eef2 | 2.452 | 3.345 | 3.723 | 4.017 | 3.700 | −1.248 |
| Chr10:83993001-83994000 | Ckap4 | 2.452 | 2.608 | 4.045 | 4.602 | 3.585 | −1.133 |
| Chr10:95254001-95255000 | 4732465J04Rik | 2.867 | 4.608 | 4.723 | 3.433 | 4.170 | −1.303 |
| Chr11:105800001-105801000 | Cyb561 | 2.452 | 3.345 | 1.571 | 4.754 | 3.585 | −1.133 |
| Chr11:113519001-113520000 | Cog1 | 0.867 | 4.023 | 2.723 | 3.433 | 2.000 | −1.133 |
| Chr11:11402001-11403000 | 4930415F15Rik | 2.867 | 4.023 | 3.308 | 4.433 | 3.907 | −1.040 |
| Chr11:114860001-114861000 | AF251705 | 0.867 | 3.345 | 2.723 | 4.017 | 3.170 | −2.303 |
| Chr11:115269001-115270000 | Ict1 | 2.452 | 4.023 | 3.723 | 3.754 | 3.907 | −1.455 |
| Chr11:115756001-115757000 | Recql5 | 2.867 | 3.608 | 3.723 | 4.017 | 3.907 | −1.040 |
| Chr11:116715001-116716000 | 1110005A03Rik | 2.452 | 4.023 | 4.531 | 3.754 | 3.807 | −1.355 |

TABLE 2-continued

| Peak | Gene | NCsh (N) | NCsh (C) | MMP-9sh (N) | MMP-9sh (C) | Input | log₂ ratio NCsh (N) vs input |
|---|---|---|---|---|---|---|---|
| Chr11:120209001-120210000 | Actg1 | 1.867 | 3.023 | 1.723 | 3.433 | 3.170 | −1.303 |
| Chr11:120807001-120808000 | Slc16a3 | 1.867 | 3.345 | 4.308 | 4.017 | 3.322 | −1.455 |
| Chr11:20235001-20236000 | Gm12033 | 2.452 | 3.608 | 3.308 | 3.754 | 4.807 | −2.355 |
| Chr11:4600001-4601000 | Uqcr10 | 2.867 | 3.345 | 1.723 | 4.602 | 4.000 | −1.133 |
| Chr11:48668001-48669000 | Gm16170 | 2.867 | 4.023 | 4.723 | 4.892 | 4.248 | −1.381 |
| Chr11:50020001-50021000 | Sqstm1 | 2.452 | 3.023 | 3.723 | 3.754 | 3.585 | −1.133 |
| Chr11:53698001-53699000 | Slc22a5 | 1.867 | 2.023 | 1.723 | 3.433 | 3.907 | −2.040 |
| Chr11:5423001-5424000 | Xbp1 | 2.452 | 4.193 | 4.308 | 4.240 | 3.807 | −1.355 |
| Chr11:54967001-54968000 | Slc36a3 | 2.452 | 3.608 | 4.045 | 3.017 | 3.700 | −1.248 |
| Chr11:55071001-55072000 | Fat2 | 2.867 | 4.023 | 1.571 | 4.754 | 4.087 | −1.220 |
| Chr11:55268001-55269000 | Atox1 | 1.867 | 3.345 | 3.723 | 1.433 | 3.807 | −1.940 |
| Chr11:58748001-58749000 | Rnf187 | 2.867 | 4.193 | 3.723 | 4.017 | 4.087 | −1.220 |
| Chr11:61037001-61038000 | Aldh3a2 | 2.867 | 3.831 | 3.308 | 4.240 | 4.000 | −1.133 |
| Chr11:61368001-61369000 | Epn2 | 2.867 | 3.608 | 3.308 | 4.240 | 3.907 | −1.040 |
| Chr11:61523001-61524000 | Slc5a10 | 2.867 | 3.831 | 4.308 | 3.433 | 3.907 | −1.040 |
| Chr11:62119001-62120000 | Ttc19 | 3.189 | 3.831 | 4.531 | 4.017 | 4.248 | −1.059 |
| Chr11:62467001-62468000 | Mmgt2 | 2.452 | 3.023 | 3.308 | 4.240 | 3.907 | −1.455 |
| Chr11:6381001-6382000 | Gm11973 | 1.867 | 3.023 | 3.308 | 3.754 | 3.807 | −1.940 |
| Chr11:69468001-69469000 | Sox15 | 2.452 | 2.608 | 4.531 | 2.433 | 4.170 | −1.718 |
| Chr11:69660001-69661000 | Plscr3 | 1.867 | 3.345 | 3.723 | 3.433 | 3.170 | −1.303 |
| Chr11:76842001-76843000 | Slc6a4 | 1.867 | 3.345 | 1.723 | 3.433 | 3.807 | −1.940 |
| Chr11:77314001-77315000 | Git1 | 2.452 | 4.345 | 5.045 | 3.754 | 3.700 | −1.248 |
| Chr11:82996001-82997000 | Slfn4 | 2.867 | 4.345 | 3.723 | 4.433 | 4.000 | −1.133 |
| Chr11:87493001-87494000 | Rnf43 | 2.867 | 3.023 | 3.723 | 4.017 | 4.644 | −1.777 |
| Chr11:88591001-88592000 | C030037D09Rik | 2.452 | 2.023 | 3.308 | 4.017 | 3.700 | −1.248 |
| Chr11:95724001-95725000 | 4833417C18Rik | 1.867 | 4.608 | 2.723 | 4.240 | 3.700 | −1.833 |
| Chr11:95903001-95904000 | Snf8 | 2.867 | 2.608 | 3.723 | 4.754 | 4.000 | −1.133 |
| Chr11:95910001-95911000 | Ube2z | 2.867 | 4.193 | 3.308 | 4.240 | 4.087 | −1.220 |
| Chr11:96710001-96711000 | Copz2 | 2.452 | 3.345 | 4.045 | 3.017 | 3.907 | −1.455 |
| Chr12:102171001-102172000 | Ccdc88c | 2.867 | 4.023 | 3.308 | 4.240 | 3.907 | −1.040 |
| Chr12:112921001-112922000 | Trmt61a | 1.867 | 3.608 | 3.308 | 3.017 | 3.807 | −1.940 |
| Chr12:113739001-113740000 | Tmem179 | 1.867 | 4.023 | 1.723 | 4.240 | 3.907 | −2.040 |
| Chr12:17888001-17889000 | Gm9222 | 1.867 | 3.023 | 1.723 | 3.433 | 4.000 | −2.133 |
| Chr12:17933001-17934000 | B430203G13Rik | 1.867 | 3.608 | 3.723 | 3.754 | 4.459 | −2.592 |
| Chr12:27159001-27160000 | Cmpk2 | 2.452 | 3.608 | 3.723 | 3.433 | 3.585 | −1.133 |
| Chr12:82636001-82637000 | 6530401F13Rik | 2.452 | 3.608 | 4.045 | 3.754 | 3.700 | −1.248 |
| Chr12:85359001-85360000 | Acot1 | 2.452 | 3.608 | 4.045 | 4.017 | 4.524 | −2.072 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr12:86814001-86815000 | Fos | 2.452 | 3.345 | 4.045 | 3.017 | 3.585 | −1.133 |
| Chr13:104825001-104826000 | Nln | 1.867 | 4.023 | 3.308 | 2.433 | 4.087 | −2.220 |
| Chr13:34334001-34335000 | Slc22a23 | 2.867 | 3.831 | 4.308 | 3.433 | 3.907 | −1.040 |
| Chr13:54890001-54891000 | Tspan17 | 2.452 | 3.345 | 3.723 | 3.433 | 3.700 | −1.248 |
| Chr13:55882001-55883000 | 4930451E10Rik | 3.452 | 4.608 | 5.045 | 4.017 | 4.700 | −1.248 |
| Chr13:65364001-65365000 | Gm10775 | 1.867 | 3.345 | 2.723 | 3.017 | 3.322 | −1.455 |
| Chr13:70147001-70148000 | Gm6132 | 1.867 | 3.345 | 1.571 | 4.017 | 3.170 | −1.303 |
| Chr13:74444001-74445000 | Pdcd6 | 0.867 | 3.831 | 4.531 | 3.017 | 3.700 | −2.833 |
| Chr13:8940001-8941000 | Rpl10a-ps2 | 2.452 | 3.023 | 4.045 | 4.602 | 3.700 | −1.248 |
| Chr13:8955001-8956000 | Idi2 | 0.867 | 3.345 | 3.723 | 4.017 | 3.000 | −2.133 |
| Chr13:94943001-94944000 | Lhfpl2 | 1.867 | 4.023 | 2.723 | 3.017 | 3.585 | −1.718 |
| Chr13:96004001-96005000 | Pde8b | 2.867 | 0.871 | 3.723 | 4.017 | 3.907 | −1.040 |
| Chr14:20414001-20415000 | Gm5458 | 2.452 | 4.023 | 4.045 | 3.754 | 4.170 | −1.718 |
| Chr14:25130001-25131000 | E330034G19Rik | 2.452 | 3.345 | 4.045 | 3.017 | 4.000 | −1.548 |
| Chr14:31752001-31753000 | Itih1 | 2.867 | 3.023 | 2.723 | 4.602 | 4.000 | −1.133 |
| Chr14:4733001-4734000 | Gm8159 | 2.452 | 4.831 | 4.308 | 3.017 | 4.000 | −1.548 |
| Chr14:47392001-47393000 | Cdkn3 | 2.867 | 4.023 | 3.723 | 4.017 | 4.000 | −1.133 |
| Chr14:55248001-55249000 | Psmb11 | 3.189 | 1.023 | 4.045 | 4.433 | 4.248 | −1.059 |
| Chr14:55260001-55261000 | Cdh24 | 1.867 | 3.608 | 2.723 | 3.017 | 3.000 | −1.133 |
| Chr14:55473001-55474000 | Homez | 0.867 | 4.193 | 4.045 | 3.017 | 3.585 | −2.718 |
| Chr14:59880001-59881000 | Gm6904 | 1.867 | 4.345 | 4.308 | 3.433 | 3.585 | −1.718 |
| Chr14:59986001-59987000 | D14Ertd668e | 2.452 | 4.023 | 4.308 | 4.017 | 3.807 | −1.355 |
| Chr14:62086001-62087000 | Rps12-ps2 | 2.452 | 3.023 | 4.308 | 4.017 | 3.907 | −1.455 |
| Chr14:8296001-8297000 | Gm3752 | 2.867 | 3.345 | 3.723 | 4.017 | 4.000 | −1.133 |
| Chr14:8390001-8391000 | Gm3558 | 2.867 | 3.608 | 4.045 | 3.754 | 3.907 | −1.040 |
| Chr15:101942001-101943000 | Tenc1 | 1.867 | 3.608 | 3.723 | 2.433 | 3.000 | −1.133 |
| Chr15:10441001-10442000 | Ttc23l | 1.867 | 4.023 | 1.723 | 3.433 | 3.322 | −1.455 |
| Chr15:52159001-52160000 | Slc30a8 | 2.452 | 4.345 | 4.045 | 3.017 | 3.700 | −1.248 |
| Chr15:73341001-73342000 | Dennd3 | 2.867 | 2.608 | 4.045 | 3.754 | 4.585 | −1.718 |
| Chr15:74714001-74715000 | 2010109I03Rik | 2.452 | 3.608 | 4.045 | 4.240 | 3.585 | −1.133 |
| Chr15:79783001-79784000 | Cbx7 | 1.867 | 3.023 | 3.308 | 2.433 | 3.459 | −1.592 |
| Chr15:85660001-85661000 | Ttc38 | 1.867 | 1.023 | 2.723 | 3.017 | 3.807 | −1.940 |
| Chr15:88950001-88951000 | Tubgcp6 | 1.867 | 3.608 | 4.045 | 3.754 | 3.700 | −1.833 |
| Chr15:9054001-9055000 | Skp2 | 2.452 | 3.608 | 4.045 | 3.433 | 4.087 | −1.635 |
| Chr16:11128001-11129000 | Txndc11 | 2.867 | 4.483 | 3.308 | 4.240 | 4.087 | −1.220 |
| Chr16:16417001-16418000 | Fgd4 | 2.867 | 3.023 | 3.723 | 4.017 | 4.170 | −1.303 |
| Chr16:18632001-18633000 | SEPT_5 | 2.452 | 4.023 | 4.045 | 4.017 | 3.459 | −1.007 |

TABLE 2-continued

| | | log₂ normalized Read count | | | | | |
|---|---|---|---|---|---|---|---|
| Peak | Gene | NCsh (N) | NCsh (C) | MMP-9sh (N) | MMP-9sh (C) | Input | log₂ ratio NCsh (N) vs input |
| Chr16:32683001-32684000 | Tnk2 | 2.867 | 4.023 | 4.045 | 3.754 | 4.000 | −1.133 |
| Chr16:38321001-38322000 | 4932425I24Rik | 2.452 | 3.023 | 3.723 | 4.017 | 3.585 | −1.133 |
| Chr16:44176001-44177000 | Gm608 | 2.867 | 4.930 | 3.723 | 4.017 | 4.087 | −1.220 |
| Chr16:77117001-77118000 | Usp25 | 3.452 | 3.831 | 4.531 | 4.433 | 4.954 | −1.502 |
| Chr16:85795001-85796000 | Adamts1 | 2.867 | 4.023 | 2.723 | 4.754 | 3.907 | −1.040 |
| Chr16:8850001-8851000 | 1810013L24Rik | 2.452 | 4.345 | 3.308 | 3.754 | 3.459 | −1.007 |
| Chr16:93610001-93611000 | Cbr1 | 2.867 | 4.193 | 4.531 | 3.754 | 4.170 | −1.303 |
| Chr16:94735001-94736000 | Dscr3 | 2.867 | 4.023 | 3.723 | 4.017 | 4.000 | −1.133 |
| Chr17:21685001-21686000 | Zfp52 | 3.452 | 4.023 | 4.531 | 4.433 | 4.700 | −1.248 |
| Chr17:24229001-24230000 | Pdpk1 | 2.452 | 4.483 | 2.723 | 4.017 | 3.459 | −1.007 |
| Chr17:24373001-24374000 | Ccnf | 3.189 | 1.023 | 2.723 | 5.133 | 4.322 | −1.133 |
| Chr17:24873001-24874000 | Rpl3l | 1.867 | 3.023 | 3.308 | 3.754 | 3.459 | −1.592 |
| Chr17:27033001-27034000 | Gm20468 | 2.452 | 3.023 | 4.308 | 4.017 | 3.459 | −1.007 |
| Chr17:27740001-27741000 | Nudt3 | 3.452 | 3.608 | 4.045 | 5.017 | 4.524 | −1.072 |
| Chr17:27816001-27817000 | Pacsin1 | 1.867 | 4.023 | 2.723 | 3.017 | 3.459 | −1.592 |
| Chr17:34072001-34073000 | Rgl2 | 0.867 | 3.345 | 2.723 | 2.433 | 3.807 | −2.940 |
| Chr17:35619001-35620000 | Gm20419 | 2.452 | 3.608 | 3.723 | 3.754 | 4.322 | −1.870 |
| Chr17:37004001-37005000 | Trim15 | 1.867 | 3.345 | 2.723 | 3.433 | 3.322 | −1.455 |
| Chr17:48573001-48574000 | Apobec2 | 0.715 | 3.023 | 1.723 | 4.240 | 3.000 | −2.285 |
| Chr17:53812001-53813000 | Kat2b | 1.867 | 2.608 | 2.723 | 3.017 | 3.322 | −1.455 |
| Chr17:57010001-57011000 | Acsbg2 | 1.867 | 3.608 | 1.723 | 3.433 | 3.322 | −1.455 |
| Chr17:57392001-57393000 | Trip10 | 2.452 | 3.023 | 4.723 | 2.433 | 3.700 | −1.248 |
| Chr17:66342001-66343000 | Ankrd12 | 1.867 | 3.345 | 1.571 | 3.754 | 3.000 | −1.133 |
| Chr17:6857001-6858000 | Dynlt1e | 2.452 | 3.608 | 4.045 | 3.754 | 3.700 | −1.248 |
| Chr17:71251001-71252000 | Gm16627 | 2.867 | 3.831 | 4.045 | 3.754 | 3.907 | −1.040 |
| Chr17:80944001-80945000 | Cdkl4 | 1.867 | 3.345 | 3.723 | 1.433 | 3.459 | −1.592 |
| Chr17:8170001-8171000 | Rsph3a | 1.867 | 3.831 | 3.308 | 2.433 | 3.807 | −1.940 |
| Chr17:85187001-85188000 | Lrprc | 2.867 | 3.831 | 4.308 | 3.433 | 3.907 | −1.040 |
| Chr18:35942001-35943000 | Ube2d2 | 2.452 | 4.023 | 1.723 | 4.240 | 3.459 | −1.007 |
| Chr18:37655001-37656000 | Pcdhb19 | 2.452 | 3.023 | 1.723 | 4.602 | 3.700 | −1.248 |
| Chr18:50200001-50201000 | Tnfaip8 | 2.867 | 3.831 | 3.723 | 4.017 | 4.000 | −1.133 |
| Chr18:57047001-57048000 | MARCH_3 | 2.452 | 4.483 | 4.308 | 3.017 | 3.700 | −1.248 |
| Chr18:60427001-60428000 | Gm4841 | 2.452 | 3.345 | 4.045 | 4.017 | 4.000 | −1.548 |
| Chr18:74948001-74949000 | Acaa2 | 2.452 | 3.023 | 3.723 | 3.433 | 4.170 | −1.718 |
| Chr18:80213001-80214000 | Gm10527 | 2.452 | 0.871 | 3.308 | 3.754 | 3.459 | −1.007 |
| Chr18:80911001-80812000 | Nfatc1 | 0.867 | 3.860 | 2.723 | 3.433 | 3.170 | −2.303 |
| Chr19:10603001-10604000 | Cpsf7 | 2.867 | 3.023 | 3.308 | 4.602 | 3.907 | −1.040 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr19:11531001-11532000 | Ms4a4b | 2.867 | 3.831 | 5.531 | 3.017 | 3.907 | −1.040 |
| Chr19:11848001-11849000 | Mrpl16 | 1.867 | 2.608 | 4.308 | 2.433 | 3.322 | −1.455 |
| Chr19:23147001-23148000 | C330002G04Rik | 2.452 | 3.345 | 2.723 | 4.017 | 3.585 | −1.133 |
| Chr19:29102001-29103000 | Ak3 | 2.452 | 4.345 | 3.308 | 4.017 | 3.807 | −1.355 |
| Chr19:41984001-41985000 | Pgam1 | 1.867 | 4.193 | 1.723 | 3.433 | 3.322 | −1.455 |
| Chr19:42219001-42220000 | Marveld1 | 3.189 | 3.831 | 3.723 | 4.602 | 4.392 | −1.203 |
| Chr19:4234001-4235000 | Pold4 | 1.867 | 3.608 | 2.723 | 3.017 | 3.459 | −1.592 |
| Chr19:47606001-47607000 | Obfc1 | 1.867 | 4.193 | 3.308 | 2.433 | 3.322 | −1.455 |
| Chr19:5418001-5419000 | 4930481A15Rik | 2.452 | 3.831 | 4.045 | 3.017 | 3.585 | −1.133 |
| Chr19:5600001-5601000 | Rnaseh2c | 1.867 | 4.483 | 3.308 | 4.017 | 3.459 | −1.592 |
| Chr19:60628001-60629000 | 2700078E11Rik | 2.452 | 4.345 | 3.723 | 3.754 | 3.700 | −1.248 |
| Chr19:6064001-6065000 | Tm7sf2 | 2.867 | 3.345 | 4.045 | 3.754 | 4.000 | −1.133 |
| Chr19:6314001-6315000 | Cdc42bpg | 0.867 | 4.023 | 3.308 | 4.240 | 3.000 | −2.133 |
| Chr19:7075001-7076000 | Fermt3 | 2.452 | 4.345 | 4.045 | 3.017 | 3.459 | −1.007 |
| Chr2:103928001-103929000 | Cd59b | 3.189 | 3.608 | 3.723 | 4.892 | 4.585 | −1.396 |
| Chr2:112164001-112165000 | Slc12a6 | 2.867 | 3.831 | 4.308 | 3.433 | 4.807 | −1.940 |
| Chr2:117160001-117161000 | Rasgrp1 | 2.867 | 3.023 | 3.308 | 4.433 | 3.907 | −1.040 |
| Chr2:119428001-119429000 | 1700020I14Rik | 2.452 | 2.608 | 3.723 | 4.433 | 3.459 | −1.007 |
| Chr2:126901001-126902000 | Blvra | 2.867 | 4.023 | 3.723 | 4.017 | 5.392 | −2.525 |
| Chr2:152565001-152566000 | Id1 | 1.867 | 2.608 | 3.723 | 3.017 | 3.000 | −1.133 |
| Chr2:154497001-154498000 | Chmp4b | 2.867 | 4.023 | 4.308 | 3.433 | 4.248 | −1.381 |
| Chr2:155358001-155359000 | Acss2 | 2.867 | 3.608 | 3.308 | 4.240 | 3.907 | −1.040 |
| Chr2:155416001-155417000 | Gss | 2.452 | 3.608 | 3.723 | 4.017 | 4.000 | −1.548 |
| Chr2:156658001-156659000 | Gm14230 | 0.867 | 4.193 | 3.308 | 4.602 | 2.000 | −1.133 |
| Chr2:158083001-158084000 | Bpi | 0.867 | 3.023 | 2.723 | 3.017 | 3.807 | −2.940 |
| Chr2:164300001-164301000 | Sys1 | 3.189 | 4.193 | 4.308 | 4.433 | 4.322 | −1.133 |
| Chr2:164595001-164596000 | Gm11457 | 1.867 | 3.608 | 1.723 | 4.602 | 3.000 | −1.133 |
| Chr2:167439001-167440000 | Ube2v1 | 2.452 | 3.023 | 2.723 | 4.017 | 3.585 | −1.133 |
| Chr2:172260001-172261000 | Gm14455 | 1.867 | 5.023 | 4.045 | 2.433 | 3.585 | −1.718 |
| Chr2:17959001-17960000 | A930004D18Rik | 0.867 | 2.608 | 3.308 | 3.433 | 3.459 | −2.592 |
| Chr2:21137001-21138000 | Thnsl1 | 2.452 | 4.608 | 4.531 | 2.433 | 3.459 | −1.007 |
| Chr2:24198001-24199000 | Il1rn | 2.867 | 4.608 | 4.531 | 4.240 | 4.087 | −1.220 |
| Chr2:25034001-25035000 | Nrarp | 1.867 | 2.608 | 2.723 | 4.017 | 3.459 | −1.592 |
| Chr2:26800001-26801000 | Gm711 | 2.452 | 3.831 | 3.723 | 3.433 | 4.644 | −2.192 |
| Chr2:26870001-26871000 | 5930434B04Rik | 2.452 | 3.608 | 3.723 | 3.433 | 3.807 | −1.355 |
| Chr2:30817001-30818000 | Tor1a | 1.867 | 3.831 | 3.308 | 3.017 | 3.700 | −1.833 |
| Chr2:3231001-3232000 | Nmt2 | 1.867 | 4.023 | 3.308 | 2.433 | 3.000 | −1.133 |

TABLE 2-continued

| | | log₂ normalized Read count | | | | | |
|---|---|---|---|---|---|---|---|
| Peak | Gene | NCsh (N) | NCsh (C) | MMP-9sh (N) | MMP-9sh (C) | Input | log₂ ratio NCsh (N) vs input |
| Chr2:33583001-33584000 | Fam125b | 1.867 | 4.193 | 3.308 | 2.433 | 3.322 | −1.455 |
| Chr2:34532001-34533000 | Gapvd1 | 2.867 | 4.724 | 4.045 | 3.754 | 3.907 | −1.040 |
| Chr2:36078001-36079000 | Gm13431 | 1.867 | 3.345 | 3.723 | 2.433 | 3.000 | −1.133 |
| Chr2:38383001-38384000 | Nek6 | 1.867 | 3.831 | 3.308 | 2.433 | 3.322 | −1.455 |
| Chr2:56967001-56968000 | Nr4a2 | 1.867 | 4.193 | 1.723 | 4.433 | 3.000 | −1.133 |
| Chr2:60076001-60077000 | MARCH_7 | 2.867 | 4.023 | 3.723 | 4.017 | 4.000 | −1.133 |
| Chr2:84647001-84648000 | Ube2l6 | 0.715 | 2.608 | 2.723 | 2.433 | 2.807 | −2.092 |
| Chr2:90741001-90742000 | Ndufs3 | 1.867 | 4.345 | 2.723 | 3.017 | 3.322 | −1.455 |
| Chr2:90894001-90895000 | Gm13778 | 2.452 | 4.023 | 3.723 | 3.433 | 3.459 | −1.007 |
| Chr2:90910001-90911000 | Slc39a13 | 1.867 | 3.608 | 4.308 | 1.280 | 3.000 | −1.133 |
| Chr2:91154001-91155000 | 1110051M20Rik | 2.867 | 3.023 | 4.723 | 2.433 | 4.000 | −1.133 |
| Chr2:93026001-93027000 | Trp53i11 | 2.452 | 4.023 | 3.723 | 3.433 | 3.585 | −1.133 |
| Chr3:145309001-145310000 | Cyr61 | 2.452 | 3.608 | 2.723 | 4.017 | 3.700 | −1.248 |
| Chr3:14610001-14611000 | 1810022K09Rik | 2.452 | 3.608 | 4.045 | 3.754 | 4.000 | −1.548 |
| Chr3:31061001-31062000 | Cldn11 | 1.867 | 3.345 | 2.723 | 3.433 | 3.000 | −1.133 |
| Chr3:32336001-32337000 | Pik3ca | 1.867 | 3.345 | 3.723 | 1.433 | 3.170 | −1.303 |
| Chr3:33703001-33704000 | Ttc14 | 2.452 | 3.831 | 2.723 | 4.017 | 3.807 | −1.355 |
| Chr3:51236001-51237000 | Naa15 | 2.452 | 4.023 | 2.723 | 4.017 | 3.700 | −1.248 |
| Chr3:90190001-90191000 | Slc27a3 | 2.867 | 4.023 | 4.531 | 3.017 | 4.392 | −1.525 |
| Chr3:90203001-90204000 | Ints3 | 3.452 | 4.345 | 4.045 | 4.892 | 4.524 | −1.072 |
| Chr4:107892001-107893000 | Zyg11a | 2.452 | 4.193 | 4.045 | 3.017 | 3.807 | −1.355 |
| Chr4:116776001-116777000 | Ptch2 | 1.867 | 3.345 | 3.308 | 2.433 | 3.585 | −1.718 |
| Chr4:117548001-117549000 | B4galt2 | 1.867 | 3.023 | 1.723 | 3.754 | 4.000 | −2.133 |
| Chr4:119308001-119309000 | Guca2a | 0.867 | 4.345 | 2.723 | 2.433 | 3.459 | −2.592 |
| Chr4:128582001-128583000 | Trim62 | 2.452 | 4.193 | 3.723 | 3.754 | 3.459 | −1.007 |
| Chr4:143208001-143209000 | Gm13083 | 2.452 | 3.831 | 3.723 | 4.017 | 3.700 | −1.248 |
| Chr4:143946001-143947000 | Gm13119 | 2.452 | 3.345 | 3.308 | 3.754 | 3.459 | −1.007 |
| Chr4:14616001-14617000 | Lrrc69 | 3.189 | 4.724 | 4.308 | 4.240 | 4.322 | −1.133 |
| Chr4:149467001-149468000 | Gpr157 | 2.452 | 2.023 | 4.045 | 3.433 | 3.807 | −1.355 |
| Chr4:150276001-150277000 | Park7 | 2.867 | 3.023 | 3.308 | 4.240 | 4.000 | −1.133 |
| Chr4:19525001-19526000 | Fam82b | 2.867 | 3.831 | 3.723 | 4.240 | 3.907 | −1.040 |
| Chr4:40995001-40996000 | Aqp7 | 2.452 | 4.345 | 2.723 | 4.240 | 3.807 | −1.355 |
| Chr4:41472001-41473000 | 2310028H24Rik | 1.867 | 4.345 | 1.723 | 3.754 | 3.322 | −1.455 |
| Chr4:45357001-45358000 | Dcaf10 | 2.867 | 3.345 | 3.723 | 4.017 | 4.000 | −1.133 |
| Chr4:49546001-49547000 | Zfp189 | 2.452 | 3.831 | 3.723 | 3.433 | 3.700 | −1.248 |
| Chr4:53802001-53803000 | Tal2 | 2.867 | 3.831 | 4.893 | 3.433 | 4.087 | −1.220 |
| Chr4:63212001-63213000 | Atp6v1g1 | 2.452 | 3.608 | 1.723 | 4.240 | 3.459 | −1.007 |

TABLE 2-continued

| | | log₂ normalized Read count | | | | |
|---|---|---|---|---|---|---|
| Peak | Gene | NCsh (N) | NCsh (C) | MMP-9sh (N) | MMP-9sh (C) | Input | log₂ ratio NCsh (N) vs input |
| Chr4:72509001-72510000 | Aldoart1 | 2.452 | 4.193 | 2.723 | 4.017 | 4.000 | −1.548 |
| Chr4:83153001-83154000 | Gm10154 | 2.452 | 1.023 | 4.045 | 3.017 | 3.459 | −1.007 |
| Chr4:88362001-88363000 | Klhl9 | 1.867 | 3.608 | 4.531 | 2.433 | 3.700 | −1.833 |
| Chr5:104534001-104535000 | Sparcl1 | 2.867 | 3.831 | 3.723 | 4.017 | 4.000 | −1.133 |
| Chr5:105466001-105467000 | Gbp8 | 1.867 | 4.193 | 1.723 | 3.433 | 3.585 | −1.718 |
| Chr5:114456001-114457000 | Dao | 1.867 | 4.193 | 1.723 | 3.754 | 3.700 | −1.833 |
| Chr5:115096001-115097000 | Trpv4 | 2.867 | 3.831 | 3.723 | 4.017 | 3.907 | −1.040 |
| Chr5:115131001-115132000 | Gltp | 2.452 | 3.023 | 4.531 | 4.017 | 3.459 | −1.007 |
| Chr5:116469001-116470000 | Prkab1 | 1.867 | 4.608 | 2.723 | 4.433 | 3.322 | −1.455 |
| Chr5:117813001-117814000 | Wsb2 | 1.867 | 4.023 | 3.723 | 3.433 | 3.322 | −1.455 |
| Chr5:123492001-123493000 | Morn3 | 2.452 | 3.831 | 3.723 | 3.754 | 4.087 | −1.635 |
| Chr5:130681001-130682000 | Rabgef1 | 2.867 | 3.608 | 1.571 | 4.892 | 4.170 | −1.303 |
| Chr5:139875001-139876000 | 3110082I17Rik | 1.867 | 3.831 | 3.723 | 2.433 | 3.807 | −1.940 |
| Chr5:141212001-141213000 | Amz1 | 2.867 | 4.193 | 1.571 | 4.754 | 3.907 | −1.040 |
| Chr5:23883001-23884000 | Nos3 | 1.867 | 3.831 | 1.723 | 4.017 | 3.907 | −2.040 |
| Chr5:25007001-25008000 | 4831440E17Rik | 1.867 | 1.023 | 3.723 | 4.240 | 3.907 | −2.040 |
| Chr5:33372001-33373000 | Ywhah | 2.867 | 3.023 | 5.045 | 3.754 | 4.000 | −1.133 |
| Chr5:36063001-36064000 | Sh3tc1 | 2.452 | 3.345 | 3.308 | 3.754 | 4.000 | −1.548 |
| Chr5:86518001-86519000 | Stap1 | 2.452 | 3.023 | 4.045 | 3.017 | 4.248 | −1.796 |
| Chr5:89861001-89862000 | Gc | 3.452 | 4.193 | 5.183 | 3.433 | 5.615 | −2.163 |
| Chr5:95385001-95386000 | Gm3176 | 1.867 | 4.345 | 5.045 | 4.017 | 3.000 | −1.133 |
| Chr6:113425001-113426000 | Il17rc | 2.452 | 4.483 | 4.723 | 4.017 | 3.907 | −1.455 |
| Chr6:113447001-113448000 | Prrt3 | 2.452 | 3.345 | 3.723 | 4.017 | 3.807 | −1.355 |
| Chr6:115898001-115899000 | H1foo | 1.867 | 3.831 | 4.045 | 3.017 | 3.322 | −1.455 |
| Chr6:116456001-116457000 | Olfr212 | 2.452 | 3.023 | 3.723 | 4.017 | 3.807 | −1.355 |
| Chr6:116574001-116575000 | Zfp422 | 3.189 | 3.345 | 3.723 | 5.017 | 4.248 | −1.059 |
| Chr6:120774001-120775000 | Atp6v1e1 | 3.452 | 5.271 | 5.045 | 4.017 | 2.322 | 1.130 |
| Chr6:125499001-125500000 | Vwf | 1.867 | 4.023 | 3.723 | 1.433 | 4.000 | −2.133 |
| Chr6:135328001-135329000 | Emp1 | 3.189 | 3.023 | 4.893 | 3.433 | 4.322 | −1.133 |
| Chr6:30862001-30863000 | 4930412F09Rik | 2.867 | 4.193 | 4.308 | 3.433 | 4.170 | −1.303 |
| Chr6:40146001-40147000 | Gm5567 | 2.452 | 4.193 | 4.308 | 2.433 | 3.459 | −1.007 |
| Chr6:40319001-40320000 | Agk | 2.867 | 3.608 | 3.308 | 4.240 | 4.087 | −1.220 |
| Chr6:71803001-71804000 | Immt | 2.867 | 3.831 | 3.723 | 4.017 | 4.322 | −1.455 |
| Chr6:83523001-83524000 | Stambp | 2.452 | 3.608 | 3.723 | 4.240 | 3.700 | −1.248 |
| Chr6:83684001-83685000 | Vax2 | 2.452 | 3.608 | 4.045 | 4.433 | 4.087 | −1.635 |
| Chr6:86344001-86345000 | Pcyox1 | 1.867 | 3.608 | 1.723 | 3.754 | 3.170 | −1.303 |
| Chr7:100063001-100064000 | Prcp | 3.452 | 4.023 | 4.531 | 4.433 | 4.644 | −1.192 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr7:106624001-106625000 | Rps3 | 2.452 | 3.831 | 3.308 | 4.240 | 3.459 | −1.007 |
| Chr7:108023001-108024000 | Arhgef17 | 2.452 | 3.023 | 3.723 | 3.433 | 4.170 | −1.718 |
| Chr7:112892001-112893000 | Taf10 | 0.867 | 2.608 | 2.723 | 1.433 | 3.585 | −2.718 |
| Chr7:113577001-113578000 | Gm4759 | 1.867 | 3.345 | 3.308 | 4.017 | 3.459 | −1.592 |
| Chr7:117120001-117121000 | Tmem41b | 1.867 | 3.345 | 4.308 | 3.433 | 3.585 | −1.718 |
| Chr7:125259001-125260000 | Rps15a | 0.867 | 2.023 | 1.723 | 2.433 | 3.459 | −2.592 |
| Chr7:135022001-135023000 | Zfp646 | 2.867 | 3.345 | 4.723 | 3.433 | 3.907 | −1.040 |
| Chr7:147284001-147285000 | 1810014F10Rik | 2.452 | 4.023 | 3.308 | 4.240 | 3.459 | −1.007 |
| Chr7:148278001-148279000 | Sigirr | 1.867 | 3.831 | 3.308 | 3.017 | 3.585 | −1.718 |
| Chr7:149085001-149086000 | Tollip | 2.452 | 3.608 | 2.723 | 4.017 | 3.459 | −1.007 |
| Chr7:151029001-151030000 | Dhcr7 | 2.452 | 3.831 | 4.045 | 3.017 | 3.807 | −1.355 |
| Chr7:25302001-25303000 | Zfp428 | 1.867 | 3.608 | 3.308 | 4.017 | 4.170 | −2.303 |
| Chr7:25348001-25349000 | Xrcc1 | 2.452 | 3.023 | 4.308 | 3.017 | 3.459 | −1.007 |
| Chr7:28299001-28300000 | Prx | 2.867 | 3.345 | 3.308 | 4.240 | 3.907 | −1.040 |
| Chr7:31429001-31430000 | Rbm42 | 2.452 | 2.023 | 2.723 | 4.433 | 3.459 | −1.007 |
| Chr7:3601001-3602000 | Cnot3 | 1.867 | 3.831 | 4.045 | 2.433 | 3.585 | −1.718 |
| Chr7:4092001-4093000 | Leng8 | 2.452 | 3.831 | 4.308 | 3.017 | 3.700 | −1.248 |
| Chr7:51486001-51487000 | 1700028J19Rik | 3.189 | 3.608 | 4.893 | 4.017 | 4.248 | −1.059 |
| Chr7:51500001-51501000 | 2410002F23Rik | 2.452 | 4.023 | 3.308 | 3.754 | 3.907 | −1.455 |
| Chr7:52246001-52247000 | Gm15545 | 2.452 | 3.608 | 3.723 | 3.754 | 3.700 | −1.248 |
| Chr7:52320001-52321000 | Nosip | 2.452 | 3.608 | 4.045 | 3.017 | 3.585 | −1.133 |
| Chr7:52890001-52891000 | Rasip1 | 2.867 | 3.608 | 4.045 | 3.754 | 3.907 | −1.040 |
| Chr7:53198001-53199000 | Ccdc114 | 2.452 | 3.023 | 2.723 | 4.017 | 3.585 | −1.133 |
| Chr7:5364001-5365000 | Vmn1r58 | 2.867 | 3.345 | 4.045 | 4.240 | 4.087 | −1.220 |
| Chr7:63103001-63104000 | Cyfip1 | 2.452 | 3.345 | 2.723 | 4.017 | 3.700 | −1.248 |
| Chr7:74884001-74885000 | Synm | 1.867 | 3.831 | 3.308 | 3.017 | 3.170 | −1.303 |
| Chr7:88302001-88303000 | Slc28a1 | 1.867 | 4.023 | 2.723 | 3.017 | 3.459 | −1.592 |
| Chr7:97767001-97768000 | Dlg2 | 3.452 | 2.608 | 4.531 | 4.433 | 4.585 | −1.133 |
| Chr7:99723001-99724000 | Ccdc90b | 1.867 | 2.608 | 4.308 | 3.017 | 3.170 | −1.303 |
| Chr7:99884001-99885000 | 4632427E13Rik | 1.867 | 4.193 | 4.045 | 4.017 | 3.807 | −1.940 |
| Chr8:107816001-107817000 | Exoc3l | 2.452 | 2.023 | 2.723 | 4.433 | 3.907 | −1.455 |
| Chr8:107932001-107933000 | Kctd19 | 2.867 | 4.345 | 4.045 | 4.017 | 4.087 | −1.220 |
| Chr8:108111001-108112000 | Gm8841 | 2.867 | 3.831 | 4.045 | 5.339 | 3.907 | −1.040 |
| Chr8:109536001-109537000 | Sntb2 | 2.867 | 3.608 | 4.045 | 3.754 | 4.000 | −1.133 |
| Chr8:112200001-112201000 | 2400003C14Rik | 2.452 | 3.831 | 3.723 | 3.754 | 3.807 | −1.355 |
| Chr8:121970001-121971000 | Osgin1 | 1.867 | 2.608 | 3.308 | 2.433 | 3.000 | −1.133 |
| Chr8:14902001-14903000 | Cln8 | 2.452 | 3.831 | 3.308 | 4.017 | 3.700 | −1.248 |

TABLE 2-continued

| Peak | Gene | log₂ normalized Read count | | | | | log₂ ratio NCsh (N) vs input |
|------|------|---------|---------|---------|---------|-------|---------|
|      |      | NCsh (N) | NCsh (C) | MMP-9sh (N) | MMP-9sh (C) | Input | |
| Chr8:26697001-26698000 | Letm2 | 2.452 | 4.345 | 3.723 | 3.433 | 4.087 | −1.635 |
| Chr8:28157001-28158000 | Prosc | 2.452 | 3.831 | 2.723 | 4.017 | 3.585 | −1.133 |
| Chr8:4106001-4107000 | Cd209f | 1.867 | 2.608 | 2.723 | 4.602 | 3.322 | −1.455 |
| Chr8:47102001-47103000 | Lrp2bp | 3.189 | 3.831 | 4.045 | 4.433 | 4.585 | −1.396 |
| Chr8:4859001-4860000 | Rpl21-ps14 | 2.867 | 3.608 | 2.723 | 5.017 | 4.170 | −1.303 |
| Chr8:72236001-72237000 | Zfp869 | 0.867 | 3.608 | 1.723 | 2.433 | 2.807 | −1.940 |
| Chr8:72834001-72835000 | Cope | 1.867 | 4.193 | 3.723 | 4.602 | 3.459 | −1.592 |
| Chr8:73056001-73057000 | Fkbp8 | 0.715 | 4.023 | 4.308 | 3.754 | 3.322 | −2.607 |
| Chr8:73900001-73901000 | Ocel1 | 1.867 | 4.345 | 2.723 | 3.433 | 3.170 | −1.303 |
| Chr8:74708001-74709000 | Rab8a | 2.452 | 3.831 | 4.045 | 3.017 | 4.000 | −1.548 |
| Chr8:83341001-83342000 | Gab1 | 1.867 | 2.608 | 2.723 | 3.017 | 3.170 | −1.303 |
| Chr8:86591001-86592000 | C330011M18Rik | 1.867 | 2.608 | 3.308 | 4.433 | 3.459 | −1.592 |
| Chr8:87414001-87415000 | Gcdh | 2.452 | 3.345 | 4.308 | 3.017 | 3.585 | −1.133 |
| Chr8:87613001-87614000 | Man2b1 | 0.867 | 2.608 | 1.571 | 4.017 | 3.700 | −2.833 |
| Chr8:97507001-97508000 | Gpr56 | 1.867 | 2.023 | 3.723 | 1.433 | 3.322 | −1.455 |
| Chr9:102494001-102495000 | Cep63 | 2.867 | 4.193 | 3.308 | 4.433 | 4.248 | −1.381 |
| Chr9:103371001-103372000 | Bfsp2 | 2.452 | 4.023 | 3.308 | 3.754 | 4.170 | −1.718 |
| Chr9:107229001-107230000 | Hemk1 | 2.452 | 3.608 | 4.531 | 2.433 | 3.585 | −1.133 |
| Chr9:107436001-107437000 | Tmem115 | 2.452 | 3.345 | 1.723 | 4.240 | 3.459 | −1.007 |
| Chr9:20294001-20295000 | Gm17523 | 1.867 | 4.345 | 2.723 | 3.017 | 3.807 | −1.940 |
| Chr9:21312001-21313000 | Dnm2 | 2.452 | 1.023 | 4.045 | 3.017 | 3.907 | −1.455 |
| Chr9:44755001-44756000 | Ube4a | 2.452 | 4.023 | 4.045 | 3.433 | 3.907 | −1.455 |
| Chr9:50447001-50448000 | Dlat | 2.452 | 4.023 | 3.308 | 4.017 | 3.585 | −1.133 |
| Chr9:51674001-51675000 | 9230115E21Rik | 1.867 | 3.023 | 3.723 | 4.017 | 3.907 | −2.040 |
| Chr9:51808001-51809000 | Gm6981 | 2.452 | 2.023 | 4.045 | 4.240 | 4.000 | −1.548 |
| Chr9:54478001-54479000 | Acsbg1 | 0.867 | 2.608 | 2.723 | 4.602 | 3.585 | −2.718 |
| Chr9:57444001-57445000 | Ulk3 | 2.452 | 3.831 | 3.308 | 4.017 | 3.807 | −1.355 |
| Chr9:64030001-64031000 | Snapc5 | 1.867 | 4.023 | 3.723 | 4.017 | 3.000 | −1.133 |
| Chr9:78223001-78224000 | Ooep | 1.867 | 3.023 | 3.308 | 4.602 | 3.459 | −1.592 |
| Chr9:96334001-96335000 | BC043934 | 2.452 | 2.023 | 4.308 | 3.433 | 3.807 | −1.355 |
| Chr9:97082001-97083000 | Rpl7a-ps10 | 1.867 | 3.345 | 3.308 | 3.433 | 3.807 | −1.940 |
| Chr9:98469001-98470000 | Copb2 | 2.452 | 3.831 | 3.723 | 3.433 | 3.907 | −1.455 |
| Gene body and promoter cleavage | | | | | | | |
| Chr1:13682001-13683000 | Xkr9 | 1.867 | 4.930 | 3.723 | 3.433 | 4.392 | −2.525 |
| Chr1:136869001-136870000 | Ube2t | 2.452 | 3.608 | 4.308 | 2.433 | 3.585 | −1.133 |
| Chr1:146094001-146095000 | Rgs1 | 1.867 | 3.831 | 4.045 | 3.754 | 4.000 | −2.133 |
| Chr1:157123001-157124000 | Xpr1 | 3.452 | 3.831 | 4.045 | 4.754 | 4.644 | −1.192 |

TABLE 2-continued

| | | log₂ normalized Read count | | | | |
|---|---|---|---|---|---|---|
| Peak | Gene | NCsh (N) | NCsh (C) | MMP-9sh (N) | MMP-9sh (C) | Input | log₂ ratio NCsh (N) vs input |
| Chr1:173214001-173215000 | Usp21 | 2.452 | 3.023 | 4.308 | 2.433 | 4.392 | −1.940 |
| Chr1:173436001-173437000 | Refbp2 | 1.867 | 3.345 | 3.308 | 4.433 | 4.000 | −2.133 |
| Chr1:173826001-173827000 | Gm10521 | 1.867 | 3.831 | 1.723 | 3.433 | 4.000 | −2.133 |
| Chr1:174020001-174021000 | Copa | 1.867 | 3.831 | 3.723 | 1.433 | 3.700 | −1.833 |
| Chr1:175530001-175531000 | Pydc4 | 2.452 | 3.608 | 4.308 | 2.433 | 3.585 | −1.133 |
| Chr1:180188001-180189000 | Gm9982 | 1.867 | 3.608 | 3.308 | 3.754 | 4.087 | −2.220 |
| Chr1:188796001-188797000 | D1Pas1 | 2.452 | 4.023 | 3.723 | 3.433 | 3.700 | −1.248 |
| Chr1:190163001-190164000 | Ush2a | 3.867 | 4.023 | 5.045 | 4.754 | 5.170 | −1.303 |
| Chr1:36669001-36670000 | Fam178b | 2.452 | 3.023 | 3.308 | 3.754 | 4.087 | −1.635 |
| Chr1:39422001-39423000 | Rpl31 | 2.452 | 3.831 | 4.045 | 3.754 | 3.459 | −1.007 |
| Chr1:4774001-4775000 | Mrpl15 | 1.867 | 2.608 | 3.308 | 2.433 | 3.170 | −1.303 |
| Chr1:55232001-55233000 | Rftn2 | 2.452 | 3.608 | 4.045 | 3.017 | 3.700 | −1.248 |
| Chr1:58744001-58745000 | Als2cr12 | 3.189 | 4.483 | 4.308 | 4.240 | 4.322 | −1.133 |
| Chr1:60784001-60785000 | Cd28 | 4.037 | 4.483 | 5.424 | 4.754 | 5.129 | −1.092 |
| Chr1:60951001-60952000 | Ctla4 | 1.867 | 3.608 | 1.723 | 3.433 | 3.807 | −1.940 |
| Chr1:64660001-64661000 | Mettl21a | 1.867 | 3.831 | 4.045 | 3.017 | 4.000 | −2.133 |
| Chr1:80380001-80381000 | Gm6189 | 2.452 | 3.023 | 4.308 | 3.017 | 3.459 | −1.007 |
| Chr10:105628001-105629000 | Gm7263 | 3.452 | 4.023 | 4.893 | 4.754 | 4.644 | −1.192 |
| Chr10:128145001-128146000 | Pmel | 2.867 | 3.345 | 4.045 | 3.754 | 4.248 | −1.381 |
| Chr10:29043001-29044000 | Echdc1 | 3.452 | 3.608 | 4.531 | 4.433 | 4.755 | −1.303 |
| Chr10:79634001-79635000 | Cirbp | 2.867 | 3.023 | 3.308 | 4.433 | 3.907 | −1.040 |
| Chr10:80070001-80071000 | Adat3 | 0.867 | 3.608 | 2.723 | 3.433 | 3.000 | −2.133 |
| Chr10:80394001-80395000 | Gadd45b | 0.867 | 3.608 | 1.723 | 2.433 | 2.322 | −1.455 |
| Chr10:80437001-80438000 | Gng7 | 1.867 | 3.608 | 2.723 | 3.017 | 3.700 | −1.833 |
| Chr10:80738001-80739000 | Tjp3 | 1.867 | 4.023 | 2.723 | 3.017 | 3.170 | −1.303 |
| Chr10:86211001-86212000 | BC030307 | 2.867 | 3.831 | 1.723 | 4.602 | 4.248 | −1.381 |
| Chr10:98910001-98911000 | Gad1-ps | 1.867 | 3.023 | 4.893 | 3.754 | 4.459 | −2.592 |
| Chr11:106618001-106619000 | Gm885 | 0.867 | 3.831 | 2.723 | 3.017 | 3.700 | −2.833 |
| Chr11:115130001-115131000 | Fdxr | 2.452 | 3.608 | 3.723 | 3.433 | 3.585 | −1.133 |
| Chr11:115720001-115721000 | Myo15b | 1.867 | 3.608 | 3.308 | 2.433 | 3.000 | −1.133 |
| Chr11:116534001-116535000 | 1810032O08Rik | 2.867 | 3.608 | 4.045 | 4.433 | 3.907 | −1.040 |
| Chr11:118345001-118346000 | Engase | 1.867 | 4.023 | 3.308 | 3.754 | 4.170 | −2.303 |
| Chr11:119141001-119142000 | Gaa | 2.452 | 3.831 | 2.723 | 4.017 | 3.807 | −1.355 |
| Chr11:120302001-120303000 | Tspan10 | 2.452 | 4.345 | 1.571 | 4.433 | 4.000 | −1.548 |
| Chr11:120510001-120511000 | Gm11768 | 1.867 | 3.608 | 3.723 | 3.754 | 3.000 | −1.133 |
| Chr11:46057001-46058000 | Cyfip2 | 2.867 | 4.193 | 3.308 | 4.240 | 4.392 | −1.525 |
| Chr11:5705001-5706000 | Pgam2 | 2.867 | 3.023 | 3.308 | 4.240 | 3.907 | −1.040 |

TABLE 2-continued

| Peak | Gene | NCsh (N) | NCsh (C) | MMP-9sh (N) | MMP-9sh (C) | Input | log₂ ratio NCsh (N) vs input |
|---|---|---|---|---|---|---|---|
| Chr11:57987001-57988000 | Mrpl22 | 0.867 | 4.483 | 4.045 | 4.240 | 3.000 | −2.133 |
| Chr11:6017001-6018000 | Nudcd3 | 1.867 | 4.023 | 1.723 | 3.433 | 4.000 | −2.133 |
| Chr11:60394001-60395000 | Gm17423 | 1.867 | 2.608 | 2.723 | 3.017 | 3.322 | −1.455 |
| Chr11:60751001-60752000 | Map2k3 | 2.452 | 3.345 | 4.308 | 4.017 | 4.322 | −1.870 |
| Chr11:6427001-6428000 | Gm11974 | 2.867 | 4.023 | 3.308 | 4.602 | 4.087 | −1.220 |
| Chr11:6535001-6536000 | Wap | 0.715 | 3.608 | 3.308 | 4.433 | 4.170 | −3.455 |
| Chr11:69712001-69713000 | 2810408A11Rik | 2.452 | 2.023 | 5.045 | 4.433 | 4.000 | −1.548 |
| Chr11:73021001-73022000 | Shpk | 1.867 | 4.023 | 3.723 | 1.433 | 3.000 | −1.133 |
| Chr11:75285001-75286000 | Tlcd2 | 1.867 | 4.023 | 3.308 | 4.433 | 4.170 | −2.303 |
| Chr11:80021001-80022000 | Rhot1 | 3.452 | 3.345 | 4.893 | 4.017 | 4.459 | −1.007 |
| Chr11:96636001-96637000 | Snx11 | 1.867 | 4.483 | 3.723 | 3.433 | 4.087 | −2.220 |
| Chr11:96910001-96911000 | Mrpl10 | 2.452 | 3.608 | 3.723 | 3.433 | 3.700 | −1.248 |
| Chr11:98634001-98635000 | Nr1d1 | 2.452 | 3.831 | 2.723 | 4.433 | 3.459 | −1.007 |
| Chr12:102142001-102143000 | Gpr68 | 2.867 | 3.345 | 2.723 | 4.754 | 3.907 | −1.040 |
| Chr12:102387001-102388000 | Kif4-ps | 2.452 | 3.831 | 1.723 | 4.433 | 3.459 | −1.007 |
| Chr12:114001001-114002000 | Pld4 | 1.867 | 3.023 | 2.723 | 3.433 | 3.322 | −1.455 |
| Chr12:4236001-4237000 | 2410017P09Rik | 0.867 | 2.023 | 3.308 | 4.240 | 3.459 | −2.592 |
| Chr12:70398001-70399000 | Klhdc2 | 2.452 | 1.023 | 3.308 | 3.754 | 3.807 | −1.355 |
| Chr12:86564001-86565000 | Eif2b2 | 1.867 | 3.345 | 3.308 | 3.754 | 3.459 | −1.592 |
| Chr13:101717001-101718000 | Gm10257 | 3.452 | 3.023 | 5.531 | 3.754 | 4.954 | −1.502 |
| Chr13:21577001-21578000 | Zkscan4 | 2.452 | 3.023 | 3.723 | 3.433 | 3.459 | −1.007 |
| Chr13:21594001-21595000 | Gm11273 | 2.452 | 3.608 | 3.308 | 4.017 | 3.585 | −1.133 |
| Chr13:23629001-23630000 | Hist1h3g | 2.867 | 1.023 | 3.723 | 4.433 | 3.907 | −1.040 |
| Chr13:23637001-23638000 | Hist1h3f | 2.452 | 3.608 | 4.723 | 1.433 | 3.459 | −1.007 |
| Chr13:23701001-23702000 | Hist1h2be | 2.452 | 3.608 | 4.308 | 3.017 | 3.907 | −1.455 |
| Chr13:33107001-33108000 | Serpinb9 | 2.452 | 3.608 | 3.723 | 4.892 | 3.807 | −1.355 |
| Chr13:40980001-40981000 | Gcnt2 | 1.867 | 3.608 | 2.723 | 3.017 | 4.000 | −2.133 |
| Chr13:43463001-43464000 | Sirt5 | 2.452 | 4.345 | 4.045 | 3.017 | 3.459 | −1.007 |
| Chr13:58439001-58440000 | Kif27 | 2.452 | 3.345 | 4.045 | 3.017 | 3.459 | −1.007 |
| Chr13:62818001-62819000 | Gm5665 | 2.867 | 4.483 | 4.308 | 4.433 | 4.170 | −1.303 |
| Chr13:73470001-73471000 | Mrpl36 | 1.867 | 3.345 | 2.723 | 3.433 | 3.322 | −1.455 |
| Chr13:76125001-76126000 | Spata9 | 2.452 | 3.023 | 3.723 | 3.433 | 3.700 | −1.248 |
| Chr13:76210001-76211000 | Arsk | 2.867 | 2.608 | 4.723 | 3.017 | 4.459 | −1.592 |
| Chr14:118518001-118519000 | Tgds | 1.867 | 4.345 | 2.723 | 4.754 | 3.322 | −1.455 |
| Chr14:26528001-26529000 | 1700054O19Rik | 1.867 | 4.483 | 4.045 | 3.754 | 3.907 | −2.040 |
| Chr14:55505001-55506000 | Bcl2l2 | 1.867 | 3.023 | 4.308 | 1.433 | 3.585 | −1.718 |
| Chr14:55721001-55722000 | Ap1g2 | 2.452 | 4.193 | 4.308 | 4.017 | 3.585 | −1.133 |

TABLE 2-continued

| Peak | Gene | NCsh (N) | NCsh (C) | MMP-9sh (N) | MMP-9sh (C) | Input | log₂ ratio NCsh (N) vs input |
|---|---|---|---|---|---|---|---|
| Chr14:59897001-59898000 | Phf11 | 0.867 | 2.608 | 1.723 | 4.602 | 2.585 | −1.718 |
| Chr14:8162001-8163000 | Gm5797 | 1.867 | 3.831 | 3.308 | 3.433 | 4.459 | −2.592 |
| Chr15:100241001-100242000 | Slc11a2 | 2.867 | 4.345 | 3.723 | 4.017 | 3.907 | −1.040 |
| Chr15:102114001-102115000 | Mfsd5 | 2.452 | 4.930 | 4.045 | 3.017 | 3.807 | −1.355 |
| Chr15:38227001-38228000 | Klf10 | 3.189 | 3.831 | 3.723 | 4.602 | 2.322 | 0.867 |
| Chr15:39584001-39585000 | Tm7sf4 | 3.252 | 3.608 | 4.045 | 4.754 | 3.720 | −0.468 |
| Chr15:58819001-58820000 | Mtss1 | 2.452 | 3.345 | 3.308 | 3.754 | 3.585 | −1.133 |
| Chr15:61821001-61822000 | Myc | 2.452 | 4.023 | 4.045 | 4.754 | 3.459 | −1.007 |
| Chr15:66430001-66431000 | Phf20l1 | 2.867 | 4.345 | 4.723 | 4.433 | 4.087 | −1.220 |
| Chr15:76505001-76506000 | Ppp1r16a | 2.867 | 3.608 | 3.723 | 4.433 | 4.170 | −1.303 |
| Chr15:76883001-76884000 | Apol6 | 0.867 | 4.345 | 2.723 | 3.433 | 3.807 | −2.940 |
| Chr15:78243001-78244000 | Mpst | 2.867 | 4.608 | 3.723 | 4.017 | 4.170 | −1.303 |
| Chr15:78984001-78985000 | Sox10 | 1.867 | 3.345 | 1.723 | 3.754 | 3.000 | −1.133 |
| Chr15:79977001-79978000 | Tab1 | 3.452 | 3.831 | 4.531 | 5.017 | 4.459 | −1.007 |
| Chr15:82842001-82843000 | Nfam1 | 2.452 | 3.831 | 4.045 | 3.017 | 3.700 | −1.248 |
| Chr15:89316001-89317000 | C230037L18Rik | 1.867 | 3.608 | 3.308 | 4.017 | 4.322 | −2.455 |
| Chr15:95908001-95909000 | D030018L15Rik | 2.867 | 4.023 | 2.723 | 4.433 | 4.087 | −1.220 |
| Chr15:98548001-98549000 | Ccdc65 | 2.867 | 3.023 | 4.308 | 3.754 | 4.392 | −1.525 |
| Chr16:11071001-11072000 | Snn | 2.452 | 3.608 | 4.308 | 3.017 | 4.000 | −1.548 |
| Chr16:11314001-11315000 | Tnfrsf17 | 3.189 | 3.831 | 4.308 | 4.240 | 4.322 | −1.133 |
| Chr16:17117001-17118000 | 2610318N02Rik | 2.867 | 4.193 | 4.308 | 3.754 | 4.087 | −1.220 |
| Chr16:18815001-18816000 | Ufd1l | 1.867 | 3.023 | 3.723 | 1.433 | 3.322 | −1.455 |
| Chr16:29585001-29586000 | Opa1 | 1.867 | 4.023 | 1.723 | 3.433 | 3.459 | −1.592 |
| Chr16:30524001-30525000 | Tmem44 | 2.452 | 4.483 | 4.045 | 3.433 | 3.700 | −1.248 |
| Chr16:32428001-32429000 | Tctex1d2 | 2.452 | 5.023 | 3.723 | 3.433 | 3.907 | −1.455 |
| Chr16:38435001-38436000 | Pla1a | 2.867 | 3.345 | 1.723 | 4.892 | 4.000 | −1.133 |
| Chr16:4882001-4883000 | Fam100a | 2.452 | 3.023 | 2.723 | 5.017 | 3.907 | −1.455 |
| Chr16:49788001-49789000 | Gm15518 | 2.452 | 3.831 | 2.723 | 4.017 | 4.322 | −1.870 |
| Chr16:50593001-50594000 | Ccdc54 | 1.867 | 4.345 | 1.571 | 4.602 | 3.907 | −2.040 |
| Chr16:52249001-52250000 | Alcam | 1.867 | 3.831 | 1.571 | 3.754 | 3.170 | −1.303 |
| Chr16:57064001-57065000 | 2310005G13Rik | 2.452 | 3.831 | 4.045 | 3.017 | 3.459 | −1.007 |
| Chr16:57194001-57195000 | Tbc1d23 | 1.867 | 3.608 | 1.723 | 3.433 | 3.170 | −1.303 |
| Chr16:87438001-87439000 | Rwdd2b | 1.867 | 3.608 | 3.723 | 3.017 | 3.170 | −1.303 |
| Chr16:92393001-92394000 | Rcan1 | 3.452 | 3.608 | 4.045 | 4.754 | 2.585 | 0.867 |
| Chr16:93599001-93600000 | Setd4 | 0.867 | 3.608 | 2.723 | 2.433 | 3.459 | −2.592 |
| Chr17:23772001-23773000 | Mmp25 | 2.867 | 2.608 | 3.723 | 4.017 | 3.907 | −1.040 |
| Chr17:26107001-26108000 | Solh | 2.452 | 3.608 | 4.308 | 3.017 | 3.459 | −1.007 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr17:33238001-33239000 | Zfp563 | 1.867 | 3.345 | 2.723 | 3.754 | 3.000 | −1.133 |
| Chr17:34201001-34202000 | Col11a2 | 1.867 | 2.608 | 3.308 | 3.017 | 3.807 | −1.940 |
| Chr17:34699001-34700000 | Notch4 | 1.867 | 3.608 | 4.045 | 2.433 | 3.907 | −2.040 |
| Chr17:35094001-35095000 | Hspa1b | 2.452 | 3.608 | 4.531 | 3.017 | 3.459 | −1.007 |
| Chr17:35887001-35888000 | Gm20442 | 2.867 | 3.345 | 3.308 | 4.240 | 4.087 | −1.220 |
| Chr17:45645001-45646000 | Aars2 | 2.452 | 4.831 | 4.045 | 4.240 | 4.000 | −1.548 |
| Chr17:6652001-6653000 | Dynlt1c | 2.452 | 4.345 | 2.723 | 4.017 | 3.700 | −1.248 |
| Chr18:33952001-33953000 | 2410004N09Rik | 0.867 | 3.023 | 3.308 | 3.433 | 3.322 | −2.455 |
| Chr18:35865001-35866000 | 1700066B19Rik | 2.452 | 4.193 | 4.723 | 4.433 | 4.322 | −1.870 |
| Chr18:37204001-37205000 | Pcdha11 | 3.867 | 3.345 | 3.308 | 5.520 | 4.907 | −1.040 |
| Chr18:38497001-38498000 | Gnpda1 | 2.452 | 2.608 | 3.308 | 3.754 | 3.459 | −1.007 |
| Chr18:4377001-4378000 | Gm17417 | 2.867 | 2.608 | 3.308 | 4.433 | 4.170 | −1.303 |
| Chr18:61100001-61101000 | Camk2a | 2.452 | 3.023 | 4.045 | 3.017 | 3.907 | −1.455 |
| Chr18:63854001-63855000 | Txnl1 | 2.867 | 4.023 | 4.531 | 3.017 | 3.907 | −1.040 |
| Chr19:24753001-24754000 | E030010A14Rik | 2.867 | 3.023 | 4.308 | 4.017 | 4.170 | −1.303 |
| Chr19:24951001-24952000 | Gm10053 | 0.867 | 4.193 | 2.723 | 4.017 | 2.322 | −1.455 |
| Chr19:28835001-28836000 | Gm6788 | 2.452 | 3.345 | 2.723 | 4.433 | 3.807 | −1.355 |
| Chr19:28958001-28959000 | Slc1a1 | 2.867 | 3.345 | 4.308 | 3.433 | 3.907 | −1.040 |
| Chr19:29884001-29885000 | Ranbp6 | 2.452 | 4.483 | 1.723 | 5.133 | 4.087 | −1.635 |
| Chr19:4011001-4012000 | Ndufv1 | 2.452 | 3.345 | 4.045 | 3.433 | 4.087 | −1.635 |
| Chr19:42201001-42202000 | Avpi1 | 2.452 | 2.023 | 4.723 | 3.754 | 3.907 | −1.455 |
| Chr19:4314001-4315000 | Kdm2a | 2.867 | 4.345 | 4.045 | 3.754 | 4.000 | −1.133 |
| Chr19:43900001-43901000 | Abcc2 | 2.452 | 4.193 | 1.723 | 4.240 | 3.459 | −1.007 |
| Chr19:44029001-44030000 | Cpn1 | 2.452 | 2.023 | 4.045 | 3.017 | 3.585 | −1.133 |
| Chr19:47916001-47917000 | Wdr96 | 3.452 | 3.831 | 3.723 | 4.892 | 4.524 | −1.072 |
| Chr19:48010001-48011000 | Ccdc147 | 1.867 | 3.023 | 2.723 | 3.017 | 3.000 | −1.133 |
| Chr19:4840001-4841000 | Ccdc87 | 2.452 | 3.023 | 4.045 | 3.017 | 3.907 | −1.455 |
| Chr19:4965001-4966000 | Mrpl11 | 1.867 | 4.345 | 3.723 | 4.017 | 4.000 | −2.133 |
| Chr19:5091001-5092000 | Yif1a | 1.867 | 3.831 | 4.308 | 3.433 | 3.585 | −1.718 |
| Chr19:60929001-60930000 | Sfxn4 | 2.452 | 3.831 | 3.308 | 3.754 | 3.807 | −1.355 |
| Chr19:7012001-7013000 | Gpr137 | 1.867 | 2.608 | 3.723 | 3.017 | 3.807 | −1.940 |
| Chr19:7026001-7027000 | Bad | 1.867 | 3.345 | 3.308 | 3.017 | 3.585 | −1.718 |
| Chr19:9053001-9054000 | Eef1g | 1.867 | 3.345 | 1.723 | 3.433 | 3.907 | −2.040 |
| Chr2:112094001-112095000 | BC125332 | 1.867 | 4.345 | 4.045 | 3.433 | 3.170 | −1.303 |
| Chr2:120141001-120142000 | Vps39 | 2.452 | 4.193 | 3.723 | 3.754 | 3.807 | −1.355 |
| Chr2:128414001-128415000 | Gm355 | 2.452 | 3.608 | 3.308 | 4.433 | 3.700 | −1.248 |
| Chr2:129007001-129008000 | Gm14029 | 2.452 | 3.831 | 4.531 | 4.433 | 3.700 | −1.248 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr2:130998001-130999000 | Spef1 | 2.452 | 3.023 | 3.308 | 4.602 | 3.585 | −1.133 |
| Chr2:131747001-131748000 | Prnp | 2.867 | 3.345 | 3.308 | 4.433 | 4.248 | −1.381 |
| Chr2:153443001-153444000 | Commd7 | 2.867 | 3.831 | 4.308 | 3.754 | 4.000 | −1.133 |
| Chr2:157296001-157297000 | Src | 2.867 | 3.345 | 3.723 | 4.017 | 3.459 | −0.592 |
| Chr2:180192001-180193000 | Slco4a1 | 1.867 | 2.608 | 3.723 | 3.017 | 3.170 | −1.303 |
| Chr2:181240001-181241000 | Tpd52l2 | 2.452 | 3.608 | 3.308 | 4.240 | 3.585 | −1.133 |
| Chr2:181453001-181454000 | Oprl1 | 2.452 | 3.345 | 3.723 | 4.754 | 3.585 | −1.133 |
| Chr2:25489001-25490000 | Gm13520 | 2.452 | 3.608 | 4.308 | 3.433 | 3.700 | −1.248 |
| Chr2:25998001-25999000 | C330006A16Rik | 1.867 | 3.831 | 3.308 | 3.433 | 4.087 | −2.220 |
| Chr2:26743001-26744000 | Surf6 | 2.867 | 4.023 | 4.308 | 3.433 | 4.248 | −1.381 |
| Chr2:26879001-26880000 | Slc2a6 | 2.452 | 2.023 | 2.723 | 4.017 | 3.907 | −1.455 |
| Chr2:29946001-29947000 | Pkn3 | 1.867 | 4.608 | 3.308 | 3.017 | 3.459 | −1.592 |
| Chr2:30572001-30573000 | Gm14488 | 0.867 | 2.608 | 1.571 | 3.754 | 2.807 | −1.940 |
| Chr2:32432001-32433000 | Pip5kl1 | 2.867 | 3.831 | 3.723 | 4.240 | 4.000 | −1.133 |
| Chr2:32482001-32483000 | Ak1 | 1.867 | 2.608 | 4.045 | 2.433 | 3.322 | −1.455 |
| Chr2:34717001-34718000 | Psmd5 | 2.452 | 3.608 | 3.723 | 3.433 | 4.907 | −2.455 |
| Chr2:38851001-38852000 | Gm13496 | 2.452 | 4.345 | 2.723 | 5.017 | 3.807 | −1.355 |
| Chr2:75773001-75774000 | Ttc30b | 2.452 | 3.345 | 3.308 | 4.433 | 4.000 | −1.548 |
| Chr2:76798001-76799000 | Ttn | 3.452 | 4.023 | 4.723 | 4.240 | 4.858 | −1.406 |
| Chr2:93818001-93819000 | 4921507L20Rik | 1.867 | 4.023 | 4.308 | 3.754 | 4.087 | −2.220 |
| Chr3:123274001-123275000 | Ndst3 | 2.867 | 3.608 | 3.308 | 4.240 | 4.087 | −1.220 |
| Chr3:142260001-142261000 | Gbp1 | 0.867 | 3.023 | 4.045 | 1.433 | 3.170 | −2.303 |
| Chr3:14865001-14866000 | Car3 | 0.867 | 2.023 | 4.531 | 2.433 | 3.170 | −2.303 |
| Chr3:32806001-32807000 | Usp13 | 1.867 | 2.608 | 2.723 | 3.017 | 3.000 | −1.133 |
| Chr3:33972001-33973000 | Dnajc19 | 0.867 | 3.608 | 1.571 | 3.754 | 2.585 | −1.718 |
| Chr4:116793001-116794000 | Btbd19 | 1.867 | 4.023 | 3.308 | 3.017 | 3.170 | −1.303 |
| Chr4:124360001-124361000 | Utp11l | 2.452 | 4.023 | 4.531 | 4.017 | 4.087 | −1.635 |
| Chr4:124380001-124381000 | Fhl3 | 1.867 | 4.023 | 4.308 | 1.433 | 3.459 | −1.592 |
| Chr4:126805001-126806000 | Gm12942 | 1.867 | 3.831 | 2.723 | 4.433 | 3.000 | −1.133 |
| Chr4:128790001-128791000 | Hpca | 1.867 | 3.831 | 3.308 | 2.433 | 3.170 | −1.303 |
| Chr4:129027001-129028000 | Zbtb8os | 2.867 | 3.831 | 2.723 | 4.433 | 3.907 | −1.040 |
| Chr4:132301001-132302000 | Smpdl3b | 1.867 | 3.608 | 3.308 | 2.433 | 3.700 | −1.833 |
| Chr4:135906001-135907000 | 9130020K20Rik | 2.452 | 3.831 | 4.045 | 3.433 | 4.170 | −1.718 |
| Chr4:135912001-135913000 | Gm17388 | 2.867 | 2.608 | 4.531 | 3.017 | 4.087 | −1.220 |
| Chr4:138730001-138731000 | Gm16287 | 2.452 | 3.608 | 3.723 | 3.754 | 4.000 | −1.548 |
| Chr4:140512001-140513000 | Gm13031 | 2.452 | 2.608 | 4.045 | 4.433 | 3.700 | −1.248 |
| Chr4:141180001-141181000 | Slc25a34 | 2.452 | 3.831 | 3.308 | 4.017 | 3.459 | −1.007 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr4:141572001-141573000 | 4930455G09Rik | 1.867 | 4.345 | 3.308 | 4.892 | 3.807 | −1.940 |
| Chr4:143484001-143485000 | Pramef6 | 1.867 | 2.608 | 3.308 | 2.433 | 3.585 | −1.718 |
| Chr4:143657001-143658000 | Pramel4 | 1.867 | 5.111 | 3.723 | 4.017 | 3.170 | −1.303 |
| Chr4:148533001-148534000 | Pgd | 1.867 | 3.023 | 3.308 | 3.017 | 4.248 | −2.381 |
| Chr4:148856001-148857000 | Nmnat1 | 2.867 | 3.831 | 4.531 | 3.433 | 3.907 | −1.040 |
| Chr4:149561001-149562000 | Car6 | 0.867 | 1.023 | 3.308 | 1.280 | 4.087 | −3.220 |
| Chr4:151493001-151494000 | Tnfrsf25 | 2.452 | 3.345 | 4.045 | 3.754 | 4.000 | −1.548 |
| Chr4:151787001-151788000 | Kcnab2 | 2.867 | 4.023 | 3.723 | 4.017 | 4.087 | −1.220 |
| Chr4:154271001-154272000 | 2810405K02Rik | 2.452 | 3.831 | 3.308 | 4.602 | 3.459 | −1.007 |
| Chr4:43459001-43460000 | Tesk1 | 2.452 | 4.023 | 3.308 | 3.754 | 3.459 | −1.007 |
| Chr4:43531001-43532000 | Tpm2 | 1.867 | 2.608 | 3.308 | 3.754 | 3.459 | −1.592 |
| Chr4:43542001-43543000 | Tln1 | 2.867 | 3.608 | 3.308 | 4.240 | 4.170 | −1.303 |
| Chr4:46393001-46394000 | 5830415F09Rik | 1.867 | 4.193 | 2.723 | 4.240 | 3.700 | −1.833 |
| Chr4:48079001-48080000 | Nr4a3 | 1.867 | 4.023 | 2.723 | 3.017 | 3.585 | −1.718 |
| Chr4:56757001-56758000 | Actl7a | 1.867 | 4.483 | 3.723 | 3.754 | 3.807 | −1.940 |
| Chr4:89894001-89895000 | Zfp352 | 3.189 | 2.608 | 4.723 | 4.240 | 4.248 | −1.059 |
| Chr4:97589001-97590000 | Nfia | 2.867 | 4.483 | 4.531 | 3.017 | 4.000 | −1.133 |
| Chr5:104040001-104041000 | Slc10a6 | 2.452 | 4.345 | 4.893 | 4.240 | 4.170 | −1.718 |
| Chr5:105760001-105761000 | Gbp11 | 2.452 | 1.023 | 4.045 | 4.017 | 4.000 | −1.548 |
| Chr5:111221001-111222000 | Ulk1 | 1.867 | 2.023 | 2.723 | 3.017 | 3.700 | −1.833 |
| Chr5:115544001-115545000 | Sppl3 | 2.867 | 4.483 | 4.308 | 3.433 | 3.907 | −1.040 |
| Chr5:117791001-117792000 | Vsig10 | 2.867 | 4.023 | 4.045 | 3.754 | 4.087 | −1.220 |
| Chr5:121770001-121771000 | Gm15800 | 2.867 | 3.345 | 3.723 | 4.017 | 3.907 | −1.040 |
| Chr5:125044001-125045000 | Gtf2h3 | 2.452 | 3.831 | 3.308 | 3.754 | 3.700 | −1.248 |
| Chr5:135658001-135659000 | Bcl7b | 0.867 | 3.608 | 3.308 | 4.017 | 4.087 | −3.220 |
| Chr5:136046001-136047000 | Ccl24 | 1.867 | 4.023 | 4.308 | 4.240 | 3.000 | −1.133 |
| Chr5:137871001-137872000 | Zan | 1.867 | 3.831 | 1.571 | 3.754 | 3.700 | −1.833 |
| Chr5:138077001-138078000 | Lrch4 | 1.867 | 4.023 | 3.308 | 2.433 | 3.459 | −1.592 |
| Chr5:144095001-144096000 | 0610040B10Rik | 1.867 | 3.608 | 3.308 | 3.433 | 3.170 | −1.303 |
| Chr5:145519001-145520000 | Tmem130 | 2.452 | 3.831 | 2.723 | 4.017 | 3.807 | −1.355 |
| Chr5:145947001-145948000 | Atp5j2 | 2.452 | 4.023 | 2.723 | 4.754 | 3.459 | −1.007 |
| Chr5:146324001-146325000 | Cyp3a41b | 3.452 | 4.608 | 5.183 | 4.017 | 4.459 | −1.007 |
| Chr5:24094001-24095000 | Chpf2 | 2.452 | 3.608 | 2.723 | 4.754 | 4.322 | −1.870 |
| Chr5:34117001-34118000 | Letm1 | 2.452 | 3.831 | 4.045 | 3.017 | 4.087 | −1.635 |
| Chr5:38444001-38445000 | Stx18 | 2.867 | 3.023 | 2.723 | 4.433 | 3.907 | −1.040 |
| Chr5:44443001-44444000 | Prom1 | 1.867 | 3.608 | 3.308 | 2.433 | 3.585 | −1.718 |
| Chr5:73720001-73721000 | Ociad2 | 2.452 | 3.831 | 2.723 | 4.754 | 3.459 | −1.007 |

TABLE 2-continued

| | | log₂ normalized Read count | | | | | |
|---|---|---|---|---|---|---|---|
| Peak | Gene | NCsh (N) | NCsh (C) | MMP-9sh (N) | MMP-9sh (C) | Input | log₂ ratio NCsh (N) vs input |
| Chr5:76348001-76349000 | Kdr | 2.452 | 3.831 | 1.723 | 4.240 | 3.807 | −1.355 |
| Chr5:87087001-87088000 | Tmprss11bnl | 2.867 | 2.023 | 3.308 | 4.433 | 4.087 | −1.220 |
| Chr6:113015001-113016000 | Thumpd3 | 2.867 | 3.608 | 3.723 | 4.892 | 4.000 | −1.133 |
| Chr6:122882001-122883000 | Clec4a1 | 0.715 | 3.608 | 3.308 | 3.754 | 3.807 | −3.092 |
| Chr6:123007001-123008000 | Clec4b1 | 2.452 | 3.608 | 4.045 | 4.017 | 3.807 | −1.355 |
| Chr6:126779001-126780000 | Ndufa9 | 2.452 | 4.345 | 1.723 | 4.240 | 3.807 | −1.355 |
| Chr6:136707001-136708000 | Gucy2c | 2.452 | 3.831 | 4.531 | 1.433 | 4.644 | −2.192 |
| Chr6:13905001-13906000 | 1110019D14Rik | 3.452 | 4.483 | 4.308 | 4.602 | 4.524 | −1.072 |
| Chr6:145083001-145084000 | Lrmp | 1.867 | 2.608 | 2.723 | 3.017 | 3.170 | −1.303 |
| Chr6:147023001-147024000 | Gm5887 | 2.452 | 4.023 | 4.045 | 3.433 | 3.459 | −1.007 |
| Chr6:29242001-29243000 | Fam71f2 | 2.452 | 4.023 | 3.308 | 5.433 | 3.459 | −1.007 |
| Chr6:49025001-49026000 | 2410003K15Rik | 2.867 | 3.831 | 4.308 | 3.754 | 4.248 | −1.381 |
| Chr6:72375001-72376000 | Ggcx | 2.452 | 4.483 | 2.723 | 4.433 | 3.585 | −1.133 |
| Chr6:83432001-83433000 | Dguok | 1.867 | 4.345 | 1.723 | 3.433 | 4.000 | −2.133 |
| Chr6:84528001-84529000 | Cyp26b1 | 2.452 | 3.608 | 4.045 | 3.433 | 3.700 | −1.248 |
| Chr6:86330001-86331000 | Snrpg | 2.867 | 3.023 | 4.045 | 4.892 | 3.907 | −1.040 |
| Chr6:89133001-89134000 | Gm6507 | 1.867 | 3.608 | 3.723 | 4.017 | 3.459 | −1.592 |
| Chr7:100184001-100185000 | Gm16744 | 2.452 | 3.608 | 3.308 | 3.754 | 3.907 | −1.455 |
| Chr7:104485001-104486000 | Kctd21 | 1.867 | 3.831 | 3.308 | 3.433 | 3.170 | −1.303 |
| Chr7:108003001-108004000 | Relt | 2.867 | 3.831 | 4.308 | 3.754 | 3.907 | −1.040 |
| Chr7:110567001-110568000 | Usp17l5 | 0.867 | 3.608 | 4.045 | 4.017 | 2.322 | −1.455 |
| Chr7:112704001-112705000 | Smpd1 | 0.867 | 3.831 | 4.045 | 4.017 | 2.585 | −1.718 |
| Chr7:11752001-11753000 | Zscan4d | 1.867 | 3.608 | 2.723 | 4.433 | 3.000 | −1.133 |
| Chr7:123239001-123240000 | 1110004F10Rik | 0.867 | 4.023 | 4.723 | 4.602 | 3.585 | −2.718 |
| Chr7:128161001-128162000 | Gm9234 | 1.867 | 4.193 | 3.308 | 3.754 | 3.700 | −1.833 |
| Chr7:129300001-129301000 | Gm15489 | 1.867 | 4.345 | 3.308 | 3.754 | 3.000 | −1.133 |
| Chr7:133554001-133555000 | Cd19 | 2.867 | 3.345 | 4.045 | 3.754 | 3.907 | −1.040 |
| Chr7:134121001-134122000 | Cdipt | 2.867 | 4.930 | 4.045 | 4.433 | 3.907 | −1.040 |
| Chr7:135045001-135046000 | Bckdk | 0.867 | 4.023 | 3.308 | 4.017 | 3.907 | −3.040 |
| Chr7:135079001-135080000 | Prss36 | 1.867 | 2.608 | 1.23 | 3.433 | 3.459 | −1.592 |
| Chr7:147309001-147310000 | Paox | 2.452 | 3.831 | 3.723 | 4.017 | 4.000 | −1.548 |
| Chr7:148036001-148037000 | Odf3 | 1.867 | 4.608 | 1.723 | 4.433 | 3.700 | −1.833 |
| Chr7:148133001-148134000 | Athl1 | 2.452 | 3.608 | 4.531 | 3.433 | 3.585 | −1.133 |
| Chr7:16808001-16809000 | Dhx34 | 1.867 | 3.345 | 3.723 | 1.433 | 3.907 | −2.040 |
| Chr7:17327001-17328000 | Ap2s1 | 1.867 | 4.345 | 4.308 | 3.754 | 4.000 | −2.133 |
| Chr7:20091001-20092000 | Bloc1s3 | 2.452 | 2.608 | 4.045 | 3.017 | 4.087 | −1.635 |
| Chr7:25381001-25382000 | Ethe1 | 3.452 | 4.023 | 3.308 | 5.017 | 4.524 | −1.072 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr7:26144001-26145000 | Megf8 | 2.452 | 2.608 | 3.723 | 3.433 | 3.459 | −1.007 |
| Chr7:27982001-27983000 | BC024978 | 1.867 | 2.023 | 2.723 | 3.017 | 3.459 | −1.592 |
| Chr7:29086001-29087000 | Dll3 | 1.867 | 3.345 | 3.308 | 4.433 | 3.459 | −1.592 |
| Chr7:31892001-31893000 | Hpn | 2.452 | 4.023 | 1.571 | 4.433 | 3.585 | −1.133 |
| Chr7:4086001-4087000 | Ttyh1 | 0.867 | 3.608 | 3.723 | 2.433 | 3.170 | −2.303 |
| Chr7:4579001-4580000 | Tmem86b | 2.867 | 4.724 | 4.045 | 4.240 | 4.000 | −1.133 |
| Chr7:4696001-4697000 | Suv420h2 | 2.452 | 4.023 | 3.308 | 4.602 | 3.459 | −1.007 |
| Chr7:50609001-50610000 | Siglec5 | 2.867 | 3.345 | 2.723 | 4.433 | 3.907 | −1.040 |
| Chr7:50706001-50707000 | Etfb | 2.452 | 4.193 | 3.723 | 3.433 | 3.459 | −1.007 |
| Chr7:52032001-52033000 | Vrk3 | 2.452 | 1.023 | 2.723 | 4.017 | 3.585 | −1.133 |
| Chr7:52229001-52230000 | Cpt1c | 2.867 | 3.831 | 4.045 | 3.754 | 3.907 | −1.040 |
| Chr7:71486001-71487000 | Gm20457 | 1.867 | 4.193 | 3.308 | 3.433 | 3.807 | −1.940 |
| Chr7:7243001-7244000 | Clcn4-2 | 1.867 | 4.193 | 3.723 | 2.433 | 3.807 | −1.940 |
| Chr7:86061001-86062000 | Isg20 | 2.452 | 2.023 | 4.045 | 3.754 | 3.700 | −1.248 |
| Chr7:86270001-86271000 | Hapln3 | 1.867 | 4.831 | 2.723 | 3.754 | 3.322 | −1.455 |
| Chr7:86529001-86530000 | Rlbp1 | 2.452 | 3.345 | 3.723 | 3.433 | 3.907 | −1.455 |
| Chr8:109919001-109920000 | Nqo1 | 2.452 | 4.023 | 4.045 | 3.433 | 3.907 | −1.455 |
| Chr8:12873001-12874000 | Gm15347 | 1.867 | 3.023 | 3.308 | 2.433 | 3.322 | −1.455 |
| Chr8:15039001-15040000 | BB014433 | 2.867 | 3.345 | 3.723 | 4.240 | 3.907 | −1.040 |
| Chr8:54598001-54599000 | Aga | 1.867 | 2.608 | 4.045 | 3.754 | 4.087 | −2.220 |
| Chr8:72279001-72280000 | Gm20422 | 1.867 | 2.608 | 2.723 | 3.017 | 4.000 | −2.133 |
| Chr8:72428001-72429000 | Tssk6 | 0.867 | 3.345 | 2.723 | 1.433 | 3.459 | −2.592 |
| Chr8:72857001-72858000 | Upf1 | 1.867 | 4.193 | 3.308 | 2.433 | 3.459 | −1.592 |
| Chr8:72895001-72896000 | Comp | 1.867 | 4.023 | 2.723 | 4.017 | 3.700 | −1.833 |
| Chr8:73361001-73362000 | Arrdc2 | 2.452 | 4.483 | 4.045 | 3.433 | 4.170 | −1.718 |
| Chr8:74438001-74439000 | Zfp882 | 2.452 | 4.193 | 3.723 | 4.240 | 3.459 | −1.007 |
| Chr8:74716001-74717000 | Hsh2d | 2.867 | 2.023 | 3.723 | 4.433 | 3.907 | −1.040 |
| Chr8:97646001-97647000 | Kifc3 | 2.452 | 4.193 | 2.723 | 4.017 | 3.907 | −1.455 |
| Chr8:98232001-98233000 | Ndrg4 | 2.452 | 3.608 | 3.308 | 3.754 | 3.907 | −1.455 |
| Chr9:100893001-100894000 | Pccb | 2.867 | 3.608 | 4.308 | 3.433 | 4.248 | −1.381 |
| Chr9:106089001-106090000 | Wdr82 | 2.452 | 4.023 | 1.723 | 4.240 | 3.907 | −1.455 |
| Chr9:106371001-106372000 | Parp3 | 2.452 | 3.831 | 3.308 | 3.754 | 3.459 | −1.007 |
| Chr9:107456001-107457000 | Rassf1 | 2.452 | 2.023 | 4.531 | 2.433 | 3.700 | −1.248 |
| Chr9:107833001-107834000 | 4921517D21Rik | 2.452 | 3.608 | 3.723 | 3.433 | 3.585 | −1.133 |
| Chr9:110522001-110523000 | Nradd | 2.452 | 4.345 | 4.308 | 3.017 | 3.459 | −1.007 |
| Chr9:110627001-110628000 | Pth1r | 1.867 | 4.023 | 2.723 | 3.017 | 3.322 | −1.455 |
| Chr9:119056001-119057000 | Dlec1 | 1.867 | 2.608 | 1.723 | 3.433 | 3.000 | −1.133 |

TABLE 2-continued

| | | log₂ normalized Read count | | | | |
|---|---|---|---|---|---|---|
| Peak | Gene | NCsh (N) | NCsh (C) | MMP-9sh (N) | MMP-9sh (C) | Input | log₂ ratio NCsh (N) vs input |
| Chr9:122809001-122810000 | A530083I20Rik | 2.452 | 3.345 | 2.723 | 4.017 | 3.459 | −1.007 |
| Chr9:15041001-15042000 | 2200002K05Rik | 0.867 | 4.023 | 3.723 | 4.240 | 3.000 | −2.133 |
| Chr9:20148001-20149000 | Zfp560 | 1.867 | 3.608 | 4.045 | 1.280 | 3.000 | −1.133 |
| Chr9:44331001-44332000 | Cxcr5 | 2.452 | 2.608 | 3.723 | 4.240 | 3.907 | −1.455 |
| Chr9:50331001-50332000 | Pts | 2.452 | 3.831 | 2.723 | 5.240 | 3.700 | −1.248 |
| Chr9:58058001-58059000 | 1600029O15Rik | 1.867 | 3.345 | 1.723 | 3.754 | 3.807 | −1.940 |
| Chr9:61217001-61218000 | Gm10655 | 2.452 | 3.023 | 4.045 | 3.017 | 3.700 | −1.248 |
| Chr9:61912001-61913000 | Glce | 2.452 | 3.023 | 3.723 | 3.754 | 4.248 | −1.796 |
| Chr9:63485001-63486000 | Aagab | 2.452 | 3.023 | 3.308 | 4.017 | 3.459 | −1.007 |
| Chr9:63968001-63969000 | Lctl | 1.867 | 4.345 | 3.308 | 3.017 | 3.807 | −1.940 |
| Chr9:64184001-64185000 | Dis3l | 2.867 | 4.023 | 4.308 | 3.754 | 3.907 | −1.040 |
| Chr9:98499001-98500000 | Mrps22 | 2.452 | 4.608 | 2.723 | 4.754 | 3.907 | −1.455 |
| ChrX:103772001-103773000 | Cysltr1 | 1.867 | 3.608 | 4.045 | 1.280 | 3.000 | −1.133 |
| Gene body cleavage | | | | | | | |
| Chr1:107175001-107176000 | Rnf152 | 1.867 | 3.023 | 1.723 | 3.433 | 3.459 | −1.592 |
| Chr1:107691001-107692000 | Tnfrsf11a | 2.867 | 4.193 | 4.308 | 3.433 | 3.322 | −0.455 |
| Chr1:129673001-129674000 | Ccnt2 | 1.867 | 3.831 | 2.723 | 3.017 | 3.585 | −1.718 |
| Chr1:133565001-133566000 | Ctse | 2.452 | 4.023 | 3.308 | 3.754 | 4.000 | −1.548 |
| Chr1:134032001-134033000 | Cdk18 | 0.715 | 3.831 | 2.723 | 2.433 | 3.459 | −2.744 |
| Chr1:141450001-141451000 | Cfhr1 | 1.867 | 3.023 | 4.308 | 4.240 | 3.585 | −1.718 |
| Chr1:141645001-141646000 | Gm4788 | 3.189 | 3.023 | 4.045 | 4.433 | 4.858 | −1.669 |
| Chr1:153298001-153299000 | 1190005F20Rik | 1.867 | 4.345 | 4.045 | 1.433 | 3.807 | −1.940 |
| Chr1:172231001-172232000 | Gm7694 | 2.452 | 3.345 | 3.308 | 3.754 | 3.807 | −1.355 |
| Chr1:173224001-173225000 | Ufc1 | 1.867 | 4.483 | 3.723 | 4.433 | 3.170 | −1.303 |
| Chr1:174416001-174417000 | Igsf9 | 0.867 | 2.608 | 3.308 | 3.017 | 3.170 | −2.303 |
| Chr1:21064001-21065000 | Tram2 | 1.867 | 2.608 | 1.723 | 3.433 | 3.585 | −1.718 |
| Chr1:34644001-34645000 | Fam123c | 2.452 | 2.608 | 2.723 | 4.017 | 3.459 | −1.007 |
| Chr1:53002001-53003000 | 1700019D03Rik | 3.867 | 4.023 | 5.424 | 4.240 | 4.954 | −1.087 |
| Chr1:58000001-58001000 | Spats2l | 1.867 | 4.345 | 3.308 | 2.433 | 4.170 | −2.303 |
| Chr1:58990001-58991000 | Trak2 | 3.452 | 4.483 | 4.045 | 4.754 | 5.129 | −1.677 |
| Chr1:74999001-75000000 | Ihh | 2.867 | 3.831 | 4.045 | 4.017 | 4.170 | −1.303 |
| Chr1:75236001-75237000 | Dnajb2 | 1.867 | 4.345 | 4.723 | 3.017 | 3.700 | −1.833 |
| Chr1:75398001-75399000 | Speg | 1.867 | 3.831 | 2.723 | 3.017 | 3.700 | −1.833 |
| Chr1:87793001-87794000 | Itm2c | 2.452 | 4.193 | 2.723 | 4.433 | 3.459 | −1.007 |
| Chr1:87834001-87835000 | 4933407L21Rik | 2.452 | 3.608 | 3.308 | 3.754 | 3.807 | −1.355 |
| Chr1:94805001-94806000 | Dusp28 | 1.867 | 4.023 | 3.723 | 4.433 | 3.000 | −1.133 |
| Chr1:95739001-95740000 | D2hgdh | 2.867 | 4.023 | 4.531 | 4.017 | 4.907 | −2.040 |

TABLE 2-continued

| Peak | Gene | NCsh (N) | NCsh (C) | MMP-9sh (N) | MMP-9sh (C) | Input | log₂ ratio NCsh (N) vs input |
|---|---|---|---|---|---|---|---|
| Chr10:103615001-103616000 | Gm6763 | 0.867 | 2.023 | 2.723 | 3.017 | 3.322 | −2.455 |
| Chr10:111631001-111632000 | Caps2 | 2.452 | 4.345 | 3.308 | 3.754 | 4.000 | −1.548 |
| Chr10:114787001-114788000 | Tmem19 | 1.867 | 3.608 | 4.045 | 4.240 | 4.087 | −2.220 |
| Chr10:119581001-119582000 | Irak3 | 1.867 | 3.608 | 3.723 | 1.433 | 3.459 | −1.592 |
| Chr10:126635001-126636000 | F420014N23Rik | 2.452 | 3.608 | 2.723 | 4.017 | 3.585 | −1.133 |
| Chr10:126683001-126684000 | Kif5a | 2.867 | 3.023 | 3.308 | 4.240 | 3.907 | −1.040 |
| Chr10:128061001-128062000 | Rps26 | 2.452 | 4.483 | 3.308 | 3.754 | 3.807 | −1.355 |
| Chr10:128113001-128114000 | Rab5b | 2.452 | 4.345 | 4.045 | 3.754 | 3.459 | −1.007 |
| Chr10:13219001-13220000 | Fuca2 | 1.867 | 3.831 | 1.723 | 4.017 | 3.170 | −1.303 |
| Chr10:34003001-34004000 | Tspyl1 | 2.452 | 3.345 | 3.723 | 3.754 | 3.700 | −1.248 |
| Chr10:42409001-42410000 | Ostm1 | 3.452 | 3.345 | 4.045 | 4.754 | 3.907 | −0.455 |
| Chr10:43669001-43670000 | Aim1 | 1.867 | 4.023 | 2.723 | 3.017 | 3.585 | −1.718 |
| Chr10:52153001-52154000 | Nus1 | 2.452 | 4.345 | 4.045 | 3.433 | 3.459 | −1.007 |
| Chr10:59184001-59185000 | Cbara1 | 2.867 | 4.483 | 3.723 | 4.017 | 3.907 | −1.040 |
| Chr10:70798001-70799000 | Cisd1 | 1.867 | 3.345 | 1.571 | 4.017 | 3.170 | −1.303 |
| Chr10:75244001-75245000 | Gstt3 | 1.867 | 3.345 | 3.308 | 3.433 | 3.170 | −1.303 |
| Chr10:77661001-77662000 | Trappc10 | 2.867 | 3.608 | 4.045 | 3.754 | 3.907 | −1.040 |
| Chr10:78995001-78996000 | Ppap2c | 0.867 | 1.023 | 1.723 | 3.017 | 3.170 | −2.303 |
| Chr10:79382001-79383000 | Kiss1r | 1.867 | 3.023 | 2.723 | 3.433 | 3.807 | −1.940 |
| Chr10:79497001-79498000 | Polr2e | 1.867 | 4.023 | 4.045 | 3.017 | 3.459 | −1.592 |
| Chr10:79757001-79758000 | Rps15 | 2.452 | 3.831 | 4.045 | 3.017 | 3.807 | −1.355 |
| Chr10:79850001-79851000 | Mex3d | 0.867 | 3.023 | 1.723 | 3.754 | 2.807 | −1.940 |
| Chr10:80049001-80050000 | Fam108a | 1.867 | 4.345 | 4.893 | 3.433 | 3.170 | −1.303 |
| Chr10:80496001-80497000 | Slc39a3 | 1.867 | 2.608 | 4.045 | 4.433 | 3.170 | −1.303 |
| Chr10:80609001-80610000 | Zbtb7a | 1.867 | 3.023 | 4.045 | 2.433 | 3.000 | −1.133 |
| Chr10:81002001-81003000 | Gna11 | 1.867 | 4.023 | 1.723 | 3.754 | 3.170 | −1.303 |
| Chr10:81155001-81156000 | Gm8112 | 1.867 | 2.608 | 2.723 | 3.017 | 3.000 | −1.133 |
| Chr10:93604001-93605000 | Fgd6 | 3.189 | 3.831 | 4.045 | 4.433 | 4.322 | −1.133 |
| Chr11:100555001-100556000 | Gm11547 | 2.452 | 4.193 | 2.723 | 4.017 | 4.000 | −1.548 |
| Chr11:100684001-100685000 | Stat5b | 2.452 | 3.345 | 3.723 | 3.433 | 4.248 | −1.796 |
| Chr11:101030001-101031000 | Plekhh3 | 2.452 | 1.023 | 4.045 | 3.017 | 3.585 | −1.133 |
| Chr11:102084001-102085000 | Hdac5 | 2.867 | 3.608 | 3.723 | 4.017 | 3.907 | −1.040 |
| Chr11:102145001-102146000 | Tmub2 | 3.452 | 3.345 | 4.308 | 4.754 | 4.459 | −1.007 |
| Chr11:102981001-102982000 | Hexim1 | 2.452 | 3.831 | 2.723 | 4.017 | 4.000 | −1.548 |
| Chr11:104458001-104459000 | Myl4 | 1.867 | 3.608 | 4.045 | 1.433 | 4.000 | −2.133 |
| Chr11:105884001-105885000 | Kcnh6 | 2.867 | 3.831 | 4.308 | 3.433 | 3.907 | −1.040 |
| Chr11:106196001-106197000 | Scn4a | 2.452 | 4.345 | 3.308 | 3.754 | 3.700 | −1.248 |

TABLE 2-continued

| | | log₂ normalized Read count | | | | | |
|---|---|---|---|---|---|---|---|
| Peak | Gene | NCsh (N) | NCsh (C) | MMP-9sh (N) | MMP-9sh (C) | Input | log₂ ratio NCsh (N) vs input |
| Chr11:107482001-107483000 | Helz | 3.189 | 3.608 | 4.531 | 4.017 | 4.644 | −1.455 |
| Chr11:109449001-109450000 | Wipi1 | 2.452 | 3.023 | 3.723 | 3.433 | 3.700 | −1.248 |
| Chr11:110261001-110262000 | Map2k6 | 2.867 | 3.023 | 4.893 | 1.433 | 3.270 | −0.403 |
| Chr11:115469001-115470000 | Mrps7 | 1.867 | 3.023 | 3.723 | 3.433 | 3.322 | −1.455 |
| Chr11:116155001-116156000 | Exoc7 | 1.867 | 3.345 | 4.045 | 3.433 | 3.322 | −1.455 |
| Chr11:116394001-116395000 | Sphk1 | 1.867 | 2.608 | 1.723 | 4.017 | 3.322 | −1.455 |
| Chr11:117477001-117478000 | 2900041M22Rik | 1.867 | 4.023 | 4.045 | 3.754 | 3.000 | −1.133 |
| Chr11:117670001-117671000 | Syngr2 | 1.867 | 3.345 | 1.723 | 4.433 | 3.459 | −1.592 |
| Chr11:118033001-118034000 | Cyth1 | 1.867 | 4.345 | 1.571 | 3.754 | 3.585 | −1.718 |
| Chr11:118899001-118900000 | Cbx8 | 0.867 | 4.023 | 3.723 | 4.433 | 3.459 | −2.592 |
| Chr11:120210001-120211000 | 0610009L18Rik | 1.867 | 3.608 | 3.308 | 2.433 | 3.000 | −1.133 |
| Chr11:120352001-120353000 | Gm11788 | 1.867 | 2.608 | 2.723 | 3.017 | 3.322 | −1.455 |
| Chr11:120410001-120411000 | Fam195b | 1.867 | 4.193 | 3.308 | 3.433 | 3.585 | −1.718 |
| Chr11:120474001-120475000 | Pcyt2 | 1.867 | 2.608 | 1.723 | 3.754 | 3.000 | −1.133 |
| Chr11:20101001-20102000 | Rab1 | 1.867 | 3.345 | 1.723 | 3.433 | 3.585 | −1.718 |
| Chr11:21903001-21904000 | Otx1 | 2.452 | 3.345 | 3.308 | 3.754 | 3.700 | −1.248 |
| Chr11:3202001-3203000 | Patz1 | 2.867 | 2.023 | 4.531 | 4.240 | 3.907 | −1.040 |
| Chr11:3823001-3824000 | Tcn2 | 2.452 | 4.023 | 3.308 | 3.754 | 3.807 | −1.355 |
| Chr11:3991001-3992000 | Mtfp1 | 1.867 | 4.193 | 3.723 | 3.754 | 3.700 | −1.833 |
| Chr11:3996001-3997000 | Sec14l2 | 2.452 | 3.608 | 4.531 | 2.433 | 3.585 | −1.133 |
| Chr11:4171001-4172000 | Lif | 1.867 | 2.023 | 3.723 | 1.433 | 4.000 | −2.133 |
| Chr11:4644001-4645000 | Cabp7 | 2.452 | 4.483 | 4.308 | 3.017 | 3.585 | −1.133 |
| Chr11:51432001-51433000 | Nhp2 | 1.867 | 3.831 | 3.308 | 3.017 | 3.585 | −1.718 |
| Chr11:51459001-51460000 | N4bp3 | 2.452 | 5.023 | 4.045 | 4.433 | 3.907 | −1.455 |
| Chr11:53431001-53432000 | Il4 | 1.867 | 1.023 | 3.308 | 3.433 | 3.585 | −1.718 |
| Chr11:5768001-5769000 | Aebp1 | 2.867 | 4.193 | 4.531 | 3.017 | 3.907 | −1.040 |
| Chr11:58972001-58973000 | A230051G13Rik | 0.867 | 3.345 | 3.723 | 3.433 | 3.585 | −2.718 |
| Chr11:59022001-59023000 | 2310033P09Rik | 1.867 | 3.345 | 4.045 | 1.433 | 3.170 | −1.303 |
| Chr11:59144001-59145000 | Wnt9a | 1.867 | 3.345 | 1.723 | 3.433 | 3.907 | −2.040 |
| Chr11:59475001-59476000 | Mprip | 1.867 | 3.608 | 3.723 | 1.433 | 3.459 | −1.592 |
| Chr11:59603001-59604000 | Flcn | 2.867 | 3.608 | 4.308 | 3.433 | 4.248 | −1.381 |
| Chr11:61307001-61308000 | Mapk7 | 0.867 | 1.023 | 2.723 | 3.754 | 2.322 | −1.455 |
| Chr11:62090001-62091000 | Zswim7 | 1.867 | 4.483 | 3.723 | 3.433 | 3.459 | −1.592 |
| Chr11:6492001-6493000 | Ccm2 | 3.189 | 3.345 | 3.723 | 4.602 | 4.524 | −1.335 |
| Chr11:66842001-66843000 | Tmem220 | 1.867 | 3.608 | 4.045 | 4.017 | 3.459 | −1.592 |
| Chr11:67777001-67778000 | Wdr16 | 2.452 | 4.345 | 2.723 | 4.017 | 3.700 | −1.248 |
| Chr11:68902001-68903000 | Vamp2 | 1.867 | 0.871 | 2.723 | 3.433 | 3.322 | −1.455 |

TABLE 2-continued

| | | log₂ normalized Read count | | | | | |
|---|---|---|---|---|---|---|---|
| Peak | Gene | NCsh (N) | NCsh (C) | MMP-9sh (N) | MMP-9sh (C) | Input | log₂ ratio NCsh (N) vs input |
| Chr11:69171001-69172000 | Chd3 | 1.867 | 3.345 | 3.723 | 1.433 | 3.585 | −1.718 |
| Chr11:69630001-69631000 | 4933402P03Rik | 2.452 | 3.608 | 4.045 | 3.433 | 3.585 | −1.133 |
| Chr11:69756001-69757000 | Slc2a4 | 0.867 | 3.608 | 3.308 | 1.280 | 3.459 | −2.592 |
| Chr11:70052001-70053000 | Rnasek | 1.867 | 3.023 | 4.893 | 4.240 | 3.000 | −1.133 |
| Chr11:70707001-70708000 | Rabep1 | 2.867 | 4.608 | 3.723 | 4.017 | 4.170 | −1.303 |
| Chr11:72212001-72213000 | Smtnl2 | 1.867 | 2.608 | 2.723 | 3.017 | 3.170 | −1.303 |
| Chr11:72248001-72249000 | Ggt6 | 2.452 | 3.345 | 2.723 | 4.240 | 3.585 | −1.133 |
| Chr11:74449001-74450000 | E130309D14Rik | 2.452 | 4.345 | 3.723 | 3.754 | 3.807 | −1.355 |
| Chr11:78003001-78004000 | Rab34 | 1.867 | 3.023 | 4.045 | 3.754 | 4.170 | −2.303 |
| Chr11:78138001-78139000 | Aldoc | 2.452 | 4.023 | 3.723 | 3.754 | 4.087 | −1.635 |
| Chr11:79965001-79966000 | Adap2 | 2.867 | 3.831 | 2.723 | 4.602 | 4.000 | −1.133 |
| Chr11:82832001-82833000 | Slfn8 | 2.867 | 3.608 | 4.308 | 3.433 | 3.907 | −1.040 |
| Chr11:94642001-94643000 | Tmem92-ps | 2.452 | 3.608 | 3.308 | 4.240 | 3.700 | −1.248 |
| Chr11:95007001-95008000 | Dlx4 | 2.452 | 2.608 | 1.723 | 4.240 | 3.459 | −1.007 |
| Chr11:95130001-95131000 | Tac4 | 2.452 | 4.193 | 4.531 | 4.017 | 3.907 | −1.455 |
| Chr11:96144001-96145000 | Hoxb8 | 0.867 | 3.023 | 3.308 | 2.433 | 2.807 | −1.940 |
| Chr11:97885001-97886000 | Gm11629 | 2.867 | 3.831 | 3.308 | 4.240 | 4.000 | −1.133 |
| Chr11:98218001-98219000 | Ppp1r1b | 2.452 | 3.345 | 2.723 | 4.017 | 3.700 | −1.248 |
| Chr12:102323001-102324000 | D130020L05Rik | 1.867 | 3.345 | 2.723 | 3.433 | 3.585 | −1.718 |
| Chr12:110854001-110855000 | Rian | 1.867 | 3.345 | 3.308 | 3.017 | 3.700 | −1.833 |
| Chr12:111764001-111765000 | Ppp2r5c | 2.867 | 3.023 | 4.308 | 3.433 | 3.907 | −1.040 |
| Chr12:112812001-112813000 | 2810029C07Rik | 1.867 | 2.608 | 4.045 | 2.433 | 3.807 | −1.940 |
| Chr12:112946001-112947000 | Bag5 | 2.452 | 1.023 | 3.308 | 3.754 | 3.907 | −1.455 |
| Chr12:113921001-113922000 | Zbtb42 | 0.867 | 3.345 | 1.723 | 3.017 | 3.000 | −2.133 |
| Chr12:114178001-114179000 | Nudt14 | 1.867 | 4.193 | 4.045 | 3.017 | 3.322 | −1.455 |
| Chr12:114279001-114280000 | Pacs2 | 2.867 | 4.193 | 3.308 | 4.240 | 3.907 | −1.040 |
| Chr12:114383001-114384000 | Crip2 | 1.867 | 3.831 | 2.723 | 3.433 | 3.459 | −1.592 |
| Chr12:25178001-25179000 | Gm16372 | 1.867 | 3.831 | 1.723 | 4.433 | 3.459 | −1.592 |
| Chr12:25670001-25671000 | Kidins220 | 2.867 | 2.608 | 4.531 | 3.017 | 3.907 | −1.040 |
| Chr12:25782001-25783000 | Id2 | 1.867 | 3.345 | 4.045 | 2.433 | 3.000 | −1.133 |
| Chr12:36911001-36912000 | Ankmy2 | 2.867 | 2.023 | 2.723 | 4.433 | 4.000 | −1.133 |
| Chr12:45585001-45586000 | Nrcam | 3.452 | 4.023 | 4.723 | 4.240 | 4.459 | −1.007 |
| Chr12:71068001-71069000 | Gm3086 | 2.452 | 4.193 | 3.308 | 4.892 | 4.087 | −1.635 |
| Chr12:80245001-80246000 | Arg2 | 3.189 | 3.345 | 4.308 | 4.433 | 4.459 | −1.270 |
| Chr12:80271001-80272000 | Vti1b | 2.867 | 3.831 | 3.308 | 5.017 | 4.087 | −1.220 |
| Chr12:81230001-81231000 | 2310015A10Rik | 2.452 | 4.023 | 4.045 | 3.017 | 3.585 | −1.133 |
| Chr13:102470001-102471000 | Pik3r1 | 3.189 | 4.023 | 4.723 | 4.017 | 3.585 | −0.396 |

TABLE 2-continued

| | | log$_2$ normalized Read count | | | | |
|---|---|---|---|---|---|---|
| Peak | Gene | NCsh (N) | NCsh (C) | MMP-9sh (N) | MMP-9sh (C) | Input | log$_2$ ratio NCsh (N) vs input |
| Chr13:103498001-103499000 | Cd180 | 1.867 | 4.193 | 2.723 | 3.017 | 3.807 | −1.940 |
| Chr13:21923001-21924000 | Hist1h4n | 1.867 | 3.831 | 3.308 | 3.754 | 3.000 | −1.133 |
| Chr13:23858001-23859000 | Hist1h1a | 2.452 | 2.608 | 3.308 | 3.754 | 3.585 | −1.133 |
| Chr13:33416001-33417000 | Serpinb9f | 1.867 | 3.608 | 2.723 | 3.433 | 3.807 | −1.940 |
| Chr13:35011001-35012000 | 1700026J04Rik | 0.715 | 3.608 | 4.723 | 1.280 | 3.322 | −2.607 |
| Chr13:43635001-43636000 | Ccdc90a | 1.867 | 2.608 | 3.308 | 3.433 | 3.459 | −1.592 |
| Chr13:45501001-45502000 | Mylip | 2.867 | 3.345 | 4.045 | 4.017 | 4.000 | −1.133 |
| Chr13:46061001-46062000 | 5033430I15Rik | 0.867 | 3.608 | 3.308 | 4.017 | 2.585 | −1.718 |
| Chr13:53063001-53064000 | Nfil3 | 1.867 | 3.345 | 2.723 | 3.433 | 4.000 | −2.133 |
| Chr13:54483001-54484000 | Cplx2 | 1.867 | 1.023 | 1.723 | 3.433 | 3.000 | −1.133 |
| Chr13:54797001-54798000 | Rnf44 | 2.867 | 4.023 | 4.045 | 4.017 | 3.907 | −1.040 |
| Chr13:54826001-54827000 | Cdhr2 | 2.452 | 3.345 | 4.308 | 2.433 | 3.907 | −1.455 |
| Chr13:59755001-59756000 | Golm1 | 1.867 | 4.023 | 4.045 | 3.754 | 3.700 | −1.833 |
| Chr13:62318001-62319000 | Gm17352 | 2.452 | 3.831 | 4.531 | 3.433 | 3.807 | −1.355 |
| Chr13:74176001-74177000 | Cep72 | 2.452 | 4.345 | 2.723 | 4.433 | 3.585 | −1.133 |
| Chr13:9110001-9111000 | Larp4b | 4.567 | 5.023 | 5.630 | 5.520 | 6.209 | −1.642 |
| Chr14:120903001-120904000 | Rap2a | 1.867 | 3.831 | 2.723 | 3.754 | 3.700 | −1.833 |
| Chr14:21132001-21133000 | Nudt13 | 2.867 | 3.831 | 3.723 | 4.017 | 4.170 | −1.303 |
| Chr14:25312001-25313000 | Rps24 | 2.452 | 4.608 | 1.723 | 4.433 | 3.700 | −1.248 |
| Chr14:26280001-26281000 | D930049A15Rik | 0.867 | 3.345 | 2.723 | 3.433 | 2.807 | −1.940 |
| Chr14:26695001-26696000 | Anxa11 | 0.715 | 2.608 | 1.571 | 3.017 | 2.000 | −1.285 |
| Chr14:32906001-32907000 | Oxnad1 | 2.452 | 2.023 | 3.723 | 3.433 | 3.459 | −1.007 |
| Chr14:35128001-35129000 | Glud1 | 2.452 | 3.608 | 1.723 | 4.433 | 3.585 | −1.133 |
| Chr14:35367001-35368000 | Ldb3 | 2.867 | 4.193 | 4.531 | 3.433 | 4.248 | −1.381 |
| Chr14:48699001-48700000 | Gm6055 | 0.867 | 4.608 | 3.308 | 4.433 | 3.585 | −2.718 |
| Chr14:52529001-52530000 | Ndrg2 | 2.452 | 3.831 | 3.308 | 3.754 | 4.000 | −1.548 |
| Chr14:54857001-54858000 | Dad1 | 1.867 | 3.023 | 2.723 | 3.433 | 3.170 | −1.303 |
| Chr14:54983001-54984000 | Oxa1l | 2.452 | 3.023 | 2.723 | 4.433 | 3.585 | −1.133 |
| Chr14:55233001-55234000 | Psmb5 | 2.452 | 4.345 | 3.308 | 4.240 | 3.700 | −1.248 |
| Chr14:56280001-56281000 | Nedd8 | 2.452 | 3.023 | 4.531 | 4.240 | 3.700 | −1.248 |
| Chr14:58448001-58449000 | Mrp63 | 1.867 | 3.608 | 3.308 | 4.240 | 3.585 | −1.718 |
| Chr14:73922001-73923000 | Nudt15 | 2.452 | 3.608 | 3.308 | 4.017 | 3.700 | −1.248 |
| Chr15:100958001-100959000 | Acvrl1 | 2.452 | 3.023 | 2.723 | 4.240 | 4.087 | −1.635 |
| Chr15:102983001-102984000 | Smug1 | 2.867 | 3.608 | 4.045 | 3.754 | 4.000 | −1.133 |
| Chr15:6559001-6560000 | Fyb | 2.867 | 3.831 | 3.308 | 4.240 | 3.907 | −1.040 |
| Chr15:66816001-66817000 | Gm2895 | 2.452 | 1.023 | 2.723 | 4.017 | 3.907 | −1.455 |
| Chr15:74409001-74410000 | Bai1 | 2.452 | 3.345 | 3.723 | 3.433 | 3.700 | −1.248 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr15:74503001-74504000 | Arc | 2.452 | 4.023 | 3.308 | 3.754 | 3.807 | −1.355 |
| Chr15:76174001-76175000 | Cyc1 | 0.867 | 3.023 | 2.723 | 4.240 | 2.807 | −1.940 |
| Chr15:76364001-76365000 | Fbxl6 | 0.867 | 2.023 | 1.723 | 3.433 | 2.322 | −1.455 |
| Chr15:78387001-78388000 | Rac2 | 2.452 | 4.193 | 1.723 | 4.240 | 3.807 | −1.355 |
| Chr15:78818001-78819000 | Triobp | 2.867 | 2.608 | 3.723 | 4.017 | 4.170 | −1.303 |
| Chr15:79555001-79556000 | Sun2 | 1.867 | 3.345 | 2.723 | 3.017 | 3.000 | −1.133 |
| Chr15:80077001-80078000 | Smcr7l | 2.867 | 3.608 | 3.308 | 4.433 | 4.087 | −1.220 |
| Chr15:82168001-82169000 | Naga | 1.867 | 3.345 | 3.308 | 3.433 | 3.170 | −1.303 |
| Chr15:83416001-83417000 | Ttll12 | 2.867 | 3.831 | 4.531 | 4.433 | 4.087 | −1.220 |
| Chr15:85403001-85404000 | Wnt7b | 1.867 | 3.831 | 2.723 | 3.017 | 3.170 | −1.303 |
| Chr15:97727001-97728000 | Vdr | 1.867 | 3.345 | 1.723 | 3.433 | 3.322 | −1.455 |
| Chr15:99222001-99223000 | Tmbim6 | 1.867 | 4.724 | 3.308 | 4.240 | 3.170 | −1.303 |
| Chr15:99335001-99336000 | Faim2 | 1.867 | 3.345 | 3.308 | 4.017 | 3.322 | −1.455 |
| Chr15:99544001-99545000 | Smarcd1 | 2.452 | 4.193 | 3.723 | 3.754 | 4.000 | −1.548 |
| Chr16:18423001-18424000 | Comt | 2.867 | 4.023 | 3.723 | 4.433 | 4.087 | −1.220 |
| Chr16:32161001-32162000 | Lrrc33 | 2.867 | 3.831 | 4.531 | 3.017 | 3.907 | −1.040 |
| Chr16:38574001-38575000 | Tmem39a | 2.452 | 4.345 | 3.723 | 3.754 | 3.459 | −1.007 |
| Chr16:45119001-45120000 | Ccdc80 | 2.867 | 2.608 | 4.045 | 3.754 | 4.087 | −1.220 |
| Chr16:4624001-4625000 | Glis2 | 2.867 | 4.608 | 4.045 | 4.017 | 3.907 | −1.040 |
| Chr16:4698001-4699000 | Dnaja3 | 2.867 | 4.930 | 3.308 | 4.240 | 4.170 | −1.303 |
| Chr16:49800001-49801000 | Gm16619 | 2.452 | 3.608 | 3.723 | 3.754 | 3.459 | −1.007 |
| Chr16:52029001-52030000 | Cblb | 3.452 | 4.193 | 4.893 | 4.017 | 4.000 | −0.548 |
| Chr16:70373001-70374000 | Gbe1 | 2.867 | 3.608 | 4.893 | 1.433 | 4.807 | −1.940 |
| Chr16:8635001-8636000 | Tmem186 | 2.452 | 3.345 | 4.723 | 3.754 | 3.459 | −1.007 |
| Chr16:93682001-93683000 | Cbr3 | 2.452 | 2.608 | 3.723 | 4.433 | 3.807 | −1.355 |
| Chr16:95933001-95934000 | Ets2 | 1.867 | 3.023 | 4.045 | 3.017 | 3.170 | −1.303 |
| Chr16:96428001-96429000 | Sh3bgr | 2.867 | 4.193 | 4.045 | 4.240 | 3.907 | −1.040 |
| Chr17:24826001-24827000 | Syngr3 | 0.715 | 3.345 | 4.531 | 3.017 | 2.322 | −1.607 |
| Chr17:33074001-33075000 | Cyp4f13 | 2.452 | 3.608 | 3.308 | 3.754 | 3.459 | −1.007 |
| Chr17:34046001-34047000 | BC051226 | 1.867 | 1.023 | 3.308 | 2.433 | 3.585 | −1.718 |
| Chr17:34087001-34088000 | B3galt4 | 1.867 | 3.345 | 3.723 | 1.433 | 3.700 | −1.833 |
| Chr17:34104001-34105000 | Vps52 | 2.452 | 4.345 | 3.723 | 4.754 | 3.459 | −1.007 |
| Chr17:34449001-34450000 | H2-Eb1 | 1.867 | 3.831 | 1.723 | 3.433 | 3.322 | −1.455 |
| Chr17:34865001-34866000 | C4b | 2.867 | 3.023 | 3.723 | 4.017 | 4.087 | −1.220 |
| Chr17:35164001-35165000 | Ng23 | 0.867 | 3.023 | 1.571 | 3.754 | 3.807 | −2.940 |
| Chr17:35331001-35332000 | Ltb | 1.867 | 2.023 | 3.308 | 3.017 | 3.170 | −1.303 |
| Chr17:36598001-36599000 | H2-M10.4 | 1.867 | 3.023 | 2.723 | 3.754 | 3.700 | −1.833 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr17:47577001-47578000 | AI661453 | 2.452 | 3.831 | 4.531 | 2.433 | 3.459 | −1.007 |
| Chr17:56929001-56930000 | Rfx2 | 1.867 | 3.023 | 2.723 | 3.017 | 3.585 | −1.718 |
| Chr17:57200001-57201000 | Crb3 | 2.452 | 3.831 | 4.045 | 4.017 | 3.807 | −1.355 |
| Chr18:35023001-35024000 | Egr1 | 2.452 | 3.608 | 4.531 | 3.433 | 3.459 | −1.007 |
| Chr18:36127001-36128000 | Psd2 | 1.867 | 3.608 | 1.723 | 3.433 | 3.807 | −1.940 |
| Chr18:39542001-39543000 | Gm15337 | 2.452 | 3.345 | 3.308 | 3.754 | 3.807 | −1.355 |
| Chr18:43476001-43477000 | Stk32a | 1.867 | 4.023 | 3.308 | 2.433 | 3.170 | −1.303 |
| Chr18:4668001-4669000 | 9430020K01Rik | 1.867 | 3.023 | 1.723 | 3.433 | 3.000 | −1.133 |
| Chr18:48206001-48207000 | Gm5506 | 2.452 | 4.193 | 2.723 | 4.017 | 3.700 | −1.248 |
| Chr18:54144001-54145000 | Gm5507 | 2.452 | 3.345 | 4.045 | 4.892 | 4.000 | −1.548 |
| Chr18:60728001-60729000 | Rbm22 | 2.452 | 4.023 | 4.045 | 3.433 | 3.585 | −1.133 |
| Chr18:61210001-61211000 | Pdgfrb | 1.867 | 3.023 | 1.571 | 3.754 | 3.459 | −1.592 |
| Chr18:67485001-67486000 | B430212C06Rik | 2.452 | 3.023 | 1.571 | 4.433 | 4.170 | −1.718 |
| Chr18:70178001-70179000 | Rab27b | 1.867 | 3.023 | 2.723 | 3.017 | 3.459 | −1.592 |
| Chr18:75120001-75121000 | Lipg | 2.452 | 4.023 | 4.045 | 3.754 | 3.459 | −1.007 |
| Chr18:75162001-75163000 | Rpl17 | 2.867 | 4.483 | 4.531 | 3.017 | 4.087 | −1.220 |
| Chr19:21346001-21347000 | Zfand5 | 0.867 | 2.608 | 2.723 | 3.433 | 2.585 | −1.718 |
| Chr19:24416001-24417000 | Pip5k1b | 1.867 | 2.608 | 1.723 | 3.433 | 4.000 | −2.133 |
| Chr19:29031001-29032000 | 4430402I18Rik | 2.452 | 3.023 | 4.308 | 2.433 | 3.807 | −1.355 |
| Chr19:3899001-3900000 | Tcirg1 | 2.452 | 4.345 | 3.308 | 3.754 | 4.000 | −1.548 |
| Chr19:4171001-4172000 | Carns1 | 1.867 | 3.831 | 1.723 | 3.433 | 3.585 | −1.718 |
| Chr19:4195001-4196000 | Ppp1ca | 2.452 | 4.023 | 4.045 | 3.017 | 4.585 | −2.133 |
| Chr19:45065001-45066000 | Sema4g | 2.452 | 3.831 | 2.723 | 4.017 | 4.000 | −1.548 |
| Chr19:45093001-45094000 | Lzts2 | 1.867 | 3.023 | 3.308 | 3.754 | 3.459 | −1.592 |
| Chr19:46402001-46403000 | Fbxl15 | 2.867 | 4.023 | 2.723 | 4.602 | 3.907 | −1.040 |
| Chr19:46743001-46744000 | Cyp17a1 | 1.867 | 3.345 | 2.723 | 3.754 | 3.585 | −1.718 |
| Chr19:4863001-4864000 | Actn3 | 2.867 | 4.023 | 3.308 | 4.433 | 3.907 | −1.040 |
| Chr19:4930001-4931000 | Peli3 | 1.867 | 4.193 | 3.723 | 2.433 | 3.807 | −1.940 |
| Chr19:5038001-5039000 | B3gnt1 | 0.867 | 3.608 | 2.723 | 4.240 | 3.000 | −2.133 |
| Chr19:5116001-5117000 | Klc2 | 2.452 | 4.023 | 2.723 | 4.017 | 3.700 | −1.248 |
| Chr19:5388001-5389000 | Sart1 | 0.867 | 4.023 | 2.723 | 1.433 | 2.807 | −1.940 |
| Chr19:5425001-5426000 | AI837181 | 1.867 | 4.023 | 4.045 | 3.433 | 3.459 | −1.592 |
| Chr19:5480001-5481000 | Efemp2 | 1.867 | 4.483 | 2.723 | 3.017 | 3.459 | −1.592 |
| Chr19:57436001-57437000 | Fam160b1 | 0.867 | 3.023 | 3.723 | 1.280 | 2.807 | −1.940 |
| Chr19:5754001-5755000 | Ltbp3 | 2.452 | 3.345 | 3.723 | 3.754 | 4.170 | −1.718 |
| Chr19:59336001-59337000 | Slc18a2 | 2.867 | 3.831 | 4.045 | 4.240 | 3.907 | −1.040 |
| Chr19:6084001-6085000 | Zfpl1 | 0.867 | 3.608 | 2.723 | 3.433 | 3.000 | −2.133 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr19:6108001-6109000 | Naaladl1 | 2.452 | 3.831 | 3.308 | 3.754 | 3.459 | −1.007 |
| Chr19:6399001-6400000 | Rasgrp2 | 0.715 | 1.023 | 3.308 | 3.017 | 3.000 | −2.285 |
| Chr19:6981001-6982000 | Prdx5 | 1.867 | 3.023 | 4.045 | 4.433 | 3.807 | −1.940 |
| Chr19:7044001-7045000 | Plcb3 | 1.867 | 2.023 | 3.308 | 2.433 | 3.000 | −1.133 |
| Chr19:7277001-7278000 | Otub1 | 2.452 | 1.023 | 3.308 | 4.754 | 4.000 | −1.548 |
| Chr2:101519001-101520000 | Traf6 | 2.452 | 4.345 | 3.308 | 3.754 | 3.000 | −0.548 |
| Chr2:116727001-116728000 | D330050G23Rik | 2.452 | 4.023 | 4.045 | 3.754 | 4.000 | −1.548 |
| Chr2:119097001-119098000 | Rhov | 2.452 | 3.023 | 2.723 | 4.017 | 3.459 | −1.007 |
| Chr2:12846001-12847000 | Pter | 1.867 | 2.608 | 3.308 | 2.433 | 3.907 | −2.040 |
| Chr2:130107001-130108000 | Idh3b | 1.867 | 2.608 | 1.723 | 4.017 | 3.585 | −1.718 |
| Chr2:131030001-131031000 | 2310035K24Rik | 1.867 | 4.023 | 3.723 | 1.433 | 3.000 | −1.133 |
| Chr2:132697001-132698000 | Lrrn4 | 1.867 | 3.831 | 4.045 | 3.433 | 3.700 | −1.833 |
| Chr2:143764001-143765000 | Dstn | 2.452 | 4.193 | 4.045 | 3.433 | 3.700 | −1.248 |
| Chr2:143808001-143809000 | Rrbp1 | 2.452 | 4.023 | 1.723 | 4.433 | 4.000 | −1.548 |
| Chr2:146002001-146003000 | 4930529M08Rik | 3.452 | 4.023 | 4.045 | 4.754 | 4.907 | −1.455 |
| Chr2:155074001-155075000 | Dynlrb1 | 3.189 | 3.608 | 1.571 | 5.240 | 4.248 | −1.059 |
| Chr2:155817001-155818000 | Cep250 | 1.867 | 3.831 | 4.308 | 1.433 | 3.807 | −1.940 |
| Chr2:160586001-160587000 | Plcg1 | 2.192 | 4.608 | 2.723 | 4.240 | 2.622 | −0.430 |
| Chr2:164667001-164668000 | Pltp | 2.452 | 4.193 | 4.045 | 3.017 | 3.807 | −1.355 |
| Chr2:164719001-164720000 | Pcif1 | 2.452 | 2.608 | 4.045 | 4.433 | 3.585 | −1.133 |
| Chr2:173076001-173077000 | Pmepa1 | 2.452 | 2.608 | 4.308 | 2.433 | 3.459 | −1.007 |
| Chr2:174165001-174166000 | Gnas | 1.867 | 2.608 | 3.308 | 2.433 | 3.000 | −1.133 |
| Chr2:174257001-174258000 | Ctsz | 0.867 | 4.023 | 3.723 | 3.754 | 3.170 | −2.303 |
| Chr2:174287001-174288000 | Atp5e | 1.867 | 4.023 | 3.723 | 4.017 | 3.807 | −1.940 |
| Chr2:176979001-176980000 | Gm14410 | 2.452 | 2.023 | 3.723 | 3.754 | 3.700 | −1.248 |
| Chr2:18923001-18924000 | 4930426L09Rik | 1.867 | 3.831 | 4.308 | 4.433 | 3.322 | −1.455 |
| Chr2:25053001-25054000 | A830007P12Rik | 2.867 | 3.608 | 4.308 | 3.433 | 4.087 | −1.220 |
| Chr2:25097001-25098000 | 2310002J15Rik | 0.867 | 3.608 | 2.723 | 3.433 | 2.000 | −1.133 |
| Chr2:25129001-25130000 | Anapc2 | 0.867 | 4.345 | 2.723 | 3.017 | 4.000 | −3.133 |
| Chr2:25165001-25166000 | Grin1 | 3.452 | 4.930 | 4.893 | 4.017 | 4.459 | −1.007 |
| Chr2:25187001-25188000 | AA543186 | 1.867 | 4.345 | 3.308 | 4.017 | 3.170 | −1.303 |
| Chr2:25947001-25948000 | Nacc2 | 1.867 | 4.023 | 3.308 | 2.433 | 3.170 | −1.303 |
| Chr2:32181001-32182000 | Dnm1 | 2.452 | 4.023 | 3.308 | 3.754 | 3.459 | −1.007 |
| Chr2:35899001-35900000 | Ndufa8 | 2.452 | 4.023 | 4.045 | 3.017 | 3.459 | −1.007 |
| Chr2:91098001-91099000 | Pacsin3 | 1.867 | 4.193 | 3.723 | 2.433 | 3.807 | −1.940 |
| Chr2:92233001-92234000 | Mapk8ip1 | 1.867 | 3.023 | 3.308 | 4.017 | 3.459 | −1.592 |
| Chr2:94231001-94232000 | Ttc17 | 1.867 | 4.023 | 1.723 | 3.433 | 4.644 | −2.777 |

TABLE 2-continued

| Peak | Gene | NCsh (N) | NCsh (C) | MMP-9sh (N) | MMP-9sh (C) | Input | log₂ ratio NCsh (N) vs input |
|---|---|---|---|---|---|---|---|
| Chr3:117529001-117530000 | Snx7 | 2.867 | 3.345 | 3.308 | 4.240 | 4.248 | −1.381 |
| Chr3:127339001-127340000 | Neurog2 | 1.867 | 3.831 | 1.723 | 3.433 | 3.807 | −1.940 |
| Chr3:151119001-151120000 | Eltd1 | 3.452 | 3.608 | 4.531 | 4.433 | 4.524 | −1.072 |
| Chr3:151905001-151906000 | Nexn | 2.867 | 3.608 | 4.308 | 4.017 | 3.907 | −1.040 |
| Chr3:27894001-27895000 | Pld1 | 1.867 | 2.023 | 3.308 | 2.433 | 3.000 | −1.133 |
| Chr3:53251001-53252000 | Nhlrc3 | 0.715 | 3.023 | 2.723 | 3.017 | 3.000 | −2.285 |
| Chr3:63734001-63735000 | E130311K13Rik | 1.867 | 4.193 | 2.723 | 3.433 | 3.170 | −1.303 |
| Chr3:68843001-68844000 | Trim59 | 1.867 | 3.345 | 3.308 | 4.240 | 3.322 | −1.455 |
| Chr4:101320001-101321000 | Leprot | 1.867 | 4.023 | 2.723 | 4.017 | 3.000 | −1.133 |
| Chr4:107356001-107357000 | Dmrtb1 | 1.867 | 3.345 | 3.308 | 2.433 | 4.087 | −2.220 |
| Chr4:114588001-114589000 | 9130206I24Rik | 2.867 | 3.023 | 4.723 | 4.240 | 3.907 | −1.040 |
| Chr4:116825001-116826000 | Rps8 | 2.867 | 3.023 | 3.308 | 4.602 | 4.000 | −1.133 |
| Chr4:118034001-118035000 | Hyi | 1.867 | 4.023 | 3.308 | 4.017 | 3.000 | −1.133 |
| Chr4:122783001-122784000 | Bmp8b | 1.867 | 2.608 | 3.723 | 3.433 | 3.000 | −1.133 |
| Chr4:123397001-123398000 | Ndufs5 | 2.452 | 4.483 | 4.308 | 2.433 | 3.807 | −1.355 |
| Chr4:123603001-123604000 | Rragc | 1.867 | 4.608 | 2.723 | 3.433 | 3.459 | −1.592 |
| Chr4:125714001-125715000 | Csf3r | 1.867 | 3.608 | 3.723 | 3.433 | 3.322 | −1.455 |
| Chr4:125925001-125926000 | Mtap7d1 | 1.867 | 4.345 | 1.723 | 4.017 | 3.585 | −1.718 |
| Chr4:126178001-126179000 | Eif2c4 | 2.867 | 3.345 | 3.308 | 4.433 | 4.644 | −1.777 |
| Chr4:128628001-128629000 | Adc | 2.452 | 4.608 | 2.723 | 4.017 | 3.700 | −1.248 |
| Chr4:129054001-129055000 | Zbtb8a | 0.867 | 2.023 | 1.723 | 3.754 | 3.459 | −2.592 |
| Chr4:130168001-130169000 | Nkain1 | 2.452 | 3.345 | 4.531 | 3.017 | 3.585 | −1.133 |
| Chr4:132961001-132962000 | Slc9a1 | 1.867 | 4.193 | 2.723 | 3.017 | 3.700 | −1.833 |
| Chr4:134478001-134479000 | D4Wsu53e | 0.867 | 3.608 | 3.308 | 3.754 | 4.000 | −3.133 |
| Chr4:135029001-135030000 | Nipal3 | 2.452 | 4.345 | 3.308 | 4.017 | 3.907 | −1.455 |
| Chr4:135522001-135523000 | Gale | 0.867 | 3.023 | 3.723 | 3.754 | 3.322 | −2.455 |
| Chr4:137115001-137116000 | Hspg2 | 1.867 | 3.608 | 2.723 | 3.017 | 3.585 | −1.718 |
| Chr4:138875001-138876000 | Akr7a5 | 1.867 | 3.023 | 2.723 | 3.017 | 3.907 | −2.040 |
| Chr4:140239001-140240000 | Gm13025 | 1.867 | 2.608 | 1.723 | 3.754 | 3.807 | −1.940 |
| Chr4:143112001-143113000 | Gm13040 | 3.452 | 3.831 | 4.723 | 4.433 | 4.907 | −1.455 |
| Chr4:143135001-143136000 | Gm13057 | 3.452 | 4.483 | 4.531 | 4.433 | 4.907 | −1.455 |
| Chr4:147322001-147323000 | 2510039O18Rik | 2.452 | 3.023 | 4.893 | 3.433 | 3.807 | −1.355 |
| Chr4:147523001-147524000 | Fbxo6 | 2.452 | 3.345 | 4.531 | 2.433 | 3.585 | −1.133 |
| Chr4:147967001-147968000 | Srm | 2.452 | 4.345 | 4.045 | 3.754 | 3.459 | −1.007 |
| Chr4:151462001-151463000 | Plekhg5 | 1.867 | 3.023 | 3.308 | 2.433 | 3.170 | −1.303 |
| Chr4:15202001-15203000 | Tmem64 | 2.452 | 4.345 | 4.045 | 3.017 | 3.807 | −1.355 |
| Chr4:155237001-155238000 | Tas1r3 | 0.867 | 3.023 | 1.571 | 3.754 | 3.170 | −2.303 |

TABLE 2-continued

| | | log₂ normalized Read count | | | | |
|---|---|---|---|---|---|---|
| Peak | Gene | NCsh (N) | NCsh (C) | MMP-9sh (N) | MMP-9sh (C) | Input | log₂ ratio NCsh (N) vs input |
| Chr4:35172001-35173000 | 3110043O21Rik | 1.867 | 3.023 | 2.723 | 3.433 | 3.000 | −1.133 |
| Chr4:43055001-43056000 | B230312A22Rik | 2.452 | 3.831 | 3.723 | 3.754 | 4.000 | −1.548 |
| Chr4:44994001-44995000 | Grhpr | 1.867 | 2.608 | 2.723 | 3.433 | 3.807 | −1.940 |
| Chr4:45911001-45912000 | E230008N13Rik | 2.452 | 4.345 | 3.308 | 3.754 | 3.700 | −1.248 |
| Chr4:48551001-48552000 | 5730528L13Rik | 2.452 | 3.831 | 4.045 | 3.754 | 4.087 | −1.635 |
| Chr4:61926001-61927000 | Slc31a2 | 1.867 | 2.608 | 2.723 | 3.017 | 3.459 | −1.592 |
| Chr5:101081001-101082000 | Coq2 | 2.452 | 3.345 | 3.308 | 4.433 | 3.459 | −1.007 |
| Chr5:108154001-108155000 | Gfi1 | 0.867 | 3.831 | 3.723 | 3.754 | 2.585 | −1.718 |
| Chr5:110119001-110120000 | 5430403G16Rik | 0.715 | 3.831 | 3.308 | 4.240 | 4.087 | −3.372 |
| Chr5:115891001-115892000 | Msi1 | 2.452 | 2.608 | 1.723 | 4.240 | 3.585 | −1.133 |
| Chr5:115963001-115964000 | Pxn | 2.452 | 3.831 | 4.045 | 3.017 | 3.585 | −1.133 |
| Chr5:122303001-122304000 | Fam109a | 2.452 | 2.608 | 4.308 | 3.017 | 3.585 | −1.133 |
| Chr5:122855001-122856000 | Arpc3 | 0.867 | 4.483 | 3.308 | 4.017 | 4.000 | −3.133 |
| Chr5:124312001-124313000 | Niacr1 | 2.452 | 3.345 | 3.308 | 3.754 | 3.459 | −1.007 |
| Chr5:135725001-135726000 | Fzd9 | 1.867 | 4.608 | 3.308 | 2.433 | 3.170 | −1.303 |
| Chr5:136213001-136214000 | Tmem120a | 1.867 | 0.871 | 4.308 | 4.240 | 4.000 | −2.133 |
| Chr5:136625001-136626000 | Orai2 | 1.867 | 3.345 | 2.723 | 3.017 | 3.000 | −1.133 |
| Chr5:137548001-137549000 | Serpine1 | 1.867 | 3.023 | 3.308 | 2.433 | 3.700 | −1.833 |
| Chr5:138637001-138638000 | Mblac1 | 1.867 | 3.023 | 4.308 | 1.280 | 3.000 | −1.133 |
| Chr5:141093001-141094000 | Lfng | 1.867 | 3.345 | 1.723 | 3.433 | 3.585 | −1.718 |
| Chr5:141183001-141184000 | Baat1 | 2.452 | 3.831 | 4.531 | 3.433 | 3.585 | −1.133 |
| Chr5:144952001-144953000 | Bhlha15 | 1.867 | 3.345 | 3.723 | 2.433 | 3.170 | −1.303 |
| Chr5:23948001-23949000 | Fastk | 2.452 | 4.345 | 4.045 | 4.754 | 3.459 | −1.007 |
| Chr5:31202001-31203000 | Agbl5 | 1.867 | 3.608 | 1.723 | 3.433 | 3.000 | −1.133 |
| Chr5:34978001-34979000 | Mfsd10 | 2.452 | 2.608 | 4.308 | 3.433 | 3.585 | −1.133 |
| Chr5:42472001-42473000 | Gm16223 | 1.867 | 2.608 | 2.723 | 3.017 | 3.170 | −1.303 |
| Chr5:44227001-44228000 | Bst1 | 2.452 | 4.023 | 4.531 | 4.017 | 4.087 | −1.635 |
| Chr5:65875001-65876000 | 1110003E01Rik | 1.867 | 3.345 | 3.723 | 1.433 | 3.459 | −1.592 |
| Chr5:67820001-67821000 | Gm16714 | 2.867 | 3.831 | 4.531 | 3.433 | 3.907 | −1.040 |
| Chr5:68240001-68241000 | Gm15477 | 2.452 | 4.023 | 4.045 | 3.017 | 3.807 | −1.355 |
| Chr5:96991001-96992000 | Fras1 | 3.867 | 4.193 | 5.424 | 4.240 | 5.358 | −1.491 |
| Chr5:97537001-97538000 | Paqr3 | 0.867 | 3.345 | 4.045 | 4.240 | 2.807 | −1.940 |
| Chr6:113236001-113237000 | Cpne9 | 2.452 | 4.023 | 3.723 | 3.754 | 3.459 | −1.007 |
| Chr6:113289001-113290000 | Camk1 | 0.867 | 3.345 | 1.723 | 4.017 | 3.585 | −2.718 |
| Chr6:113340001-113341000 | Arpc4 | 2.867 | 3.023 | 2.723 | 4.602 | 4.000 | −1.133 |
| Chr6:121216001-121217000 | Usp18 | 2.452 | 3.345 | 2.723 | 4.017 | 3.700 | −1.248 |
| Chr6:124344001-124345000 | Pex5 | 2.452 | 3.608 | 3.308 | 3.754 | 3.807 | −1.355 |

TABLE 2-continued

| Peak | Gene | log₂ normalized Read count ||||| log₂ ratio NCsh (N) vs input |
|------|------|-------|-------|-------|-------|-------|-------|
|      |      | NCsh (N) | NCsh (C) | MMP-9sh (N) | MMP-9sh (C) | Input | |
| Chr6:124715001-124716000 | Eno2 | 2.452 | 4.023 | 3.308 | 3.754 | 3.585 | −1.133 |
| Chr6:125095001-125096000 | Iffo1 | 1.867 | 3.023 | 3.308 | 2.433 | 3.322 | −1.455 |
| Chr6:126802001-126803000 | Akap3 | 2.867 | 4.023 | 3.723 | 4.240 | 3.907 | −1.040 |
| Chr6:129453001-129454000 | Olr1 | 2.867 | 4.345 | 4.308 | 4.240 | 4.087 | −1.220 |
| Chr6:29356001-29357000 | Ccdc136 | 2.867 | 4.023 | 3.308 | 4.240 | 4.087 | −1.220 |
| Chr6:36799001-36800000 | Dgki | 1.867 | 4.193 | 4.045 | 1.280 | 3.322 | −1.455 |
| Chr6:47804001-47805000 | Zfp398 | 3.189 | 4.193 | 4.308 | 4.240 | 4.700 | −1.511 |
| Chr6:48359001-48360000 | Krba1 | 2.867 | 3.831 | 4.308 | 3.433 | 3.907 | −1.040 |
| Chr6:48546001-48547000 | Repin1 | 1.867 | 4.345 | 2.723 | 3.433 | 3.700 | −1.833 |
| Chr6:54640001-54641000 | 2410066E13Rik | 1.867 | 3.831 | 2.723 | 3.017 | 3.459 | −1.592 |
| Chr6:83090001-83091000 | Rtkn | 1.867 | 3.608 | 1.571 | 4.017 | 3.170 | −1.303 |
| Chr6:83104001-83105000 | Wdr54 | 1.867 | 3.831 | 4.045 | 3.017 | 3.700 | −1.833 |
| Chr6:85077001-85078000 | Gm5878 | 2.452 | 3.608 | 4.045 | 3.433 | 3.459 | −1.007 |
| Chr6:88860001-88861000 | Tpra1 | 2.452 | 2.023 | 4.308 | 3.017 | 3.459 | −1.007 |
| Chr6:89273001-89274000 | Gm16896 | 2.452 | 3.608 | 1.571 | 4.433 | 3.700 | −1.248 |
| Chr6:97766001-97767000 | Mitf | 2.867 | 3.023 | 4.308 | 3.433 | 4.392 | −1.525 |
| Chr7:105333001-105334000 | Gm16938 | 2.867 | 3.345 | 3.723 | 4.017 | 4.087 | −1.220 |
| Chr7:105511001-105512000 | Tsku | 2.867 | 3.831 | 3.308 | 4.433 | 4.000 | −1.133 |
| Chr7:107648001-107649000 | Ucp2 | 0.867 | 3.831 | 3.723 | 4.240 | 3.322 | −2.455 |
| Chr7:107660001-107661000 | Dnajb13 | 2.867 | 4.023 | 4.045 | 4.240 | 3.907 | −1.040 |
| Chr7:109361001-109362000 | Pgap2 | 1.867 | 2.023 | 3.723 | 5.017 | 3.807 | −1.940 |
| Chr7:111538001-111539000 | Trim30c | 3.189 | 4.193 | 4.531 | 4.240 | 4.248 | −1.059 |
| Chr7:130607001-130608000 | Aqp8 | 2.867 | 3.345 | 3.308 | 4.433 | 4.000 | −1.133 |
| Chr7:13082001-13083000 | Zfp606 | 1.867 | 4.023 | 4.045 | 3.017 | 3.459 | −1.592 |
| Chr7:133942001-133943000 | Aldoa | 1.867 | 3.345 | 2.723 | 3.017 | 3.170 | −1.303 |
| Chr7:134350001-134351000 | Tbc1d10b | 1.867 | 4.345 | 1.723 | 3.433 | 3.459 | −1.592 |
| Chr7:134358001-134359000 | SEPT_1 | 0.715 | 4.345 | 2.723 | 3.017 | 3.000 | −2.285 |
| Chr7:134635001-134636000 | Fbrs | 0.867 | 3.023 | 3.308 | 3.017 | 3.907 | −3.040 |
| Chr7:134978001-134979000 | Stx4a | 2.452 | 3.608 | 4.045 | 3.433 | 3.807 | −1.355 |
| Chr7:135242001-135243000 | Itgam | 2.867 | 3.023 | 3.723 | 4.017 | 4.000 | −1.133 |
| Chr7:148050001-148051000 | Sirt3 | 0.867 | 3.608 | 3.723 | 3.754 | 3.700 | −2.833 |
| Chr7:148396001-148397000 | 1600016N20Rik | 1.867 | 1.023 | 4.893 | 3.433 | 3.000 | −1.133 |
| Chr7:148672001-148673000 | Tspan4 | 0.867 | 4.345 | 4.308 | 3.754 | 3.585 | −2.718 |
| Chr7:149244001-149245000 | Mob2 | 1.867 | 3.608 | 1.723 | 3.433 | 3.170 | −1.303 |
| Chr7:150970001-150971000 | Mrgpre | 1.867 | 3.831 | 1.723 | 4.017 | 4.000 | −2.133 |
| Chr7:17478001-17479000 | Gng8 | 0.867 | 3.345 | 3.308 | 3.017 | 3.459 | −2.592 |
| Chr7:19713001-19714000 | Fbxo46 | 2.867 | 3.831 | 3.308 | 4.240 | 3.907 | −1.040 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr7:19799001-19800000 | Gpr4 | 2.452 | 3.345 | 2.723 | 4.602 | 3.585 | −1.133 |
| Chr7:20229001-20230000 | Clptm1 | 2.452 | 3.023 | 4.045 | 3.017 | 3.585 | −1.133 |
| Chr7:20320001-20321000 | Pvrl2 | 2.452 | 4.193 | 4.045 | 3.433 | 3.459 | −1.007 |
| Chr7:20352001-20353000 | Bcam | 2.452 | 4.193 | 4.045 | 4.602 | 3.700 | −1.248 |
| Chr7:25169001-25170000 | Kcnn4 | 1.867 | 2.023 | 3.308 | 4.017 | 3.322 | −1.455 |
| Chr7:28453001-28454000 | Map3k10 | 0.867 | 3.608 | 3.723 | 4.017 | 2.807 | −1.940 |
| Chr7:29137001-29138000 | Rps16 | 2.867 | 2.608 | 4.045 | 3.754 | 4.000 | −1.133 |
| Chr7:29174001-29175000 | Med29 | 1.867 | 3.345 | 4.531 | 3.017 | 3.700 | −1.833 |
| Chr7:29329001-29330000 | Nccrp1 | 2.452 | 3.023 | 3.308 | 3.754 | 3.585 | −1.133 |
| Chr7:29513001-29514000 | Fbxo17 | 2.867 | 3.831 | 3.723 | 4.602 | 4.000 | −1.133 |
| Chr7:29669001-29670000 | Capn12 | 2.867 | 3.023 | 4.723 | 3.433 | 4.170 | −1.303 |
| Chr7:30555001-30556000 | Zfp84 | 2.452 | 3.831 | 4.045 | 3.017 | 4.000 | −1.548 |
| Chr7:30602001-30603000 | Zfp790 | 2.867 | 3.345 | 4.531 | 3.433 | 4.322 | −1.455 |
| Chr7:3112001-3113000 | Gm7353 | 2.867 | 3.831 | 4.308 | 4.017 | 4.170 | −1.303 |
| Chr7:31241001-31242000 | Kirrel2 | 2.452 | 3.345 | 3.723 | 3.754 | 3.907 | −1.455 |
| Chr7:3624001-3625000 | Tmc4 | 2.452 | 3.345 | 3.308 | 4.017 | 3.807 | −1.355 |
| Chr7:3758001-3759000 | Pira5 | 3.452 | 4.483 | 5.183 | 3.433 | 4.907 | −1.455 |
| Chr7:3866001-3867000 | Lilra6 | 1.867 | 4.345 | 2.723 | 3.017 | 3.585 | −1.718 |
| Chr7:4651001-4652000 | Brsk1 | 2.867 | 3.608 | 4.045 | 3.754 | 4.248 | −1.381 |
| Chr7:50743001-50744000 | Iglon5 | 2.452 | 3.023 | 4.045 | 3.017 | 3.585 | −1.133 |
| Chr7:51917001-51918000 | Myh14 | 2.452 | 4.193 | 3.723 | 3.433 | 4.087 | −1.635 |
| Chr7:52113001-52114000 | Pnkp | 1.867 | 3.608 | 3.723 | 3.433 | 3.585 | −1.718 |
| Chr7:52122001-52123000 | Ptov1 | 0.867 | 1.023 | 1.723 | 2.433 | 2.585 | −1.718 |
| Chr7:52258001-52259000 | Irf3 | 1.867 | 3.023 | 4.045 | 1.433 | 3.170 | −1.303 |
| Chr7:52408001-52409000 | Aldh16a1 | 2.452 | 3.023 | 3.308 | 3.754 | 3.907 | −1.455 |
| Chr7:52901001-52902000 | Mamstr | 2.452 | 4.345 | 4.045 | 3.754 | 3.459 | −1.007 |
| Chr7:53113001-53114000 | Grin2d | 2.452 | 3.023 | 3.308 | 3.754 | 3.807 | −1.355 |
| Chr7:53971001-53972000 | Saa3 | 2.452 | 4.193 | 3.308 | 4.433 | 3.907 | −1.455 |
| Chr7:69619001-69620000 | Atp5l-ps1 | 3.452 | 2.608 | 4.893 | 4.433 | 4.807 | −1.355 |
| Chr7:86857001-86858000 | Kif7 | 2.452 | 3.345 | 4.308 | 3.017 | 3.585 | −1.133 |
| Chr7:86958001-86959000 | Mesp2 | 2.452 | 3.831 | 4.045 | 4.017 | 3.807 | −1.355 |
| Chr7:87188001-87189000 | Zfp710 | 1.867 | 3.345 | 2.723 | 3.017 | 3.700 | −1.833 |
| Chr7:87333001-87334000 | Sema4b | 2.867 | 4.023 | 3.723 | 4.017 | 3.907 | −1.040 |
| Chr7:87472001-87473000 | Unc45a | 1.867 | 3.345 | 3.308 | 2.433 | 3.322 | −1.455 |
| Chr7:95676001-95677000 | Gm10159 | 2.452 | 3.608 | 3.308 | 3.754 | 4.170 | −1.718 |
| Chr8:107870001-107871000 | Fhod1 | 0.867 | 3.023 | 3.723 | 3.754 | 3.700 | −2.833 |
| Chr8:107879001-107880000 | Slc9a5 | 1.867 | 4.724 | 1.723 | 3.433 | 3.459 | −1.592 |

TABLE 2-continued

| Peak | Gene | NCsh (N) | NCsh (C) | MMP-9sh (N) | MMP-9sh (C) | Input | log₂ ratio NCsh (N) vs input |
|---|---|---|---|---|---|---|---|
| Chr8:108050001-108051000 | Atp6v0d1 | 1.867 | 3.608 | 3.308 | 2.433 | 3.170 | −1.303 |
| Chr8:108380001-108381000 | Thap11 | 2.452 | 3.345 | 4.308 | 3.754 | 3.585 | −1.133 |
| Chr8:108469001-108470000 | Gm16156 | 2.452 | 3.831 | 3.723 | 4.240 | 3.700 | −1.248 |
| Chr8:114259001-114260000 | Bcar1 | 1.867 | 3.023 | 2.723 | 3.017 | 4.322 | −2.455 |
| Chr8:114397001-114398000 | Tmem170 | 0.867 | 3.608 | 3.723 | 3.017 | 3.700 | −2.833 |
| Chr8:15026001-15027000 | Kbtbd11 | 2.452 | 2.023 | 2.723 | 4.017 | 3.585 | −1.133 |
| Chr8:26202001-26203000 | Plekha2 | 1.867 | 3.345 | 1.723 | 3.433 | 3.322 | −1.455 |
| Chr8:28086001-28087000 | Zfp703 | 2.867 | 3.023 | 3.723 | 4.017 | 4.170 | −1.303 |
| Chr8:28137001-28138000 | Erlin2 | 2.452 | 2.608 | 2.723 | 4.240 | 3.807 | −1.355 |
| Chr8:37088001-37089000 | Gm10063 | 0.867 | 4.608 | 1.723 | 2.433 | 3.170 | −2.303 |
| Chr8:4135001-4136000 | Cd209g | 2.452 | 3.608 | 3.308 | 3.754 | 3.459 | −1.007 |
| Chr8:4245001-4246000 | Map2k7 | 0.867 | 3.608 | 3.308 | 1.280 | 2.585 | −1.718 |
| Chr8:4681001-4682000 | Gm6410 | 3.189 | 4.023 | 4.531 | 4.017 | 4.248 | −1.059 |
| Chr8:48763001-48764000 | AA386476 | 2.452 | 3.608 | 2.723 | 4.433 | 3.459 | −1.007 |
| Chr8:72447001-72448000 | Gatad2a | 1.867 | 4.193 | 2.723 | 3.017 | 3.700 | −1.833 |
| Chr8:72822001-72823000 | Ddx49 | 1.867 | 4.345 | 3.308 | 2.433 | 3.585 | −1.718 |
| Chr8:73039001-73040000 | 2810422J05Rik | 2.867 | 3.608 | 3.723 | 4.240 | 4.000 | −1.133 |
| Chr8:73140001-73141000 | Lrrc25 | 1.867 | 4.724 | 2.723 | 3.433 | 3.000 | −1.133 |
| Chr8:73198001-73199000 | Lsm4 | 2.452 | 0.871 | 3.723 | 4.602 | 3.907 | −1.455 |
| Chr8:73257001-73258000 | Pde4c | 1.867 | 3.608 | 2.723 | 3.017 | 3.000 | −1.133 |
| Chr8:73408001-73409000 | Slc5a5 | 1.867 | 4.193 | 3.723 | 1.433 | 3.907 | −2.040 |
| Chr8:73789001-73790000 | Haus8 | 1.867 | 3.345 | 2.723 | 3.017 | 4.000 | −2.133 |
| Chr8:74087001-74088000 | Nxnl1 | 2.867 | 3.023 | 3.723 | 4.017 | 3.907 | −1.040 |
| Chr8:74114001-74115000 | Pgls | 2.452 | 4.023 | 4.045 | 3.017 | 3.807 | −1.355 |
| Chr8:85688001-85689000 | Gm10645 | 2.452 | 3.023 | 3.308 | 3.754 | 3.907 | −1.455 |
| Chr8:86649001-86650000 | Podnl1 | 1.867 | 3.023 | 2.723 | 3.017 | 3.170 | −1.303 |
| Chr8:87542001-87543000 | Asna1 | 2.452 | 4.193 | 3.308 | 3.754 | 3.700 | −1.248 |
| Chr8:98339001-98340000 | 4930513N10Rik | 1.867 | 4.023 | 2.723 | 4.240 | 3.700 | −1.833 |
| Chr9:106346001-106347000 | Abhd14a | 2.452 | 2.608 | 4.308 | 2.433 | 3.459 | −1.007 |
| Chr9:107444001-107445000 | Cyb561d2 | 1.867 | 2.608 | 2.723 | 3.433 | 3.700 | −1.833 |
| Chr9:107476001-107477000 | Hyal2 | 1.867 | 4.345 | 1.723 | 3.754 | 3.700 | −1.833 |
| Chr9:114277001-114278000 | 4930520O04Rik | 0.867 | 3.023 | 2.723 | 3.433 | 3.000 | −2.133 |
| Chr9:114399001-114400000 | Ccr4 | 2.452 | 3.608 | 4.045 | 3.433 | 4.000 | −1.548 |
| Chr9:119392001-119393000 | Scn5a | 2.867 | 3.831 | 3.723 | 4.017 | 4.000 | −1.133 |
| Chr9:120484001-120485000 | Rpl14 | 2.867 | 4.023 | 4.531 | 3.754 | 4.322 | −1.455 |
| Chr9:122933001-122934000 | Tmem42 | 2.452 | 4.345 | 3.723 | 3.433 | 3.700 | −1.248 |
| Chr9:15393001-15394000 | Ccdc67 | 2.452 | 4.193 | 2.723 | 4.017 | 3.700 | −1.248 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr9:20453001-20454000 | Ubl5 | 2.452 | 3.608 | 1.723 | 5.017 | 4.392 | −1.940 |
| Chr9:20876001-20877000 | Fdx1l | 0.867 | 2.023 | 3.723 | 3.754 | 3.459 | −2.592 |
| Chr9:21150001-21151000 | Slc44a2 | 2.867 | 4.608 | 4.045 | 4.017 | 3.907 | −1.040 |
| Chr9:21932001-21933000 | Acp5 | 2.867 | 2.608 | 4.308 | 3.433 | 3.459 | −0.592 |
| Chr9:22087001-22088000 | Zfp810 | 2.867 | 3.608 | 2.723 | 4.754 | 4.170 | −1.303 |
| Chr9:24933001-24934000 | Herpud2 | 2.452 | 3.023 | 2.723 | 4.017 | 4.322 | −1.870 |
| Chr9:35236001-35237000 | Cdon | 2.867 | 4.345 | 4.045 | 3.754 | 3.907 | −1.040 |
| Chr9:42062001-42063000 | Sc5d | 2.867 | 3.831 | 4.308 | 4.017 | 3.907 | −1.040 |
| Chr9:44577001-44578000 | Ift46 | 2.452 | 3.023 | 4.045 | 3.017 | 4.087 | −1.635 |
| Chr9:46078001-46079000 | Apoa5 | 1.867 | 4.023 | 2.723 | 3.433 | 3.000 | −1.133 |
| Chr9:50573001-50574000 | 1110032A03Rik | 0.867 | 4.193 | 1.723 | 4.602 | 3.322 | −2.455 |
| Chr9:55205001-55206000 | AI118078 | 2.452 | 4.193 | 4.308 | 2.433 | 3.907 | −1.455 |
| Chr9:57001001-57002000 | Commd4 | 2.867 | 3.023 | 4.045 | 4.433 | 4.000 | −1.133 |
| Chr9:57109001-57110000 | 1700017B05Rik | 1.867 | 1.023 | 1.571 | 3.754 | 3.000 | −1.133 |
| Chr9:59453001-59454000 | Celf6 | 1.867 | 4.483 | 2.723 | 4.017 | 3.807 | −1.940 |
| Chr9:59506001-59507000 | Pkm2 | 2.452 | 3.831 | 1.723 | 4.240 | 3.585 | −1.133 |
| Chr9:62715001-62716000 | Gm10653 | 1.867 | 4.345 | 1.723 | 3.433 | 4.585 | −2.718 |
| Chr9:65061001-65062000 | Parp16 | 2.452 | 4.023 | 4.045 | 3.433 | 3.700 | −1.248 |
| Chr9:66648001-66649000 | BC050972 | 1.867 | 4.193 | 2.723 | 3.433 | 3.700 | −1.833 |
| Chr9:70507001-70508000 | Gm10642 | 2.867 | 4.193 | 1.723 | 4.602 | 4.524 | −1.657 |
| Chr9:78092001-78093000 | Dppa5b | 1.867 | 3.831 | 3.723 | 3.754 | 3.000 | −1.133 |
| Chr9:7838001-7839000 | C330006D17Rik | 1.867 | 3.345 | 3.723 | 3.017 | 3.585 | −1.718 |
| Chr9:81538001-81539000 | D430036J16Rik | 2.452 | 5.111 | 3.723 | 4.433 | 4.087 | −1.635 |
| Chr9:86462001-86463000 | Pgm3 | 1.867 | 4.483 | 3.308 | 2.433 | 3.459 | −1.592 |
| ChrX:12195001-12196000 | Atp6ap2 | 1.867 | 1.023 | 4.045 | 1.433 | 3.000 | −1.133 |
| ChrX:15513001-15514000 | Drr1 | 2.452 | 3.608 | 4.045 | 4.240 | 4.700 | −2.248 |
| ChrX:34911001-34912000 | Rhox2d | 0.867 | 1.023 | 3.308 | 3.017 | 3.459 | −2.592 |
| Cleavage in any region and don't show differential expression | | | | | | | |
| Chr1:146619001-146620000 | Rgs18 | 4.189 | 2.608 | 1.723 | 1.433 | 2.585 | 1.604 |
| Chr1:159290001-159291000 | Rasal2 | 2.867 | 1.023 | 1.571 | 2.433 | 3.000 | −0.133 |
| Chr1:166005001-166006000 | Sell | 5.115 | 3.023 | 3.308 | 1.433 | 4.524 | 0.591 |
| Chr1:196548001-196549000 | Plxna2 | 4.954 | 3.345 | 2.723 | 1.433 | 3.459 | 1.495 |
| Chr1:37087001-37088000 | Vwa3b | 5.259 | 2.023 | 3.308 | 2.433 | 3.807 | 1.452 |
| Chr1:44709001-44710000 | Gulp1 | 5.037 | 1.023 | 3.308 | 3.433 | 3.807 | 1.230 |
| Chr1:60466001-60467000 | Abi2 | 4.037 | 3.023 | 1.571 | 1.280 | 2.000 | 2.037 |
| Chr1:65410001-65411000 | Pth2r | 4.189 | 2.023 | 1.571 | 3.017 | 3.585 | 0.604 |
| Chr1:70884001-70885000 | Vwc2l | 4.452 | 0.871 | 3.723 | 2.433 | 3.000 | 1.452 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr10:13276001-13277000 | Adat2 | 4.189 | 1.023 | 1.571 | 3.017 | 3.459 | 0.730 |
| Chr11:58088001-58089000 | 4930438A08Rik | 4.674 | 1.023 | 3.723 | 2.433 | 3.000 | 1.674 |
| Chr11:67609001-67610000 | Dhrs7c | 4.954 | 3.023 | 1.723 | 3.433 | 3.459 | 1.495 |
| Chr11:97066001-97067000 | Npepps | 0.867 | 0.871 | 1.571 | 1.280 | 1.585 | −0.718 |
| Chr12:114952001-114953000 | Gm16594 | 4.452 | 1.023 | 1.571 | 1.433 | 3.322 | 1.130 |
| Chr12:67657001-67658000 | Mdga2 | 4.189 | 0.871 | 3.308 | 2.433 | 3.807 | 0.382 |
| Chr12:76023001-76024000 | Kcnh5 | 4.452 | 2.608 | 1.723 | 1.280 | 3.170 | 1.282 |
| Chr12:85792001-85793000 | Lin52 | 4.326 | 2.023 | 1.571 | 2.433 | 3.807 | 0.519 |
| Chr12:88997001-88998000 | BB287469 | 0.715 | 0.871 | 1.571 | 1.280 | −0.152 | 0.867 |
| Chr13:105254001-105255000 | Adamts6 | 3.089 | 2.023 | 1.571 | 1.280 | 3.585 | −0.496 |
| Chr13:27941001-27942000 | Prl2c1 | 4.674 | 3.023 | 2.723 | 1.280 | 3.000 | 1.674 |
| Chr13:39952001-39953000 | U1 | 4.452 | 2.023 | 2.723 | 2.433 | 3.322 | 1.130 |
| Chr13:62252001-62253000 | Zfp808 | 4.037 | 1.023 | 1.723 | 1.433 | 3.807 | 0.230 |
| Chr13:63532001-63533000 | Fancc | 3.189 | 2.023 | 1.723 | 1.280 | 1.585 | 1.604 |
| Chr13:63963001-63964000 | 0610007P08Rik | 3.867 | 2.023 | 1.723 | 1.433 | 1.585 | 2.282 |
| Chr13:67199001-67200000 | Zfp708 | 4.774 | 2.023 | 3.723 | 1.280 | 3.585 | 1.189 |
| Chr14:17610001-17611000 | Rarb | 3.067 | 2.608 | 1.723 | 1.280 | 3.700 | −0.633 |
| Chr14:19507001-19508000 | Ube2e2 | 3.867 | 1.023 | 1.571 | 3.017 | 2.322 | 1.545 |
| Chr14:63628001-63629000 | Defb43 | 4.567 | 2.608 | 3.308 | 1.280 | 3.000 | 1.567 |
| Chr14:79733001-79734000 | Naa16 | 4.037 | 2.608 | 1.723 | 1.280 | 3.807 | 0.230 |
| Chr15:54105001-54106000 | Tnfrsf11b | 4.674 | 2.608 | 3.723 | 1.280 | 2.585 | 2.089 |
| Chr15:7207001-7208000 | Egflam | 4.954 | 2.023 | 3.723 | 3.017 | 3.700 | 1.254 |
| Chr15:91341001-91342000 | Slc2a13 | 4.567 | 2.023 | 1.723 | 2.433 | 3.322 | 1.246 |
| Chr16:50529001-50530000 | G730013B05Rik | 4.189 | 2.023 | 2.723 | 1.433 | 2.585 | 1.604 |
| Chr16:96367001-96368000 | Wrb | 4.037 | 2.023 | 1.723 | 2.433 | 4.087 | −0.051 |
| Chr17:35480001-35481000 | H2-Q2 | 2.452 | 1.023 | 1.571 | 1.433 | 1.585 | 0.867 |
| Chr17:52907001-52908000 | Kcnh8 | 3.867 | 2.023 | 2.723 | 1.433 | 2.585 | 1.282 |
| Chr19:29999001-30000000 | Il33 | 4.326 | 2.608 | 1.723 | 1.433 | 3.807 | 0.519 |
| Chr19:30250001-30251000 | Gldc | 4.567 | 2.023 | 3.723 | 1.280 | 3.000 | 1.567 |
| Chr2:103271001-103272000 | Elf5 | 4.189 | 2.023 | 1.571 | 2.433 | 3.700 | 0.489 |
| Chr2:147699001-147700000 | U6 | 4.037 | 1.023 | 1.571 | 2.433 | 2.322 | 1.715 |
| Chr2:17445001-17446000 | Nebl | 4.326 | 3.023 | 1.571 | 1.433 | 3.459 | 0.867 |
| Chr2:178164001-178165000 | Cdh26 | 3.674 | 2.023 | 1.723 | 1.433 | 2.000 | 1.674 |
| Chr2:3631001-3632000 | Fam107b | 4.189 | 2.023 | 1.571 | 3.017 | 2.322 | 1.867 |
| Chr2:36667001-36668000 | Olfr3 | 4.567 | 2.608 | 2.723 | 1.433 | 0.000 | 4.567 |
| Chr2:5182001-5183000 | U2 | 4.037 | 2.608 | 1.571 | 1.280 | 2.585 | 1.452 |
| Chr2:52189001-52190000 | Neb | 4.867 | 1.023 | 2.723 | 3.017 | 3.700 | 1.167 |

TABLE 2-continued

| Peak | Gene | log₂ normalized Read count | | | | | log₂ ratio NCsh (N) vs input |
|---|---|---|---|---|---|---|---|
| | | NCsh (N) | NCsh (C) | MMP-9sh (N) | MMP-9sh (C) | Input | |
| Chr2:6159001-6160000 | A230108P19Rik | 4.326 | 1.023 | 1.723 | 3.017 | 3.807 | 0.519 |
| Chr2:82806001-82807000 | Fsip2 | 4.452 | 1.023 | 1.723 | 3.017 | 3.459 | 0.993 |
| Chr3:101408001-101409000 | Atp1a1 | 4.452 | 3.023 | 1.571 | 2.433 | 3.322 | 1.130 |
| Chr3:105490001-105491000 | Ddx20 | 3.452 | 1.023 | 1.723 | 1.280 | 4.392 | −0.940 |
| Chr3:122843001-122844000 | Synpo2 | 4.774 | 3.023 | 1.571 | 2.433 | 3.907 | 0.867 |
| Chr3:19231001-19232000 | 7SK | 3.189 | 1.023 | 1.571 | 2.433 | 2.585 | 0.604 |
| Chr3:33290001-33291000 | SNORA48 | 4.452 | 2.023 | 2.723 | 2.433 | 2.322 | 2.130 |
| Chr3:39700001-39701000 | SNORA17 | 3.452 | 0.871 | 1.723 | 1.433 | 3.000 | 0.452 |
| Chr3:80921001-80922000 | Pdgfc | 3.674 | 1.023 | 1.571 | 2.433 | 2.322 | 1.352 |
| Chr3:83959001-83960000 | Mnd1 | 1.867 | 1.023 | 1.571 | 1.433 | 2.585 | −0.718 |
| Chr3:85157001-85158000 | Arfip1 | 4.567 | 0.871 | 3.308 | 3.433 | 4.170 | 0.398 |
| Chr4:109321001-109322000 | Gm12811 | 4.326 | 2.023 | 2.723 | 2.433 | 3.807 | 0.519 |
| Chr4:134319001-134320000 | Ldlrap1 | 4.954 | 2.023 | 2.723 | 2.433 | 3.585 | 1.370 |
| Chr4:19331001-19332000 | Cngb3 | 4.452 | 3.345 | 1.723 | 1.433 | 2.807 | 1.645 |
| Chr4:3943001-3944000 | Sdr16c5 | 4.452 | 2.023 | 2.723 | 2.433 | 3.459 | 0.993 |
| Chr4:59130001-59131000 | AI481877 | 4.867 | 3.023 | 3.308 | 1.280 | 3.700 | 1.167 |
| Chr4:61060001-61061000 | Mup15 | 3.867 | 2.023 | 1.723 | 1.280 | 3.322 | 0.545 |
| Chr4:95349001-95350000 | Fggy | 5.259 | 3.023 | 3.308 | 3.017 | 3.700 | 1.559 |
| Chr5:127787001-127788000 | Tmem132c | 3.867 | 2.023 | 1.571 | 1.433 | 3.170 | 0.697 |
| Chr5:143871001-143872000 | Rnf216 | 3.867 | 1.023 | 1.571 | 3.017 | 3.000 | 0.867 |
| Chr5:3397001-3398000 | Cdk6 | 4.867 | 3.023 | 2.723 | 2.433 | 3.000 | 1.867 |
| Chr5:96390001-96391000 | Cxcl13 | 4.567 | 1.023 | 3.308 | 3.017 | 3.000 | 1.567 |
| Chr5:9704001-9705000 | Grm3 | 3.452 | 2.023 | 1.723 | 1.280 | 3.170 | 0.282 |
| Chr6:67321001-67322000 | Il12rb2 | 4.452 | 2.023 | 2.723 | 2.433 | 3.322 | 1.130 |
| Chr6:87777001-87778000 | Isy1 | 4.452 | 1.023 | 3.308 | 1.280 | 3.000 | 1.452 |
| Chr7:109121001-109122000 | Numa1 | 3.674 | 1.023 | 1.723 | 1.433 | 3.170 | 0.504 |
| Chr7:10945001-10946000 | Nlrp4d | 4.326 | 2.608 | 2.723 | 1.280 | 3.000 | 1.326 |
| Chr7:114032001-114033000 | Olfr706 | 4.954 | 2.023 | 3.308 | 3.017 | 1.585 | 3.370 |
| Chr7:135137001-135138000 | Pycard | 4.674 | 2.023 | 2.723 | 2.433 | 3.000 | 1.674 |
| Chr7:22454001-22455000 | Gm4545 | 0.867 | 0.871 | 1.723 | 1.280 | −0.152 | 1.019 |
| Chr7:66704001-66705000 | SNORD115 | 2.867 | 1.023 | 1.571 | 1.280 | 3.170 | −0.303 |
| Chr7:68880001-68881000 | Mir344e | 3.867 | 2.023 | 1.571 | 2.433 | 2.585 | 1.282 |
| Chr7:79223001-79224000 | Mctp2 | 4.189 | 1.023 | 2.723 | 2.433 | 2.322 | 1.867 |
| Chr7:92563001-92564000 | Vmn2r69 | 4.674 | 3.023 | 1.723 | 2.433 | 3.170 | 1.504 |
| Chr8:46798001-46799000 | Sorbs2 | 4.452 | 0.871 | 3.723 | 2.433 | 3.170 | 1.282 |
| Chr8:48627001-48628000 | Rwdd4a | 4.326 | 2.023 | 1.723 | 2.433 | 4.392 | −0.066 |
| Chr8:55162001-55163000 | Vegfc | 3.867 | 0.871 | 3.308 | 1.433 | 2.000 | 1.867 |

TABLE 2-continued

| Peak | Gene | log₂ normalized Read count | | | | | log₂ ratio NCsh |
| --- | --- | --- | --- | --- | --- | --- | --- |
| | | NCsh (N) | NCsh (C) | MMP-9sh (N) | MMP-9sh (C) | Input | (N) vs input |
| Chr9:103220001-103221000 | Topbp1 | 5.115 | 2.608 | 3.308 | 3.433 | 2.585 | 2.530 |
| Chr9:108982001-108983000 | Ccdc72 | 3.867 | 1.023 | 2.723 | 1.433 | 4.322 | −0.455 |
| Chr9:39200001-39201000 | Olfr951 | 5.037 | 3.831 | 1.571 | 2.433 | 4.170 | 0.867 |
| Chr9:54323001-54324000 | Dmxl2 | 4.954 | 3.023 | 1.723 | 3.017 | 3.907 | 1.048 |
| Chr9:73361001-73362000 | Unc13c | 4.567 | 2.608 | 1.571 | 3.433 | 2.585 | 1.982 |
| Chr9:7763001-7764000 | Tmem123 | 4.189 | 1.023 | 2.723 | 1.433 | 3.322 | 0.867 |
| ChrX:144496001-144497000 | U3 | 2.867 | 0.871 | 1.723 | 1.433 | 1.585 | 1.282 |
| ChrX:51094001-51095000 | Xlr | 4.037 | 3.023 | 1.723 | 1.280 | 2.585 | 1.452 |
| ChrX:74032001-74033000 | 5S_rRNA | 2.867 | 1.023 | 1.571 | 1.433 | 2.585 | 0.282 |
| ChrX:91596001-91597000 | snoU13 | 3.674 | 1.023 | 1.571 | 2.433 | 2.000 | 1.674 |
| ChrX:98440001-98441000 | U11 | 4.189 | 2.023 | 2.723 | 1.280 | 3.700 | 0.489 |

What is claimed is:

1. A method to identify a polynucleotide fragment bound to an H3 histone comprising a cleaved N-terminal tail (H3NT) in a cell, the method comprising:
   a. crosslinking the genomic DNA of the cell to the histones of the cell, thereby producing crosslinked chromatin;
   b. generating fragments of the crosslinked chromatin;
   c. acetylating all unmodified lysine residues in the histones by contacting the fragmented, crosslinked chromatin with acetic anhydride or an equivalent thereof,
   d. conducting parallel chromatin immunoprecipitations on the acetylated chromatin produced in step c. with (1) an H3 C-terminal tail control antibody and (2) one or more antibodies directed to acetylated lysine residues in the cleaved region of the H3NT; and
   e. identifying the polynucleotide fragment bound to an H3NT by detecting reduction in polynucleotide fragment enrichment with the one or more antibodies directed to acetylated lysine residues in the cleaved region relative to polynucleotide fragment enrichment with the H3 C-terminal tail control antibody.

2. The method of claim 1, wherein step a. is performed by fixation with methylene blue or an equivalent thereof.

3. The method of claim 1, wherein step b. is performed by sonication, enzymatic fragmentation, or an equivalent of each thereof.

4. The method of claim 1, wherein the one or more antibodies directed to acetylated lysine residues in the cleaved region of the H3NT are selected from an H3K4ac antibody, an H3K9ac antibody, and an H3K14ac antibody.

5. The method of claim 4, wherein the one or more antibodies directed to acetylated lysine residues in the cleaved region of the H3NT is an H3K14ac antibody.

6. The method of claim 1, wherein step e. is performed by a method comprising quantitative PCR (qPCR) or NextGen sequencing analysis.

7. The method of claim 1, further comprising identifying a subject for therapy with MMP-9.

8. The method of claim 1, further comprising identifying a region of the genome of the cell at which a matrix metalloproteinase cleaves an H3 N terminal tail.

* * * * *

SEQUENCE LISTING

<160> NUMBER OF SEQ ID NOS: 47

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gaagtggtag cccacgtgat                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
tcttggcacc acataaacca                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gggtcagtgt gaccgaagat                                              20

<210> SEQ ID NO 4
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 4
ggaagtcaga agtgggtgga                                                     20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcgaaagac agcactggag cat                                                 23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggctgcctt ccgtctcata g                                                   21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctctggctgt cctggaactc                                                     20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccaggaccag gtgaaacact                                                     20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atcttgtggc tttgccaact                                                     20

<210> SEQ ID NO 10
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 10
agtccttgcc tgtctttcca                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaaggtcct gaaccccact                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agaaggtcct gaaccccact                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggaccttcg gaagagcagt                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagcaagcag ctcataacca                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtgggttcc actgaaagaa                                                   20

<210> SEQ ID NO 16
<211> LENGTH: 20
<212> TYPE: DNA
<213> ORGANISM: Artificial Sequence
<220> FEATURE:
```

<223> OTHER INFORMATION: Description of Artificial Sequence: Synthetic
       primer

<400> SEQUENCE: 16
ggttcctctg accaaaagca                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 17
aggagcgtgt ccaacatagg                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 18
ccacgagatg tttccaggat                                                    20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 19
gaggcatact tgtaccgcta t                                                  21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 20
ccctggatta agtttgataa a                                                  21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 21
taactctggc catagcttaa t                                                  21

<210> SEQ ID NO 22
<211> LENGTH: 707
<212> TYPE: PRT
<213> ORGANISM: Homo sapiens

<400> SEQUENCE: 22

```
Met Ser Leu Trp Gln Pro Leu Val Leu Val Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
        50                  55                  60

Lys Ser Leu Gly Pro Ala Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415
```

```
Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
            435                 440                 445

Pro Glu Pro Arg Pro Pro Thr Thr Thr Thr Pro Gln Pro Thr Ala Pro
    450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
            530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
                595                 600                 605

Asp Val Ala Gln Val Thr Gly Ala Leu Arg Ser Gly Arg Gly Lys Met
610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
                675                 680                 685

Asn Gln Val Asp Gln Val Gly Tyr Val Thr Tyr Asp Ile Leu Gln Cys
            690                 695                 700

Pro Glu Asp
705

<210> SEQ ID NO 23
<211> LENGTH: 4
<212> TYPE: PRT
<213> ORGANISM: Mus musculus

<400> SEQUENCE: 23

Asp Glu Ala His
1

<210> SEQ ID NO 24
<211> LENGTH: 4
<212> TYPE: PRT
<213> ORGANISM: Mus musculus

<400> SEQUENCE: 24

Asp Glu Ala Asp
1
```

-continued

```
<210> SEQ ID NO 25
<211> LENGTH: 5
<212> TYPE: PRT
<213> ORGANISM: Homo sapiens

<400> SEQUENCE: 25

Gln Leu Ala Thr Lys
1               5

<210> SEQ ID NO 26
<211> LENGTH: 10
<212> TYPE: PRT
<213> ORGANISM: Homo sapiens

<400> SEQUENCE: 26

Lys Ser Ala Pro Ala Thr Gly Gly Val Lys
1               5                   10

<210> SEQ ID NO 27
<211> LENGTH: 9
<212> TYPE: PRT
<213> ORGANISM: Homo sapiens

<400> SEQUENCE: 27

Ser Ala Pro Ala Thr Gly Gly Val Lys
1               5

<210> SEQ ID NO 28
<211> LENGTH: 9
<212> TYPE: PRT
<213> ORGANISM: Homo sapiens

<400> SEQUENCE: 28

Tyr Arg Pro Gly Thr Val Ala Leu Arg
1               5

<210> SEQ ID NO 29
<211> LENGTH: 7
<212> TYPE: PRT
<213> ORGANISM: Homo sapiens

<400> SEQUENCE: 29

Ser Thr Glu Leu Leu Ile Arg
1               5

<210> SEQ ID NO 30
<211> LENGTH: 6
<212> TYPE: PRT
<213> ORGANISM: Homo sapiens

<400> SEQUENCE: 30

Lys Leu Pro Phe Gln Arg
1               5

<210> SEQ ID NO 31
<211> LENGTH: 5
<212> TYPE: PRT
<213> ORGANISM: Homo sapiens

<400> SEQUENCE: 31

Leu Pro Phe Gln Arg
1               5

<210> SEQ ID NO 32
```

```
<211> LENGTH: 11
<212> TYPE: PRT
<213> ORGANISM: Homo sapiens

<400> SEQUENCE: 32

Glu Ile Ala Gln Asp Phe Lys Thr Asp Leu Arg
1               5                   10

<210> SEQ ID NO 33
<211> LENGTH: 7
<212> TYPE: PRT
<213> ORGANISM: Homo sapiens

<400> SEQUENCE: 33

Arg Val Thr Ile Met Pro Lys
1               5

<210> SEQ ID NO 34
<211> LENGTH: 6
<212> TYPE: PRT
<213> ORGANISM: Homo sapiens

<400> SEQUENCE: 34

Val Thr Ile Met Pro Lys
1               5

<210> SEQ ID NO 35
<211> LENGTH: 12
<212> TYPE: PRT
<213> ORGANISM: Homo sapiens

<400> SEQUENCE: 35

Val Thr Ile Met Pro Lys Asp Ile Gln Leu Ala Arg
1               5                   10

<210> SEQ ID NO 36
<211> LENGTH: 6
<212> TYPE: PRT
<213> ORGANISM: Homo sapiens

<400> SEQUENCE: 36

Asp Ile Gln Leu Ala Arg
1               5

<210> SEQ ID NO 37
<211> LENGTH: 5
<212> TYPE: PRT
<213> ORGANISM: Homo sapiens

<400> SEQUENCE: 37

Ile Arg Gly Glu Arg
1               5

<210> SEQ ID NO 38
<211> LENGTH: 6
<212> TYPE: PRT
<213> ORGANISM: Homo sapiens

<400> SEQUENCE: 38

Pro Arg Lys Gln Leu Ala
1               5

<210> SEQ ID NO 39
<211> LENGTH: 136
<212> TYPE: PRT
```

<213> ORGANISM: Homo sapiens

<400> SEQUENCE: 39

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 40
<211> LENGTH: 8
<212> TYPE: PRT
<213> ORGANISM: Homo sapiens

<400> SEQUENCE: 40

Leu Ala Arg Arg Ile Arg Gly Glu
1               5

<210> SEQ ID NO 41
<211> LENGTH: 8
<212> TYPE: PRT
<213> ORGANISM: Homo sapiens

<400> SEQUENCE: 41

Ser Ser Ala Val Met Ala Leu Gln
1               5

<210> SEQ ID NO 42
<211> LENGTH: 8
<212> TYPE: PRT
<213> ORGANISM: Homo sapiens

<400> SEQUENCE: 42

Met Pro Lys Asp Ile Gln Leu Ala
1               5

<210> SEQ ID NO 43
<211> LENGTH: 8
<212> TYPE: PRT
<213> ORGANISM: Homo sapiens

<400> SEQUENCE: 43

Lys Pro His Arg Tyr Arg Pro Gly
1               5

<210> SEQ ID NO 44
<211> LENGTH: 8
<212> TYPE: PRT

```
<213> ORGANISM: Homo sapiens

<400> SEQUENCE: 44

Leu Ile Arg Lys Leu Pro Phe Gln
1               5

<210> SEQ ID NO 45
<211> LENGTH: 8
<212> TYPE: PRT
<213> ORGANISM: Homo sapiens

<400> SEQUENCE: 45

Ala Pro Arg Lys Gln Leu Ala Thr
1               5

<210> SEQ ID NO 46
<211> LENGTH: 8
<212> TYPE: PRT
<213> ORGANISM: Homo sapiens

<400> SEQUENCE: 46

Ala Val Met Ala Leu Gln Glu Ala
1               5

<210> SEQ ID NO 47
<211> LENGTH: 8
<212> TYPE: PRT
<213> ORGANISM: Homo sapiens

<400> SEQUENCE: 47

Gln Ser Ser Ala Val Met Ala Leu
1               5
```